(12) United States Patent
Li et al.

(10) Patent No.: US 12,351,643 B2
(45) Date of Patent: Jul. 8, 2025

(54) DOSING FOR TREATMENT WITH ANTI-CD20/ANTI-CD3 BISPECIFIC ANTIBODIES

(71) Applicant: Genentech, Inc., South San Francisco, CA (US)

(72) Inventors: Chi-Chung Li, South San Francisco, CA (US); Carol Elaine O'Hear, South San Francisco, CA (US); Brendan Christian Bender, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 56 days.

(21) Appl. No.: 17/517,236

(22) Filed: Nov. 2, 2021

(65) Prior Publication Data

US 2022/0162329 A1    May 26, 2022

Related U.S. Application Data

(60) Provisional application No. 63/188,545, filed on May 14, 2021, provisional application No. 63/109,863, filed on Nov. 4, 2020.

(51) Int. Cl.
| | |
|---|---|
| *C07K 16/28* | (2006.01) |
| *A61K 31/573* | (2006.01) |
| *A61K 39/00* | (2006.01) |
| *A61P 35/00* | (2006.01) |

(52) U.S. Cl.
CPC ........ *C07K 16/2887* (2013.01); *A61K 31/573* (2013.01); *A61P 35/00* (2018.01); *C07K 16/2809* (2013.01); *C07K 16/2827* (2013.01); *C07K 16/2866* (2013.01); *A61K 2039/507* (2013.01); *A61K 2039/545* (2013.01); *C07K 2317/24* (2013.01); *C07K 2317/31* (2013.01); *C07K 2317/41* (2013.01)

(58) Field of Classification Search
CPC ............ C07K 16/2887; C07K 16/2809; C07K 2317/31; C07K 2317/565; A61K 31/573; A61K 2039/545; A61P 35/00
See application file for complete search history.

(56) References Cited

U.S. PATENT DOCUMENTS

| | | | |
|---|---|---|---|
| 5,500,362 A | 3/1996 | Robinson et al. | |
| 5,595,756 A * | 1/1997 | Bally et al. ........... | A61K 9/1272 264/4.1 |
| 5,624,821 A | 4/1997 | Winter et al. | |
| 5,648,260 A | 7/1997 | Winter et al. | |
| 5,731,168 A | 3/1998 | Carter et al. | |
| 5,821,337 A | 10/1998 | Carter et al. | |
| 5,869,046 A | 2/1999 | Presta et al. | |
| 6,194,551 B1 | 2/2001 | Idusogie et al. | |
| 6,248,516 B1 | 6/2001 | Winter et al. | |
| 6,455,043 B1 | 9/2002 | Grillo-Lopez | |
| 6,602,684 B1 | 8/2003 | Umana et al. | |
| 6,737,056 B1 | 5/2004 | Presta | |
| 7,332,581 B2 | 2/2008 | Presta | |
| 7,371,826 B2 | 5/2008 | Presta | |
| 7,612,181 B2 | 11/2009 | Wu et al. | |
| 7,682,612 B1 | 3/2010 | White et al. | |
| 7,695,936 B2 | 4/2010 | Carter et al. | |
| 7,799,900 B2 | 9/2010 | Adams et al. | |
| 8,219,149 B2 | 7/2012 | Lafata et al. | |
| 8,258,268 B2 | 9/2012 | Wu et al. | |
| 8,562,992 B2 | 10/2013 | Adams et al. | |
| 8,709,421 B2 | 4/2014 | Heiss et al. | |
| 8,722,859 B2 | 5/2014 | Miller et al. | |
| 8,895,702 B2 | 11/2014 | Williams et al. | |
| 8,969,526 B2 | 3/2015 | Baehner et al. | |
| 9,011,864 B2 | 4/2015 | Schulz et al. | |
| 9,017,676 B2 | 4/2015 | Lindhofer | |
| 9,308,257 B2 | 4/2016 | Sharma, Sr. et al. | |
| 9,315,567 B2 | 4/2016 | Chang et al. | |
| 9,493,563 B2 | 11/2016 | Blein et al. | |
| 9,587,021 B2 | 3/2017 | Huang et al. | |
| 9,657,102 B2 | 5/2017 | Smith et al. | |
| 10,000,576 B1 | 6/2018 | Weisser et al. | |
| 10,105,391 B2 | 10/2018 | Wu et al. | |
| 10,357,571 B2 | 7/2019 | Williams et al. | |

(Continued)

FOREIGN PATENT DOCUMENTS

| | | |
|---|---|---|
| CN | 102369218 A | 3/2012 |
| EP | 1870459 A1 | 12/2007 |

(Continued)

OTHER PUBLICATIONS

Heppner et al., Tumor heterogeneity: biological implications and therapeutic consequences, 1983, Cancer Metastasis Reviews 2: 5-23 (Year: 1983).*
Jain RK, Barriers to Drug Delivery in Solid Tumors, 1994, Scientific American, pp. 58-645 (Year: 1994).*
Gura T, Systems for Identifying New Drugs are Often Faulty, Science, 1997, 278(5340): 1041-1042 (Year: 1997).*
Sporn et al. Chemoprevention of Cancer, Carcinogenesis, vol. 21 (2000), 525-530 (Year: 2000).*
Auerbach et al, Angiogenesis assays: Problems and pitfalls, Cancer and Metastasis Reviews, 2000, 19: 167-172 (Year: 2000).*

(Continued)

*Primary Examiner* — Vanessa L. Ford
*Assistant Examiner* — Danaya L Middleton
(74) *Attorney, Agent, or Firm* — Clark & Elbing LLP; Karen L. Elbing

(57) ABSTRACT

The present invention relates to the treatment of subjects having CD20-positive cell proliferative disorders (e.g., B cell proliferative disorders, such as non-Hodgkin's lymphomas). More specifically, the invention pertains to the treatment of subjects having a B cell proliferative disorder by intravenous administration of an anti-CD20/anti-CD3 bispecific antibody (e.g., mosunetuzumab).

80 Claims, 14 Drawing Sheets

Specification includes a Sequence Listing.

(56) References Cited

U.S. PATENT DOCUMENTS

| | | | |
|---|---|---|---|
| 10,561,686 | B2 | 2/2020 | Xiao et al. |
| 11,466,094 | B2 * | 10/2022 | Chu et al. ............... A61P 35/02 |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0014934 | A1 | 1/2005 | Hinton et al. |
| 2005/0095243 | A1 | 5/2005 | Chan et al. |
| 2005/0123546 | A1 | 6/2005 | Umana et al. |
| 2009/0075279 | A1 | 3/2009 | Frantz et al. |
| 2009/0252683 | A1 | 10/2009 | Kischel et al. |
| 2009/0304719 | A1 | 12/2009 | Daugherty et al. |
| 2010/0015133 | A1 | 1/2010 | Igawa et al. |
| 2010/0150918 | A1 | 6/2010 | Kufer et al. |
| 2010/0331527 | A1 | 12/2010 | Davis et al. |
| 2011/0020322 | A1 | 1/2011 | Wilkins et al. |
| 2011/0123532 | A1 | 5/2011 | Gurney et al. |
| 2011/0178279 | A1 | 7/2011 | Williams et al. |
| 2012/0244577 | A1 | 9/2012 | Dixit et al. |
| 2012/0251531 | A1 | 10/2012 | Baehner et al. |
| 2013/0129723 | A1 | 5/2013 | Blankenship et al. |
| 2013/0165638 | A1 | 6/2013 | Hsu et al. |
| 2013/0171095 | A1 | 7/2013 | Bernett et al. |
| 2013/0266568 | A1 | 10/2013 | Brinkmann et al. |
| 2013/0287774 | A1 | 10/2013 | Zugmaier et al. |
| 2014/0079689 | A1 | 3/2014 | Elliott et al. |
| 2014/0088295 | A1 | 3/2014 | Smith et al. |
| 2014/0112914 | A1 | 4/2014 | Nezu et al. |
| 2014/0170149 | A1 | 6/2014 | Neijssen et al. |
| 2014/0187753 | A1 | 7/2014 | Blein et al. |
| 2014/0302064 | A1 | 10/2014 | Moore |
| 2014/0377270 | A1 | 12/2014 | Moore et al. |
| 2015/0098900 | A1 | 4/2015 | Ebens et al. |
| 2015/0133640 | A1 | 5/2015 | Blein et al. |
| 2015/0166661 | A1 * | 6/2015 | Chen et al. ............... A61P 9/08 |
| | | | 435/254.2 |
| 2015/0266966 | A1 | 9/2015 | Smith et al. |
| 2015/0284475 | A1 | 10/2015 | Zhou et al. |
| 2016/0000916 | A1 | 1/2016 | Crotts et al. |
| 2016/0017058 | A1 | 1/2016 | Kim et al. |
| 2016/0075785 | A1 | 3/2016 | Ast et al. |
| 2016/0090416 | A1 | 3/2016 | Gunde et al. |
| 2016/0145339 | A1 | 5/2016 | Zhou et al. |
| 2016/0152711 | A1 | 6/2016 | Williams et al. |
| 2016/0159906 | A1 | 6/2016 | Sun et al. |
| 2016/0194399 | A1 | 7/2016 | Irving et al. |
| 2016/0368985 | A1 | 12/2016 | Hotzel et al. |
| 2016/0368994 | A1 | 12/2016 | Kelley et al. |
| 2017/0008971 | A1 | 1/2017 | Dennis et al. |
| 2017/0022274 | A1 | 1/2017 | Chang et al. |
| 2017/0158773 | A1 | 6/2017 | Adams et al. |
| 2017/0204194 | A1 | 7/2017 | Chen et al. |
| 2017/0209573 | A1 | 7/2017 | Bacac et al. |
| 2017/0218074 | A1 | 8/2017 | Williams et al. |
| 2017/0224818 | A1 | 8/2017 | Lindhofer et al. |
| 2017/0267783 | A1 | 9/2017 | Nezu et al. |
| 2018/0057593 | A1 | 3/2018 | Dennis |
| 2018/0148508 | A1 | 5/2018 | Wang et al. |
| 2018/0193479 | A1 | 7/2018 | Williams et al. |
| 2020/0129617 | A1 * | 4/2020 | Brownstein et al. ......................... |
| | | | A61K 31/675 |
| 2020/0164077 | A1 | 5/2020 | Williams et al. |
| 2020/0199578 | A1 | 6/2020 | Short et al. |
| 2020/0339686 | A1 | 10/2020 | Sato et al. |

FOREIGN PATENT DOCUMENTS

| | | | |
|---|---|---|---|
| EP | 1923072 | A1 | 5/2008 |
| EP | 1870459 | A4 | 9/2010 |
| EP | 2482212 | A1 | 8/2012 |
| EP | 2578230 | A1 | 4/2013 |
| EP | 2647707 | A1 | 10/2013 |
| EP | 2647707 | A4 | 4/2014 |
| EP | 2769989 | A1 | 8/2014 |
| EP | 2840091 | A1 | 2/2015 |
| EP | 1870459 | B1 | 6/2016 |
| JP | 2013-528569 | A | 7/2013 |
| JP | 2015-509952 | A | 4/2015 |
| JP | 2018-527887 | A | 9/2018 |
| RU | 2539112 | C2 | 1/2015 |
| TW | 201508008 | A | 3/2015 |
| TW | 201827075 | A | 8/2018 |
| WO | WO-91/03493 | A1 | 3/1991 |
| WO | WO-92/22653 | A1 | 12/1992 |
| WO | WO-94/04679 | A1 | 3/1994 |
| WO | WO-94/29351 | A2 | 12/1994 |
| WO | WO-96/01126 | A1 | 1/1996 |
| WO | WO-96/27011 | A1 | 9/1996 |
| WO | WO-97/30087 | A1 | 8/1997 |
| WO | WO-98/50431 | A2 | 11/1998 |
| WO | WO-98/58964 | A1 | 12/1998 |
| WO | WO-98/50431 | A3 | 1/1999 |
| WO | WO-99/22764 | A1 | 5/1999 |
| WO | WO-99/51642 | A1 | 10/1999 |
| WO | WO-00/61739 | A1 | 10/2000 |
| WO | WO-01/29246 | A1 | 4/2001 |
| WO | WO-02/31140 | A1 | 4/2002 |
| WO | WO-03/011878 | A2 | 2/2003 |
| WO | WO-03/084570 | A1 | 10/2003 |
| WO | WO-03/085107 | A1 | 10/2003 |
| WO | WO-03/085119 | A1 | 10/2003 |
| WO | WO-2004/056312 | A2 | 7/2004 |
| WO | WO-2005/035586 | A1 | 4/2005 |
| WO | WO-2005/035778 | A1 | 4/2005 |
| WO | WO-2005/053742 | A1 | 6/2005 |
| WO | WO-2005/083431 | A2 | 9/2005 |
| WO | WO-2005/100402 | A1 | 10/2005 |
| WO | WO-2006/029879 | A2 | 3/2006 |
| WO | WO-2007/005874 | A2 | 1/2007 |
| WO | WO-2007/042261 | A2 | 4/2007 |
| WO | WO-2007/110205 | A2 | 10/2007 |
| WO | WO-2007/146968 | A2 | 12/2007 |
| WO | WO-2008/077546 | A1 | 7/2008 |
| WO | WO-2008/119566 | A2 | 10/2008 |
| WO | WO-2008/119567 | A2 | 10/2008 |
| WO | WO-2009/070642 | A1 | 6/2009 |
| WO | WO-2009/106321 | A1 | 9/2009 |
| WO | WO-2010/057109 | A1 | 5/2010 |
| WO | WO-2010/077643 | A1 | 7/2010 |
| WO | WO-2010/114940 | A1 | 10/2010 |
| WO | WO-2011/028945 | A1 | 3/2011 |
| WO | WO-2011/028952 | A1 | 3/2011 |
| WO | WO-2011/090754 | A1 | 7/2011 |
| WO | WO-2011/090762 | A1 | 7/2011 |
| WO | WO-2011/121110 | A1 | 10/2011 |
| WO | WO-2011/131746 | A2 | 10/2011 |
| WO | WO-2011/143545 | A1 | 11/2011 |
| WO | WO-2012/025525 | A1 | 3/2012 |
| WO | WO-2012/058768 | A1 | 5/2012 |
| WO | WO-2012/058768 | A8 | 5/2012 |
| WO | WO-2012/073985 | A1 | 6/2012 |
| WO | WO-2012/075581 | A1 | 6/2012 |
| WO | WO-2012/123949 | A1 | 9/2012 |
| WO | WO-2012/143524 | A2 | 10/2012 |
| WO | WO-2012/158818 | A2 | 11/2012 |
| WO | WO-2012/162067 | A2 | 11/2012 |
| WO | WO-2013/026831 | A1 | 2/2013 |
| WO | WO-2013/128027 | A1 | 9/2013 |
| WO | WO-2013/128194 | A1 | 9/2013 |
| WO | WO-2014/022540 | A1 | 2/2014 |
| WO | WO-2014/028560 | A2 | 2/2014 |
| WO | WO-2014/047231 | A1 | 3/2014 |
| WO | WO-2014/028560 | A3 | 5/2014 |
| WO | WO-2014/083178 | A1 | 6/2014 |
| WO | WO-2014/108483 | A1 | 7/2014 |
| WO | WO-2014/122251 | A2 | 8/2014 |
| WO | WO-2014/141152 | A2 | 9/2014 |
| WO | WO-2014/144722 | A2 | 9/2014 |
| WO | WO-2014/153002 | A1 | 9/2014 |

(56) References Cited

FOREIGN PATENT DOCUMENTS

| | | |
|---|---|---|
| WO | WO-2014/122251 A3 | 10/2014 |
| WO | WO-2014/170063 A1 | 10/2014 |
| WO | WO-2014/141152 A3 | 12/2014 |
| WO | WO-2014/191113 A1 | 12/2014 |
| WO | WO-2014/193973 A2 | 12/2014 |
| WO | WO-2014/210064 A1 | 12/2014 |
| WO | WO-2015/006749 A2 | 1/2015 |
| WO | WO-2014/191113 A8 | 2/2015 |
| WO | WO-2015/095392 A1 | 6/2015 |
| WO | WO-2015/143079 A1 | 9/2015 |
| WO | WO-2015/184203 A1 | 12/2015 |
| WO | WO-2015/184207 A1 | 12/2015 |
| WO | WO-2016/014942 A1 | 1/2016 |
| WO | WO-2016/019969 A1 | 2/2016 |
| WO | WO-2016/020065 A1 | 2/2016 |
| WO | WO-2016/036678 A1 | 3/2016 |
| WO | WO-2016/049214 A1 | 3/2016 |
| WO | WO-2016/081490 A1 | 5/2016 |
| WO | WO-2016/090210 A1 | 6/2016 |
| WO | WO-2016/110576 A1 | 7/2016 |
| WO | WO-2016/179003 A1 | 11/2016 |
| WO | WO-2016/191261 A1 | 12/2016 |
| WO | WO-2016/201300 A1 | 12/2016 |
| WO | WO-2016/204966 A1 | 12/2016 |
| WO | WO-2016/205520 A1 | 12/2016 |
| WO | WO-2016/205531 A2 | 12/2016 |
| WO | WO-2017/132279 A1 | 8/2017 |
| WO | WO-2018/093821 A1 | 5/2018 |
| WO | WO-2020/232169 A1 | 11/2020 |
| WO | WO-2022/098648 A2 | 5/2022 |

OTHER PUBLICATIONS

Harris et al., The World Health Organization Classi® cation of Neoplasms of the Hematopoietic and Lymphoid Tissues: Report of the Clinical Advisory Committee Meeting—Airlie House, Virginia, Nov. 1997, (2000), The Hematology Journal (2000) 1, 53-66 (Year: 2000).*

Dornan et al., Therapeutic potential of an anti-CD79b antibody-drug conjugate, anti-CD79b-vc-MMAE, for the treatment of non-Hodgkin lymphoma, (2009), Blood. 2009;114:2721-2729 (Year: 2009).*

Buhmann et al., Immunotherapy of recurrent B-cell malignancies after allo-SCT with Bi20 (FBT A05), a trifunctional anti-CD3 x anti-CD20 antibody and donor lymphocyte infusion, Bone Marrow Transplantation (2009) 43, 383-397 (Year: 2009).*

Hait., Anticancer drug development: the grand challenges, Nature Reviews/Drug Discovery, 2010, 9, pp. 253-254 (Year: 2010).*

Shao et al., Distinguishing Hairy Cell Leukemia Variant from Hairy Cell Leukemia: Development and Validation of Diagnostic Criteria, Leuk Res. Apr. 2013 ; 37(4): 401-409 (Year: 2013).*

Gravanis et al., The changing world of cancer drug development: the regulatory bodies' perspective, Chin Clin Oncol, 2014, 3, pp. 1-5 (Year: 2014).*

Seung et al., Immunotherapy with Long-Lived Anti-CD20 x Anti-CD3 Bispecific Antibodies Stimulates Potent T Cell-Mediated Killing of Human B Cell Lines and of Circulating and Lymphoid B Cells in . . . , (2014), Blood, 124(21):3111 (Year: 2014).*

Sun et al., Anti-CD20/CD3 T cell-dependent bispecific antibody for the treatment of B cell malignancies, Sci Transl Med, 2015, 7 (287)(287ra70):1-10 (Year: 2015).*

Stieglmaier et al., Utilizing the BiTE (bispecific T-cell engager) platform for immunotherapy of cancer, Exp Opin on Biol Ther, 2015, 15(8): 1093-1099 (Year: 2015).*

Schuster et al., BJH, 2015, 169: 90-102 (Year: 2015).*

Choi et al., Reference values of hematology, biochemistry, and blood type in cynomolgus monkeys from cambodia origin, (2016), Lab Anim Res 2016: 32(1), 46-55 (Year: 2016).*

Goebeler et al., Journal of Clinical Oncology, 2016, 34(10): 1104-1111) (Year: 2016).*

Beans, Targeting metastasis to halt cancer's spread, PNAS 2018; 115(50): 12539-12543 (Year: 2018).*

Curigliano et al., Safety and Tolerability of Phosphatidylinositol-3-Kinase (PI3K) Inhibitors in Oncology, (2019), Drug Safety 42:247-262 (Year: 2019).*

Schuster et al., Blood (2019) 134 (Supplement_1): 6 (Year: 2019).*

Lazar et al., Mol. Cell. Biol., 8:1247-1252, 1988 (Year: 1988).*

Bowie et al., Science, 1990, 247:1306-1310 (Year: 1990).*

Burgess et al., J. Cell Biol. 111: 2129-2138, 1990 (Year: 1990).*

Greenspan et al., 1999, Nature Biotechnology, 17:936-937 (Year: 1999).*

Bork. Genome Research, 2000, 10:398-400 (Year: 2000).*

American Cancer Society, cancer.org; last revised Jan. 29, 2019 (Year: 2019).*

Bartlett et al., Blood (2022) 140 (Supplement 1): 1467-1470; Abstract only (Year: 2022).*

Budde et al, J Clin Oncol 40:481-49, 2021 (Year: 2021).*

The Cleveland Clinic, https://my.clevelandclinic.org/health/diseases/15662-non-hodgkin-lymphoma; accessed online Jul. 29, 2024 (Year: 2024).*

Hosseini et al, Systems Biology and Applications (2020) 6:28, 11 pages; published online Aug. 28, 2020 (Year: 2020).*

"Purified Mouse Anti-Human CD3-epsilon Clone SP34," BD Biosciences, <https://www.bdbiosciences.com/us/reagents/research/antibodies- buffers/immunology-reagents/anti-non-human-primate-antibodies/cell-surface-antigens/purified-mouse-anti-human-cd3-sp34/p/556610>, retrieved on Jan. 4, 2021 (4 pages).

Anderson et al., "G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. 80(11):2826-34 (1992) (10 pages).

Atwell et al., "Stable heterodimers from remodeling the domain interface of a homodimer using a phage display library," J Mol Biol. 270(1):26-35 (1997).

Baeuerle et al., "Bispecific T-cell engaging antibodies for cancer therapy," Cancer Res. 69(12):4941-4 (2009).

Bortoletto et al., "Optimizing anti-CD3 affinity for effective T cell targeting against tumor cells," Eur J Immunol. 32(11):3102-7 (2002).

Brack et al., "A Bispecific HER2-Targeting FynomAb with Superior Antitumor Activity and Novel Mode of Action," Mol Cancer Ther. 13(8):2030-39 (2014) (11 pages).

Brinkmann et al., "The making of bispecific antibodies," MAbs. 9(2):182-212 (2017).

Brown et al., "Tolerance to single, but not multiple, amino acid replacements in antibody $V_H$ CDR2: a means of minimizing B cell wastage from somatic hypermutation?" J Immunol. 156(9):3285-91 (1996).

Brüggemann et al., "Comparison of the effector functions of human immunoglobulins using a matched set of chimeric antibodies," J Exp Med. 166(5):1351-61 (1987).

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).

Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," J Transl Med. 11:160 (2013) (9 pages).

Carter, "Bispecific human IgG by design," J Immunol Methods. 248(1-2):7-15 (2001).

Choi et al., "Bispecific antibodies engage T cells for antitumor immunotherapy," Expert Opin Biol Ther. 11(7):843-53 (2011).

Chu et al., "Immunotherapy with long-lived anti-CD20 x anti-CD3 bispecific antibodies stimulates potent T cell-mediated killing of human B cell lines and of circuating and lymphoid B cells in monkeys: a potential therapy for B cell lymphomas and lukemias," Blood. 124(21):311 (2014) (1 page).

Clynes et al., "Fc receptors are required in passive and active immunity to melanoma," Proc Natl Acad Sci U S A. 95(2):652-6 (1998).

(56) References Cited

OTHER PUBLICATIONS

Cragg et al., "Antibody specificity controls in vivo effector mechanisms of anti-CD20 reagents," Blood. 103(7):2738-43 (2004).
Cragg et al., "Complement-mediated lysis by anti-CD20 mAb correlates with segregation into lipid rafts," Blood. 101(3):1045-52 (2003).
Desnoyers et al., "Tumor-Specific Activation of an EGFR-Targeting Probody Enhances Therapeutic Index," Sci Transl Med. 5(207):207ra144 (2013) (10 pages).
Desnoyers et al., "Tumor-specific activation of an EGFR-targeting probody enhances therapeutic index," Sci Transl Med. 5(207):207ra144 (2013) (2 pages) (Abstract only).
Diefenbach et al., "An individualized risk mitigation approach for safety: experience from the mosunetuzumab (CD20/CD3 bispecific antibody) development program in relation to neurotoxicity risk," 61st ASH Annual Meeting & Exposition, Dec. 7-10, Orlando, Florida, Poster P-4728 (2019) (1 page).
Donaldson et al., "Design and development of masked therapeutic antibodies to limit off-target effects: application to anti-EGFR antibodies," available in PMC Jan. 16, 2013, published in final edited form as: Cancer Biol Ther. 8(22): 2147-52 (2009) (12 pages).
Donaldson et al., "Design and development of masked therapeutic antibodies to limit off-target effects: application to anti-EGFR antibodies," Cancer Biol Ther. 8(22): 2145-50 (2009) (6 pages).
Drent et al., "A Rational Strategy for Reducing On-Target Off-Tumor Effects of CD38-Chimeric Antigen Receptors by Affinity Optimization," Mol Ther. 25(8):1946-58 (2017).
Duncan et al., "The binding site for C1q on IgG," Nature. 332(6166):738-40 (1988).
Edelman et al., "The covalent structure of an entire gammaG immunoglobulin molecule," Proc Natl Acad Sci U S A. 63(1):78-85 (1969).
Erster et al., "Site-specific targeting of antibody activity in vivo mediated by disease-associated proteases," J Control Release. 161(3): 804-12 (2012) (2 pages) (Abstract only).
Gaston et al., "Intracellular delivery of therapeutic antibodies into specific cells using antibody-peptide fusions," Sci Rep. 9(1):18688 (2019) (12 pages).
Gazzano-Santoro et al., "A non-radioactive complement-dependent cytotoxicity assay for anti-CD20 monoclonal antibody," J Immunol Methods. 202(2):163-71 (1997).
Gonzales et al., "Minimizing the Immunogenicity of Antibodies for Clinical Application," Tumour Biol. 26(1):31-43 (2005) (1 page) (Abstract only).
Guyer et al., "Immunoglobulin binding by mouse intestinal epithelial cell receptors," J Immunol. 117(2):587-93 (1976).
Haile et al., "Soluble CD80 Restores T Cell Activation and Overcomes Tumor Cell Programmed Death Ligand 1-Mediated Immune Suppression," J Immunol. 191(5):2829-36 (2013) (9 pages).
Han et al., "Masked Chimeric Antigen Receptor for Tumor-Specific Activation," Mol Ther. 25(1):274-84 (2017).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-502 (1985).
Holliger et al., "Diabodies': small bivalent and bispecific antibody fragments," Proc Natl Acad Sci USA. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).
Hosseini et al., "Mitigating The Risk Of Cytokine Release Syndrome In A Phase I Trial Of CD20/CD3 Bispecific Antibody Mosunetuzumab In NHL: Impact Of Translational System Modeling," NPJ Syst Biol Appl. 6(1):28 (2020) (11 pages).
Hosseini et al., "Systems pharmacology modeling of anti-CD20/CD3 T-cell dependent bispecific antibody and its application to clinical trial design," American Conference on Pharmacometrics 7; Oct. 25; Bellevue, WA. (2016) (1 page).
Huang et al., "In Vivo Deamidation Characterization of Monoclonal Antibody by LC/MS/MS," Anal Chem. 77(5):1432-9 (2005).
Huang et al., "Structural chemistry and therapeutic intervention of protein-protein interactions in immune response, human immunodeficiency virus entry, and apoptosis," Pharmacol Ther. 86(3):201-215 (2000).
Hudson et al., "Engineered antibodies," Nat Med. 9(1):129-34 (2003).
Huehls et al., "Bispecific T-cells engagers for cancer immunotherapy," Immunol Cell Biol. 93(3):290-6 (2015).
Idusogie et al., "Mapping of the C1q Binding Site on Rituxan, A Chimeric Antibody with a Human IgG1 Fc," J Immunol. 164(8):4178-84 (2000).
Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).
Jager et al., "The trifunctional antibody ertumaxomab destroys tumor cells that express low levels of human epidermal growth factor receptor 2," Cancer Res. 69(10):4270-6 (2009).
Junttila et al., "Antitumor Efficacy of a Bispecific Antibody That Targets HER2 and Activates T Cells," Cancer Res. 74(19):5561-71 (2014).
Kanda et al., "Comparison of cell lines for stable production of fucose-negative antibodies with enhanced ADCC," Biotechnol Bioeng. 94(4):680-8 (2006).
Kelley et al., " Thermodynamic Analysis of an Antibody Functional Epitope," Biochemistry. 32(27):6828-35 (1993).
Kiewe et al., "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005) (1 page).
Kiewe et al., "Phase I trial of the trifunctional anti-HER2 x anti-CD3 antibody ertumaxomab in metastatic breast cancer," Clin Cancer Res. 12(10):3085-91 (2006).
Kim et al., "Localization of the site of the murine IgG1 molecule that is involved in binding to the murine intestinal Fc receptor," Eur J Immunol. 24(10):2429-34 (1994).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," mAbs. 4(2):182-97 (2012).
Kortt et al., "Dimeric and trimeric antibodies: high avidity scFvs for cancer targeting," Biomol Eng. 18(3):95-108 (2001) (15 pages).
Law et al., "Expression and characterization of recombinant soluble human CD3 molecules: presentation of antigenic epitopes defined on the native TCR-CD3 complex" Int Immunol 14(4):389-400 (2002).
Leabman et al., "Effects of altered FcγR binding on antibody pharmacokinetics in cynomolgus monkeys, " MAbs. 5(6):896-903 (2013) (27 pages).
Lee et al., "Current concepts in the diagnosis and management of cytokine release syndrome," Blood. 124(2):188-95 (2014) (18 pages).
Li et al., "Exposure-response analyses indicate a promising benefit/risk profile of mosunetuzumab in relapsed and refractory non-Hodgkin lymphoma," 61st ASH Annual Meeting & Exposition, Dec. 7-10, 2019, Orlando, Florida. Poster P-1285 (2019).

(56) References Cited

OTHER PUBLICATIONS

Li, "Successful QSP modeling in drug development starts with the right questions," American Conference on Pharmacometrics 8, Oct. 16, Fort Lauderdale, FL. (2017) (20 pages).
Lippow et al., "Computational Design of Antibody-Affinity Improvement Beyond in Vivo Maturation," available in PMC Jan. 7, 2010, published in final edited form as: Nat Biotechnol. 25(10):1171-6 (2007) (14 pages).
Liu et al., "Affinity-Tuned ErbB2 or EGFR Chimeric Antigen Receptor T Cells Exhibit an Increased Therapeutic Index against Tumors in Mice," Cancer Res. 75(17):3596-607 (2015) (13 pages).
Liu et al., "Heteroantibody duplexes target cells for lysis by cytotoxic T lymphocytes," Proc Natl Acad Sci U S A. 82(24):8648-52 (1985).
Liu et al., "Improvement in soluble expression levels of a diabody by exchanging expression vectors," Protein Expr Purif. 62(1): 15-20 (2008) (6 pages).
Lord et al., "Structure-based engineering to restore high affinity binding of an isoform-selective anti-TGFβ1 antibody," MAbs. 10(3):444-452 (2018).
Lu et al., "Tetravalent anti-CD20/CD3 bispecific antibody for the treatment of B cell lymphoma," Biochem Biophys Res Commun. 473(4):808-813 (2016) (3 pages) (Abstract only).
Lum et al., "Targeting T cells with bispecific antibodies for cancer therapy," available in PMC Oct. 8, 2013, published in final edited form as: BioDrugs. 25(6):365-79 (2011) (24 pages).
Mariuzza et al., "The structural basis of antigen-antibody recognition," Annu Rev Biophys Biophys Chem. 16:139-159 (1987) (2 pages) (Abstract only).
Merchant et al., "An efficient route to human bispecific IgG," Nat Biotechnol. 16(7):677-81 (1998).
Metz et al., "Bispecific antibody derivatives with restricted binding functionalities that are activated by proteolytic processing," Protein Eng Des Sel. 25(10):571-80 (2012).
Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
NIH/NCI, "anti-PD-1 fusion protein AMP-224," dated Jul. 10, 2015, accessed Jul. 31, 2019 (1 page).
Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Okazaki et al., "Fucose depletion from human IgG1 oligosaccharide enhances binding enthalpy and association rate between IgG1 and FcgammaRIIIa," J Mol Biol. 336(5):1239-49 (2004).
Paino et al., "Reply to 'Response to "CD20 Positive Cells Are Undetectable in the Majority of Multiple Myeloma Cell Lines and Are Not Associated With a Cancer Stem Cell Phenotype,"'" Haematologica. 97(7):1110-1114 (2012) (1 page).
Pessano et al., "The T3/T cell receptor complex: antigenic distinction between the two 20-kd T3 (T3-δ and T3-ε) subunits," EMBO J. 4(2):337-44 (1985).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Polu et al., "Probody therapeutics for targeting antibodies to diseased tissue," Expert Opin Biol Ther. 14(8):1049-53 (2014).
Ravetch et al., "Fc receptors," Annu Rev Immunol. 9:457-92 (1991).
Reusch et al., "A tetravalent bispecific TandAb (CD19/CD3), AFM11, efficiently recruits T cells for the potent lysis of CD19(+) tumor cells," MAbs. 7(3):584-604 (2015) (22 pages).
Reusch et al., "Anti-CD3 x anti-epidermal growth factor receptor (EGFR) bispecific antibody redirects T-cell cytolytic activity to EGFR-positive cancers in vitro and in an animal model," Clin Cancer Res. 12(1):183-190 (2006) (9 pages).
Ridgway et al., "Knobs-into-holes' engineering of antibody $C_h3$ domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Ripka et al., "Two Chinese hamster ovary glycosylation mutants affected in the conversion of GDP-mannose to GDP-fucose," Arch Biochem Biophys. 249(2):533-45 (1986).
Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).
Salmerón et al., "A conformational epitope expressed upon association of CD3-epsilon with either CD3-delta or CD3-gamma is the main target for recognition by anti-CD3 monoclonal antibodies," J Immunol. 147(9): 3047-52 (1991) (2 pages) (Abstract only).
Saphire et al., "Crystal structure of a neutralizing human IgG against HIV-1: a template for vaccine design," Science. 293(5532):1155-9 (2001).
Schuster et al., "Immunotherapy with the trifunctional anti-CD20 x anti-CD3 antibody FBTA05 (Lymphomun) in paediatric high-risk patients with recurrent CD20-positive B cell malignancies," Br J Haematol. 169:90-102 (2015) (13 pages).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Sen et al., "Use of Anti-CD3 x Anti-HER2/neu Bispecific Antibody for Redirecting Cytotoxicity of Activated T Cells Toward HER2/neu$^+$ Tumors," J Hematother Stem Cell Res. 10(2):247-60 (2001).
Shalaby et al., "Bispecific HER2 x CD3 antibodies enhance T-cell cytotoxicity in vitro and localize to HER2-overexpressing xenografts in nude mice," Clin Immunol Immunopathol. 74(2):185-92 (1995).
Shen et al., "Preparation and characterization for bispecific antibodies of anti-CD3 x anti-idiotype to B cell lymphocytic leukemia," J Tongji Med Univ. 19(3):166-9 (1999) (4 pages).
Shi et al., "Margin-Infiltrating CD20$^+$ B Cells Display an Atypical Memory Phenotype and Correlate with Favorable Prognosis in Hepatocellular Carcinoma," Clin Cancer Res. 19(21):5994-6005 (2013).
Shields et al., "High resolution mapping of the binding site on human IgG1 for FcγRI, FcγRII, FcγRIII, and FcRn and design of IgG1 variants with improved binding to the FcγR," J Biol Chem. 276(9):6591-604 (2001).
Somasundaram et al., "Will Engineered T Cells Expressing CD20 scFv Eradicate Melanoma?" Mol Ther. 19(4):638-40 (2011).
Sondermann et al., "The 3.2-A crystal structure of the human IgG1 Fc fragment-FcγRIII complex," Nature. 406(6793):267-73 (2000).
Spiess et al., "Alternative molecular formats and therapeutic applications for bispecific antibodies," Mol Immunol. 67(2 pt A):95-106 (2015).
Spiess et al., "Bispecific antibodies with natural architecture produced by co-culture of bacteria expressing two distinct half-antibodies," Nat Biotechnol. 31(8):753-8 (2013) (7 pages).
Stanglmaier et al., "Bi20 (FBTA05), a novel trifunctional bispecific antibody (anti-CD20 x anti-CD3), mediates efficient killing of B-cell lymphoma cells even with very low CD20 expression levels," Int J Cancer. 123(5):1181-9 (2008).
Stein et al., "Novel and Emerging Drugs for Acute Myeloid Leukemia," available in PMC May 22, 2014, published in final edited form as: Curr Cancer Drug Targets. 12(5):522-530 (2012) (19 pages).
Stieglmaier et al., "Utilizing the BiTE (bispecific T-cell engager) platform for immunotherapy of cancer," Expert Opin Biol Ther. 15(8):1093-9 (2015) (8 pages).

(56) References Cited

OTHER PUBLICATIONS

Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Wakefield et al., "Addition of a C-terminal extension sequence to transforming growth factor-beta 1 interferes with biosynthetic processing and abolishes biological activity," Growth Factors. 5(3):243-53 (1991) (2 pages) (Abstract only).
Wark et al., "Latest technologies for the enhancement of antibody affinity," Adv Drug Deliv Rev. 58(5-6):657-70 (2006).
Weidle et al., "The Intriguing Options of Multispecific Antibody Formats for Treatment of Cancer," Cancer Genomics Proteomics. 10(1):1-18 (2013) (18 pages).
Wells et al., "Reaching for high-hanging fruit in drug discovery at protein-protein interfaces," Nature. 450(7172):1001-9 (2007).
Westin et al., "Safety and activity of PD1 blockade by pidilizumab in combination with rituximab in patients with relapsed follicular lymphoma: a single group, open-label, phase 2 trial," Lancet Oncol. 15(1):69-77 (2014).
Wright et al., "Effect of glycosylation on antibody function: implications for genetic engineering," Trends Biotechnol. 15(1):26-32 (1997).
Wu et al., "Humanization of a Murine Monoclonal Antibody by Simultaneous Optimization of Framework and CDR Residues," J Mol Biol. 294(1):151-162 (1999).
Wuellner et al., "Bispecific CD3/HER2 Targeting FynomAb Induces Redirected T Cell-Mediated Cytolysis with High Potency and Enhanced Tumor Selectivity," Antibodies. 4(4):426-440 (2015) (15 pages).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. 87(5):614-22 (2004).
Yan et al., "Succinimide Formation at Asn 55 in the Complementarity Determining Region of a Recombinant Monoclonal Antibody IgG1 Heavy Chain," J Pharm Sci. 98(10):3509-21 (2009).
Yang et al., "Generation and characterization of a target-selectively activated antibody against epidermal growth factor receptor with enhanced anti-tumor potency," MAbs. 7(2):440-50 (2015).
Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).
Zhu et al., "Identification of heavy chain residues in a humanized anti-CD3 antibody important for efficient antigen binding and T cell activation," J Immunol. 155(4):1903-10 (1995).
Budde et al., "Mosunetuzumab, a Full-Length Bispecific CD20/CD3 Antibody, Displays Clinical Activity in Relapsed/Refractory B-Cell Non-Hodgkin Lymphoma (NHL): Interim Safety and Efficacy Results from a Phase 1 Study," Blood. 132(Supplement 1):399 (2018) (6 pages).
Hernandez et al., "Pharmacodynamic Effects and Immune Correlates of Response to the CD20/CD3 Bispecific Antibody Mosunetuzumab in Relapsed or Refractory Non-Hodgkin Lymphoma," Blood. 134(Supplement 1):1585 (2019) (4 pages).
Li et al., "Exposure-response analyses indicate a promising benefit/risk profile of mosunetuzumab in relapsed and refractory non-Hodgkin lymphoma," Blood. 134(Supplement 1):1285 (2019) (8 pages).
Schuster et al., "Mosunetuzumab Induces Complete Remissions in Poor Prognosis Non-Hodgkin Lymphoma Patients, Including Those Who Are Resistant to or Relapsing After Chimeric Antigen Receptor T-Cell (CAR-T) Therapies, and Is Active in Treatment through Multiple Lines," Blood. 134(Supplement 1):6 (2019) (5 pages).
International Search Report and Written Opinion for International Application No. PCT/US2021/057694, mailed Mar. 21, 2022 (20 pages).
Audino et al., "Polatuzumab Vedotin, an Antibody-Drug Conjugate Targeting CD79b, Is a Highly Active Agent Against Burkitt Lymphoma and Primary Mediastinal B-Cell Lymphoma," Blood. 134(Supplement 1):3963 (2019) (5 pages).
Engelberts et al., "DuoBody-CD3xCD20 induces potent T-cell-mediated killing of malignant B cells in preclinical models and provides opportunities for subcutaneous dosing," EBioMedicine 52:102625 (Jan. 2020) (13 pages).
Falchi et al., "An Evidence-based Review of Anti-CD20 Antibody-containing Regimens for the Treatment of Patients With Relapsed or Refractory Chronic Lymphocytic Leukemia, Diffuse Large B-cell Lymphoma, or Follicular Lymphoma," Clin Lymphoma Myeloma Leuk. 18(8):508-18.e14 (May 23, 2018) (25 pages).
Forero-Torres et al., "Polatuzumab Vedotin Combined with Obinutuzumab, Cyclophosphamide, Doxorubicin, and Prednisone (G-CHP) for Patients with Previously Untreated Diffuse Large B-Cell Lymphoma (DLBCL): Preliminary Results of a Phase Ib/II Dose-Escalation Study," Blood. 128(22):1856 (2016) (2 pages).
Goebeler et al., "Bispecific T-cell Engager (BITE) Antibody Construct Blinatumomab for the Treatment of Patients With Relapsed/Refractory Non-Hodgkin Lymphoma: Final Results From a Phase I Study," J Clin Oncol. 34(10):1104-11 (2016) (13 pages).
Olszewski et al., "401 Single-agent mosunetuzumab is a promising safe and efficacious chemotherapy-free regimen for elderly/unfit patients with previously untreated diffuse large B-cell lymphoma," 62nd American Society of Hematology (ASH) Annual Meeting and Exposition, Dec. 5-8, Oral Abstract, <https://ash.confex.com/ash/2020/webprogram/Paper136255.html>, retrieved on Apr. 21, 2022 (2020) (4 pages).
Office Action and Search Report for Taiwanese Patent Application No. 110140854, dated Dec. 14, 2022 (18 pages).
Yuraszeck et al., "A quantitative systems pharmacology (QSP) model to assess the action of blinatumomab in NHL patients (pts)," Journal of Clinical Oncology 34(15_suppl) Abstract e14511 (May 20, 2016) (3 pages).
Xu et al., "Production of bispecific antibodies in 'knobs-into-holes' using a cell-free expression system," MAbs. 7(1):231-42 (Nov. 26, 2014) (13 pages).
International Preliminary Report on Patentability for International Patent Application No. PCT/US2021/057694, dated May 8, 2023 (8 pages).
"History of Changes for Study: NCT02500407: A Safety, Efficacy and Pharmacokinetic Study of BTCT4465A (Mosunetuzumab) as a Single Agent and Combined With Atezolizumab in Non-Hodgkin's Lymphoma (NHL) and Chronic Lymphocytic Leukemia (CLL) ," ClinicalTrials.gov, last updated Mar. 17, 2022, retrieved Jul. 17, 2023, from <https://classic.clinicaltrials.gov/ct2/history/NCT02500407?V_74=View#StudyPageTop> (10 pages).
Bartlett et al., "610 Mosunetuzumab Monotherapy Demonstrates Durable Efficacy with a Manageable Safety Profile in Patients with Relapsed/Refractory Follicular Lymphoma Who Received greater than or equal to 2 Prior Therapies: Updated Results from a Pivotal Phase II Study." American Society of Hematology (ASH) Annual Meeting and Exposition, Dec. 10-13, 2022 (3 pages).
World Health Organization, "International Nonproprietary Names for Pharmaceutical Substances (INN)," WHO Drug Information. 31(2):241-383 (2017).

* cited by examiner

FIG. 12

| | 0.05 mg (N=1) | 0.1 mg (N=1) | 0.4 mg (N=3) | 0.8 mg (N=4) | 1.2 mg (N=7) | 1.6 mg (N=6) | 2.0 mg (N=3) | 2.8 mg (N=8) | SUBTOTAL (N=33) |
|---|---|---|---|---|---|---|---|---|---|
| Total number of patients with at least one adverse event | 1 (100.0%) | 1 (100.0%) | 3 (100.0%) | 4 (100.0%) | 7 (100.0%) | 6 (100.0%) | 2 (66.7%) | 8 (100.0%) | 32 (97.0%) |
| Total number of events | 1 | 9 | 10 | 36 | 59 | 40 | 41 | 76 | 298 |
| Total number of deaths | 1 (100.0%) | 0 | 2 (66.7%) | 2 (50.0%) | 3 (42.9%) | 2 (33.3%) | 1 (33.3%) | 5 (62.5%) | 16 (48.5%) |
| Total number of subjects withdrawn from study due to an AE | 0 | 0 | 0 | 0 | 0 | 0 | 0 | 0 | 0 |
| Total number of subjects with at least one | | | | | | | | | |
| Fatal AE | 0 | 0 | 0 | 1 (25.0%) | 1 (14.3%) | 1 (16.7%) | 0 | 2 (25.0%) | 5 (15.2%) |
| Fatal AE (not including PD) | 0 | 0 | 0 | 0 | 0 | 0 | 0 | 1 (12.5%) | 1 (3.0%) |
| Serious AE | 0 | 0 | 0 | 2 (50.0%) | 2 (28.6%) | 2 (33.3%) | 0 | 3 (37.5%) | 9 (27.3%) |
| Serious AE (not including PD) | 0 | 0 | 0 | 2 (50.0%) | 1 (14.3%) | 2 (33.3%) | 0 | 2 (25.0%) | 7 (21.2%) |
| Serious AE leading to withdrawal from study treatment | 0 | 0 | 0 | 0 | 0 | 0 | 0 | 1 (12.5%) | 1 (3.0%) |

Investigator text for AEs encoded using MedDRA Version 21.1. Percentages are based on N in the column headings.
Only treatment emergent AEs are considered.
Data Cutoff Date - 31Jul2020

FIG. 13

```
                       SEQUENCE LISTING

<160> NUMBER OF SEQ ID NOS: 54

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Ser Tyr Asn Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Ala Ile Tyr Pro Gly Asn Gly Asp Thr Ser Tyr Asn Gln Lys Phe Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Val Val Tyr Tyr Ser Asn Ser Tyr Trp Tyr Phe Asp Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Arg Ala Ser Ser Ser Val Ser Tyr Met His
1               5                   10
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Pro Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Trp Ser Phe Asn Pro Pro Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
```

```
                    50                  55                  60
Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Phe Asn Pro Pro Thr
                 85                  90                  95

Phe Gly Gln Gly Thr Lys Val Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Asn Tyr Tyr Ile His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Trp Ile Tyr Pro Gly Asp Gly Asn Thr Lys Tyr Asn Glu Lys Phe Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Asp Ser Tyr Ser Asn Tyr Tyr Phe Asp Tyr
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Lys Ser Ser Gln Ser Leu Leu Asn Ser Arg Thr Arg Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Trp Ala Ser Thr Arg Glu Ser
1               5
```

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Thr Gln Ser Phe Ile Leu Arg Thr
1               5

<210> SEQ ID NO 15
<211> LENGTH: 119
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

```
<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Trp Val Arg Gln Ala Pro Gly Lys Gly Leu Glu Trp Val Gly
1               5                   10

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Arg Phe Thr Ile Ser Val Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Trp Gly Gln Gly Thr Leu Val Thr Val Ser Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 22
<211> LENGTH: 15
<212> TYPE: PRT
<213> ORGANISM: Artificial Sequence
```

```
<220> FEATURE:
<223> OTHER INFORMATION: Synthetic Construct

<400> SEQUENCE: 22

Trp Tyr Gln Gln Lys Pro Gly Lys Ala Pro Lys Pro Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Phe Gly Gln Gly Thr Lys Val Glu Ile Lys
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Trp Val Arg Gln Ala Pro Gly Gln Gly Leu Glu Trp Ile Gly
1               5                   10

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Arg Ala Thr Leu Thr Ala Asp Thr Ser Thr Ser Thr Ala Tyr Leu Glu
1               5                   10                  15
```

Leu Ser Ser Leu Arg Ser Glu Asp Thr Ala Val Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Trp Gly Gln Gly Thr Leu Val Thr Val Ser Ser
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp Tyr Gln Gln Lys Pro Gly Gln Pro Pro Lys Leu Leu Ile Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Phe Gly Gln Gly Thr Lys Val Glu Ile Lys
1               5                   10

<210> SEQ ID NO 33
<211> LENGTH: 10
<212> TYPE: PRT
<213> ORGANISM: Artificial Sequence

```
<220> FEATURE:
<223> OTHER INFORMATION: Synthetic Construct

<400> SEQUENCE: 33

Gly Tyr Thr Phe Ser Ser Tyr Trp Ile Glu
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Synthetic Construct

<400> SEQUENCE: 34

Gly Glu Ile Leu Pro Gly Gly Gly Asp Thr Asn Tyr Asn Glu Ile Phe
1               5                   10                  15

Lys Gly

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Thr Arg Arg Val Pro Ile Arg Leu Asp Tyr
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Synthetic Construct

<400> SEQUENCE: 36

Lys Ala Ser Gln Ser Val Asp Tyr Glu Gly Asp Ser Phe Leu Asn
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ala Ala Ser Asn Leu Glu Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln Gln Ser Asn Glu Asp Pro Leu Thr
1               5

<210> SEQ ID NO 39
<211> LENGTH: 25
<212> TYPE: PRT
```

```
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 40
<211> LENGTH: 13
<212> TYPE: PRT
<213> ORGANISM: Artificial Sequence
<220> FEATURE:
<223> OTHER INFORMATION: Synthetic Construct

<400> SEQUENCE: 40

Trp Val Arg Gln Ala Pro Gly Lys Gly Leu Glu Trp Ile
1               5                   10

<210> SEQ ID NO 41
<211> LENGTH: 30
<212> TYPE: PRT
<213> ORGANISM: Artificial Sequence
<220> FEATURE:
<223> OTHER INFORMATION: Synthetic Construct

<400> SEQUENCE: 41

Arg Ala Thr Phe Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Trp Gly Gln Gly Thr Leu Val Thr Val Ser Ser
1               5                   10

<210> SEQ ID NO 43
<211> LENGTH: 23
<212> TYPE: PRT
<213> ORGANISM: Artificial Sequence
<220> FEATURE:
<223> OTHER INFORMATION: Synthetic Construct

<400> SEQUENCE: 43

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44
```

Trp Tyr Gln Gln Lys Pro Gly Lys Ala Pro Lys Leu Leu Ile Tyr
1               5                   10                  15

<210> SEQ ID NO 45
<211> LENGTH: 32
<212> TYPE: PRT
<213> ORGANISM: Artificial Sequence
<220> FEATURE:
<223> OTHER INFORMATION: Synthetic Construct

<400> SEQUENCE: 45

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Phe Gly Gln Gly Thr Lys Val Glu Ile Lys Arg
1               5                   10

<210> SEQ ID NO 47
<211> LENGTH: 117
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 48
<211> LENGTH: 112
<212> TYPE: PRT
<213> ORGANISM: Artificial Sequence
<220> FEATURE:
<223> OTHER INFORMATION: Synthetic Construct

<400> SEQUENCE: 48

Asp Ile Gln Leu Thr Gln Ser Pro Ser Ser Leu Ser Ala Ser Val Gly
1               5                   10                  15

```
Asp Arg Val Thr Ile Thr Cys Lys Ala Ser Gln Ser Val Asp Tyr Glu
             20                  25                  30

Gly Asp Ser Phe Leu Asn Trp Tyr Gln Gln Lys Pro Gly Lys Ala Pro
         35                  40                  45

Lys Leu Leu Ile Tyr Ala Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Leu Thr Phe Gly Gln Gly Thr Lys Val Glu Ile Lys Arg
             100                 105                 110

<210> SEQ ID NO 49
<211> LENGTH: 447
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Ser Ser Tyr
             20                  25                  30

Trp Ile Glu Trp Val Arg Gln Ala Pro Gly Lys Gly Leu Glu Trp Ile
         35                  40                  45

Gly Glu Ile Leu Pro Gly Gly Gly Asp Thr Asn Tyr Asn Glu Ile Phe
 50                  55                  60

Lys Gly Arg Ala Thr Phe Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Arg Arg Val Pro Ile Arg Leu Asp Tyr Trp Gly Gln Gly Thr Leu
             100                 105                 110

Val Thr Val Ser Ser Ala Ser Thr Lys Gly Pro Ser Val Phe Pro Leu
         115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 50
<211> LENGTH: 218
<212> TYPE: PRT
<213> ORGANISM: Artificial Sequence
<220> FEATURE:
<223> OTHER INFORMATION: Synthetic Construct

<400> SEQUENCE: 50

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 51
<211> LENGTH: 452
<212> TYPE: PRT
<213> ORGANISM: Artificial Sequence
<220> FEATURE:
<223> OTHER INFORMATION: Synthetic Construct

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gly Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Trp Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 52
<211> LENGTH: 213
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
            85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 53
```

<211> LENGTH: 449
<212> TYPE: PRT
<213> ORGANISM: Artificial Sequence
<220> FEATURE:
<223> OTHER INFORMATION: Synthetic Construct

<400> SEQUENCE: 53

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380
```

```
Ser Asn Gly Gln Pro Glu Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 54
<211> LENGTH: 219
<212> TYPE: PRT
<213> ORGANISM: Artificial Sequence
<220> FEATURE:
<223> OTHER INFORMATION: Synthetic Construct

<400> SEQUENCE: 54

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

DOSING FOR TREATMENT WITH ANTI-CD20/ANTI-CD3 BISPECIFIC ANTIBODIES

CROSS-REFERENCE TO RELATED APPLICATIONS

This application claims benefit of priority to U.S. Provisional Application No. 63/109,863, filed on Nov. 4, 2020 and U.S. Provisional Application No. 63/188,545, filed on May 14, 2021, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 28, 2021, is named 50474-234003_Sequence_Listing_10_28_21_ST25 and is 35,298 bytes in size.

FIELD OF THE INVENTION

The present invention relates to the treatment of CD20-positive cell proliferative disorders. More specifically, the invention pertains to treatment of subjects having a CD20-positive cell proliferative disorders by administration of a bispecific antibody that binds to anti-cluster of differentiation 20 (CD20) and anti-cluster of differentiation 3 (CD3).

BACKGROUND

Cancers are characterized by the uncontrolled growth of cell subpopulations. Cancers are the leading cause of death in the developed world and the second leading cause of death in developing countries, with over 14 million new cancer cases diagnosed and over eight million cancer deaths occurring each year. Cancer care thus represents a significant and ever-increasing societal burden.

CD20-positive cell proliferative disorders, such as B cell proliferative disorders, are a leading cause of cancer-related deaths. For example, non-Hodgkin's lymphoma (NHL) advances quickly and is fatal if untreated. In the United States, B-cell lymphomas constitute approximately 80%-85% of all cases of NHL. Diffuse large B-cell lymphoma (DLBCL) is the most common type of NHL accounting for approximately 30%-40% of all NHL diagnosis, followed by follicular lymphoma (FL; 20%-25% of all NHL diagnosis) and mantle cell lymphoma (MCL; 6%-10% of all NHL diagnosis). B-cell chronic lymphocytic leukemia (CLL) is the most common leukemia in adults, with approximately 15,000 new cases per year in the United States (American Cancer Society, 2015).

Bispecific antibodies are capable of simultaneously binding cell surface antigens on cytotoxic cells (e.g., T cells, via binding to cluster of differentiation 3 (CD3)) and cancer cells (e.g., B cells, via binding to CD20), with the intent that the bound cytotoxic cell will destroy the bound cancer cell. However, use of such antibody-based immunotherapies can be limited by unwanted effects, including cytokine-driven toxicities (e.g., cytokine release syndrome (CRS)), infusion-related reactions (IRRs), severe tumor lysis syndrome (TLS), and central nervous system (CNS) toxicities.

Thus, there is an unmet need in the field for the development of efficacious methods of dosing therapeutic bispecific antibodies (e.g., bispecific antibodies that bind to CD20 and CD3) for the treatment of CD20-positive cell proliferative disorders (e.g., B cell proliferative disorders) that achieve a more favorable benefit-risk profile.

SUMMARY OF THE INVENTION

The present invention relates to methods of treating a subject having a CD20-positive cell proliferative disorder (e.g., a B cell proliferative disorder) by administration (e.g., intravenous administration) of a bispecific antibody that binds to anti-cluster of differentiation 20 (CD20) and anti-cluster of differentiation 3 (CD3) that decreases the risk of unwanted side effects, such as cytokine-driven toxicities, such as CRS.

The invention is based, in part, on the discovery that dosing regimens involving administration of a bispecific antibody that binds to CD20 and CD3 (e.g., mosunetuzumab) over multiple dosing cycles (e.g., wherein the first dosing cycle is a step-up, fractionated dosing cycle) including a relatively high third dose (C1D3) and/or a dose of a second dosing cycle (C2D1) ("loading doses") that is greater in amount than a dose of the third dosing cycle (C3D1) and/or additional dosing cycles ("base doses") can effectively treat subjects having a CD20-positive cell proliferative disorder (e.g., B cell proliferative disorder) while reducing toxicity (e.g., cytokine release syndrome). The loading doses can increase efficacy in the critical day 0-42 time period during which patients may have residual anti-CD20 monoclonal antibody present from prior therapies, and for those patients who have high tumor burdens. Step-up dosing reduces cytokine release syndrome toxicity, and administering a base dose that is lower than the loading dose can potentially reduce chronic toxicity (e.g., neutropenia, infections, etc.).

In one aspect, the invention features a method of treating a subject having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL or Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) comprising administering to the subject a bispecific antibody that binds to CD20 and CD3 in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., from about 0.02 to about 1.8 mg, from about 0.02 to about 1.6 mg, from about 0.02 to about 1.4 mg, from about 0.02 to about 1.2 mg, from about 0.05 to about 1.8 mg, from about 0.1 to about 1.8 mg, from about 0.4 to about 1.8 mg, from about 0.6 to about 1.8 mg, from about 0.8 to about 1.8 mg, from about 0.5 to about 1.5 mg, from about 0.8 to about 1.2 mg; e.g., about 1 mg), the C1D2 is from about 0.05 mg to about 4.0 mg (e.g., from about 0.05 to about 3.5 mg, from about 0.05 to about 3.0 mg, from about 0.05 to about 2.5 mg, from about 0.05 to about 2.2 mg, from about 0.1 to about 3.5 mg, from about 0.5 to about 3.5 mg, from about 1.0 to about 3.5 mg, from about 1.5 to about 3.5 mg, from about 1.8 to about 3.5 mg, from about 1.0 to about 3.0 mg, from about 1.5 to about 2.5 mg; e.g., about 2 mg), and the C1D3 is greater than about 50 mg; and (b) the second dosing cycle comprises a single dose (C2D1) of the bispecific antibody.

In some embodiments, the C1D3 is from 50 mg to 200 mg (e.g., from 50 mg to 175 mg, from 50 mg to 150 mg, from 50 mg to 125 mg, from 50 mg to 100 mg, from 50 mg to 75 mg, from 50 mg to 70 mg, from 52 mg to 100 mg, from 52 mg to 75 mg, from 50 mg to 180 mg, from 55 mg to 150 mg, from 55 mg to 100 mg, from 55 mg to 70 mg, from 55 mg to 65 mg, from 58 mg to 62 mg; e.g., about 60 mg). In some embodiments, the C1D3 is about 60 mg. In some embodiments, the C1D1 is about 1 mg. In some embodiments, the C1D2 is about 2 mg. In some embodiments, the C2D1 is about equivalent in amount to the C1D3.

In some embodiments, the C1D1, the C1D2, and the C1D3 are administered to the subject on or about Days 1, 8, and 15, respectively, of the first dosing cycle. In some embodiments, the C2D1 is administered to the subject on Day 1 of the second dosing cycle.

In some embodiments, the first and second dosing cycles are 21-day dosing cycles. In some embodiments, the second dosing cycle is a 28-day dosing cycle.

In some embodiments, the dosing regimen further comprises one or more additional dosing cycles beyond the second dosing cycle. In some embodiments, the dosing regimen comprises from six to 15 additional dosing cycles (e.g., from six to ten additional dosing cycles (e.g., six additional dosing cycles, seven additional dosing cycles, eight additional dosing cycles, nine additional dosing cycles, or ten additional dosing cycles) or from 11-15 additional dosing cycles (e.g., 11 additional dosing cycles, 12 additional dosing cycles, 13 additional dosing cycles, 14 additional dosing cycles, or 15 additional dosing cycles) beyond the second dosing cycle. In some embodiments, the additional dosing cycles are 21-day dosing cycles. In some embodiments, the additional dosing cycles are 28-day dosing cycles.

In some embodiments, one or more of the additional dosing cycles comprise an additional single dose of the bispecific antibody. In some embodiments, the additional single dose of the bispecific antibody is administered to the subject on Day 1 of each additional dosing cycle.

In some embodiments, the additional single dose (e.g., base dose) of the bispecific antibody is greater than the C1D1 and less than the C1D3 and/or the C2D1 (e.g., loading doses). In some embodiments, the additional single dose (e.g., base dose) of the bispecific antibody is from 20% to 80% (e.g., from 20% to 70%, from 20% to 60%, from 20% to 55%, from 30% to 80%, from 30% to 70%, from 40% to 70%, from 45% to 70%, from 40% to 60%, from 45% to 55%, from 48% to 52%; e.g., about 50%) of the C1D3 and/or the C2D1 (e.g., loading doses). In some embodiments, the additional single dose of the bispecific antibody is about 50% of the C1D3 and/or the C2D1 (e.g., loading doses).

In some embodiments, the additional single dose of the bispecific antibody is about 30 mg.

In another aspect, the invention features a method of treating a subject having a CD20-positive cell proliferative disorder comprising administering to the subject a bispecific antibody that binds to CD20 and CD3 in a dosing regimen comprising at least a first dosing cycle, a second dosing cycle, and a third dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; and (c) the third dosing cycle comprises a single dose (C3D1) of the bispecific antibody, wherein the C3D1 is greater than the C1D1 and less than the C2D1.

In some embodiments, the C1D3 and the C2D1 (e.g., loading doses) are each from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; about 20 mg, about 30 mg, about 45 mg, or e.g., about 60 mg). In some embodiments, the C1D3 and the C2D1 are each about 60 mg. In some embodiments, the C3D1 is from about 20% to about 80% (e.g., from about 20% to about 70%, from about 20% to about 60%, from about 20% to about 55%, from about 30% to about 80%, from about 30% to about 70%, from about 40% to about 70%, from about 45% to about 70%, from about 40% to about 60%, from about 45% to about 55%, or from about 48% to about 52%; e.g., about 40%, about 45%, about 50%, about 55%, or about 60%) of the C2D1. In some embodiments, the C3D1 is about 50% of the C2D1. In some embodiments, the C3D1 is from about 12 mg to about 48 mg (e.g., from about 12 mg to about 42 mg, from about 12 mg to about 36 mg, from about 12 mg to about 30 mg, from about 18 mg to about 48 mg, from about 18 mg to about 42 mg, from about 24 mg to about 42 mg, from about 27 mg to about 42 mg, from about 24 mg to about 36 mg, from about 27 mg to about 33 mg, from about 28 mg to about 32 mg; e.g., about 24 mg, about 27 mg, about 30 mg, about 33 mg, or about 36 mg). In a particular embodiment, the C3D1 is about 30 mg.

In some embodiments, the C3D1 is about 30 mg. In some embodiments, the C1D1 is about 1 mg. In some embodiments, the C1D2 is about 2 mg.

In some embodiments, the C1D1, the C1D2, and the C1D3 are administered to the subject on or about Days 1, 8, and 15, respectively, of the first dosing cycle. In some embodiments, the C2D1 is administered to the subject on Day 1 of the second dosing cycle and the C3D1 is administered to the subject on Day 1 of the third dosing cycle. In some embodiments, the first, second, and third dosing cycles are 21-day dosing cycles. In some embodiments, the second and/or third dosing cycles are 28-day dosing cycles.

In some embodiments, the dosing regimen further comprises one or more additional dosing cycles beyond the third dosing cycle. In some embodiments, the dosing regimen comprises from five to 14 additional dosing cycles (e.g., from five to ten additional dosing cycles (e.g., five additional dosing cycles, six additional dosing cycles, seven additional dosing cycles, eight additional dosing cycles, nine additional dosing cycles, or ten additional dosing cycles) or from 11-14 additional dosing cycles (e.g., 11 additional dosing cycles, 12 additional dosing cycles, 13 additional dosing cycles, 14 additional dosing cycles)) beyond the third dosing cycle. In some embodiments, the additional dosing cycles are 21-day dosing cycles. In some embodiments, the additional dosing cycles are 28-day dosing cycles.

In some embodiments, one or more of the additional dosing cycles comprise an additional single dose (e.g., base dose) of the bispecific antibody. In some embodiments, the additional single dose of the bispecific antibody is administered to the subject on Day 1 of each additional dosing cycle. In some embodiments, the additional single dose of the bispecific antibody is about equivalent in amount to the C3D1.

In an additional aspect, the invention features a method of treating a subject having a CD20-positive cell proliferative disorder comprising administering to the subject a bispecific antibody that binds to CD20 and CD3 in a dosing regimen comprising eight or more dosing cycles, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; (c) the third dosing cycle comprises a single dose (C3D1) of the bispecific antibody, wherein the C3D1 is greater than the C1D1 and less than the C2D1; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 (e.g., base doses) are about equivalent in amount.

In some embodiments, the C1D3 and the C2D1 (e.g., loading doses) are each from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; e.g., about 60 mg). In some embodiments, the C1D3 and the C2D1 are each about 60 mg.

In some embodiments, the C3D1 is from about 20% to about 80% (e.g., from about 20% to about 70%, from about 20% to about 60%, from about 20% to about 55%, from about 30% to about 80%, from about 30% to about 70%, from about 40% to about 70%, from about 45% to about 70%, from about 40% to about 60%, from about 45% to about 55%, or from about 48% to about 52%; e.g., about 40%, about 45%, about 50%, about 55%, or about 60%) of the C2D1. In some embodiments, the C3D1 is about 50% of the C2D1. In some embodiments, the C3D1 is from about 12 mg to about 48 mg (e.g., from about 12 mg to about 42 mg, from about 12 mg to about 36 mg, from about 12 mg to about 30 mg, from about 18 mg to about 48 mg, from about 18 mg to about 42 mg, from about 24 mg to about 42 mg, from about 27 mg to about 42 mg, from about 24 mg to about 36 mg, from about 27 mg to about 33 mg, from about 28 mg to about 32 mg; e.g., about 24 mg, about 27 mg, about 30 mg, about 33 mg, or about 36 mg). In a particular embodiment, the C3D1 is about 30 mg.

In some embodiments, wherein the C3D1 is about 30 mg. In some embodiments, the C1D1 is about 1 mg. In some embodiments, the C1D2 is about 2 mg.

In some embodiments, the C1D1, the C1D2, and the C1D3 are administered to the subject on or about Days 1, 8, and 15, respectively, of the first dosing cycle. In some embodiments, the C2D1-C8D1 are each administered to the subject on Day 1 of the second-eighth dosing cycle, respectively.

In some embodiments, dosing cycles are 21-day dosing cycles. In some embodiments, dosing cycles after the first dosing cycle are 28-day dosing cycles.

In some embodiments, the dosing regimen comprises one or more additional dosing cycles beyond the eighth dosing cycle. In some embodiments, the additional dosing cycles are 21-day dosing cycles. In some embodiments, the additional dosing cycles are 28-day dosing cycles.

In some embodiments, one or more of the additional dosing cycles comprise an additional single dose of the bispecific antibody. In some embodiments, the additional single dose of the bispecific antibody is administered to the subject on Day 1 of each additional dosing cycle. In some embodiments, the additional single dose of the bispecific antibody is about equivalent in amount to any one of the C3D1-C8D1 (e.g., base doses).

In a further aspect, the invention features a method of treating a subject having a CD20-positive cell proliferative disorder comprising administering to the subject a bispecific antibody that binds to CD20 and CD3 in a dosing regimen comprising eight or more 21- or 28-day dosing cycles, wherein: (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg; (b) the second dosing cycle comprises a single dose (C2D1) of the bispecific antibody, wherein the C2D1 is about 60 mg; (c) the third dosing cycle comprises a single dose (C3D1) of the bispecific antibody; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 (e.g., base doses) are each about 30 mg. In some embodiments, the dosing cycles after the first dosing cycle are 28-day dosing cycles.

In some embodiments, the subject has received a prior systemic therapy for the CD20-positive cell proliferative disorder. In some embodiments, the subject has received a first-line systemic therapy and a second-line systemic therapy for the CD20-positive cell proliferative disorder.

In some embodiments, the subject has exhibited progression of the CD20-positive cell proliferative disorder within 24 months of the prior systemic therapy.

In some embodiments, the prior systemic therapy comprises an anti-CD20 antibody. In some embodiments, the anti-CD20 antibody is rituximab. In some embodiments, the anti-CD20 antibody is obinutuzumab.

In some embodiments, the prior systemic therapy comprises a chemotherapeutic agent. In some embodiments, the chemotherapeutic agent is an alkylating agent. In some embodiments, the alkylating agent is bendamustine. In some embodiments, the chemotherapeutic agent is lenalidomide.

In some embodiments, the prior systemic therapy comprises a radio-immunotherapy. In some embodiments, the radio-immunotherapy is ibritumomab tiuxetan.

In some embodiments, the prior systemic therapy comprises a phosphoinositide 3-kinase inhibitor. In some embodiments, the phosphoinositide 3-kinase inhibitor is selected from the group comprising idelalisib, alpelisib, copanlisib, and duvelisib.

In some embodiments, the prior systemic therapy comprises a CAR-T therapy.

In some embodiments, the subject is a human.

In some embodiments of any of the methods of the present invention, the bispecific antibody is administered intravenously.

In yet another aspect, the invention features a method of treating a population of subjects having a CD20-positive cell proliferative disorder comprising administering to the subjects a bispecific antibody that binds to CD20 and CD3 in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than 50 mg; and (b) the second dosing cycle comprises a single dose (C2D1) of the bispecific antibody.

In some embodiments, the C1D3 is from 50 mg to 200 mg (e.g., from 50 mg to 175 mg, from 50 mg to 150 mg, from 50 mg to 125 mg, from 50 mg to 100 mg, from 50 mg to 75 mg, from 50 mg to 70 mg, from 52 mg to 100 mg, from 52 mg to 75 mg, from 50 mg to 180 mg, from 55 mg to 150 mg, from 55 mg to 100 mg, from 55 mg to 70 mg, from 55 mg to 65 mg, from 58 mg to 62 mg; e.g., about 60 mg).

In another aspect, the invention features a method of treating a population of subjects having a CD20-positive cell proliferative disorder comprising administering to the subjects a bispecific antibody that binds to CD20 and CD3 in a dosing regimen comprising at least a first dosing cycle, a second dosing cycle, and a third dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; and (c) the third dosing cycle comprises a single dose (C3D1) of the bispecific antibody, wherein the C3D1 is greater than the C1D1 and less than the C2D1.

In yet another aspect, the invention features a method of treating a population of subjects having a CD20-positive cell proliferative disorder comprising administering to the subjects a bispecific antibody that binds to CD20 and CD3 in a dosing regimen comprising eight or more dosing cycles, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; (c) the third dosing cycle comprises a single dose (C3D1) of the bispecific antibody, wherein the C3D1 is greater than the C1D1 and less than the C2D1; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 (e.g., base doses) are about equivalent in amount.

In some embodiments, the C1D3 and the C2D1 (e.g., loading doses) are each from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; e.g., about 20 mg, about 30 mg, about 45 mg, or about 60 mg). In some embodiments, the C1D3 and the C2D1 are each about 60 mg.

In a further aspect, the invention features a method of treating a population of subjects having a CD20-positive cell proliferative disorder comprising administering to the subjects a bispecific antibody that binds to CD20 and CD3 in a dosing regimen comprising eight or more 21- or 28-day dosing cycles, wherein: (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg; (b) the second dosing cycle comprises a single dose (C2D1) of the bispecific antibody, wherein the C2D1 is about 60 mg; (c) the third dosing cycle comprises a single dose (C3D1) of the bispecific antibody; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 (e.g., base doses) are each about 30 mg. In some embodiments, dosing cycles after the first dosing cycle are 28-day dosing cycles.

In some embodiments, the complete response rate is at least about 15% (e.g., from about 15% to about 30%, from about 15% to about 40%, from about 15% to about 50%, from about 15% to about 60%, from about 15% to about 75%, from about 15% to about 80%, from about 15% to about 90%, from about 15% to about 100%, from about 20% to about 100%, from about 20% to about 75%, from about 20% to about 50%, from about 25% to about 100%, from about 25% to about 75%, from about 25% to about 50%, from about 30% to about 75%, from about 30% to about 100%, or from about 30% to about 50%; e.g., about 15%, about 20%, about 25%, about 30%, about 35%, about 40%, or about 45%). In some embodiments, the complete response rate is at least about 45% (e.g., from about 45% to about 60%, from about 45% to about 70%, from about 45% to about 80%, from about 45% to about 95%, from about 45% to about 100%, from about 50% to about 100%, from about 50% to about 95%, or from about 50% to about 75%; e.g., about 45%, about 50%, about 55%, or about 60%).

In some embodiments, the objective response rate is at least about 60% (e.g., from about 60% to about 70%, from about 60% to about 80%, from about 60% to about 90%, or from about 60% to about 100%; e.g., about 60%, about 65%, about 70%, about 75%, about 80%, or about 85%). In some embodiments, the objective response rate at about 20 months after the initiation of treatment is at least about 70% (e.g., from about 70% to about 80%, from about 70% to about 90%, from about 70% to about 95%, or from about 70% to about 100%; e.g., about 70%, about 75%, about 80%, about 85%, or about 90%).

In some embodiments, the objective response rate at about 24 months after the initiation of treatment is at least about 75% (e.g., from about 75% to about 80%, from about 75% to about 90%, from about 75% to about 95%, from about 75% to about 100%, from about 80% to about 100%, or from about 90% to about 100%; e.g., about 75%, about 80%, about 85%, or about 90%).

In some embodiments, the median duration of response (mDOR) is at least about 12 months (e.g., at least about 14 months, at least about 16 months, at least about 18 months; e.g., between about 12 and about 14 months, between about 12 and about 16 months, between about 12 and about 18 months, or between about 12 and about 20 months; e.g., about 12 months, about 14 months, about 16 months, or about 18 months). In some embodiments, the mDOR is at least about 20 months (e.g., at least about 22 months, at least about 24 months, at least about 26 months, at least about 28 months, at least about 30 months, at least about 32 months, at least about 34 months, or at least about 36 months; e.g., between about 20 and about 24 months, between about 20 and about 30 months, between about 20 and about 36 months, between about 20 and about 48 months, between about 20 and about 60 months, between about 20 and about 72 months, between about 24 and about 36 months, between about 24 and about 48 months, between about 24 and about 60 months, between about 36 and about 48 months, or between about 36 and about 60 months; e.g., about 20 months, about 24 months, about 28 months, about 32 months, about 36 months, about 40 months, about 48 months, about 56 months, or about 60 months). In some embodiments, the population of subjects has a rate of subjects in the population having a DOR of at least 12 months, and wherein the rate of subjects in the population having a DOR of at least 12 months is at least about 60% (e.g., from about 60% to about 70%, from about 60% to about 80%, from about 60% to about 90%, or from about 60% to about 100%; e.g., about 60%, about 65%, about 70%, about 75%, about 80%, about 85%, about 90%, or about 95%).

In some embodiments, the population of subjects exhibits cytokine release syndrome after administering the bispecific antibody, and wherein the rate of the cytokine release syndrome in the population of subjects is less than or equal to about 25% (e.g., less than or equal to about 23%, less than or equal to about 20%, less than or equal to about 18%, less than or equal to about 16%, less than or equal to about 15%, less than or equal to about 14%, less than or equal to about 13%, less than or equal to about 12%, less than or equal to about 11%, less than or equal to about 10%; e.g., between about 1% and about 25%, between about 5% and about 25%, between about 10% and about 25%, between about 15% and about 25%, between about 20% and about 25%, between about 5% and about 15%, between about 5% and about 10%, between about 1% and about 15%, or between about 1% and about 10%; e.g., about 24%, about 22%, about 20%, about 18%, about 16%, about 14%, about 12%, about 10%, about 8%, about 6%, about 5%, about 4%, about 3%, about 2%, about 1%, or about 0%). In some embodiments, the rate of cytokine release syndrome in the population of subjects is less than or equal to about 10%.

In some embodiments, the rate of cytokine release syndrome having a grade of 2 or greater (as defined by the American Society for Transplantation and Cellular Therapy, 2018; ASTCT; e.g., a grade between 2 and 5, e.g., a grade of 2, 3, 4, or 5) is less than or equal to about 10% (e.g., less than or equal to about 9%, less than or equal to about 8%, less than or equal to about 7%, less than or equal to about 6%, less than or equal to about 5%, less than or equal to about 4%, less than or equal to about 3%, less than or equal to about 2%, less than or equal to about 1%; e.g. between about 0.1% to about 10%, between about 0.5% and about 10%, between about 1% and about 10%, between about 1% and about 7%, between about 1% and about 5%, between about 1% and about 3%, or between about 5% and about 10%; e.g., about 10%, about 8%, about 6%, about 5%, about 4%, about 3%, about 2%, about 1%, or about 0%). In some embodiments, the rate of cytokine release syndrome having a grade of 2 or greater (as defined by the ASTCT) is less than or equal to about 5% (e.g., less than or equal to about 4%, less than or equal to about 3%, less than or equal to about 2%, less than or equal to about 1%; e.g., between about 0% and about 5%, between about 1% and about 5%, between about 2% and about 5%, between about 3% and about 5%, between about 4% and about 5%, between about 1% and about 3%, between about 2% and about 5%, or between about 0% and about 2%; e.g., about 5%, about 4%, about 3%, about 2%, about 1%, or about 0%). In some embodiments, the rate of cytokine release syndrome having a grade of 3 or greater (as defined by the ASTCT e.g., a grade between 3 and 5, e.g., a grade of 3, 4, or 5) is about 0.

In some embodiments, the CD20-positive cell proliferative disorder is a B cell proliferative disorder. In some embodiments, the CD20-positive cell proliferative disorder is a relapsed or refractory B cell proliferative disorder. In some embodiments, the CD20-positive cell proliferative disorder is a non-Hodgkin's lymphoma (NHL) or a chronic lymphoid leukemia (CLL). In some embodiments, the NHL is a diffuse large B cell lymphoma (DLBCL). In some embodiments, the DLBCL is a Richter's transformation. In some embodiments, the NHL is follicular lymphoma (FL). In some embodiments, the FL is Grade 1, 2, 3a, or 3b FL. In some embodiments, the FL is a transformed FL. In some embodiments, the NHL is a mantle cell lymphoma (MCL) or a marginal zone lymphoma (MZL).

In some embodiments, the bispecific antibody comprises an anti-CD20 arm comprising a first binding domain comprising the following six hypervariable regions (HVRs): (a) an HVR-H1 comprising the amino acid sequence of GYTFTSYNMH (SEQ ID NO: 1); (b) an HVR-H2 comprising the amino acid sequence of AIYPGNGDTSYN-QKFKG (SEQ ID NO: 2); (c) an HVR-H3 comprising the amino acid sequence of VVYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6).

In some embodiments, the bispecific antibody comprises an anti-CD20 arm comprising a first binding domain comprising (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b).

In some embodiments, the first binding domain comprises a VH domain comprising an amino acid sequence of SEQ ID NO: 7 and a VL domain comprising an amino acid sequence of SEQ ID NO: 8.

In some embodiments, the bispecific antibody comprises an anti-CD3 arm comprising a second binding domain comprising the following six HVRs: (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYS-NYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14).

In some embodiments, the bispecific antibody comprises an anti-CD3 arm comprising a second binding domain comprising (a) a VH domain comprising an amino acid sequence having at least 95% sequence identity to the amino acid sequence of SEQ ID NO: 15; (b) a VL domain comprising an amino acid sequence having at least 95% sequence identity to the amino acid sequence of SEQ ID NO: 16; or (c) a VH domain as in (a) and a VL domain as in (b).

In some embodiments, the second binding domain comprises a VH domain comprising an amino acid sequence of SEQ ID NO: 15 and a VL domain comprising an amino acid sequence of SEQ ID NO: 16.

In some embodiments, the bispecific antibody comprises (a) an anti-CD20 arm comprising (i) a heavy chain comprising an amino acid sequence having at least 95% sequence identity to the amino acid sequence of SEQ ID NO: 51, and (ii) a light chain comprising an amino acid sequence having at least 95% sequence identity to the amino acid sequence of SEQ ID NO: 52; and (b) an anti-CD3 arm comprising (i) a heavy chain comprising an amino acid sequence having at least 95% sequence identity to the amino acid sequence of SEQ ID NO: 53, and (ii) a light chain comprising an amino acid sequence having at least 95% sequence identity to the amino acid sequence of SEQ ID NO: 54. In some antibodies, (a) the anti-CD20 arm comprises a heavy chain comprising an amino acid sequence of SEQ ID NO: 51 and a light chain comprising an amino acid sequence of SEQ ID NO: 52, and (b) the anti-CD3 arm comprises a heavy chain comprising an amino acid sequence of SEQ ID NO: 53 and a light chain comprising an amino acid sequence of SEQ ID NO: 54.

In some embodiments, the bispecific antibody is a humanized antibody. In some embodiments, the bispecific antibody is a chimeric antibody.

In some embodiments, the bispecific antibody is an antibody fragment that binds CD20 and CD3. In some embodiments, the antibody fragment is selected from the group consisting of Fab, Fab'-SH, Fv, scFv, and (Fab')$_2$ fragments.

In some embodiments, the bispecific antibody is a full-length antibody.

In some embodiments, the bispecific antibody is an IgG antibody. In some embodiments, the IgG antibody is an IgG1 antibody.

In some embodiments, the IgG antibody comprises a mutation at amino acid residue N297 (EU numbering) that results in the absence of glycosylation. In some embodiments, the mutation at amino acid residue N297 is a substitution mutation. In some embodiments, the mutation at amino acid residue N297 reduces effector function of the Fc region. In some embodiments, the mutation is an N297G or N297A mutation.

In some embodiments, the bispecific antibody comprises a mutation in the Fc region that reduces effector function. In some embodiments, the mutation is a substitution mutation. In some embodiments, the substitution mutation is at amino acid residue L234, L235, D265, and/or P329 (EU numbering). In some embodiments, the substitution mutation is selected from the group consisting of L234A, L235A, D265A, and P329G.

In some embodiments, the bispecific antibody comprises one or more heavy chain constant domains, wherein the one or more heavy chain constant domains are selected from a first CH1 (CH1$_1$) domain, a first CH2 (CH2$_1$) domain, a first CH3 (CH3$_1$) domain, a second CH1 (CH1$_2$) domain, second CH2 (CH2$_2$) domain, and a second CH3 (CH3$_2$) domain. In some embodiments, at least one of the one or more heavy chain constant domains is paired with another heavy chain constant domain.

In some embodiments, the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain. In some embodiments, the CH3$_1$ and CH3$_2$ domains meet at an interface between the protuberance and cavity.

In some embodiments the anti-CD20 arm of the bispecific antibody further comprises T366W and N297G substitution mutations (EU numbering). In some embodiments, the anti-CD3 arm of the bispecific antibody further comprises T366S, L368A, Y407V, and N297G substitution mutations (EU numbering). In some embodiments, (a) the anti-CD20 arm further comprises T366W and N297G substitution mutations and (b) the anti-CD3 arm further comprises T366S, L368A, Y407V, and N297G substitution mutations (EU numbering).

In some embodiments, the dosing regimen further comprises administering to the subject a PD-1 axis binding antagonist. In some embodiments, the PD-1 axis binding antagonist is administered at a dose of between about 1100 mg to about 1300 mg (e.g., between about 1150 mg to about 1250 mg, between about 1175 mg to about 1225 mg, between about 1190 mg to about 1210 mg; e.g., 1200 mg±5 mg, e.g., 1200±2.5 mg, e.g., 1200±1.0 mg, e.g., 1200±0.5 mg; e.g., about 1200 mg). In particular embodiments, the PD-1 axis binding antagonist is administered at a dose of about 1200 mg. In some embodiments, the PD-1 axis binding antagonist is administered on Day 1 (±1 day) of each dosing cycle after the first dosing cycle comprising administration of the bispecific antibody. In some embodiments, the PD-1 axis binding antagonist is atezolizumab. In some embodiments, the subject is a human.

BRIEF DESCRIPTION OF THE DRAWINGS

FIG. 12 is a table reporting adverse events experienced by patients in Group A, grouped by mosunetuzumab doses. AE=adverse event; PD=progressive disease.

FIG. 13 is a table reporting adverse events experienced by patients in Group B, grouped by mosunetuzumab doses. AE=adverse event; PD=progressive disease.

DETAILED DESCRIPTION

Figure 1:
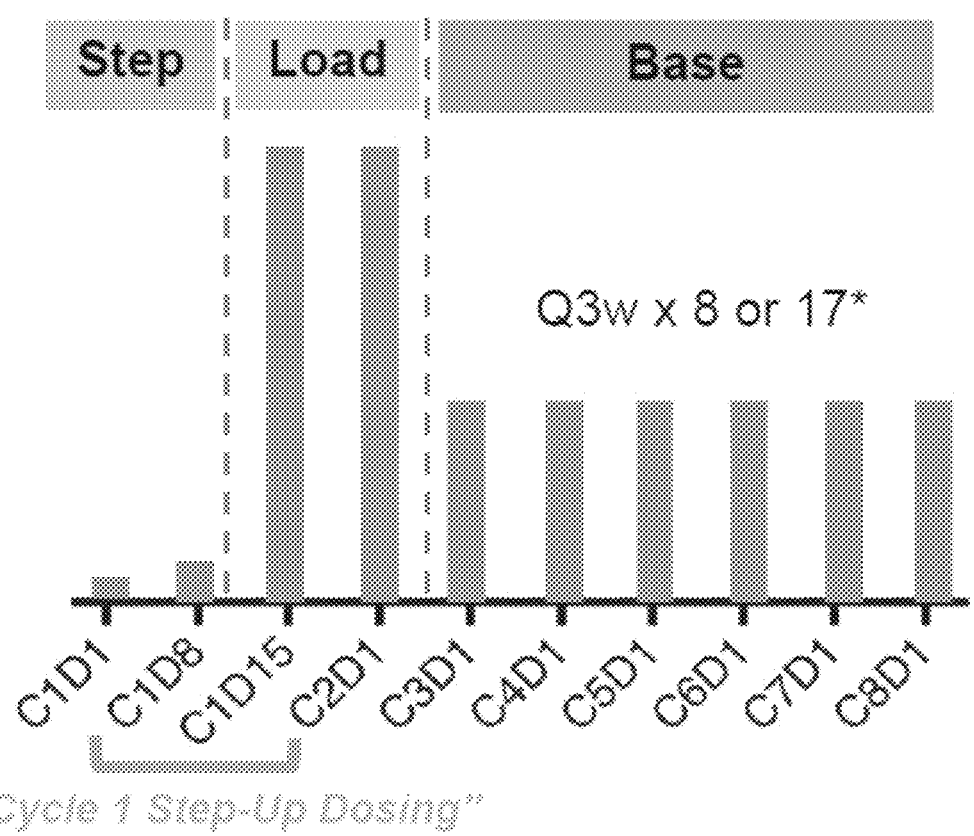
FIG. 1 is a schematic diagram showing the overview of the step-load-base dosing of mosunetuzumab. The vertical bars indicate the relative amount of administered mosunetuzumab. Described is a step load-base dosing of 1/2/60/30 (mg). Patients are administered a first step dose of about 1 mg mosunetuzumab on Cycle 1 Day 1 (C1D1), followed by a second step dose of about 2 mg mosunetuzumab on Cycle 1 Day 8 (C1D8). The patients are then administered a first loading dose of about 60 mg mosunetuzumab on Cycle 1 Day 15 (C1D15), followed by a second loading dose of about 60 mg mosunetuzumab on Cycle 2 Day 1 (C2D1). Thereafter, the patient is administered base doses of about 30 mg mosunetuzumab on Day 1 of each subsequent cycle. The patients are initially administered 6 base doses on Cycle 3 Day 1 (C3D1) to Cycle 8 Day 1 (C8D1). Patients who do not achieve CR following 8 cycles of treatment continue to receive base doses of about 30 mg mosunetuzumab for 8 or 17 additional cycles of treatment. Base=base dose; C=cycle; CR=complete response; D=Day; Load=loading dose; Q3w=dosing occurs once every dosing cycle, i.e., about every three weeks; Step=step dose.

The present invention involves methods of treating a subject (or a population of subjects) having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL or a Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory (MZL)) or a relapsed or refractory CLL) by administering (e.g., intravenously administering) to the subject a bispecific antibody that binds to CD20 and CD3 (e.g., mosunetuzumab) in a dosing regimen comprising at least a first dosing cycle and a second dosing cycle. In some instances, the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 50 mg. In some instances, the second dosing cycle includes a single dose (C2D1) of the bispecific antibody. In some instances, the C1D3 and C2D1 are collectively termed the "loading doses."

In some instances, the invention features administration to the subject a bispecific antibody that binds to CD20 and CD3 (e.g., mosunetuzumab) in a dosing regimen comprising at least a first dosing cycle, a second dosing cycle, and a third dosing cycle, wherein the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg; the second dosing cycle comprises a single dose (C2D1) of the bispecific antibody, wherein the C2D1 is about equivalent in amount to the C1D3; and the third dosing cycle comprises a single dose (C3D1) of the bispecific antibody, wherein the C3D1 is greater than the C1D1 and less than the C2D1.

As previously noted, the invention is based, in part, on the discovery that dosing regimens involving administration of a bispecific antibody that binds to CD20 and CD3 (e.g., mosunetuzumab) over multiple dosing cycles (e.g., wherein the first dosing cycle is a step-up, fractionated dosing cycle) including a relatively high third dose (C1D3) and/or a dose of a second dosing cycle (C2D1) ("loading doses") that is greater in amount than a dose of the third dosing cycle (C3D1) and/or additional dosing cycles ("base doses") can effectively treat subjects having a CD20-positive cell proliferative disorder (e.g., B cell proliferative disorder) while reducing toxicity (e.g., cytokine release syndrome). The loading doses can increase efficacy in the critical day 0-42 time period during which patients may have residual anti-CD20 monoclonal antibody present from prior therapies, and for those patients who have high tumor burdens. Step-up dosing reduces cytokine release syndrome toxicity, and administering a base dose that is lower than the loading dose can potentially reduce chronic toxicity (e.g., neutropenia, infections, etc.).

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3*d edition* (2001) Cold Spring Harbor Laboratory Press, Cold Spring Harbor, N.Y.; *Current Protocols in Molecular Biology* (F. M. Ausubel, et al., eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual*(E. Harlow and D. Lane (Cold Spring Harbor Laboratory Press, 1999); *The Antibodies* (M.

Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

It is to be understood that aspects and embodiments of the invention described herein include "comprising," "consisting," and "consisting essentially of" aspects and embodiments.

As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

The terms "cancer" and "cancerous" refer to or describe the physiological condition in mammals that is typically characterized by unregulated cell growth. Examples of cancer include, but are not limited to, hematologic cancers, such as mature B cell cancers, excluding Hodgkin's lymphoma, but including non-Hodgkin's lymphoma (NHL), such as diffuse large B cell lymphoma (DLBCL), which may be relapsed or refractory DLBCL. A cancer may be a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL or Grade 3b FL), or a transformed FL), a mantle cell lymphoma (MCL) or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL. In some instances, specific examples of cancer include germinal-center B cell-like (GCB) diffuse large B cell lymphoma (DLBCL), activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), high-grade B cell lymphoma, primary mediastinal (thymic) large B cell lymphoma (PMLBCL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, heavy chain diseases, α heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and Burkitt lymphoma, and B cell lymphoma, unclassifiable, with features intermediate between DLBCL and classical Hodgkin's lymphoma. Further examples of cancer include, but are not limited to, carcinoma, lymphoma, blastoma, sarcoma, and leukemia or lymphoid malignancies, including B cell lymphomas. More particular examples of such cancers include, but are not limited to, multiple myeloma (MM); low grade/follicular NHL; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; AIDS-related lymphoma; and acute lymphoblastic leukemia (ALL); chronic myeloblastic leukemia; and post-transplant lymphoproliferative disorder (PTLD).

"Tumor," as used herein, refers to all neoplastic cell growth and proliferation, whether malignant or benign, and all pre-cancerous and cancerous cells and tissues.

The terms "cancer", "cancerous", "cell proliferative disorder", "proliferative disorder," and "tumor" are not mutually exclusive as referred to herein.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In another embodiment, the cell proliferative disorder is a tumor.

The terms "B cell proliferative disorder" or "B cell malignancy" refer to disorders that are associated with some degree of abnormal B cell proliferation and include, for example, lymphomas, leukemias, myelomas, and myelodysplastic syndromes. In one embodiment, the B cell proliferative disorder is a lymphoma, such as non-Hodgkin's lymphoma (NHL), including, for example, diffuse large B cell lymphoma (DLBCL) (e.g., relapsed or refractory DLBCL or a Richter's transformation), FL (e.g., relapsed and/or refractory FL or transformed FL), mantle cell lymphoma (MCL), marginal zone lymphoma (MZL), high-grade B cell lymphoma, or PMLBCL). In another embodiment, the B cell proliferative disorder is a leukemia, such as chronic lymphocytic leukemia (CLL).

As used herein, "treatment" (and grammatical variations thereof, such as "treat" or "treating") refers to clinical intervention in an attempt to alter the natural course of the subject being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a CD20-positive cell proliferative disorder, e.g., a B cell proliferative disorder, e.g., NHL, e.g., DLBCL). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the reduction or inhibition of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the fractionated, dose-escalation dosing regimen of the invention relative to intravenous administration with the bispecific antibody. In other embodiments, reduce or inhibit can refer to effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

As used herein, "administering" is meant a method of giving a dosage of a compound (e.g., a bispecific antibody) or a composition (e.g., a pharmaceutical composition, e.g., a pharmaceutical composition including a bispecific antibody) to a subject. The compounds and/or compositions utilized in the methods described herein can be administered intravenously (e.g., by intravenous infusion).

A "fixed" or "flat" dose of a therapeutic agent (e.g., a bispecific antibody) herein refers to a dose that is administered to a patient without regard for the weight or body surface area (BSA) of the patient. The fixed or flat dose is therefore not provided as a mg/kg dose or a mg/m$^2$ dose, but rather as an absolute amount of the therapeutic agent (e.g., mg).

A "subject" or an "individual" is a mammal. Mammals include, but are not limited to, primates (e.g., humans and non-human primates such as monkeys), domesticated animals (e.g., cows, sheep, cats, dogs, and horses), rabbits, and rodents (e.g., mice and rats). In certain embodiments, the subject or individual is a human.

"Individual response" or "response" can be assessed using any endpoint indicating a benefit to the subject, including, without limitation, (1) inhibition, to some extent, of disease progression (e.g., progression of a CD20-positive cell proliferative disorder, e.g., a B cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL or Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e., reduction, slowing down or complete stopping) of metastasis; (5) relief, to some extent, of one or more symptoms associated with the CD20-positive cell proliferative disorder, e.g., a B cell proliferative disorder; (6) increase or extend in the length of survival, including overall survival and progression-free survival; and/or (7) decreased mortality at a given point of time following treatment.

As used herein, "complete response" or "CR" refers to disappearance of all target lesions (i.e., all evidence of disease).

As used herein, "partial response" or "PR" refers to at least a 30% decrease in the sum of the longest diameters (SLD) of target lesions, taking as reference the baseline SLD, or at least a 50% decrease in the product of the diameters (SPD) of target lesions, taking as reference the baseline SPD.

As used herein, "objective response rate" (ORR) refers to the sum of complete response (CR) rate and partial response (PR) rate.

As used herein, "duration of objective response" or "duration of response" (DOR) is defined as the time from the first occurrence of a documented objective response to disease progression, or death from any cause within 30 days of the last dose of a treatment, whichever occurs first.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

An "effective response" of a subject or a subject's "responsiveness" to treatment with a medicament and similar wording refers to the clinical or therapeutic benefit imparted to a subject as risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

A subject who "does not have an effective response" to treatment refers to a subject who does not have any one of extending survival (including overall survival and progression free survival); resulting in an objective response (including a complete response or a partial response); or improving signs or symptoms of cancer.

As used herein, "survival" refers to the patient remaining alive, and includes overall survival as well as progression-free survival.

As used herein, "overall survival" (OS) refers to the percentage of subjects in a group who are alive after a particular duration of time, e.g., 1 year or 5 years from the time of diagnosis or treatment.

As used herein, "progression-free survival" (PFS) refers to the length of time during and after treatment during which the disease being treated (e.g., CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL or Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) does not get worse. Progression-free survival may include the amount of time patients have experienced a complete response or a partial response, as well as the amount of time patients have experienced stable disease.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD, or at least a 50% increase in the SPD of target legions, taking as reference the smallest SPD, recorded since the treatment started or the presence of one or more new lesions.

As used herein, "delaying progression" of a disorder or disease means to defer, hinder, slow, retard, stabilize, and/or postpone development of the disease or disorder (e.g., CD20-positive cell proliferative disorder (e.g., a B cell proliferative disorder (e.g., an NHL (e.g., a DLBCL (e.g., relapsed and/or refractory DLBCL or a Richter's transformation), an FL (e.g., a relapsed and/or refractory FL or a transformed FL), an MCL, an MZL, a high-grade B cell lymphoma, or a PMLBCL) or a CLL)). This delay can be of varying lengths of time, depending on the history of the disease and/or subject being treated. As is evident to one skilled in the art, a sufficient or significant delay can, in effect, encompass prevention, in that the subject does not develop the disease. For example, in a late stage cancer, development of central nervous system (CNS) metastasis, may be delayed.

As used herein, the term "reducing or inhibiting cancer relapse" means to reduce or inhibit tumor or cancer relapse, or tumor or cancer progression.

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated (e.g., CD20-positive cell proliferative disorder (e.g., a B cell proliferative disorder (e.g., an NHL (e.g., a DLBCL (e.g., relapsed and/or refractory DLBCL or a Richter's transformation), an FL (e.g., a relapsed and/or refractory FL or a transformed FL), an MCL, an MZL, a high-grade B cell lymphoma, or a PMLBCL) or a CLL)), the presence or size of metastases, or the size of the primary tumor.

By "extending survival" is meant increasing overall or progression-free survival in a treated patient relative to an untreated patient (e.g., relative to a patient not treated with the medicament), or relative to a patient who does not express a biomarker at the designated level, and/or relative to a patient treated with an approved anti-tumor agent. An objective response refers to a measurable response, including complete response (CR) or partial response (PR).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The terms "full-length antibody," "intact antibody," and "whole antibody" are used herein interchangeably to refer to an antibody having a structure substantially similar to a native antibody structure or having heavy chains that contain an Fc region as defined herein.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'$_2$, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term IgG "isotype" or "subclass" as used herein is meant any of the subclasses of immunoglobulins defined by the chemical and antigenic characteristics of their constant regions.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al., *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al., *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, e.g., Flatman et al., *J. Chromatogr. B* 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The term "cluster of differentiation 3" or "CD3," as used herein, refers to any native CD3 from any vertebrate source, including mammals such as primates (e.g., humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

The term "cluster of differentiation 20" or "CD20," as used herein, refers to any native CD20 from any vertebrate source, including mammals such as primates (e.g., humans) and rodents (e.g., mice and rats), unless otherwise indicated. The term encompasses "full-length," unprocessed CD20, as well as any form of CD20 that results from processing in the cell. The term also encompasses naturally occurring variants of CD20, including, for example, splice variants or allelic variants. CD20 includes, for example, human CD20 protein (see, e.g., NCBI RefSeq Nos. NP_068769.2 and NP_690605.1), which is 297 amino acids in length and may be generated, for example, from variant mRNA transcripts that lack a portion of the 5' UTR (see, e.g., NCBI RefSeq No. NM_021950.3) or longer variant mRNA transcripts (see, e.g., NCBI RefSeq No. NM_152866.2).

The terms "anti-CD20/anti-CD3 bispecific antibody," "bispecific anti-CD20/anti-CD3 antibody," and "antibody that binds to CD20 and CD3," or variants thereof, refer to a multispecific antibody (e.g., a bispecific antibody) that is capable of binding to CD20 and CD3 with sufficient affinity such that the antibody is useful as a diagnostic and/or therapeutic agent in targeting CD20 and/or CD3. In one embodiment, the extent of binding of a bispecific antibody that binds to CD20 and CD3 to an unrelated, non-CD3 protein and/or non-CD20 protein is less than about 10% of the binding of the antibody to CD3 and/or CD20 as measured, e.g., by a radioimmunoassay (RIA). In certain embodiments, a bispecific antibody that binds to CD20 and CD3 has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, a bispecific antibody that binds to CD20 and CD3 binds to an epitope of CD3 that is conserved among CD3 from different species and/or an epitope of CD20 that is conserved among CD20 from different species. Examples of anti-CD20/anti-CD3 bispecific antibodies are discussed below under "Therapeutic Methods—Bispecific Antibodies that Bind to CD20 and CD3." In one embodiment, a bispecific antibody that binds to CD20 and CD3 is mosunetuzumab.

As used herein, the term "mosunetuzumab" refers to an anti-CD20/anti-CD3 bispecific antibody having the International Nonproprietary Names for Pharmaceutical Substances (INN) List 117 (WHO Drug Information, Vol. 31, No. 2, 2017, p. 303), or the CAS Registry Number 1905409-39-3.

As used herein, the term "binds," "specifically binds to," or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, for example, by a radioimmunoassay (RIA). In certain embodiments, an antibody that specifically binds to a target has a dissociation constant ($K_D$) of $\leq 1$ µM, $\leq 100$ nM, $\leq 10$ nM, $\leq 1$ nM, or $\leq 0.1$ nM. In certain embodiments, an antibody specifically binds to an epitope on a protein that is conserved among the protein from different species. In another embodiment, specific binding can include, but does not require exclusive binding. The term as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN® (DNASTAR®) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX® operating system, including digital UNIX® V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "chemotherapeutic agent" refers to a compound useful in the treatment of cancer, such as a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a marginal zone lymphoma (MZL)) or a relapsed or refractory CLL). Examples of chemotherapeutic agents include EGFR inhibitors (including small molecule inhibitors (e.g., erlotinib (TARCEVA®, Genentech/OSI Pharm.); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl) amino]-1H-pyrrolo[2,3-d]pyrimidin-6-yl]-phenol); (R)-6-(4-hydroxyphenyl)-4-[(1-phenylethyl)amino]-7H-pyrrolo [2,3-d]pyrimidine); CL-387785 (N-[4-[(3-bromophenyl) amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino] methyl]-2-furanyl]-4-quinazolinamine)); a tyrosine kinase inhibitor (e.g., an EGFR inhibitor; a small molecule HER2 tyrosine kinase inhibitor such as TAK165 (Takeda); CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; PKI-166 (Novartis); pan-HER inhibitors such as canertinib (CI-1033; Pharmacia); Raf-1 inhibitors such as antisense agent ISIS-5132 (ISIS Pharmaceuticals) which inhibit Raf-1 signaling; non-HER-targeted tyrosine kinase inhibitors such as imatinib mesylate (GLEEVEC®, Glaxo SmithKline); multi-targeted tyrosine kinase inhibitors such as sunitinib (SUTENT®, Pfizer); VEGF receptor tyrosine kinase inhibitors such as vatalanib (PTK787/ZK222584, Novartis/Schering AG); MAPK extracellular regulated kinase I inhibitor CI-1040 (Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino) phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®)); proteasome inhibitors such as bortezomib (VELCADE®, Millennium Pharm.); disulfiram; epigallocatechin gallate; salinosporamide A; carfilzomib; 17-AAG (geldanamycin); radicicol; lactate dehydrogenase A (LDH-A); fulvestrant (FASLODEX®, AstraZeneca); letrozole (FEMARA®, Novartis), finasunate (VATALANIB®, Novartis); oxaliplatin (ELOXATIN®, Sanofi); 5-FU (5-fluorouracil); leucovorin; lonafamib (SCH 66336); sorafenib (NEXAVAR®, Bayer Labs); AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1 and calicheamicin ω1); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, cactinomycin, carabicin, caminomycin, carzinophilin, chromomycinis, dactinomycin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; chloranmbucil; GEMZAR® (gemcitabine); 6-thioguanine; mercaptopurine; methotrexate; etoposide (VP-16); ifosfamide; mitoxantrone; novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids, prodrugs, and derivatives of any of the above.

Chemotherapeutic agents also include (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; (ix) growth inhibitory agents including vincas (e.g., vincristine and vinblastine), NAVELBINE® (vinorelbine), taxanes (e.g., paclitaxel, nab-paclitaxel, and docetaxel), topoisomerase II inhibitors (e.g., doxorubicin, epirubicin, daunorubicin, etoposide, and bleomycin), and DNA alkylating agents (e.g., tamoxigen, dacarbazine, mechlorethamine, cisplatin, methotrexate, 5-fluorouracil, and ara-C); and (x) pharmaceutically acceptable salts, acids, prodrugs, and derivatives of any of the above.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, Sm$^{153}$, Bi$^{212}$, P$^{32}$, Pb$^{212}$ and radioactive isotopes of Lu); chemotherapeutic agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one instance, the cytotoxic agent is a platinum-based chemotherapeutic agent (e.g., carboplatin or cisplatin). In one instance, the cytotoxic agent is an antagonist of EGFR, e.g., N-(3-ethynylphenyl)-6,7-bis(2-methoxyethoxy)quinazolin-4-amine (e.g., erlotinib). In one instance the cytotoxic agent is a RAF inhibitor, e.g., a BRAF and/or CRAF inhibitor. In one instance the RAF inhibitor is vemurafenib. In one instance, the cytotoxic agent is a PI3K inhibitor.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis, with a result being to restore or enhance T-cell function (e.g., proliferation, cytokine production, target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab). In another specific aspect, a PD-1 binding antagonist is pembrolizumab (formerly lambrolizumab (MK-3475)). In another specific aspect, a PD-1 binding antagonist is AMP-224. In some embodiments, the PD-1 binding antagonist is MDX-1106 (nivolumab). In some embodiments, the PD-1 binding antagonist is MK-3475 (pembrolizumab). In some embodiments, the PD-1 binding antagonist is MEDI-0680. In some instances, the PD-1 binding antagonist is PDR001 (spartalizumab). In some instances, the PD-1 binding antagonist is REGN2810 (cemiplimab). In some instances, the PD-1 binding antagonist is BGB-108. In other instances, the PD-1 binding antagonist is prolgolimab, camrelizumab, sintilimab, tislelizumab, or toripalimab.

Further examples of PD-1 axis binding antagonists include cemiplimab, prolgolimab, camrelizumab, sintilimab, tislelizumab, toripalimab, dostarlimab, retifanlimab, spartalizumab, sasanlimab, penpulimab, CS1003, HLX10, SCT-I10A, SHR-1316, CS1001, envafolimab, TQB2450, ZKAB001, LP-002, zimberelimab, balstilimab, genolimzumab, BI 754091, cetrelimab, YBL-006, BAT1306, HX008, CX-072, IMC-001, KL-A167, budigalimab, CX-188, JTX-4014, 609A, Sym021, LZM009, F520, SG001, APL-502, cosibelimab, lodapolimab, GS-4224, INCB086550, FAZ053, TG-1501, BGB-A333, BCD-135, AK-106, LDP, GR1405, HLX20, MSB2311, MAX-10181, RC98, BION-004, AM0001, CB201, ENUM 244C8, ENUM 388D4, AUNP-012, STI-1110, ADG104, AK-103, LBL-006, hAb21, AVA-004, PDL-GEX, INCB090244, KD036, KY1003, LYN192, MT-6035, VXM10, YBL-007, ABSK041, GB7003, JS-003, and HS-636.

The term "PD-L1 binding antagonist" refers to a molecule that decreases, blocks, inhibits, abrogates, or interferes with signal transduction resulting from the interaction of PD-L1 with either one or more of its binding partners, such as PD-1 or R7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or R7-1. In some embodiments, the PD-L1 binding antagonists include anti-PD-L1 antibodies, antigen-binding fragments thereof, immunoadhesins, fusion proteins, oligopeptides, and other molecules that decrease, block, inhibit, abrogate, or interfere with signal transduction resulting from the interaction of PD-L1 with one or more of its binding partners, such as PD-1 or R7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific embodiment, the anti-PD-L1 antibody is atezolizumab, also known as MPDL3280A. In another specific embodiment, the anti-PD-L1 antibody is MDX-1105. In still another specific aspect, the anti-PD-L1 antibody is MEDI4736.

As used herein, the term "atezolizumab" refers to anti-PD-L1 antagonist antibody having the International Nonproprietary Names for Pharmaceutical Substances (INN) List 112 (WHO Drug Information, Vol. 28, No. 4, 2014, p. 488), or the CAS Registry Number 1380723-44-3.

The term "PD-L2 binding antagonist" refers to a molecule that decreases, blocks, inhibits, abrogates, or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen-binding fragments thereof, immunoadhesins, fusion proteins, oligopeptides, and other molecules that decrease, block, inhibit, abrogate, or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "package insert" is used to refer to instructions customarily included in commercial packages of therapeutic products, that contain information about the indications, usage, dosage, administration, combination therapy, contraindications and/or warnings concerning the use of such therapeutic products.

III. Therapeutic Methods

Provided herein are methods of treating a subject having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering (e.g., intravenously administering) to the subject a bispecific antibody that binds to CD20 and CD3 (e.g., mosunetuzumab) in a dosing regimen comprising at least a first dosing cycle and a second dosing cycle (e.g., a first dosing cycle, a second dosing cycle, and a third dosing cycle).

Also provided herein are methods of treating a population of subjects having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering (e.g., intravenously administering) to one or more of the subjects a bispecific antibody that binds to CD20 and CD3 (e.g., mosunetuzumab) in a dosing regimen comprising at least a first dosing cycle and a second dosing cycle (e.g., a first dosing cycle, a second dosing cycle, and a third dosing cycle).

In some instances, the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 50 mg. In some instances, the second dosing cycle includes a single dose (C2D1) of the bispecific antibody. In some instances, the invention features administration to the subject a bispecific antibody that binds to CD20 and CD3 (e.g., mosunetuzumab) in a dosing regimen comprising at least a first dosing cycle, a second dosing cycle, and a third dosing cycle, wherein the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg; the second dosing cycle comprises a single dose (C2D1) of the bispecific antibody, wherein the C2D1 is about equivalent in amount to the C1D3; and the third dosing cycle comprises a single dose (C3D1) of the bispecific antibody, wherein the C3D1 is greater than the C1D1 and less than the C2D1. In some instances of any of the methods of the invention, the dosing regimen provides a reduction in the rate of cytokine release syndrome.

First, dosing regimens are discussed, followed by anti-CD20/anti-CD3 bispecific antibodies. Various formats and properties of antibodies are then discussed, as well as additional therapeutic agents that can be used in the disclosed methods.

A. Dosing Regimens

In some instances, the invention provides a method of treating a subject (e.g., a human subject) having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL) or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering to the subject a bispecific antibody that binds to CD20 and CD3 (e.g., mosunetuzumab) in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., from about 0.02 to about 1.8 mg, from about 0.02 to about 1.6 mg, from about 0.02 to about 1.4 mg, from about 0.02 to about 1.2 mg, from about 0.05 to about 1.8 mg, from about 0.1 to about 1.8 mg, from about 0.4 to about 1.8 mg, from about 0.6 to about 1.8 mg, from about 0.8 to about 1.8 mg, from about 0.5 to about 1.5 mg, from about 0.8 to about 1.2 mg; e.g., about 1 mg), the C1D2 is from about 0.05 mg to about 4.0 mg (e.g., from about 0.05 to about 3.5 mg, from about 0.05 to about 3.0 mg, from about 0.05 to about 2.5 mg, from about 0.05 to about 2.2 mg, from about 0.1 to about 3.5 mg, from about 0.5 to about 3.5 mg, from about 1.0 to about 3.5 mg, from about 1.5 to about 3.5 mg, from about 1.8 to about 3.5 mg, from about 1.0 to about 3.0 mg, from about 1.5 to about 2.5 mg; e.g., about 2 mg), and the C1D3 is greater than about 50 mg; and (b) the second dosing cycle comprises a single dose (C2D1) of the bispecific antibody.

In some instances, the C1D3 is from 50 mg to 200 mg (e.g., from 50 mg to 175 mg, from 50 mg to 150 mg, from 50 mg to 125 mg, from 50 mg to 100 mg, from 50 mg to 75 mg, from 50 mg to 70 mg, from 52 mg to 100 mg, from 52 mg to 75 mg, from 50 mg to 180 mg, from 55 mg to 150 mg, from 55 mg to 100 mg, from 55 mg to 70 mg, from 55 mg to 65 mg, from 58 mg to 62 mg; e.g., about 60 mg). In some embodiments, the C1D3 is about 60 mg. In some embodiments, the C1D1 is about 1 mg and/or the C1D2 is about 2 mg. In some embodiments, the C2D1 is about equivalent in amount to the C1D3.

In some instances, the C1D1, the C1D2, and the C1D3 are administered to the subject on or about Days 1, 8, and 15, respectively, of the first dosing cycle (e.g., a 21-day dosing cycle). In some embodiments, the C2D1 is administered to the subject on Day 1 of the second dosing cycle (e.g., a 21- or 28-day dosing cycle).

In some instances, the dosing regimen further includes one or more additional dosing cycles beyond the second dosing cycle. For example, in some embodiments, the dosing regimen comprises from six to 15 additional dosing cycles (e.g., from six to ten additional dosing cycles (e.g., six additional dosing cycles, seven additional dosing cycles, eight additional dosing cycles, nine additional dosing cycles, or ten additional dosing cycles) or from 11-15 additional dosing cycles (e.g., 11 additional dosing cycles, 12 additional dosing cycles, 13 additional dosing cycles, 14 additional dosing cycles, or 15 additional dosing cycles) beyond the second dosing cycle.

In some embodiments, one or more of the additional dosing cycles comprise an additional single dose of the bispecific antibody (e.g., mosunetuzumab). In some embodiments, the additional single dose of the bispecific antibody is administered to the subject on Day 1 of each additional dosing cycle.

In some instances, the additional single dose of the bispecific antibody is greater than the C1D1 and less than the C1D3 and/or the C2D1. In some embodiments, the additional single dose of the bispecific antibody is from 20% to 80% (e.g., from 20% to 70%, from 20% to 60%, from 20% to 55%, from 30% to 80%, from 30% to 70%, from 40% to 70%, from 45% to 70%, from 40% to 60%, from 45% to 55%, from 48% to 52%; e.g., about 50%) of the C1D3 and/or the C2D1. In particular instances, the additional single dose of the bispecific antibody is about 50% of the C1D3 and/or the C2D1.

In some instances, the additional single dose of the bispecific antibody is about 30 mg.

In some instances, the invention features a method of treating a subject having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering (e.g., intravenously administering) to the subject a bispecific antibody that binds to CD20 and CD3 (e.g., mosunetuzumab) in a dosing regimen comprising at least a first dosing cycle, a second dosing cycle, and a third dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; and (c) the third dosing cycle comprises a single dose (C3D1) of the bispecific antibody, wherein the C3D1 is greater than the C1D1 and less than the C2D1. In some instances, the C1D3 and the C2D1 are each from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; e.g., about 20 mg, about 30 mg, about 45 mg, or about 60 mg). In some embodiments, the C1D3 and the C2D1 are each about 60 mg. In some embodiments, the C3D1 is from 20% to 80% (e.g., from 20% to 70%, from 20% to 60%, from 20% to 55%, from 30% to 80%, from 30% to 70%, from 40% to 70%, from 45% to 70%, from 40% to 60%, from 45% to 55%, or from 48% to 52%; e.g., about 40%, about 45%, about 50%, about 55%, or about 60%) of the C2D1. In some embodiments, the C3D1 is about 50% of the C2D1. In some embodiments, the C3D1 is from about 12 mg to about 48 mg (e.g., from about 12 mg to about 42 mg, from about 12 mg to about 36 mg, from about 12 mg to about 30 mg, from about 18 mg to about 48 mg, from about 18 mg to about 42 mg, from about 24 mg to about 42 mg, from about 27 mg to about 42 mg, from about 24 mg to about 36 mg, from about 27 mg to about 33 mg, from about 28 mg to about 32 mg; e.g., about 24 mg, about 27 mg, about 30 mg, about 33 mg, or about 36 mg). In a particular embodiment, the C3D1 is about 30 mg.

In some instances, the C3D1 is about 30 mg. In some embodiments, the C1D1 is about 1 mg. In some embodiments, the C1D2 is about 2 mg. For examples, in particular instances, the C1D1 is about 1 mg, the C1D2 is about 2 mg, and the C1D3 is about 30 mg.

In some instances, the C1D1, the C1D2, and the C1D3 are administered to the subject on or about Days 1, 8, and 15, respectively, of the first dosing cycle (e.g., a 21-day dosing cycle). In some embodiments, the C2D1 is administered to the subject on Day 1 of the second dosing cycle and the C3D1 is administered to the subject on Day 1 of the third dosing cycle (e.g., wherein the second and third dosing cycles are 21- or 28-day dosing cycles).

In some embodiments, a dosing regimen of the invention further comprises one or more additional dosing cycles beyond the third dosing cycle. For example, in some instances, the dosing regimen comprises from five to 14 additional dosing cycles (e.g., from five to ten additional dosing cycles (e.g., five additional dosing cycles, six additional dosing cycles, seven additional dosing cycles, eight additional dosing cycles, nine additional dosing cycles, or ten additional dosing cycles) or from 11-14 additional dosing cycles (e.g., 11 additional dosing cycles, 12 additional dosing cycles, 13 additional dosing cycles, 14 additional dosing cycles)) beyond the third dosing cycle.

In some embodiments, one or more of the additional dosing cycles comprise an additional single dose of the bispecific antibody. In some embodiments, the additional single dose of the bispecific antibody is administered to the subject on Day 1 of each additional dosing cycle. In some embodiments, the additional single dose of the bispecific antibody is about equivalent in amount to the C3D1.

The invention also features a method of treating a subject having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL;

e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering (e.g., intravenously administering) to the subject a bispecific antibody that binds to CD20 and CD3 (e.g., mosunetuzumab) in a dosing regimen comprising eight or more dosing cycles, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; (c) the third dosing cycle comprises a single dose (C3D1) of the bispecific antibody, wherein the C3D1 is greater than the C1D1 and less than the C2D1; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 are about equivalent in amount.

In some instances, the C1D3 and the C2D1 are each from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; e.g., about 20 mg, about 30 mg, about 45 mg, or about 60 mg). In some embodiments, the C1D3 and the C2D1 are each about 60 mg. In some embodiments, the C3D1 is from 20% to 80% (e.g., from 20% to 70%, from 20% to 60%, from 20% to 55%, from 30% to 80%, from 30% to 70%, from 40% to 70%, from 45% to 70%, from 40% to 60%, from 45% to 55%, or from 48% to 52%; e.g., about 40%, about 45%, about 50%, about 55%, or about 60%) of the C2D1. In some embodiments, the C3D1 is about 50% of the C2D1. In some embodiments, the C3D1 is from about 12 mg to about 48 mg (e.g., from about 12 mg to about 42 mg, from about 12 mg to about 36 mg, from about 12 mg to about 30 mg, from about 18 mg to about 48 mg, from about 18 mg to about 42 mg, from about 24 mg to about 42 mg, from about 27 mg to about 42 mg, from about 24 mg to about 36 mg, from about 27 mg to about 33 mg, from about 28 mg to about 32 mg; e.g., about 24 mg, about 27 mg, about 30 mg, about 33 mg, or about 36 mg). In a particular embodiment, the C3D1 is about 30 mg. In some embodiments, the C1D1 is about 1 mg. In some embodiments, the C1D2 is about 2 mg.

In some instances, the C1D1, the C1D2, and the C1D3 are administered to the subject on or about Days 1, 8, and 15, respectively, of the first dosing cycle. In some embodiments, the C2D1-C8D1 are each administered to the subject on Day 1 of the second-eighth dosing cycle, respectively. In some embodiments, dosing cycles are 21- or 28-day dosing cycles. In some embodiments, the dosing regimen comprises one or more additional dosing cycles beyond the eighth dosing cycle. In some embodiments, the additional dosing cycles are 21-day dosing cycles. In some embodiments, the additional dosing cycles are 28-day dosing cycles.

In some instances, one or more of the additional dosing cycles include an additional single dose of the bispecific antibody. In some embodiments, the additional single dose of the bispecific antibody is administered to the subject on Day 1 of each additional dosing cycle. In some embodiments, the additional single dose of the bispecific antibody is about equivalent in amount to any one of the C3D1-C8D1.

In some embodiments, the dosing regimen further comprises administering to the subject a PD-1 axis binding antagonist. In some embodiments, the PD-1 axis binding antagonist is administered at a dose of between about 1100 mg to about 1300 mg (e.g., between about 1150 mg to about 1250 mg, between about 1175 mg to about 1225 mg, between about 1190 mg to about 1210 mg; e.g., 1200 mg±5 mg, e.g., 1200±2.5 mg, e.g., 1200±1.0 mg, e.g., 1200±0.5 mg; e.g., about 1200 mg). In particular embodiments, the PD-1 axis binding antagonist is administered at a dose of about 1200 mg. In some embodiments, the PD-1 axis binding antagonist is administered on Day 1 (±1 day) of each dosing cycle after the first dosing cycle comprising administration of the bispecific antibody. In some embodiments, the PD-1 axis binding antagonist is atezolizumab. In some embodiments, the subject is a human The present invention further provides methods of treating a subject having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering (e.g., intravenously administering) to the subject a bispecific antibody that binds to CD20 and CD3 (e.g., mosunetuzumab) in a dosing regimen comprising eight or more 21- or 28-day dosing cycles, wherein: (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg; (b) the second dosing cycle comprises a single dose (C2D1) of the bispecific antibody, wherein the C2D1 is about 60 mg; (c) the third dosing cycle comprises a single dose (C3D1) of the bispecific antibody; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 are each about 30 mg. In some embodiments, dosing cycles after the first dosing cycle are 28-day dosing cycles.

In some instances of any of the aforementioned methods, the subject has received a prior systemic therapy for the CD20-positive cell proliferative disorder (e.g., a prior systemic therapy for the B cell proliferative disorder (e.g., relapsed or refractory B cell proliferative disorder), e.g., non-Hodgkin's lymphoma (NHL; e.g., diffuse large B cell lymphoma (DLBCL; e.g., Richter's Transformation), follicular lymphoma (FL; e.g., a Grade 1 FL, a Grade 2 FL, a Grade 3 FL (e.g., a Grade 3a FL, Grade 3b FL), or transformed FL), mantle cell lymphoma (MCL), or a marginal zone lymphoma (MZL)) or chronic lymphoid leukemia (CLL). In some instances, the subject has received a first-line systemic therapy and a second-line systemic therapy for the CD20-positive cell proliferative disorder (e.g., the dosing regimen provided herein can be a third-line therapy). In some embodiments, the subject has exhibited progression of the CD20-positive cell proliferative disorder within 24 months of any prior systemic therapy.

In some instances, the prior systemic therapy comprises an anti-CD20 antibody (e.g., rituximab or obinutuzumab). In some instances, the prior systemic therapy includes a chemotherapeutic agent, e.g., an alkylating agent (e.g., bendamustine). In some embodiments, prior systemic therapy includes lenalidomide. In some instances, the prior systemic therapy includes a radio-immunotherapy (e.g., ibritumomab tiuxetan). In some instances, the prior systemic therapy includes a phosphoinositide 3-kinase inhibitor (e.g., idelalisib, alpelisib, copanlisib, or duvelisib). In some instances, the prior systemic therapy includes a CAR-T therapy.

The invention also provides methods of treating a population of subjects having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL or a relapsed or refractory MZL) or a relapsed or refractory CLL) by administering (e.g., intravenously administering) to one or more of the subjects a bispecific antibody that binds to CD20 and CD3 (e.g., mosunetuzumab) in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than 50 mg; and (b) the second dosing cycle comprises a single dose (C2D1) of the bispecific antibody.

In other particular instances, the invention includes a method of treating a population of subjects having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering to one or more of the subjects a bispecific antibody that binds to CD20 and CD3 (e.g., mosunetuzumab) in a dosing regimen comprising at least a first dosing cycle, a second dosing cycle, and a third dosing cycle, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; and (c) the third dosing cycle comprises a single dose (C3D1) of the bispecific antibody, wherein the C3D1 is greater than the C1D1 and less than the C2D1.

Also provided herein is a method of treating a population of subjects having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering to one or more of the subjects a bispecific antibody that binds to CD20 and CD3 in a dosing regimen comprising eight or more dosing cycles, wherein: (a) the first dosing cycle comprises a first dose (C1D1), a second dose (C1D2), and a third dose (C1D3) of the bispecific antibody, wherein the C1D1 is from about 0.02 mg to about 2.0 mg (e.g., about 0.02 to about 1.8 mg, about 0.02 to about 1.6 mg, about 0.02 to about 1.4 mg, about 0.02 to about 1.2 mg, about 0.05 to about 1.8 mg, about 0.1 to about 1.8 mg, about 0.4 to about 1.8 mg, about 0.6 to about 1.8 mg, about 0.8 to about 1.8 mg, about 0.5 to about 1.5 mg, about 0.8 to about 1.2 mg; e.g., about 1 mg), the C1D2 is from about 0.05 mg to about 4.0 mg (e.g., about 0.05 to about 3.5 mg, about 0.05 to about 3.0 mg, about 0.05 to about 2.5 mg, about 0.05 to about 2.2 mg, about 0.1 to about 3.5 mg, about 0.5 to about 3.5 mg, about 1.0 to about 3.5 mg, about 1.5 to about 3.5 mg, about 1.8 to about 3.5 mg, about 1.0 to about 3.0 mg, about 1.5 to about 2.5 mg; e.g., about 2 mg), and the C1D3 is greater than about 20 mg; (b) the second dosing cycle comprises a single dose (C2D1) of the bispecific antibody, wherein the C2D1 is about equivalent in amount to the C1D3; (c) the third dosing cycle comprises a single dose (C3D1) of the bispecific antibody, wherein the C3D1 is greater than the C1D1 and less than the C2D1; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 are about equivalent in amount.

Methods of the invention also include treating a population of subjects having a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL) by administering (e.g., intravenously administering) to one or more of the subjects a bispecific antibody that binds to CD20 and CD3 (e.g., mosunetuzumab) in a dosing regimen comprising eight or more 21- or 28-day dosing cycles, wherein: (a) the first 21-day dosing cycle comprises a first dose (C1D1), a second dose (C1D2), and a third dose C1D3) of the bispecific antibody, wherein the C1D1 is about 1 mg, the C1D2 is about 2 mg, and the C1D3 is about 60 mg; (b) the second dosing cycle comprises a single dose (C2D1) of the bispecific antibody, wherein the C2D1 is about 60 mg; (c) the third dosing cycle comprises a single dose (C3D1) of the bispecific antibody; (d) the fourth dosing cycle comprises a single dose (C4D1) of the bispecific antibody; (e) the fifth dosing cycle comprises a single dose (C5D1) of the bispecific antibody; (f) the sixth dosing cycle comprises a single dose (C6D1) of the bispecific antibody; (g) the seventh dosing cycle comprises a single dose (C7D1) of the bispecific antibody; and (h) the eighth dosing cycle comprises a single dose (C8D1) of the bispecific antibody, wherein the C3D1-C8D1 are each about 30 mg. In some embodiments, dosing cycles after the first dosing cycle are 28-day dosing cycles.

In some embodiments, the rate of cytokine release syndrome having a grade of 2 or greater (as defined by the American Society for Transplantation and Cellular Therapy, 2018; ASTCT) is less than or equal to about 10% (e.g., less than or equal to about 9%, less than or equal to about 8%, less than or equal to about 7%, less than or equal to about 6%, less than or equal to about 5%, less than or equal to about 4%, less than or equal to about 3%, less than or equal to about 2%, less than or equal to about 1%; e.g. between about 0.1% to about 10%, between about 0.5% and about 10%, between about 1% and about 10%, between about 1% and about 7%, between about 1% and about 5%, between about 1% and about 3%, or between about 5% and about 10%; e.g., about 9%, about 8%, about 7%, about 6%, about 5%, about 4%, about 3%, about 2%, about 1%, or about 0%). In some embodiments, the rate of cytokine release syndrome having a grade of 2 or greater (as defined by the ASTCT) is less than or equal to about 5% (e.g., less than or equal to about 4%, less than or equal to about 3%, less than or equal to about 2%, less than or equal to about 1%; e.g., between about 0% and about 5%, between about 1% and about 5%, between about 2% and about 5%, between about 3% and about 5%, between about 4% and about 5%, between about 1% and about 3%, between about 2% and about 5%, or between about 0% and about 2%; e.g., about 5%, about 4%, about 3%, about 2%, about 1%, or about 0%). In some embodiments, the rate of cytokine release syndrome having a grade of 3 or greater (as defined by the ASTCT) is about 0.

Any of the methods described herein may involve monitoring a subject for cytokine release syndrome (CRS), e.g., a CRS event following commencement of any of the methods described above. Current clinical management focuses on treating the individual signs and symptoms, providing supportive care, and attempting to dampen the inflammatory response using a high dose of corticosteroids. However, this approach is not always successful, especially in the case of late intervention. The CRS grading criteria used by the methods described herein are published by the American Society for Transplantation and Cellular Therapy (ASTCT) to define mild, moderate, severe, or life-threatening CRS and harmonize reporting across clinical trials to allow rapid recognition and treatment of CRS (Lee et al., *Biology of Blood and Marrow Transplantation*. 25(4): 625-638, 2019). The ASTCT criteria is intended to be objective, easy to apply, and more accurately categorize the severity of CRS. This revised CRS grading system is shown below in Table 1.

TABLE 1

CRS Grading System

| CRS Parameter | Grade 1 | Grade 2 | Grade 3 | Grade 4 |
|---|---|---|---|---|
| Fever | Temperature ≥ 38° C. | Temperature ≥ 38° C. | Temperature ≥ 38° C. | Temperature ≥ 38° C. |
| | | with | | |
| Hypotension | None | Not requiring vasopressors | Requiring a vasopressor with or without vasopressin and/or | Requiring multiple vasopressors (excluding vasopressin) |
| Hypoxia | None | Requiring low-glow nasal cannula or blow-by | Requiring high-flow nasal cannula, facemask, nonrebreather mask or Venturi mask | Requiring positive pressure (e.g., CPAP, BiPAP, intubation and mechanical ventilation) |

ASTCT = American Society for Transplantation and Cellular Therapy; BiPAP = bilevel positive airway pressure; CPAP = continuous positive airway pressure; CRS = cytokine release syndrome; CTCAE = Common Terminology Criteria for Adverse Events.

Fever is defined as a temperature 38° C. not attributable to any other cause. In subjects who have CRS then receive antipyretic or anticytokine therapy such as tocilizumab or steroids, fever is no longer required to grade subsequent CRS severity. In this case, CRS grading is determined by hypotension and/or hypoxia.

CRS grade is determined by the more severe event, hypotension or hypoxia not attributable to any other cause. For example, a subject with temperature of 39.5° C., hypotension requiring 1 vasopressor, and hypoxia requiring low-flow nasal cannula is classified as Grade 3 CRS.

Low-flow nasal cannula is defined as oxygen delivered at 6 L/minute. Low flow also includes blow-by oxygen delivery, sometimes used in pediatrics. High-flow nasal cannula is defined as oxygen delivered at >6 L/minute.

CRS is associated with elevations in a wide array of cytokines, including marked elevations in IFNγ, IL-6, and TNF-α levels. Emerging evidence implicates IL-6, in particular, as a central mediator in CRS. IL-6 is a proinflammatory, multi-functional cytokine produced by a variety of cell types, which has been shown to be involved in a diverse array of physiological processes, including T cell activation. Regardless of the inciting agent, CRS is associated with high IL-6 levels (Nagorsen et al., *Cytokine.* 25(1): 31-5, 2004; Lee et al., *Blood.* 124(2): 188-95, 2014); Doesegger et al., *Clin. Transl. Immunology.* 4(7): e39, 2015), and IL-6 correlates with the severity of CRS, with subjects who experience a grade 4 or 5 CRS event having much higher IL-6 levels compared to subjects who do not experience CRS or experience milder CRS (grades 0-3) (Chen et al., *J. Immunol. Methods.* 434:1-8, 2016).

Therefore, blocking the inflammatory action of IL-6 using an agent that inhibits IL-6-mediated signaling to manage CRS observed in subjects during the double-step fractionated, dose-escalation dosing regimen is an alternative to steroid treatment that would not be expected to negatively impact T cell function or diminish the efficacy or clinical benefit of anti-CD20/anti-CD3 bispecific antibody therapy in the treatment of CD20-positive cell proliferative disorders (e.g., a B cell proliferative disorders).

Tocilizumab (ACTEMRA®/RoACTEMRA®) is a recombinant, humanized, anti-human monoclonal antibody directed against soluble and membrane-bound IL-6R, which inhibits IL-6-mediated signaling (see, e.g., WO 1992/019579, which is incorporated herein by reference in its entirety).

If the subject has a cytokine release syndrome (CRS) event following administration of the bispecific antibody, the method may further involve administering to the subject an effective amount of an interleukin-6 receptor (IL-6R) antagonist (e.g., an anti-IL-6R antibody, e.g., tocilizumab (ACTEMRA®/RoACTEMRA®)) to manage the event. In some instances, tocilizumab is administered intravenously to the subject as a single dose of about 8 mg/kg. Other anti-IL-6R antibodies that could be used instead of, or in combination with, tocilizumab include sarilumab, vobarilizumab (ALX-0061), SA-237, and variants thereof.

If the subject has a CRS event that does not resolve or worsens within 24 hours of administering the IL-6R antagonist to treat the symptoms of the CRS event, and the method may further comprise administering to the subject one or more additional doses of the IL-6R antagonist (e.g., an anti-IL-6R antibody, e.g., tocilizumab) to manage the CRS event. The subject may be administered a corticosteroid, such as methylprednisolone or dexamethasone if CRS event is not managed through administration of the IL-6R antagonist.

Management of the CRS events may be tailored based on the Stage of the CRS and the presence of comorbidities. For example, if the subject has a Grade 2 cytokine release syndrome (CRS) event in the absence of comorbidities or in the presence of minimal comorbidities following administration of the bispecific antibody, the method may further include treating the symptoms of the Grade 2 CRS event while suspending treatment with the bispecific antibody. If the Grade 2 CRS event then resolves to a grade≤1 CRS event for at least three consecutive days, the method may further include resuming treatment with the bispecific antibody without altering the dose. On the other hand, if the Grade 2 CRS event does not resolve or worsens to a grade 3 CRS event within 24 hours of treating the symptoms of the Grade 2 CRS event, the method may further involve administering to the subject an effective amount of an interleukin-6 receptor (IL-6R) antagonist (e.g., an anti-IL-6R antibody, e.g., tocilizumab (ACTEMRA®/RoACTEMRA®)) to manage the Grade 2 or grade 3 CRS event. In some instances, tocilizumab is administered intravenously to the subject as a single dose of about 8 mg/kg. Other anti-IL-6R antibodies that could be used instead of, or in combination with, tocilizumab include sarilumab, vobarilizumab (ALX-0061), SA-237, and variants thereof.

If the subject has a Grade 2, 3, or 4 CRS event in the presence of extensive comorbidities following administration of the bispecific antibody, the method may further include methods understood in the art to mitigate the CRS event, such as administering to the subject a first dose of an IL-6R antagonist (e.g., an anti-IL-6R antibody, e.g., tocilizumab (ACTEMRA®/RoACTEMRA®)) to manage the CRS event while suspending treatment with the bispecific antibody. Other anti-IL-6R antibodies that could be used instead of, or in combination with, tocilizumab include sarilumab, vobarilizumab (ALX-0061), SA-237, and variants thereof. In some instances, the method further includes administering to the subject an effective amount of a corticosteroid, such as methylprednisolone or dexamethasone.

In some instances, a method of the invention results in a complete response rate that is at least about 15% (e.g., from 15% to 30%, 15% to 40%, from 15% to 50%, from 15% to 60%, from 15% to 75%, from 15% to 80%, from 15% to 90%, from 15% to 100%, from 20% to 100%, from 20% to 75%, from 20% to 50%, from 25% to 100%, from 25% to 75%, from 25% to 50%, from 30% to 75%, from 30% to 100%, or from 30% to 50%; e.g., about 15%, about 20%, about 25%, about 30%, about 35%, about 40%, or about 45%). In some embodiments, the complete response rate is at least about 45% (e.g., from 45% to 60%, from 45% to 70%, from 45% to 80%, from 45% to 95%, from 45% to 100%, from 50% to 100%, from 50% to 95%, or from 50% to 75%; e.g., about 45%, about 50%, about 55%, or about 60%). In some embodiments, the objective response rate is at least about 60% (e.g., from 60% to 70%, from 60% to 80%, from 60% to 90%, or from 60% to 100%; e.g., about 60%, about 65%, about 70%, about 75%, about 80%, or about 85%). In some embodiments, the objective response rate at about 20 months after the initiation of treatment is at least about 70% (e.g., from 70% to 80%, from 70% to 90%, from 70% to 95%, or from 70% to 100%; e.g., about 70%, about 75%, about 80%, about 85%, or about 90%). In some embodiments, the objective response rate at about 24 months after the initiation of treatment is at least about 75% (e.g., from 75% to 80%, from 75% to 90%, from 75% to 95%, from 75% to 100%, from 80% to 100%, or from 90% to 100%; e.g., about 75%, about 80%, about 85%, or about 90%). In some embodiments, the median duration of response (mDOR) is at least about 12 months (e.g., at least about 14 months, at least about 16 months, or at least about 18 months; e.g., between 12 and 14 months, between 12 and 16 months, between 12 and 18 months, or between 12 and 20 months; e.g., about 12 months, about 14 months, about 16 months, or about 18 months). In some embodiments, the mDOR is at least about 20 months (e.g., at least about 22 months, at least about 24 months, at least about 26 months, at least about 28 months, at least about 30 months, at least about 32 months, at least about 34 months, or at least about 36 months; e.g., between 20 and 24 months, between 20 and 30 months, between 20 and 36 months, between 20 and 48 months, between 20 and 60 months, between 20 and 72 months, between 24 and 36 months, between 24 and 48 months, between 24 and 60 months, between 36 and 48 months, or between 36 and 60 months; e.g., about 20 months, about 24 months, about 28 months, about 32 months, about 36 months, about 40 months, about 48 months, about 56 months, or about 60 months).

In some embodiments, the population of subjects has a rate of subjects in the population having a DOR of at least 12 months, and wherein the rate of subjects in the population having a DOR of at least 12 months is at least about 60% (e.g., from 60% to 70%, from 60% to 80%, from 60% to 90%, or from 60% to 100%; e.g., about 60%, about 65%, about 70%, about 75%, about 80%, about 85%, about 90%, or about 95%).

In some embodiments, the population of subjects exhibits cytokine release syndrome after administering the bispecific antibody, and wherein the rate of the cytokine release syndrome in the population of subjects is less than or equal to about 25% (e.g., less than or equal to about 23%, less than or equal to about 20%, less than or equal to about 18%, less than or equal to about 16%, less than or equal to about 15%, less than or equal to about 14%, less than or equal to about 13%, less than or equal to about 12%, less than or equal to about 11%, or less than or equal to about 10%; e.g., between about 1% and about 25%, between about 5% and about 25%, between about 10% and about 25%, between about 15% and about 25%, between about 20% and about 25%, between about 5% and about 15%, between about 5% and about 10%, between about 1% and about 15%, or between about 1% and about 10%; e.g., about 5%, about 10%, about 15%, about 20%, or about 25%). In some embodiments, the rate of cytokine release syndrome in the population of subjects is less than or equal to about 10% (e.g., less than or equal to about 9%, less than or equal to about 8%, less than or equal to about 7%, less than or equal to about 6%, less than or equal to about 5%, less than or equal to about 4%, less than or equal to about 3%, less than or equal to about 2%, or less than or equal to about 1%; e.g. between about 0.1% to about 10%, between about 0.5% and about 10%, between about 1% and about 10%, between about 1% and about 7%, between about 1% and about 5%, between about 1% and about 3%, or between about 5% and about 10%; e.g., about 1%, about 2%, about 3%, about 4%, about 5%, about 6%, about 7%, or about 8%).

In some instances, a dosing regimen of the present invention results in a median progression-free survival (PFS) of a population of subjects of greater than four months (e.g., at least 4.5 months, at least 5 months, at least 5.5. months, at least 6 months, at least 6.5 months, at least 7 months, at least 7.5 months, at least 8 months, at least 8.5 months, at least 9.0 months, at least 9.5 months, at least 10 months, at least 11 months, at least 12 months, at least 13 months, at least 14 months, at least 15 months, at least 16 months, at least 17 months, at least 18 months, at least 20 months, at least 24 months, at least 30 months, at least 36 months, at least 42 months, at least 48 months, at least 54 months, or more; e.g., between about 4 months and about 48 months, between about 4 months about 36 months, between about 4 months and about 24 months, between about 4 months and about 12 months, between about 4 months and about 10 months; between about 4 months and about 8 months, between about 8 months and about 24 months, between about 12 months and about 24 months, or between about 8 months and about 16 months; e.g., about 4.5 months, about 5 months, about 5.5 months, about 6 months, about 6.5 months, about 7 months, about 7.5 months, about 8 months, about 8.5 months, about 9.0 months, about 9.5 months, about 10 months, about 11 months, about 12 months, about 13 months, about 14 months, about 15 months, about 16 months, about 17 months, about 18 months, about 20 months, about 24 months, about 30 months, about 36 months, about 42 months, about 48 months, about 54 months, or more).

In some instances, a dosing regimen of the present invention results in a median PFS of a population of subjects having an FL (e.g., relapsed and/or refractory FL) of greater than four months (e.g., at least 4.5 months, at least 5 months, at least 5.5. months, at least 6 months, at least 6.5 months, at least 7 months, at least 7.5 months, at least 8 months, at least 8.5 months, at least 9.0 months, at least 9.5 months, at least 10 months, at least 11 months, at least 12 months, at least 13 months, at least 14 months, at least 15 months, at least 16 months, at least 17 months, at least 18 months, at least 20 months, at least 24 months, at least 30 months, at least 36 months, at least 42 months, at least 48 months, at least 54 months, or more; e.g., between about 4 months and about 48 months, between about 4 months about 36 months, between about 4 months and about 24 months, between about 4 months and about 12 months, between about 4 months and about 10 months; between about 4 months and about 8 months, between about 8 months and about 24 months, between about 12 months and about 24 months, or between about 8 months and about 16 months; e.g., about 4.5 months, about 5 months, about 5.5 months, about 6 months, about 6.5 months, about 7 months, about 7.5 months, about 8 months, about 8.5 months, about 9.0 months, about 9.5 months, about 10 months, about 11 months, about 12 months, about 13 months, about 14 months, about 15 months, about 16 months, about 17 months, about 18 months, about 20 months, about 24 months, about 30 months, about 36 months, about 42 months, about 48 months, about 54 months, or more).

In some instances, a dosing regimen of the present invention results in a median PFS of a population of subjects having DLBCL (e.g., relapsed and/or refractory DLBCL) of greater than or equal to about two months (e.g., at least 2 months, at least 2.5 months, at least 3 months, at least 3.5 months, at least 4 months, at least 4.5 months, at least 5 months, at least 5.5. months, at least 6 months, at least 6.5 months, at least 7 months, at least 7.5 months, at least 8 months, at least 8.5 months, at least 9.0 months, at least 9.5 months, at least 10 months, at least 11 months, at least 12 months, at least 13 months, at least 14 months, at least 15 months, at least 16 months, at least 17 months, at least 18 months, at least 20 months, at least 24 months, at least 30 months, at least 36 months, at least 42 months, at least 48 months, at least 54 months, or more; e.g., between about 2 months and about 48 months, between about 2 months about 36 months, between about 2 months and about 24 months, between about 2 months and about 12 months, between about 2 months and about 10 months; between about 2 months and about 8 months, between about 2 months and about 6 months, between about 2 months and about 4 months, between about 4 months and about 12 months, between about 8 months and about 12 months, or between about 4 months and about 8 months; e.g., about 2.5 months, about 3 months, about 3.5 months, about 4 months, about 4.5 months, about 5 months, about 5.5 months, about 6 months, about 6.5 months, about 7 months, about 7.5 months, about 8 months, about 8.5 months, about 9.0 months, about 9.5 months, about 10 months, about 11 months, about 12 months, about 13 months, about 14 months, about 15 months, about 16 months, about 17 months, about 18 months, about 20 months, about 24 months, about 30 months, about 36 months, about 42 months, about 48 months, about 54 months, or more).

In some instances, a dosing regimen of the present invention results in a median PFS of a population of subjects having DLBCL (e.g., relapsed and/or refractory DLBCL) of greater than 6.3 months (e.g., at least 6.5 months, at least 6.7 months, at least 7 months, at least 7.3 months, at least 7.5 months, at least 8 months, at least 8.5 months, at least 9.0 months, at least 9.5 months, at least 10 months, at least 11 months, at least 12 months, at least 13 months, at least 14 months, at least 15 months, at least 16 months, at least 17 months, at least 18 months, at least 20 months, at least 24 months, at least 30 months, at least 36 months, at least 42 months, at least 48 months, at least 54 months, or more; e.g., between about 6 months and about 48 months, between about 6 months about 36 months, between about 6 months and about 24 months, between about 6 months and about 12 months, between about 6 months and about 10 months; between about 6 months and about 8 months, between about 8 months and about 24 months, between about 12 months and about 24 months, or between about 8 months and about 16 months; e.g., about 6.3 months, about 6.5 months, about 7 months, about 7.5 months, about 8 months, about 8.5 months, about 9.0 months, about 9.5 months, about 10 months, about 11 months, about 12 months, about 13 months, about 14 months, about 15 months, about 16 months, about 17 months, about 18 months, about 20 months, about 24 months, about 30 months, about 36 months, about 42 months, about 48 months, about 54 months, or more). In some instances, a dosing regimen of the present invention results in a median PFS of a population of subjects having DLBCL (e.g., relapsed and/or refractory DLBCL) of at least 6.7 months. In some instances, a dosing regimen of the present invention results in a median PFS of a population of subjects having DLBCL (e.g., relapsed and/or refractory DLBCL) of at least 7.3 months. In some instances, a dosing regimen of the present invention results in a median PFS of a population of subjects having DLBCL (e.g., relapsed and/or refractory DLBCL) of at least 8.0 months.

In some instances, a dosing regimen of the present invention results in a median overall survival (OS) of a population of subjects of greater than 9.5 months (e.g., at least 10 months, at least 11 months, at least 12 months, at least 13 months, at least 14 months, at least 15 months, at least 16 months, at least 17 months, at least 18 months, at least 20 months, at least 24 months, at least 30 months, at least 36 months, at least 42 months, at least 48 months, at least 54 months, or more; e.g., between about 9 months and about 48 months, between about 9 months about 36 months, between about 9 months and about 24 months, between about 9 months and about 12 months, between about 10 months and about 18 months; between about 12 months and about 24 months, between about 18 months and about 36 months, between about 12 months and about 36 months, or between about 24 months and about 48 months; e.g., about 10 months, about 11 months, about 12 months, about 13 months, about 14 months, about 15 months, about 16 months, about 17 months, about 18 months, about 20 months, about 24 months, about 30 months, about 36 months, about 42 months, about 48 months, about 54 months, or more).

In some instances, a dosing regimen of the present invention results in a median OS of a population of subjects having an FL (e.g., relapsed and/or refractory FL) of greater than 9.5 months (e.g., at least 10 months, at least 11 months, at least 12 months, at least 13 months, at least 14 months, at least 15 months, at least 16 months, at least 17 months, at least 18 months, at least 20 months, at least 24 months, at least 30 months, at least 36 months, at least 42 months, at least 48 months, at least 54 months, or more; e.g., between about 9 months and about 48 months, between about 9 months about 36 months, between about 9 months and about 24 months, between about 9 months and about 12 months, between about 10 months and about 18 months; between about 12 months and about 24 months, between about 18 months and about 36 months, between about 12 months and about 36 months, or between about 24 months and about 48 months; e.g., about 10 months, about 11 months, about 12 months, about 13 months, about 14 months, about 15 months, about 16 months, about 17 months, about 18 months, about 20 months, about 24 months, about 30 months, about 36 months, about 42 months, about 48 months, about 54 months, or more).

In some instances, a dosing regimen of the present invention results in a median OS of a population of subjects having DLBCL (e.g., relapsed and/or refractory DLBCL) of greater than 9.5 months (e.g., at least 10 months, at least 11 months, at least 12 months, at least 13 months, at least 14 months, at least 15 months, at least 16 months, at least 17 months, at least 18 months, at least 20 months, at least 24 months, at least 30 months, at least 36 months, at least 42 months, at least 48 months, at least 54 months, or more; e.g., between about 9 months and about 48 months, between about 9 months about 36 months, between about 9 months and about 24 months, between about 9 months and about 12 months, between about 10 months and about 18 months; between about 12 months and about 24 months, between about 18 months and about 36 months, between about 12 months and about 36 months, or between about 24 months and about 48 months; e.g., about 10 months, about 11 months, about 12 months, about 13 months, about 14 months, about 15 months, about 16 months, about 17 months, about 18 months, about 20 months, about 24 months, about 30 months, about 36 months, about 42 months, about 48 months, about 54 months, or more).

In some instances, a dosing regimen of the present invention results in a median OS of a population of subjects having DLBCL (e.g., relapsed and/or refractory DLBCL) of greater than 12.5 months (e.g., at least 13 months, at least 14 months, at least 14.6 months, at least 15 months, at least 15.8 months, at least 16 months, at least 17 months, at least 17.3 months, at least 18 months, at least 20 months, at least 24 months, at least 30 months, at least 36 months, at least 42 months, at least 48 months, at least 54 months, or more; e.g., between about 13 months and about 48 months, between about 13 months about 36 months, between about 13 months and about 24 months, between about 16 months and about 60 months, between about 24 months and about 36 months; between about 12 months and about 24 months, between about 18 months and about 36 months, between about 24 months and about 36 months, between about 24 months and about 48 months; e.g., about 13 months, about 14 months, about 15 months, about 16 months, about 17 months, about 18 months, about 20 months, about 24 months, about 30 months, about 36 months, about 42 months, about 48 months, about 54 months, or more). In some instances, a dosing regimen of the present invention results in a median OS of a population of subjects having DLBCL (e.g., relapsed and/or refractory DLBCL) of greater than 14.6 months. In some instances, a dosing regimen of the present invention results in a median OS of a population of subjects having DLBCL (e.g., relapsed and/or refractory DLBCL) of greater than 15.8 months. In some instances, a dosing regimen of the present invention results in a median OS of a population of subjects having DLBCL (e.g., relapsed and/or refractory DLBCL) of greater than 17.3 months.

In some instances, a dosing regimen of the present invention results in a complete response (CR) in a population of subjects at a rate of at least about 42% (e.g., at least about 45%, at least about 50%, at least about 55%, at least about 60%, at least about 65%, at least about 70%, at least about 75%, at least about 80%, at least about 85%, at least about 90%, at least about 95%, or more, e.g., from 42% to 45%, from 45% to 50%, from 50% to 55%, from 55% to 60%, from 60% to 65%, from 65% to 70%, from 70% to 75%, or more, e.g., about 42%, about 45%, about 50%, about 55%, about 65%, about 70%, about 75%, about 80%, about 85%, about 90%, about 95%, or more).

In some instances, a dosing regimen of the present invention results in a CR in a population of subjects having a FL (e.g., a relapsed and/or refractory FL) at a rate of at least about 50%. In some instances, a dosing regimen of the present invention results in a CR in a population of subjects having a FL (e.g., a relapsed and/or refractory FL) at a rate of at least about 55% (e.g., at least about 60%, at least about 65%, at least about 70%, at least about 75%, at least about 80%, at least about 85%, at least about 90%, at least about 95%, or more, e.g., from 55% to 60%, from 60% to 65%, from 65% to 70%, from 70% to 75%, or more, e.g., about 42%, about 45%, about 50%, about 55%, about 65%, about 70%, about 75%, about 80%, about 85%, about 90%, about 95%, or more).

In some instances, a dosing regimen of the present invention results in a CR in a population of subjects having a DLBCL (e.g., a relapsed and/or refractory DLBCL) at a rate of at least about 20% (e.g., at least about 20%, at least about 25%, at least about 30%, at least about 35%, at least about 40%). In some instances, a dosing regimen of the present invention results in a CR in a population of subjects having a DLBCL (e.g., a relapsed and/or refractory DLBCL) at a rate of at least about 42% (e.g., at least about 45%, at least about 50%, at least about 55%, at least about 60%, at least about 65%, at least about 70%, at least about 75%, at least about 80%, at least about 85%, at least about 90%, at least about 95%, or more, e.g., from 42% to 45%, from 45% to 50%, from 50% to 55%, from 55% to 60%, from 60% to 65%, from 65% to 70%, from 70% to 75%, or more, e.g., about 42%, about 45%, about 50%, about 55%, about 65%, about 70%, about 75%, about 80%, about 85%, about 90%, about 95%, or more).

In some instances, a dosing regimen of the present invention results in a CR in a population of subjects having a DLBCL (e.g., a relapsed and/or refractory DLBCL) at a rate of at least about 50% (e.g., at least about 50%, at least about 55%, at least about 60%, at least about 65%, at least about 70%, at least about 75%, at least about 80%, at least about 85%, at least about 90%, at least about 95%, or more, e.g., from 50% to 55%, from 55% to 60%, from 60% to 65%, from 65% to 70%, from 70% to 75%, or more, e.g., about 42%, about 45%, about 50%, about 55%, about 65%, about 70%, about 75%, about 80%, about 85%, about 90%, about 95%, or more). In some instances, a dosing regimen of the present invention results in a CR in a population of subjects having a DLBCL (e.g., a relapsed and/or refractory DLBCL) at a rate of at least about 55%. In some instances, a dosing regimen of the present invention results in a CR in a population of subjects having a DLBCL (e.g., a relapsed and/or refractory DLBCL) at a rate of at least about 60%. In some instances, a dosing regimen of the present invention results in a CR in a population of subjects having a DLBCL (e.g., a relapsed and/or refractory DLBCL) at a rate of at least about 65%. In some instances, a dosing regimen of the present invention results in a CR in a population of subjects having a DLBCL (e.g., a relapsed and/or refractory DLBCL) at a rate of at least about 20%.

B. Bispecific Antibodies that Bind to CD20 and CD3

The invention provides bispecific antibodies that bind to CD20 and CD3 (i.e., anti-CD20/anti-CD3 antibodies) useful for treating CD20-positive cell proliferative disorder, e.g., a B cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL or a relapsed or refractory MZL) or a relapsed or refractory CLL).

In some instances, the invention provides a bispecific antibody that includes an anti-CD20 arm having a first binding domain comprising at least one, two, three, four, five, or six hypervariable regions (HVRs) selected from (a) an HVR-H1 comprising the amino acid sequence of GYTFTSYNMH (SEQ ID NO: 1); (b) an HVR-H2 comprising the amino acid sequence of AIYPGNGDTSYN-QKFKG (SEQ ID NO: 2); (c) an HVR-H3 comprising the amino acid sequence of VVYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-1, FR-L2, FR-L3, and FR-L4 comprising the sequences of SEQ ID NOs: 21-24, respectively. In some instances, the bispecific antibody comprises an anti-CD20 arm comprising a first binding domain comprising (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b). Accordingly, in some instances, the first binding domain comprises a VH domain comprising an amino acid sequence of SEQ ID NO: 7 and a VL domain comprising an amino acid sequence of SEQ ID NO: 8.

In some instances, the invention provides a bispecific antibody that includes an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYSNYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, the bispecific antibody comprises an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). Accordingly, in some instances, the second binding domain comprises a VH domain comprising an amino acid sequence of SEQ ID NO: 15 and a VL domain comprising an amino acid sequence of SEQ ID NO: 16.

In some instances, the invention provides a bispecific antibody that includes (1) an anti-CD20 arm having a first binding domain comprising at least one, two, three, four, five, or six HVRs selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6); and (2) an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYSNYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, the anti-CD20/anti-CD3 bispecific antibody comprises (1) at least one (e.g., 1, 2, 3, or 4) of heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively, and (2) at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, the anti-CD20/anti-CD3 bispecific antibody comprises (1) an anti-CD20 arm comprising a first binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b), and (2) an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). In some instances, the anti-CD20/anti-CD3 bispecific antibody comprises (1) a first binding domain comprising a VH domain comprising an amino acid sequence of SEQ ID NO: 7 and a VL domain comprising an amino acid sequence of SEQ ID NO: 8 and (2) a second binding domain comprising a VH domain comprising an amino acid sequence of SEQ ID NO: 15 and a VL domain comprising an amino acid sequence of SEQ ID NO: 16.

In some cases, the antibody is mosunetuzumab, having the International Nonproprietary Names for Pharmaceutical Substances (INN) List 117 (WHO Drug Information, Vol. 31, No. 2, 2017, p. 303), or CAS Registry No. 1905409-39-3. In some embodiments, the anti-CD20/anti-CD3 bispecific antibody comprises (1) an anti-CD20 arm comprising a first binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 51; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 52; or (c) a heavy chain as in (a) and a light chain as in (b), and (2) an anti-CD3 arm comprising a second binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 53; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 54; or (c) a heavy chain as in (a) and a light chain as in (b). In some embodiments, the anti-CD20/anti-CD3 bispecific antibody comprises (1) an anti-CD20 arm comprising a first binding domain comprising a heavy chain comprising an amino acid sequence of SEQ ID NO: 51 and a light chain comprising an amino acid sequence of SEQ ID NO: 52 and (2) an anti-CD3 arm comprising a second binding domain comprising a heavy chain comprising an amino acid sequence of SEQ ID NO: 53 and a light chain comprising an amino acid sequence of SEQ ID NO: 54.

Amino acid sequences of mosunetuzumab are provided in Table 2 below.

TABLE 2

Sequence IDs for mosunetuzumab

Sequence IDs (mosunetuzumab)

| CD3 Arm SEQ ID NO: | Description | CD20 Arm SEQ ID NO: | Description |
|---|---|---|---|
| 9 | CD3 HVR-H1 | 1 | CD20 HVR-H1 |
| 10 | CD3 HVR-H2 | 2 | CD20 HVR-H2 |
| 11 | CD3 HVR-H3 | 3 | CD20 HVR-H3 |
| 12 | CD3 HVR-L1 | 4 | CD20 HVR-L1 |
| 13 | CD3 HVR-L2 | 5 | CD20 HVR-L2 |
| 14 | CD3 HVR-L3 | 6 | CD20 HVR-L3 |
| 15 | CD3 VH | 7 | CD20 VH |
| 16 | CD3 VL | 8 | CD20 VL |
| 53 | CD3 heavy chain | 51 | CD20 heavy chain |
| 54 | CD3 light chain | 52 | CD20 light chain |

The anti-CD20/anti-CD3 bispecific antibody may be produced using recombinant methods and compositions, for example, as described in U.S. Pat. No. 4,816,567.

In some instances, the anti-CD20/anti-CD3 bispecific antibody according to any of the above embodiments described above may incorporate any of the features, singly or in combination, as described in Section C below.

C. Antibody Formats and Properties

The methods described herein may further include any of the antibodies described above, wherein the antibody comprises any of the features, singly or in combination, as described below.

1. Antibody Affinity

In certain instances, an anti-CD20/anti-CD3 bispecific antibody has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one instance, $K_D$ is measured by a radiolabeled antigen binding assay (RIA). In one instance, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µL/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another instance, $K_D$ is measured using a BIACORE® surface plasmon resonance assay. For example, an assay using a BIACORE®-2000 or a BIACORE®-3000 (BIACORE®, Inc., Piscataway, NJ) is performed at 25° C. with immobilized antigen CM5 chips at ~10 response units (RU). In one instance, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at 25° C. at a flow rate of approximately 25 µL/min. Association rates ($k_{on}$) and dissociation rates ($k_{off}$) are calculated using a simple one-to-one Langmuir binding model (BIACORE®Evaluation Software version 3.2) by simultaneously fitting the association and dissociation sensorgrams. The equilibrium dissociation constant ($K_D$) is calculated as the ratio $k_{off}/k_{on}$. See, for example, Chen et al., J. Mol. Biol. 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain instances, an anti-CD20/anti-CD3 bispecific antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al., Nat. Med. 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain instances, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain instances, an anti-CD20/anti-CD3 bispecific antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain instances, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some instances, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Natl Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al., *J. Immunol.* 151:2296 (1993)); framework regions derived from the consensus sequence of human antibodies of a particular subgroup of light or heavy chain variable regions (see, e.g., Carter et al., *Proc. Natl. Acad. Sci. USA,* 89:4285 (1992); and Presta et al., *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain instances, an anti-CD20/anti-CD3 bispecific antibody is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Anti-CD20/anti-CD3 bispecific antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA*

101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

Anti-CD20/anti-CD3 bispecific antibodies or antibody fragments isolated from human antibody libraries are considered human antibodies or human antibody fragments herein.

6. Antibody Variants

In certain instances, amino acid sequence variants of anti-CD20/anti-CD3 bispecific antibodies of the invention are contemplated. As described in detail herein, anti-CD20/anti-CD3 bispecific antibodies may be optimized based on desired structural and functional properties. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain instances, anti-CD20/anti-CD3 bispecific antibody variants having one or more amino acid substitutions are provided. Sites of interest for substitutional mutagenesis include the HVRs and FRs. Conservative substitutions are shown in Table 3 under the heading of "preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 3

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, NJ, (2001).) In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain instances of the variant VH and VL sequences provided above, each HVR either is unaltered, or includes no more than one, two, or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain instances, anti-CD20/anti-CD3 bispecific antibodies of the invention can be altered to increase or decrease the extent to which the antibody is glycosylated. Addition or deletion of glycosylation sites to anti-CD20/anti-CD3 bispecific antibodies of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention are made in order to create antibody variants with certain improved properties.

In one instance, anti-CD20/anti-CD3 bispecific antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., U.S. Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249:533-545 (1986); U.S. Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.,* 94(4):680-688 (2006); and WO 2003/085107).

In view of the above, in some instances, the methods of the invention involve administering to the subject in the context of a fractionated, dose-escalation dosing regimen an anti-CD20/anti-CD3 bispecific antibody variant that comprises an aglycosylation site mutation. In some instances, the aglycosylation site mutation reduces effector function of the antibody. In some instances, the aglycosylation site mutation is a substitution mutation. In some instances, the antibody comprises a substitution mutation in the Fc region that reduces effector function. In some instances, the substitution mutation is at amino acid residue N297, L234, L235, and/or D265 (EU numbering). In some instances, the substitution mutation is selected from the group consisting of N297G, N297A, L234A, L235A, D265A, and P329G. In some instances, the substitution mutation is at amino acid residue N297. In a preferred instance, the substitution mutation is N297A.

In some embodiments the anti-CD20 arm of the anti-CD20/anti-CD3 bispecific antibody further comprises T366W and N297G substitution mutations (EU numbering). In some embodiments, the anti-CD3 arm of the anti-CD20/anti-CD3 bispecific antibody further comprises T366S, L368A, Y407V, and N297G substitution mutations (EU numbering). In some embodiments, (a) the anti-CD20 arm further comprises T366W and N297G substitution mutations and (b) the anti-CD3 arm further comprises T366S, L368A, Y407V, and N297G substitution mutations (EU numbering).

Anti-CD20/anti-CD3 bispecific antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain instances, one or more amino acid modifications are introduced into the Fc region of an anti-CD20/anti-CD3 bispecific antibody of the invention, thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain instances, the invention contemplates an anti-CD20/anti-CD3 bispecific antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al., *Proc. Natl Acad. Sci. USA* 83:7059-7063 (1986)) and Hellstrom, I et al., *Proc. Natl Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood.* 101:1045-1052 (2003); and Cragg, M. S. and M. J. Glennie *Blood.* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain instances, the proline at position 329 of a wild-type human Fc region in the antibody is substituted with glycine or arginine or an amino acid residue large enough to destroy the proline sandwich within the Fc/Fc.gamma receptor interface that is formed between the proline 329 of the Fc and tryptophan residues Trp 87 and Trp 110 of FcγRIII (Sondermann et al.: *Nature* 406, 267-273 (20 Jul. 2000)). In certain instances, the antibody comprises at least one further amino acid substitution. In one instance, the further amino acid substitution is S228P, E233P, L234A, L235A, L235E, N297A, N297D, or P331S, and still in another instance the at least one further amino acid substitution is L234A and L235A of the human IgG1 Fc region or S228P and L235E of the human IgG4 Fc region (see e.g., US 2012/0251531), and still in another instance the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain instance, an antibody variant comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US 2005/0014934 A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some aspects, the anti-CD20/anti-CD3 bispecific antibody comprises an Fc region comprising an N297G mutation (EU numbering).

In some instances, the anti-CD20/anti-CD3 bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some instances, the $CH3_1$ and $CH3_2$ domains meet at an interface between said protuberance and cavity. In some instances, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In other instances, the $CH2_1$ and $CH2_2$ domains meet at an interface between said protuberance and cavity. In some instances, the anti-CD20/anti-CD3 bispecific antibody is an IgG1 antibody.

d. Cysteine Engineered Antibody Variants

In certain instances, it is desirable to create cysteine engineered anti-CD20/anti-CD3 bispecific antibodies, e.g., "thioMAbs," in which one or more residues of an antibody are substituted with cysteine residues. In particular instances, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain instances, any one or more of the following residues are substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521, 541.

e. Antibody Derivatives

In certain instances, an anti-CD20/anti-CD3 bispecific antibody provided herein is further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and non-proteinaceous moiety that may be selectively heated by exposure to radiation are provided. In one instance, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

7. Recombinant Production Methods

Anti-CD20/anti-CD3 bispecific antibodies of the invention may be produced using recombinant methods and compositions, for example, as described in U.S. Pat. No. 4,816,567, which is incorporated herein by reference in its entirety.

For recombinant production of an anti-CD20/anti-CD3 bispecific antibody, nucleic acid encoding an antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

8. Immunoconjugates

The invention also provides immunoconjugates comprising an anti-CD20/anti-CD3 bispecific antibody of the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some instances, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises an anti-CD20/anti-CD3 bispecific antibody conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another instance, an immunoconjugate comprises an anti-CD20/anti-CD3 bispecific antibody conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$I, $^{212}$Pb and radioactive isotopes of Lu. When the radioconjugate is used for detection, it may comprise a radioactive atom for scintigraphic studies, for example $^{99m}$Tc or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker, or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

D. Additional Therapeutic Agents

In some instances, the methods described herein include administering the bispecific anti-CD20/anti-CD3 antibody in combination with an additional therapeutic agent (e.g., an antibody-drug conjugate (ADC) and/or a further chemotherapy agent and/or). In some instances, the bispecific anti-CD20/anti-CD3 antibody is co-administered with one or more additional chemotherapy agents selected from cyclophosphamide, doxorubicin, rituximab, and prednisolone. In some instances, the bispecific anti-CD20/anti-CD3 antibody is co-administered with CHOP, wherein vincristine is replaced with an ADC. In some instances, the bispecific anti-CD20/anti-CD3 antibody is co-administered with an anti-CD19 antibody drug conjugate, an anti-CD22 antibody drug conjugate, an anti-CD45 antibody drug conjugate, or an anti-CD32 antibody drug conjugate.

In some instances, the additional therapeutic agent is an anti-CD79b ADC, e.g., any of the anti-CD79b antibody drug conjugates described in U.S. Pat. No. 8,088,378, which is incorporated herein by reference in its entirety. In some instances, the anti-CD79b antibody drug conjugate includes an anti-CD79b binding domain comprising at least one, two, three, four, five, or six hypervariable regions (HVRs) selected from (a) an HVR-H1 comprising the amino acid sequence of SEQ ID NO: 33; (b) an HVR-H2 comprising the amino acid sequence of SEQ ID NO: 34; (c) an HVR-H3 comprising the amino acid sequence of SEQ ID NO:35; (d) an HVR-L1 comprising the amino acid sequence of SEQ ID NO: 36; (e) an HVR-L2 comprising the amino acid sequence of SEQ ID NO: 37; and (f) an HVR-L3 comprising the amino acid sequence of SEQ ID NO: 38. In some instances, the anti-CD79b antibody drug conjugate includes an anti-79b binding domain comprising all six of the following HVRs: (a) an HVR-H1 comprising the amino acid sequence of SEQ ID NO: 33; (b) an HVR-H2 comprising the amino acid sequence of SEQ ID NO: 34; (c) an HVR-H3 comprising the amino acid sequence of SEQ ID NO: 35; (d) an HVR-L1 comprising the amino acid sequence of SEQ ID NO: 36; (e) an HVR-L2 comprising the amino acid sequence of SEQ ID NO: 37; and (f) an HVR-L3 comprising the amino acid sequence of SEQ ID NO: 38. In some instances, the anti-CD79b antibody drug conjugate comprises at least one (e.g., 1, 2, 3, or 4) of heavy chain framework regions FR-H1, FR-H2, FR-H3, and FR-H4 comprising the sequences of SEQ ID NOs: 39-42, respectively, and/or at least one (e.g., 1, 2, 3, or 4) of the light chain framework regions FR-L1, FR-L2, FR-L3, and FR-L4 comprising the sequences of SEQ ID NOs: 43-46, respectively. In some instances, the anti-CD79b antibody drug conjugate comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 47; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 48; or (c) a VH domain as in (a) and a VL domain as in (b). Accordingly, in some instances, the first binding domain comprises a VH domain comprising an amino acid sequence of SEQ ID NO: 47 and a VL domain comprising an amino acid sequence of SEQ ID NO: 48.

In some instances, the anti-CD79b antibody is linked to a toxin such as monomethyl auristatin E (MMAE, i.e., vedotin). In some instances, the anti-CD79b antibody drug conjugate is polatuzumab vedotin (immunoglobulin G1-kappa auristatin E conjugate, anti-[Homo sapiens CD79B (immunoglobulin-associated CD79 beta)], humanized monoclonal antibody conjugated to auristatin E; gamma1 heavy chain (1-447) [humanized VH (Homo sapiens IGHV3-23*04 (76.50%)-(IGHD)-IGHJ4*01) [8.8.10](1-117)-Homo sapiens IGHG1*03 (CH1 R120>K (214)(118-215), hinge (216-230), CH2 (231-340), CH3 (341-445), CHS (446-447)) (118-447)], (220-218')-disulfide with kappa light chain (1'-218') [humanized V-KAPPA (Homo sapiens IGKV1-39*01 (85.90%)-IGKJ1*01) [10.3.9](1'-111')-Homo sapiens IGKC*01 (112'-218')]; dimer (226-226":229-229")-bisdisulfide; conjugated, on an average of 3 to 4 cysteinyl, to monomethylauristatin E (MMAE), via a cleavable maleimidocaproyl-valyl-citrullinyl-p-aminobenzyloxycarbonyl (mc-val-cit-PABC) type linker; also known as RG-7596, or RO5541077-000)), as defined by International Nonproprietary Names for Pharmaceutical Substances (INN) List 110 (WHO Drug Information, Vol. 27, No. 4, 2016, p. 443). Polatuzumab vedotin is also referred to as IUPHAR/BPS Number 8404, the KEGG Number D10761, or the CAS Registry Number 1313206-42-6. Polatuzumab vedotin-piiq is also interchangeably referred to as "polatuzumab vedotin-piiq," "huMA79bv28-MC-vc-PAB-MMAE," or "DCDS4501A." In some instances, the anti-CD79b antibody or anti-CD79b ADC includes the heavy chain sequence of SEQ ID NO: 49 and the light chain sequence of SEQ ID NO: 50.

In some instances, the additional therapeutic agent is a biological modifier. In one instance, the bispecific anti-CD20/anti-CD3 antibody is co-administered with one or more biological modifiers selected from a BCL-2 inhibitor (such as GDC-0199/ABT-199), lenalidomide (REVLIMID®), a PI3K-delta inhibitor (such as idelalisib (ZYDELIG®)), a PI3K inhibitor (such as alpelisib, copanlisib, or duvelisib), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some of the methods described herein, the dosing regimen may include administration of one or more additional therapeutic agents. For example, in a particular instance, the bispecific anti-CD20/anti-CD3 antibody can be co-administered with obinutuzumab (GAZYVA®) or tocilizumab (ACTEMRA®/RoACTEMRA®), wherein the subject is first administered with obinutuzumab (GAZYVA®) or tocilizumab (ACTEMRA®/RoACTEMRA®) and then separately administered with the bispecific anti-CD20/anti-CD3 antibody (e.g., the subject is pre-treated with obinutuzumab (GAZYVA®) or tocilizumab (ACTEMRA®/RoACTEMRA®)). In some instances, administration of tocilizumab as an additional therapeutic agent is to reduce the effects of certain adverse effects associated with CRS. In some instances, the subject is pre-treated with tocilizumab as a prophylactic approach against CRS. In some instances, the prophylactic treatment against CRS includes administration of tocilizumab and/or adalimumab.

In some instances, the PD-1 binding antagonist is an anti-PD-1 antibody. A variety of anti-PD-1 antibodies can be utilized in the methods and uses disclosed herein. In any of the instances herein, the PD-1 antibody can bind to a human PD-1 or a variant thereof. In some instances the anti-PD-1 antibody is a monoclonal antibody. In some instances, the anti-PD-1 antibody is an antibody fragment selected from the group consisting of Fab, Fab', Fab'-SH, Fv, scFv, and (Fab')2 fragments. In some instances, the anti-PD-1 antibody is a humanized antibody. In other instances, the anti-PD-1 antibody is a human antibody. Exemplary anti-PD-1 antagonist antibodies include nivolumab, pembrolizumab, MEDI-0680, PDR001 (spartalizumab), REGN2810 (cemiplimab), BGB-108, prolgolimab, camrelizumab, sintilimab, tislelizumab, toripalimab, dostarlimab, retifanlimab, sasanlimab, penpulimab, CS1003, HLX10, SCT-I10A, zimberelimab, balstilimab, genolimzumab, BI 754091, cetrelimab, YBL-006, BAT1306, HX008, budigalimab, CX-188, JTX-4014, 609A, Sym021, LZM009, F520, SG001, AM0001, ENUM 244C8, ENUM 388D4, STI-1110, AK-103, and hAb21. In some instances, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO 2006/121168. In some instances, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA®, is an anti-PD-1 antibody described in WO 2009/114335. In some instances, the anti-PD-1 antibody is MEDI-0680 (AMP-514; AstraZeneca). MEDI-0680 is a humanized IgG4 anti-PD-1 antibody. In some instances, the anti-PD-1 antibody is PDR001 (CAS Registry No. 1859072-53-9; Novartis). PDR001 is a humanized IgG4 anti-PD-1 antibody that blocks the binding of PD-L1 and PD-L2 to PD-1. In some instances, the anti-PD-1 antibody is REGN2810 (Regeneron). REGN2810 is a human anti-PD-1 antibody. In some instances, the anti-PD-1 antibody is BGB-108 (BeiGene). In some instances, the anti-PD-1 antibody is BGB-A317 (BeiGene). In some instances, the anti-PD-1 antibody is JS-001 (Shanghai Junshi). JS-001 is a humanized anti-PD-1 antibody. In some instances, the anti-PD-1 antibody is STI-A1110 (Sorrento). STI-A1110 is a human anti-PD-1 antibody. In some instances, the anti-PD-1 antibody is INCSHR-1210 (Incyte). INCSHR-1210 is a human IgG4 anti-PD-1 antibody. In some instances, the anti-PD-1 antibody is PF-06801591 (Pfizer). In some instances, the anti-PD-1 antibody is TSR-042 (also known as ANB011; Tesaro/AnaptysBio). In some instances, the anti-PD-1 antibody is AM0001 (ARMO Biosciences). In some instances, the anti-PD-1 antibody is ENUM 244C8 (Enumeral Biomedical Holdings). ENUM 244C8 is an anti-PD-1 antibody that inhibits PD-1 function without blocking binding of PD-L1 to PD-1. In some instances, the anti-PD-1 antibody is ENUM 388D4 (Enumeral Biomedical Holdings). ENUM 388D4 is an anti-PD-1 antibody that competitively inhibits binding of PD-L1 to PD-1. In some instances, the anti-PD-1 antibody comprises the six HVR sequences (e.g., the three heavy chain HVRs and the three light chain HVRs) and/or the heavy chain variable domain and light chain variable domain from an anti-PD-1 antibody described in WO 2015/112800, WO 2015/112805, WO 2015/112900, US 20150210769, WO2016/089873, WO 2015/035606, WO 2015/085847, WO 2014/206107, WO 2012/145493, U.S. Pat. No. 9,205,148, WO 2015/119930, WO 2015/119923, WO 2016/032927, WO 2014/179664, WO 2016/106160, and WO 2014/194302.

In other instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In other instances, the PD-1 binding antagonist is AMP-224. AMP-224, also known as B7-DCIg, is a PD-L2-Fc fusion soluble receptor described in PCT Pub. Nos. WO 2010/027827 and WO 2011/066342.

In some instances, the PD-L1 binding antagonist is an anti-PD-L1 antibody. A variety of anti-PD-L1 antibodies are contemplated and described herein. In any of the instances herein, the isolated anti-PD-L1 antibody can bind to a human PD-L1, for example a human PD-L1 as shown in UniProtKB/Swiss-Prot Accession No. Q9NZQ7-1, or a variant thereof. In some instances, the anti-PD-L1 antibody is capable of inhibiting binding between PD-L1 and PD-1 and/or between PD-L1 and B7-1. In some instances, the anti-PD-L1 antibody is a monoclonal antibody. In some instances, the anti-PD-L1 antibody is an antibody fragment selected from the group consisting of Fab, Fab'-SH, Fv, scFv, and (Fab')2 fragments. In some instances, the anti-PD-L1 antibody is a humanized antibody. In some instances, the anti-PD-L1 antibody is a human antibody. Exemplary anti-PD-L1 antibodies include atezolizumab, MDX-1105, MEDI4736 (durvalumab), MSB0010718C (avelumab), SHR-1316, CS1001, envafolimab, TQB2450, ZKAB001, LP-002, CX-072, IMC-001, KL-A167, APL-502, cosibelimab, lodapolimab, FAZ053, TG-1501, BGB-A333, BCD-135, AK-106, LDP, GR1405, HLX20, MSB2311, RC98, PDL-GEX, KD036, KY1003, YBL-007, HS-636, LY3300054 (Eli Lilly), STI-A1014 (Sorrento), and KN035 (Suzhou Alphamab). In some instances, the anti-PD-L1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some instances, the anti-PD-L1 antibody is CX-072 (CytomX Therapeutics). In some instances, the anti-PD-L1 antibody comprises the six HVR sequences (e.g., the three heavy chain HVRs and the three light chain HVRs) and/or the heavy chain variable domain and light chain variable domain from an anti-PD-L1 antibody described in US 20160108123, WO 2016/000619, WO 2012/145493, U.S. Pat. No. 9,205,148, WO 2013/181634, or WO 2016/061142. Examples of anti-PD-L1 antibodies useful in the methods of this invention and methods of making them are described in International Patent Application Publication No. WO 2010/077634 and U.S. Pat. No. 8,217,149, each of which is incorporated herein by reference in its entirety.

In other instances, the PD-L2 binding antagonist is an anti-PD-L2 antibody (e.g., a human, a humanized, or a chimeric anti-PD-L2 antibody). In some instances, the PD-L2 binding antagonist is an immunoadhesin.

An effective amount of a PD-1 axis binding antagonist (e.g., anti-PD-L1 antagonist antibody (e.g., atezolizumab)) is a fixed dose of between about 80 mg to about 2000 mg (e.g., between about 100 mg to about 1600 mg, e.g., between about 200 mg to about 1600 mg, e.g., between about 300 mg to about 1600 mg, e.g., between about 400 mg to about 1600 mg, e.g., between about 500 mg to about 1600 mg, e.g., between about 600 mg to about 1600 mg, e.g., between about 700 mg to about 1600 mg, e.g., between about 800 mg to about 1600 mg, e.g., between about 900 mg to about 1500 mg, e.g., between about 1000 mg to about 1400 mg, e.g., between about 1050 mg to about 1350 mg, e.g., between about 1100 mg to about 1300 mg, e.g., between about 1150 mg to about 1250 mg, e.g., between about 1175 mg to about 1225 mg, e.g., between about 1190 mg to about 1210 mg, e.g., 1200 mg±5 mg, e.g., 1200±2.5 mg, e.g., 1200±1.0 mg, e.g., 1200±0.5 mg, e.g., 1200 mg) every three weeks (Q3W). In some instances, the effective amount of the PD-1 axis binding antagonist (e.g., anti-PD-L1 antagonist antibody (e.g., atezolizumab)) is a fixed dose of about 1200 mg every three weeks (e.g., 1200 mg±10 mg, e.g., 1200±6 mg, e.g., 1200±5 mg, e.g., 1200±3 mg, e.g., 1200±1 mg, e.g., 1200±0.5 mg, e.g., 1200 mg every three weeks). In some instances, the PD-1 axis binding antagonist (e.g., anti-PD-L1 antagonist antibody (e.g., atezolizumab)) is administered at a dose of about 200 mg to about 1400 mg every three weeks (e.g., at a dose of about 200 mg to about 1200 mg every three weeks, e.g., about 200 mg to about 1000 mg every three weeks, e.g., about 200 mg to about 800 mg every three weeks, e.g., about 200 mg to about 600 mg every three weeks, e.g., about 200 mg to about 500 mg every three weeks, e.g., about 200 mg to about 450 mg every three weeks, e.g., about 250 mg to about 450 mg every three weeks).

In some instances, the bispecific anti-CD20/anti-CD3 antibody is co-administered with rituximab and one or more chemotherapy agents. In one instance, the bispecific anti-CD20/anti-CD3 antibody is co-administered with rituximab and CHOP. In one instance, the bispecific anti-CD20/anti-CD3 antibody is co-administered with rituximab and an ADC. In one instance, the bispecific anti-CD20/anti-CD3 antibody is co-administered with rituximab and CHOP, wherein vincristine is replaced with an ADC. In one instance, the bispecific anti-CD20/anti-CD3 antibody is co-administered with an ADC selected from an anti-CD19 antibody drug conjugate, an anti-CD22 antibody drug conjugate, an anti-CD45 antibody drug conjugate, and an anti-CD32 drug conjugate.

In some instances, the bispecific anti-CD20/anti-CD3 antibody is co-administered with rituximab and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PI3K inhibitor (such as alpelisib, copanlisib, or duvelisib), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody is co-administered with rituximab, one or more chemotherapy agents, and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PD-1 axis binding antagonist tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody is co-administered with obinutuzumab and one or more chemotherapy agents. In one instance, the bispecific anti-CD20/anti-CD3 antibody is co-administered with obinutuzumab and CHOP. In one instance, the bispecific anti-CD20/anti-CD3 antibody is co-administered with obinutuzumab and an ADC. In one instance, the bispecific anti-CD20/anti-CD3 antibody is co-administered with obinutuzumab and CHOP, wherein vincristine is replaced with an ADC. In one instance, the bispecific anti-CD20/anti-CD3 antibody is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate. In one instance, the bispecific anti-CD20/anti-CD3 antibody is co-administered with obinutuzumab and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PI3K inhibitor (such as alpelisib, copanlisib, or duvelisib), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances the bispecific anti-CD20/anti-CD3 antibody is co-administered with obinutuzumab and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PI3K inhibitor (such as alpelisib, copanlisib, or duvelisib), a PD-1 axis binding antagonist, tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the additional therapy includes an alkylating agent. In one instance, the alkylating agent is 4-[5-[bis(2-chloroethyl)amino]-1-methylbenzimidazol-2-yl]butanoic acid and salts thereof. In one instance, the alkylating agent is bendamustine.

In some instances, the additional therapy comprises a BCL-2 inhibitor. In one embodiment, the BCL-2 inhibitor is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide and salts thereof. In one instance, the BCL-2 inhibitor is venetoclax (CAS #: 1257044-40-8).

In some instances, the additional therapy comprises a phosphoinositide 3-kinase (PI3K) inhibitor. In one instance, the PI3K inhibitor inhibits delta isoform PI3K (i.e., P1106). In some instances, the PI3K inhibitor is 5-Fluoro-3-phenyl-2-[(1 S)-1-(7H-purin-6-ylamino)propyl]-4(3H)-quinazolinone and salts thereof. In some instances, the PI3K inhibitor is idelalisib (CAS #: 870281-82-6). In one instance, the PI3K inhibitor inhibits alpha and delta isoforms of PI3K. In some instances, the PI3K inhibitor is 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide and salts thereof. In some instance, the PI3K inhibitor is taselisib (CAS #: 1282512-48-4). In some instances, the PI3K inhibitor is 2-amino-N-[2,3-dihydro-7-methoxy-8-[3-(4-morpholinyl)propoxy]imidazo[1,2-c]quinazolin-5-yl]-5-pyrimidinecarboxamide and salts thereof. In some instance, the PI3K inhibitor is copanlisib (CAS #: 1032568-63-0). In some instances, the PI3K inhibitor is 8-chloro-2-phenyl-3-[(1S)-1-(9H-purin-6-ylamino)ethyl]-1(2H)-isoquinolinone and salts thereof. In some instance, the PI3K inhibitor is duvelisib (CAS #: 1201438-56-3). In some instances, the PI3K inhibitor is (2S)—N1-[4-methyl-5-[2-(2,2,2-trifluoro-1,1-dimethylethyl)-4-pyridinyl]-2-thiazolyl]-1,2-pyrrolidinedicarboxamide and salts thereof. In some instance, the PI3K inhibitor is alpelisib (CAS #: 1217486-61-7). In some instances, the PI3K inhibitor is 2-[(1S)-1-[4-amino-3-[3-fluoro-4-(1-methylethoxy)phenyl]-1H-pyrazolo[3,4-d]pyrimidin-1-yl]ethyl]-6-fluoro-3-(3-fluorophenyl)-4H-1-benzopyran-4-one and salts thereof. In some instance, the PI3K inhibitor is umbralisib (CAS #: 1532533-67-7).

In a further aspect of the invention, the additional therapy comprises a Bruton's tyrosine kinase (BTK) inhibitor. In one instance, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one and salts thereof. In one instance, the BTK inhibitor is ibrutinib (CAS #: 936563-96-1). In some instances, the BTK inhibitor is (7S)-4,5,6,7-tetrahydro-7-[1-(1-oxo-2-propen-1-yl)-4-piperidinyl]-2-(4-phenoxyphenyl)-pyrazolo[1,5-a]pyrimidine-3-carboxamide and salts thereof. In some instances, the BTK inhibitor is zanubrutimib (CAS #: 1691249-45-2). In some instances, the BTK inhibitor is 4-[8-amino-3-[(2S)-1-(1-oxo-2-butyn-1-yl)-2-pyrrolidinyl]imidazo[1,5-a]pyrazin-1-yl]-N-2-pyridinyl-benzamide and salts thereof. In some instances, the BTK inhibitor is acalabrutinib (CAS #: 1420477-60-6).

In some instances, the additional therapy comprises thalidomide or a derivative thereof. In one instance, the thalidomide or a derivative thereof is (RS)-3-(4-Amino-1-oxo-1,3-dihydro-2H-isoindol-2-yl)piperidine-2,6-dione and salts thereof. In one instance, the thalidomide or a derivative thereof is lendalidomide (CAS #: 191732-72-6).

In instances for which the methods described herein involve a combination therapy, such as a particular combination therapy noted above, the combination therapy encompasses the administration of the bispecific anti-CD20/anti-CD3 antibody with one or more additional therapeutic agents, and such co-administration may be combined administration (where two or more therapeutic agents are included in the same or separate formulations) or separate administration, in which case, the administration of the anti-CD20/anti-CD3 bispecific antibody can occur prior to, simultaneously, and/or following, administration of the additional therapeutic agent or agents. In one embodiment, the administration of the anti-CD20/anti-CD3 bispecific antibody administration of an additional therapeutic agent or exposure to radiotherapy can occur within about one month, or within about one, two or three weeks, or within about one, two, three, four, five, or six days, of each other. In a particular instance, the bispecific anti-CD20/anti-CD3 antibody can be co-administered with obinutuzumab (GAZYVA®), wherein the subject is first administered with obinutuzumab (GAZYVA®) and then separately administered with the bispecific anti-CD20/anti-CD3 antibody (e.g., the subject is pre-treated with obinutuzumab (GAZYVA®)). In another particular instance, the bispecific anti-CD20/anti-CD3 antibody and the anti-CD79b ADC can be co-administered with tocilizumab (ACTEMRA®/RoACTEMRA®), wherein the subject is first administered with tocilizumab (ACTEMRA®/RoACTEMRA®) and then separately administered with the bispecific anti-CD20/anti-CD3 antibody (e.g., the subject is pre-treated with tocilizumab (ACTEMRA®/RoACTEMRA®)). In some instances, administration of tocilizumab as an additional therapeutic agent is to reduce the effects of certain adverse effects associated with CRS. In some instances, the subject is pre-treated with tocilizumab as a prophylactic approach against CRS. In some instances, the prophylactic treatment against CRS includes administration of tocilizumab and/or adalimumab.

The methods described herein may result in an improved benefit-risk profile for subjects having a CD20-positive cell proliferative disorder, e.g., a B cell proliferative disorder (e.g., a relapsed or refractory B cell proliferative disorder), e.g., a non-Hodgkin's lymphoma (NHL; e.g., a diffuse large B cell lymphoma (DLBCL; e.g., a Richter's Transformation), a follicular lymphoma (FL; e.g., a Grade 1 FL, a Grade 2 FL, a Grade 3 FL (e.g., a Grade 3a FL or Grade 3b FL), or a transformed FL), a mantle cell lymphoma (MCL), or a marginal zone lymphoma (MZL)) or a chronic lymphoid leukemia (CLL), e.g., a relapsed or refractory NHL (e.g., a relapsed or refractory DLBCL, a relapsed or refractory FL, a relapsed or refractory MCL, or a relapsed or refractory MZL) or a relapsed or refractory CLL being treated with an anti-CD20/anti-CD3 bispecific antibody. In some instances, treatment using the methods described herein that result in administering the anti-CD20/anti-CD3 bispecific antibody in the context of a fractionated, dose-escalation dosing regimen results in a reduction (e.g., by 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater; e.g., between 20% and 100%, between 20% and 90%, between 20% and 80%, between 20% and 70%, between 20% and 60%, between 20% and 50%, between 20% and 40%, between 20% and 30%, between 40% and 100%, between 60% and 100%, between 80% and 100%, between 30% and 70%, between 40% and 60%, between 30% and 50%, between 50% and 80%, or between 90% and 100%; e.g., about 20%, about 25%, about 30%, about 35%, about 40%, about 45%, about 50%, about 55%, about 60%, about 65%, about 70%, about 75%, about 80%, about 85%, about 90%, about 95%, about 97%, about 99%, or about 100%) or complete inhibition (100% reduction) of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or hepatotoxicities, following treatment with an anti-CD20/anti-CD3 bispecific antibody using the fractionated, dose-escalation dosing regimen of the invention relative to treatment with an anti-CD20/anti-CD3 bispecific antibody using an non-fractioned dosing regimen.

For all the methods described herein, the anti-CD20/anti-CD3 bispecific antibody is formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The anti-CD20/anti-CD3 bispecific antibody need not be, but is optionally formulated with, one or more agents currently used to prevent or treat the disorder in question. The effective amount of such other agents depends on the amount of the anti-CD20/anti-CD3 bispecific antibody present in the formulation, the type of disorder or treatment, and other factors discussed above. The anti-CD20/anti-CD3 bispecific antibody may be suitably administered to the subject over a series of treatments.

In some instances, additional therapeutic agents useful in the present invention include therapeutic antibodies, such as alemtuzumab (CAMPATH®), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), and tositumomab (BEXXAR®, Corixia). Additional humanized monoclonal antibodies with therapeutic potential as agents in combination with the compounds of the invention include: apolizumab, aselizumab, atlizumab, bapineuzumab, bivatuzumab mertansine, briakinumab, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, tafasitamab, talizumab, tefibazumab, tocilizumab, toralizumab, tucotuzumab celmoleukin, tucusituzumab, umavizumab, urtoxazumab, ustekinumab, and visilizumab.

IV. Pharmaceutical Compositions and Formulations

Any of the antibodies (e.g., anti-CD20/anti-CD3 bispecific antibodies) described herein can be used in pharmaceutical compositions and formulations. Pharmaceutical compositions and formulations of antibodies and/or other agents describe herein can be prepared by mixing one, two, or all three agents having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

V. Kits and Articles of Manufacture

In another aspect of the invention, a kit or an article of manufacture containing materials useful for the treatment, prevention, and/or diagnosis of the disorders described above is provided.

The kit or article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be a vial having a stopper pierceable by a hypodermic injection needle). At least one active agent in the composition is an anti-CD20/anti-CD3 bispecific antibody described herein. The label or package insert indicates that the composition is used for treating the condition of choice (e.g., a B cell proliferation disorder, e.g., non-Hodgkin's lymphoma (NHL), e.g., diffuse large B cell lymphoma (DLBCL), e.g., relapsed or refractory DLBCL) and further includes information related to at least one of the dosing regimens described herein. Moreover, the kit or article of manufacture may comprise (a) a first container with a composition contained therein, wherein the composition comprises an anti-CD20/anti-CD3 bispecific antibody described herein; and (b) a second container with a composition contained therein, wherein the composition comprises a further cytotoxic or otherwise therapeutic agent. Alternatively, or additionally, the kit or article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

VI. Embodiments

Some embodiments of the technology described herein can be defined according to any of the following numbered embodiments:

1. A method of treating a subject having a CD20-positive cell proliferative disorder comprising administering to the subject a bispecific antibody that binds to CD20 and CD3 in a dosing regimen comprising at least a first dosing cycle and a second dosing cycle, wherein:
   (a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 50 mg; and
   (b) the second dosing cycle comprises a single dose (C2D1) of the bispecific antibody.

2. A bispecific antibody that binds to CD20 and CD3 for use in treating a subject having a CD20-positive cell proliferative disorder, wherein the bispecific antibody is formulated for administration to the subject in a dosing regimen comprising at least a first dosing cycle and a second dosing cycle, wherein:
   (a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 50 mg; and
   (b) the second dosing cycle comprises a single dose (C2D1) of the bispecific antibody.

3. Use of a bispecific antibody that binds to CD20 and CD3 in treating a subject having a CD20-positive cell proliferative disorder, wherein the bispecific antibody is formulated for administration to the subject in a dosing regimen comprising at least a first dosing cycle and a second dosing cycle, wherein:
  (a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 50 mg; and
  (b) the second dosing cycle comprises a single dose (C2D1) of the bispecific antibody.

4. Use of a bispecific antibody that binds to CD20 and CD3 in the manufacture of a medicament treating a subject having a CD20-positive cell proliferative disorder, wherein the bispecific antibody is formulated for administration to the subject in a dosing regimen comprising at least a first dosing cycle and a second dosing cycle, wherein:
  (a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 50 mg; and
  (b) the second dosing cycle comprises a single dose (C2D1) of the bispecific antibody.

5. The method, bispecific antibody for use, or use of any one of embodiments 1-4, wherein the C1D3 is from 50 mg to 200 mg.

6. The method, bispecific antibody for use, or use of embodiment 5, wherein the C1D3 is about 60 mg.

7. The method, bispecific antibody for use, or use of any one of embodiments 1-6, wherein the C1D1 is about 1 mg.

8. The method, bispecific antibody for use, or use of any one of embodiments 1-7, wherein the C1D2 is about 2 mg.

9. The method, bispecific antibody for use, or use of any one of embodiments 1-8, wherein the C2D1 is about equivalent in amount to the C1D3.

10. The method, bispecific antibody for use, or use of any one of embodiments 1-9, wherein the C1D1, the C1D2, and the C1D3 are administered or are to be administered to the subject on or about Days 1, 8, and 15, respectively, of the first dosing cycle.

11. The method, bispecific antibody for use, or use of any one of embodiments 1-10, wherein the C2D1 is administered or is to be administered to the subject on Day 1 of the second dosing cycle.

12. The method, bispecific antibody for use, or use of any one of embodiments 1-11, wherein the first and second dosing cycles are 21-day dosing cycles.

13. The method, bispecific antibody for use, or use of any one of embodiments 1-12, wherein the first dosing cycle is a 21-day dosing cycle and the second dosing cycle is a 28-day dosing cycle.

14. The method, bispecific antibody for use, or use of any one of embodiments 1-13, wherein the dosing regimen further comprises one or more additional dosing cycles beyond the second dosing cycle.

15. The method, bispecific antibody for use, or use of embodiment 14, wherein the dosing regimen comprises from six to 15 additional dosing cycles beyond the second dosing cycle.

16. The method, bispecific antibody for use, or use of embodiment 14 or 15, wherein the additional dosing cycles are 21-day dosing cycles.

17. The method, bispecific antibody for use, or use of embodiment 15 or 16, wherein the additional dosing cycles are 28-day dosing cycles.

18. The method, bispecific antibody for use, or use of any one of embodiments 14-17, wherein one or more of the additional dosing cycles comprise an additional single dose of the bispecific antibody.

19. The method, bispecific antibody for use, or use of embodiment 18, wherein the additional single dose of the bispecific antibody is administered or is to be administered to the subject on Day 1 of each additional dosing cycle.

20. The method, bispecific antibody for use, or use of embodiment 18 or 19, wherein the additional single dose of the bispecific antibody is greater than the C1D1 and less than the C1D3 and/or the C2D1.

21. The method, bispecific antibody for use, or use of any one of embodiments 18-20, wherein the additional single dose of the bispecific antibody is from 20% to 80% of the C1D3 and/or the C2D1.

22. The method, bispecific antibody for use, or use of embodiment 21, wherein the additional single dose of the bispecific antibody is about 50% of the C1D3 and/or the C2D1.

23. The method, bispecific antibody for use, or use of any one of embodiments 18-22, wherein the additional single dose of the bispecific antibody is about 30 mg.

24. A method of treating a subject having a CD20-positive cell proliferative disorder comprising administering to the subject a bispecific antibody that binds to CD20 and CD3 in a dosing regimen comprising at least a first dosing cycle, a second dosing cycle, and a third dosing cycle, wherein:
  (a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
  (b) the second dosing cycle comprises a single dose (C2D1) of the bispecific antibody, wherein the C2D1 is about equivalent in amount to the C1D3; and
  (c) the third dosing cycle comprises a single dose (C3D1) of the bispecific antibody, wherein the C3D1 is greater than the C1D1 and less than the C2D1.

25. A bispecific antibody that binds to CD20 and CD3 for use in treating a subject having a CD20-positive cell proliferative disorder, wherein the bispecific antibody is formulated for administration to the subject in a dosing regimen comprising at least a first dosing cycle, a second dosing cycle, and a third dosing cycle, wherein:
  (a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
  (b) the second dosing cycle comprises a single dose (C2D1) of the bispecific antibody, wherein the C2D1 is about equivalent in amount to the C1D3; and
  (c) the third dosing cycle comprises a single dose (C3D1) of the bispecific antibody, wherein the C3D1 is greater than the C1D1 and less than the C2D1.

26. Use of a bispecific antibody that binds to CD20 and CD3 in treating a subject having a CD20-positive cell proliferative disorder, wherein the bispecific antibody is formulated for administration to the subject in a dosing regimen comprising at least a first dosing cycle, a second dosing cycle, and a third dosing cycle, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3; and (c) the third dosing cycle comprises a single dose (C3D1) of the bispecific antibody, wherein the C3D1 is greater than the C1D1 and less than the C2D1.

27. Use of a bispecific antibody that binds to CD20 and CD3 in the manufacture of a medicament treating a subject having a CD20-positive cell proliferative disorder, wherein the bispecific antibody is formulated for administration to the subject in a dosing regimen comprising at least a first dosing cycle, a second dosing cycle, and a third dosing cycle, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3; and (c) the third dosing cycle comprises a single dose (C3D1) of the bispecific antibody, wherein the C3D1 is greater than the C1D1 and less than the C2D1.

28. The method, bispecific antibody for use, or use of any one of embodiments 24-27, wherein the C1D3 and the C2D1 are each from 20 mg to 200 mg.

29. The method, bispecific antibody for use, or use of embodiment 28 wherein the C1D3 and the C2D1 are each about 60 mg.

30. The method, bispecific antibody for use, or use of any one of embodiments 24-29, wherein the C3D1 is from 20% to 80% of the C2D1.

31. The method, bispecific antibody for use, or use of embodiment 30, wherein the C3D1 is about 50% of the C2D1.

32. The method, bispecific antibody for use, or use of any one of embodiments 24-31, wherein the C3D1 is about 30 mg.

33. The method, bispecific antibody for use, or use of any one of embodiments 24-32, wherein the C1D1 is about 1 mg.

34. The method, bispecific antibody for use, or use of any one of embodiments 24-33, wherein the C1D2 is about 2 mg.

35. The method, bispecific antibody for use, or use of any one of embodiments 24-34, wherein the C1D1, the C1D2, and the C1D3 are administered or are to be administered to the subject on or about Days 1, 8, and 15, respectively, of the first dosing cycle.

36. The method, bispecific antibody for use, or use of any one of embodiments 24-35, wherein the C2D1 is administered or is to be administered to the subject on Day 1 of the second dosing cycle and the C3D1 is administered or is to be administered to the subject on Day 1 of the third dosing cycle.

37. The method, bispecific antibody for use, or use of any one of embodiments 24-36, wherein the first, second, and third dosing cycles are 21-day dosing cycles.

38. The method, bispecific antibody for use, or use of any one of embodiments 24-36, wherein the first dosing cycle is a 21-day dosing cycle and the second and third dosing cycles are 28-day dosing cycles.

39. The method, bispecific antibody for use, or use of any one of embodiments 24-38, wherein the dosing regimen further comprises one or more additional dosing cycles beyond the third dosing cycle.

40. The method, bispecific antibody for use, or use of embodiment 39, wherein the dosing regimen comprises from five to 14 additional dosing cycles beyond the third dosing cycle.

41. The method, bispecific antibody for use, or use of embodiment 39 or 40, wherein the additional dosing cycles are 21-day dosing cycles.

42. The method, bispecific antibody for use, or use of embodiment 39 or 40, wherein the additional dosing cycles are 28-day dosing cycles 43. The method, bispecific antibody for use, or use of any one of embodiments 39-42, wherein one or more of the additional dosing cycles comprise an additional single dose of the bispecific antibody.

44. The method, bispecific antibody for use, or use of embodiment 43, wherein the additional single dose of the bispecific antibody is administered or is to be administered to the subject on Day 1 of each additional dosing cycle.

45. The method, bispecific antibody for use, or use of embodiment 43 or 44, wherein the additional single dose of the bispecific antibody is about equivalent in amount to the C3D1.

46. A method of treating a subject having a CD20-positive cell proliferative disorder comprising administering to the subject a bispecific antibody that binds to CD20 and CD3 in a dosing regimen comprising eight or more dosing cycles, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3;

(c) the third dosing cycle comprises a single dose (C3D1) of the bispecific antibody, wherein the C3D1 is greater than the C1D1 and less than the C2D1;

(d) the fourth dosing cycle comprises a single dose (C4D1) of the bispecific antibody;

(e) the fifth dosing cycle comprises a single dose (C5D1) of the bispecific antibody;

(f) the sixth dosing cycle comprises a single dose (C6D1) of the bispecific antibody;

(g) the seventh dosing cycle comprises a single dose (C7D1) of the bispecific antibody; and (h) the eighth dosing cycle comprises a single dose (C8D1) of the bispecific antibody, wherein the C3D1-C8D1 are about equivalent in amount.

47. A bispecific antibody that binds to CD20 and CD3 for use in treating a subject having a CD20-positive cell proliferative disorder, wherein the bispecific antibody is formulated for administration to the subject in a dosing regimen comprising eight or more dosing cycles, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
(b) the second dosing cycle comprises a single dose (C2D1) of the bispecific antibody, wherein the C2D1 is about equivalent in amount to the C1D3;
(c) the third dosing cycle comprises a single dose (C3D1) of the bispecific antibody, wherein the C3D1 is greater than the C1D1 and less than the C2D1;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are about equivalent in amount.

48. Use of a bispecific antibody that binds to CD20 and CD3 in treating a subject having a CD20-positive cell proliferative disorder, wherein the bispecific antibody is formulated for administration to the subject in a dosing regimen comprising eight or more dosing cycles, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
(b) the second dosing cycle comprises a single dose (C2D1) of the bispecific antibody, wherein the C2D1 is about equivalent in amount to the C1D3;
(c) the third dosing cycle comprises a single dose (C3D1) of the bispecific antibody, wherein the C3D1 is greater than the C1D1 and less than the C2D1;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are about equivalent in amount.

49. Use of a bispecific antibody that binds to CD20 and CD3 in the manufacture of a medicament treating a subject having a CD20-positive cell proliferative disorder, wherein the bispecific antibody is formulated for administration to the subject in a dosing regimen comprising eight or more dosing cycles, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
(b) the second dosing cycle comprises a single dose (C2D1) of the bispecific antibody, wherein the C2D1 is about equivalent in amount to the C1D3;
(c) the third dosing cycle comprises a single dose (C3D1) of the bispecific antibody, wherein the C3D1 is greater than the C1D1 and less than the C2D1;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are about equivalent in amount.

50. The method, bispecific antibody for use, or use of any one of embodiments 46-49, wherein the C1D3 and the C2D1 are each from 20 mg to 200 mg.

51. The method, bispecific antibody for use, or use of embodiment 50, wherein the C1D3 and the C2D1 are each about 60 mg.

52. The method, bispecific antibody for use, or use of any one of embodiments 46-51, wherein the C3D1 is from 20% to 80% of the C2D1.

53. The method, bispecific antibody for use, or use of embodiment 52, wherein the C3D1 is about 50% of the C2D1.

54. The method, bispecific antibody for use, or use of any one of embodiments 46-53, wherein the C3D1 is about 30 mg.

55. The method, bispecific antibody for use, or use of any one of embodiments 46-54, wherein the C1D1 is about 1 mg.

56. The method, bispecific antibody for use, or use of any one of embodiments 46-55, wherein the C1D2 is about 2 mg.

57. The method, bispecific antibody for use, or use of any one of embodiments 46-56, wherein the C1D1, the C1D2, and the C1D3 are administered or are to be administered to the subject on or about Days 1, 8, and 15, respectively, of the first dosing cycle.

58. The method, bispecific antibody for use, or use of any one of embodiments 46-57, wherein the C2D1-C8D1 are each administered to the subject on Day 1 of the second-eighth dosing cycle, respectively.

59. The method, bispecific antibody for use, or use of any one of embodiments 46-58, wherein dosing cycles are 21-ay dosing cycles.

60. The method, bispecific antibody for use, or use of any one of embodiments 46-58, wherein the first dosing cycle is a 21-day dosing cycle and the second-eighth dosing cycles are 28-day dosing cycles.

61. The method, bispecific antibody for use, or use of any one of embodiments 46-60, wherein the dosing regimen comprises one or more additional dosing cycles beyond the eighth dosing cycle.

62. The method, bispecific antibody for use, or use of embodiment 61, wherein the additional dosing cycles are 21-day dosing cycles.

63. The method, bispecific antibody for use, or use of embodiment 61, wherein the additional dosing cycles are 28-day dosing cycles.

64. The method, bispecific antibody for use, or use of any one of embodiments embodiment 61-63, wherein one or more of the additional dosing cycles comprise an additional single dose of the bispecific antibody.

65. The method, bispecific antibody for use, or use of embodiment 64, wherein the additional single dose of the bispecific antibody is administered or is to be administered to the subject on Day 1 of each additional dosing cycle.

66. The method, bispecific antibody for use, or use of embodiment 64 or 65, wherein the additional single dose of the bispecific antibody is about equivalent in amount to any one of the C3D1-C8D1.

67. A method of treating a subject having a CD20-positive cell proliferative disorder comprising administering to the subject a bispecific antibody that binds to CD20 and CD3 in a dosing regimen comprising eight or more 21-day dosing cycles, wherein:
    (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
    (b) the second dosing cycle comprises a single dose (C2D1) of the bispecific antibody, wherein the C2D1 is about 60 mg;
    (c) the third dosing cycle comprises a single dose (C3D1) of the bispecific antibody;
    (d) the fourth dosing cycle comprises a single dose (C4D1) of the bispecific antibody;
    (e) the fifth dosing cycle comprises a single dose (C5D1) of the bispecific antibody;
    (f) the sixth dosing cycle comprises a single dose (C6D1) of the bispecific antibody;
    (g) the seventh dosing cycle comprises a single dose (C7D1) of the bispecific antibody; and
    (h) the eighth dosing cycle comprises a single dose (C8D1) of the bispecific antibody, wherein the C3D1-C8D1 are each about 30 mg.

68. A bispecific antibody that binds to CD20 and CD3 for use in treating a subject having a CD20-positive cell proliferative disorder, wherein the bispecific antibody is formulated for administration to the subject in a dosing regimen comprising eight or more 21-day dosing cycles, wherein:
    (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
    (b) the second dosing cycle comprises a single dose (C2D1) of the bispecific antibody, wherein the C2D1 is about 60 mg;
    (c) the third dosing cycle comprises a single dose (C3D1) of the bispecific antibody;
    (d) the fourth dosing cycle comprises a single dose (C4D1) of the bispecific antibody;
    (e) the fifth dosing cycle comprises a single dose (C5D1) of the bispecific antibody;
    (f) the sixth dosing cycle comprises a single dose (C6D1) of the bispecific antibody;
    (g) the seventh dosing cycle comprises a single dose (C7D1) of the bispecific antibody; and
    (h) the eighth dosing cycle comprises a single dose (C8D1) of the bispecific antibody, wherein the C3D1-C8D1 are each about 30 mg.

69. Use of a bispecific antibody that binds to CD20 and CD3 in treating a subject having a CD20-positive cell proliferative disorder, wherein the bispecific antibody is formulated for administration to the subject in a dosing regimen comprising eight or more 21-day dosing cycles, wherein:
    (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
    (b) the second dosing cycle comprises a single dose (C2D1) of the bispecific antibody, wherein the C2D1 is about 60 mg;
    (c) the third dosing cycle comprises a single dose (C3D1) of the bispecific antibody;
    (d) the fourth dosing cycle comprises a single dose (C4D1) of the bispecific antibody;
    (e) the fifth dosing cycle comprises a single dose (C5D1) of the bispecific antibody;
    (f) the sixth dosing cycle comprises a single dose (C6D1) of the bispecific antibody;
    (g) the seventh dosing cycle comprises a single dose (C7D1) of the bispecific antibody; and
    (h) the eighth dosing cycle comprises a single dose (C8D1) of the bispecific antibody, wherein the C3D1-C8D1 are each about 30 mg.

70. Use of a bispecific antibody that binds to CD20 and CD3 in the manufacture of a medicament treating a subject having a CD20-positive cell proliferative disorder, wherein the bispecific antibody is formulated for administration to the subject in a dosing regimen comprising eight or more 21-day dosing cycles, wherein:
    (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
    (b) the second dosing cycle comprises a single dose (C2D1) of the bispecific antibody, wherein the C2D1 is about 60 mg;
    (c) the third dosing cycle comprises a single dose (C3D1) of the bispecific antibody;
    (d) the fourth dosing cycle comprises a single dose (C4D1) of the bispecific antibody;
    (e) the fifth dosing cycle comprises a single dose (C5D1) of the bispecific antibody;
    (f) the sixth dosing cycle comprises a single dose (C6D1) of the bispecific antibody;
    (g) the seventh dosing cycle comprises a single dose (C7D1) of the bispecific antibody; and
    (h) the eighth dosing cycle comprises a single dose (C8D1) of the bispecific antibody, wherein the C3D1-C8D1 are each about 30 mg.

71. A method of treating a subject having a CD20-positive cell proliferative disorder comprising administering to the subject a bispecific antibody that binds to CD20 and CD3 in a dosing regimen comprising a 21-day dosing cycle and seven or more 28-day dosing cycles, wherein:
    (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
    (b) the second dosing cycle comprises a single dose (C2D1) of the bispecific antibody, wherein the C2D1 is about 60 mg;
    (c) the third dosing cycle comprises a single dose (C3D1) of the bispecific antibody;
    (d) the fourth dosing cycle comprises a single dose (C4D1) of the bispecific antibody;
    (e) the fifth dosing cycle comprises a single dose (C5D1) of the bispecific antibody;
    (f) the sixth dosing cycle comprises a single dose (C6D1) of the bispecific antibody;
    (g) the seventh dosing cycle comprises a single dose (C7D1) of the bispecific antibody; and (h) the eighth dosing cycle comprises a single dose (C8D1) of the bispecific antibody, wherein the C3D1-C8D1 are each about 30 mg.

72. A bispecific antibody that binds to CD20 and CD3 for use in treating a subject having a CD20-positive cell proliferative disorder, wherein the bispecific antibody is formulated for administration to the subject in a dosing regimen comprising a 21-day dosing cycle and seven or more 28-day dosing cycles, wherein:
  (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
  (b) the second dosing cycle comprises a single dose (C2D1) of the bispecific antibody, wherein the C2D1 is about 60 mg;
  (c) the third dosing cycle comprises a single dose (C3D1) of the bispecific antibody;
  (d) the fourth dosing cycle comprises a single dose (C4D1) of the bispecific antibody;
  (e) the fifth dosing cycle comprises a single dose (C5D1) of the bispecific antibody;
  (f) the sixth dosing cycle comprises a single dose (C6D1) of the bispecific antibody;
  (g) the seventh dosing cycle comprises a single dose (C7D1) of the bispecific antibody; and
  (h) the eighth dosing cycle comprises a single dose (C8D1) of the bispecific antibody, wherein the C3D1-C8D1 are each about 30 mg.

73. Use of a bispecific antibody that binds to CD20 and CD3 in treating a subject having a CD20-positive cell proliferative disorder, wherein the bispecific antibody is formulated for administration to the subject in a dosing regimen comprising a 21-day dosing cycle and seven or more 28-day dosing cycles, wherein:
  (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
  (b) the second dosing cycle comprises a single dose (C2D1) of the bispecific antibody, wherein the C2D1 is about 60 mg;
  (c) the third dosing cycle comprises a single dose (C3D1) of the bispecific antibody;
  (d) the fourth dosing cycle comprises a single dose (C4D1) of the bispecific antibody;
  (e) the fifth dosing cycle comprises a single dose (C5D1) of the bispecific antibody;
  (f) the sixth dosing cycle comprises a single dose (C6D1) of the bispecific antibody;
  (g) the seventh dosing cycle comprises a single dose (C7D1) of the bispecific antibody; and
  (h) the eighth dosing cycle comprises a single dose (C8D1) of the bispecific antibody, wherein the C3D1-C8D1 are each about 30 mg.

74. Use of a bispecific antibody that binds to CD20 and CD3 in the manufacture of a medicament treating a subject having a CD20-positive cell proliferative disorder, wherein the bispecific antibody is formulated for administration to the subject in a dosing regimen comprising a 21-day dosing cycle and seven or more 28-day dosing cycles, wherein:
  (a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
  (b) the second dosing cycle comprises a single dose (C2D1) of the bispecific antibody, wherein the C2D1 is about 60 mg;
  (c) the third dosing cycle comprises a single dose (C3D1) of the bispecific antibody;
  (d) the fourth dosing cycle comprises a single dose (C4D1) of the bispecific antibody;
  (e) the fifth dosing cycle comprises a single dose (C5D1) of the bispecific antibody;
  (f) the sixth dosing cycle comprises a single dose (C6D1) of the bispecific antibody;
  (g) the seventh dosing cycle comprises a single dose (C7D1) of the bispecific antibody; and
  (h) the eighth dosing cycle comprises a single dose (C8D1) of the bispecific antibody, wherein the C3D1-C8D1 are each about 30 mg.

75. The method, bispecific antibody for use, or use of any one of embodiments 1-74, wherein the subject has received a prior systemic therapy for the CD20-positive cell proliferative disorder.

76. The method, bispecific antibody for use, or use of embodiment 75, wherein the subject has received a first-line systemic therapy and a second-line systemic therapy for the CD20-positive cell proliferative disorder.

77. The method, bispecific antibody for use, or use of embodiment 75 or 76, wherein the subject has exhibited progression of the CD20-positive cell proliferative disorder within 24 months of the prior systemic therapy.

78. The method, bispecific antibody for use, or use of any one of embodiments 75-77, wherein the prior systemic therapy comprises an anti-CD20 antibody.

79. The method, bispecific antibody for use, or use of embodiment 78, wherein the anti-CD20 antibody is rituximab.

80. The method, bispecific antibody for use, or use of embodiment 78, wherein the anti-CD20 antibody is obinutuzumab.

81. The method, bispecific antibody for use, or use of any one of embodiments 75-80, wherein the prior systemic therapy comprises a chemotherapeutic agent.

82. The method, bispecific antibody for use, or use of embodiment 81, wherein the chemotherapeutic agent is an alkylating agent.

83. The method, bispecific antibody for use, or use of embodiment 82, wherein the alkylating agent is bendamustine.

84. The method, bispecific antibody for use, or use of embodiment 81, wherein the chemotherapeutic agent is lenalidomide.

85. The method, bispecific antibody for use, or use of any one of embodiments 75-84, wherein the prior systemic therapy comprises a radio-immunotherapy.

86. The method, bispecific antibody for use, or use of embodiment 85, wherein the radio-immunotherapy is ibritumomab tiuxetan.

87. The method, bispecific antibody for use, or use of any one of embodiments 75-86, wherein the prior systemic therapy comprises a phosphoinositide 3-kinase inhibitor.

88. The method, bispecific antibody for use, or use of embodiment 87, wherein the phosphoinositide 3-kinase inhibitor is selected from the group consisting of idelalisib, alpelisib, copanlisib, and duvelisib.

89. The method, bispecific antibody for use, or use of any one of embodiments 75-88, wherein the prior systemic therapy comprises a CAR-T therapy.

90. The method, bispecific antibody for use, or use of any one of embodiments 1-89, wherein the subject is a human.

91. The method, bispecific antibody for use, or use of any one of embodiments 1-90, wherein the bispecific antibody is administered intravenously.

92. A method of treating a population of subjects having a CD20-positive cell proliferative disorder comprising administering to the subjects a bispecific antibody that binds to CD20 and CD3 in a dosing regimen comprising at least a first dosing cycle and a second dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than 50 mg; and
(b) the second dosing cycle comprises a single dose (C2D1) of the bispecific antibody.

93. A bispecific antibody that binds to CD20 and CD3 for use in treating a population of subjects having a CD20-positive cell proliferative disorder, wherein the bispecific antibody is formulated for administration to the subjects in a dosing regimen comprising at least a first dosing cycle and a second dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than 50 mg; and
(b) the second dosing cycle comprises a single dose (C2D1) of the bispecific antibody.

94. Use of a bispecific antibody that binds to CD20 and CD3 in treating a population of subjects having a CD20-positive cell proliferative disorder, wherein the bispecific antibody is formulated for administration to the subjects in a dosing regimen comprising at least a first dosing cycle and a second dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than 50 mg; and
(b) the second dosing cycle comprises a single dose (C2D1) of the bispecific antibody.

95. Use of a bispecific antibody that binds to CD20 and CD3 in the manufacture of a medicament treating a population of subjects having a CD20-positive cell proliferative disorder, wherein the bispecific antibody is formulated for administration to the subjects in a dosing regimen comprising at least a first dosing cycle and a second dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than 50 mg; and
(b) the second dosing cycle comprises a single dose (C2D1) of the bispecific antibody.

96. The method, bispecific antibody for use, or use of any one of embodiments 91-95, wherein the C1D3 and the C2D1 are each from 50 mg to 200 mg.

97. A method of treating a population of subjects having a CD20-positive cell proliferative disorder comprising administering to the subjects a bispecific antibody that binds to CD20 and CD3 in a dosing regimen comprising at least a first dosing cycle, a second dosing cycle, and a third dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
(b) the second dosing cycle comprises a single dose (C2D1) of the bispecific antibody, wherein the C2D1 is about equivalent in amount to the C1D3; and
(c) the third dosing cycle comprises a single dose (C3D1) of the bispecific antibody, wherein the C3D1 is greater than the C1D1 and less than the C2D1.

98. A bispecific antibody that binds to CD20 and CD3 for use in treating a population of subjects having a CD20-positive cell proliferative disorder, wherein the bispecific antibody is formulated for administration to the subjects in a dosing regimen comprising at least a first dosing cycle, a second dosing cycle, and a third dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
(b) the second dosing cycle comprises a single dose (C2D1) of the bispecific antibody, wherein the C2D1 is about equivalent in amount to the C1D3; and
(c) the third dosing cycle comprises a single dose (C3D1) of the bispecific antibody, wherein the C3D1 is greater than the C1D1 and less than the C2D1.

99. Use of a bispecific antibody that binds to CD20 and CD3 in treating a population of subjects having a CD20-positive cell proliferative disorder, wherein the bispecific antibody is formulated for administration to the subjects in a dosing regimen comprising at least a first dosing cycle, a second dosing cycle, and a third dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;
(b) the second dosing cycle comprises a single dose (C2D1) of the bispecific antibody, wherein the C2D1 is about equivalent in amount to the C1D3; and
(c) the third dosing cycle comprises a single dose (C3D1) of the bispecific antibody, wherein the C3D1 is greater than the C1D1 and less than the C2D1.

100. Use of a bispecific antibody that binds to CD20 and CD3 in the manufacture of a medicament treating a population of subjects having a CD20-positive cell proliferative disorder, wherein the bispecific antibody is formulated for administration to the subjects in a dosing regimen comprising at least a first dosing cycle, a second dosing cycle, and a third dosing cycle, wherein:
(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3; and (c) the third dosing cycle comprises a single dose (C3D1) of the bispecific antibody, wherein the C3D1 is greater than the C1D1 and less than the C2D1.

101. A method of treating a population of subjects having a CD20-positive cell proliferative disorder comprising administering to the subjects a bispecific antibody that binds to CD20 and CD3 in a dosing regimen comprising eight or more dosing cycles, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3;

(c) the third dosing cycle comprises a single dose (C3D1) of the bispecific antibody, wherein the C3D1 is greater than the C1D1 and less than the C2D1;

(d) the fourth dosing cycle comprises a single dose (C4D1) of the bispecific antibody;

(e) the fifth dosing cycle comprises a single dose (C5D1) of the bispecific antibody;

(f) the sixth dosing cycle comprises a single dose (C6D1) of the bispecific antibody;

(g) the seventh dosing cycle comprises a single dose (C7D1) of the bispecific antibody; and (h) the eighth dosing cycle comprises a single dose (C8D1) of the bispecific antibody, wherein the C3D1-C8D1 are about equivalent in amount.

102. A bispecific antibody that binds to CD20 and CD3 for use in treating a population of subjects having a CD20-positive cell proliferative disorder, wherein the bispecific antibody is formulated for administration to the subjects in a dosing regimen comprising eight or more dosing cycles, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3;

(c) the third dosing cycle comprises a single dose (C3D1) of the bispecific antibody, wherein the C3D1 is greater than the C1D1 and less than the C2D1;

(d) the fourth dosing cycle comprises a single dose (C4D1) of the bispecific antibody;

(e) the fifth dosing cycle comprises a single dose (C5D1) of the bispecific antibody;

(f) the sixth dosing cycle comprises a single dose (C6D1) of the bispecific antibody;

(g) the seventh dosing cycle comprises a single dose (C7D1) of the bispecific antibody; and (h) the eighth dosing cycle comprises a single dose (C8D1) of the bispecific antibody, wherein the C3D1-C8D1 are about equivalent in amount.

103. Use of a bispecific antibody that binds to CD20 and CD3 in treating a population of subjects having a CD20-positive cell proliferative disorder, wherein the bispecific antibody is formulated for administration to the subjects in a dosing regimen comprising eight or more dosing cycles, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3;

(c) the third dosing cycle comprises a single dose (C3D1) of the bispecific antibody, wherein the C3D1 is greater than the C1D1 and less than the C2D1;

(d) the fourth dosing cycle comprises a single dose (C4D1) of the bispecific antibody;

(e) the fifth dosing cycle comprises a single dose (C5D1) of the bispecific antibody;

(f) the sixth dosing cycle comprises a single dose (C6D1) of the bispecific antibody;

(g) the seventh dosing cycle comprises a single dose (C7D1) of the bispecific antibody; and (h) the eighth dosing cycle comprises a single dose (C8D1) of the bispecific antibody, wherein the C3D1-C8D1 are about equivalent in amount.

104. Use of a bispecific antibody that binds to CD20 and CD3 in the manufacture of a medicament treating a population of subjects having a CD20-positive cell proliferative disorder, wherein the bispecific antibody is formulated for administration to the subjects in a dosing regimen comprising eight or more dosing cycles, wherein:

(a) the first dosing cycle comprises a first dose (C1D1), a second dose (C1D2), and a third dose (C1D3) of the bispecific antibody, wherein the C1D1 is from about 0.02 mg to about 2.0 mg, the C1D2 is from about 0.05 mg to about 4.0 mg, and the C1D3 is greater than about 20 mg;

(b) the second dosing cycle comprises a single dose (C2D1) of the bispecific antibody, wherein the C2D1 is about equivalent in amount to the C1D3;

(c) the third dosing cycle comprises a single dose (C3D1) of the bispecific antibody, wherein the C3D1 is greater than the C1D1 and less than the C2D1;

(d) the fourth dosing cycle comprises a single dose (C4D1) of the bispecific antibody;

(e) the fifth dosing cycle comprises a single dose (C5D1) of the bispecific antibody;

(f) the sixth dosing cycle comprises a single dose (C6D1) of the bispecific antibody;

(g) the seventh dosing cycle comprises a single dose (C7D1) of the bispecific antibody; and (h) the eighth dosing cycle comprises a single dose (C8D1) of the bispecific antibody, wherein the C3D1-C8D1 are about equivalent in amount.

105. The method, bispecific antibody for use, or use of any one of embodiments 97-104, wherein the C1D3 and the C2D1 are each from 20 mg to 200 mg.

106. A method of treating a population of subjects having a CD20-positive cell proliferative disorder comprising administering to the subjects a bispecific antibody that binds to CD20 and CD3 in a dosing regimen comprising eight or more 21-day dosing cycles, wherein:

(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

107. A bispecific antibody that binds to CD20 and CD3 for use in treating a population of subjects having a CD20-positive cell proliferative disorder, wherein the bispecific antibody is formulated for administration to the subjects in a dosing regimen comprising eight or more 21-day dosing cycles, wherein:
(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

108. Use of a bispecific antibody that binds to CD20 and CD3 in treating a population of subjects having a CD20-positive cell proliferative disorder, wherein the bispecific antibody is formulated for administration to the subjects in a dosing regimen comprising eight or more 21-day dosing cycles, wherein:
(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

109. Use of a bispecific antibody that binds to CD20 and CD3 in the manufacture of a medicament treating a population of subjects having a CD20-positive cell proliferative disorder, wherein the bispecific antibody is formulated for administration to the subjects in a dosing regimen comprising eight or more 21-day dosing cycles, wherein:
(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

110. A method of treating a population of subjects having a CD20-positive cell proliferative disorder comprising administering to the subjects a bispecific antibody that binds to CD20 and CD3 in a dosing regimen comprising a 21-day dosing cycle and seven or more 28-day dosing cycles, wherein:
(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

111. A bispecific antibody that binds to CD20 and CD3 for use in treating a population of subjects having a CD20-positive cell proliferative disorder, wherein the bispecific antibody is formulated for administration to the subjects in a dosing regimen comprising a 21-day dosing cycle and seven or more 28-day dosing cycles, wherein:

(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

112. Use of a bispecific antibody that binds to CD20 and CD3 in treating a population of subjects having a CD20-positive cell proliferative disorder, wherein the bispecific antibody is formulated for administration to the subjects in a dosing regimen comprising a 21-day dosing cycle and seven or more 28-day dosing cycles, wherein:
(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

113. Use of a bispecific antibody that binds to CD20 and CD3 in the manufacture of a medicament treating a population of subjects having a CD20-positive cell proliferative disorder, wherein the bispecific antibody is formulated for administration to the subjects in a dosing regimen comprising a 21-day dosing cycle and seven or more 28-day dosing cycles, wherein:
(a) the first 21-day dosing cycle comprises a first dose (C1D1), a second dose (C1D2), and a third dose (C1D3) of the bispecific antibody, wherein the C1D1 is about 1 mg, the C1D2 is about 2 mg, and the C1D3 is about 60 mg;
(b) the second dosing cycle comprises a single dose (C2D1) of the bispecific antibody, wherein the C2D1 is about 60 mg;
(c) the third dosing cycle comprises a single dose (C3D1) of the bispecific antibody;
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody, wherein the C3D1-C8D1 are each about 30 mg.

114. The method, bispecific antibody for use, or use of any one of embodiments 92-113, wherein the population of subjects has a complete response rate, wherein the complete response rate is the rate of subjects in the population having a complete response, and wherein the complete response rate is at least about 15%.

115. The method, bispecific antibody for use, or use of embodiment 114, wherein the complete response rate is at least about 25%.

116. The method, bispecific antibody for use, or use of embodiment 115, wherein the complete response rate is at least about 35%.

117. The method, bispecific antibody for use, or use of embodiment 116, wherein the complete response rate is at least about 45%.

118. The method, bispecific antibody for use, or use of any one of embodiments 92-117, wherein the population of subjects has an objective response rate, wherein the objective response rate is the rate of subjects in the population having an objective response, and wherein the objective response rate is at least about 60%.

119. The method, bispecific antibody for use, or use of any one of embodiments 92-118, wherein the objective response rate at about 20 months after the initiation of treatment is at least about 70%.

120. The method, bispecific antibody for use, or use of any one of embodiments 92-119, wherein the objective response rate at about 24 months after the initiation of treatment is at least about 75%.

121. The method, bispecific antibody for use, or use of any one of embodiments 92-120, wherein the population of subjects has a median duration of response (mDOR), wherein the mDOR is the median of the durations of response of subjects in the population, and wherein mDOR is at least about 12 months.

122. The method, bispecific antibody for use, or use of embodiment 121, wherein the mDOR is at least about 20 months.

123. The method, bispecific antibody for use, or use of any one of embodiments 92-122, wherein the population of subjects has a rate of subjects in the population having a mDOR of at least 12 months, and wherein the rate of subjects in the population having a mDOR of at least 12 months is at least about 60%.

124. The method, bispecific antibody for use, or use of any one of embodiments 92-123, wherein the population of subjects exhibits cytokine release syndrome after administering the bispecific antibody, and wherein the rate of the cytokine release syndrome in the population of subjects is less than or equal to about 40%.

125. The method, bispecific antibody for use, or use of embodiment 124, wherein the rate of cytokine release syndrome in the population of subjects is less than or equal to about 10%.

126. The method, bispecific antibody for use, or use of any one of embodiments 92-125, wherein the rate of cytokine release syndrome having a grade of 2 or greater (as defined by the American Society for Transplantation and Cellular Therapy, 2018; ASTCT) is less than or equal to about 20%.

127. The method, bispecific antibody for use, or use of embodiment 126, wherein the rate of cytokine release syndrome having a grade of 2 or greater (as defined by the ASTCT) is less than or equal to about 5%.

128. The method, bispecific antibody for use, or use of any one of embodiments 92-127, wherein the rate of cytokine release syndrome having a grade of 3 or greater (as defined by the ASTCT) is about 0%.

129. The method, bispecific antibody for use, or use of any one of embodiments 92-128, wherein the bispecific antibody is administered intravenously.

130. The method, bispecific antibody for use, or use of any one of embodiments 1-128 wherein the CD20-positive cell proliferative disorder is a B cell proliferative disorder.

131. The method, bispecific antibody for use, or use of any one of embodiments 1-130, wherein the CD20-positive cell proliferative disorder is a relapsed or refractory B cell proliferative disorder.

132. The method, bispecific antibody for use, or use of any one of embodiments 1-131, wherein the CD20-positive cell proliferative disorder is a non-Hodgkin's lymphoma (NHL) or a chronic lymphoid leukemia (CLL).

133. The method, bispecific antibody for use, or use of embodiment 132, wherein the NHL is a diffuse large B cell lymphoma (DLBCL).

134. The method, bispecific antibody for use, or use of embodiment 133, wherein the DLBCL is a Richter's transformation.

135. The method, bispecific antibody for use, or use of embodiment 134, wherein the NHL is follicular lymphoma (FL).

136. The method, bispecific antibody for use, or use of embodiment 135, wherein the FL is Grade 1, 2, 3a, or 3b FL.

137. The method, bispecific antibody for use, or use of embodiment 135 or 136, wherein the FL is a transformed FL.

138. The method, bispecific antibody for use, or use of embodiment 135, wherein the NHL is a mantle cell lymphoma (MCL) or a marginal zone lymphoma (MZL).

139. The method, bispecific antibody for use, or use of any one of embodiments 1-138, wherein the bispecific antibody comprises an anti-CD20 arm comprising a first binding domain comprising the following six hypervariable regions (HVRs):
  (a) an HVR-H1 comprising the amino acid sequence of GYTFTSYNMH (SEQ ID NO: 1);
  (b) an HVR-H2 comprising the amino acid sequence of AIYPGNGDTSYNQKFKG (SEQ ID NO: 2);
  (c) an HVR-H3 comprising the amino acid sequence of VVYYSNSYWYFDV (SEQ ID NO: 3);
  (d) an HVR-L1 comprising the amino acid sequence of RASSSVSYMH (SEQ ID NO: 4);
  (e) an HVR-L2 comprising the amino acid sequence of APSNLAS (SEQ ID NO: 5); and
  (f) an HVR-L3 comprising the amino acid sequence of QQWSFNPPT (SEQ ID NO: 6).

140. The method, bispecific antibody for use, or use of any one of embodiments 1-139, wherein the bispecific antibody comprises an anti-CD20 arm comprising a first binding domain comprising (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b).

141. The method, bispecific antibody for use, or use of embodiment 140, wherein the first binding domain comprises a VH domain comprising an amino acid sequence of SEQ ID NO: 7 and a VL domain comprising an amino acid sequence of SEQ ID NO: 8.

142. The method, bispecific antibody for use, or use of any one of embodiments 1-141, wherein the bispecific antibody comprises an anti-CD3 arm comprising a second binding domain comprising the following six HVRs:
  (a) an HVR-H1 comprising the amino acid sequence of NYYIH (SEQ ID NO: 9);
  (b) an HVR-H2 comprising the amino acid sequence of WIYPGDGNTKYNEKFKG (SEQ ID NO: 10);
  (c) an HVR-H3 comprising the amino acid sequence of DSYSNYYFDY (SEQ ID NO: 11);
  (d) an HVR-L1 comprising the amino acid sequence of KSSQSLLNSRTRKNYLA (SEQ ID NO: 12);
  (e) an HVR-L2 comprising the amino acid sequence of WASTRES (SEQ ID NO: 13); and
  (f) an HVR-L3 comprising the amino acid sequence of TQSFILRT (SEQ ID NO: 14).

143. The method, bispecific antibody for use, or use of any one of embodiments 1-142, wherein the bispecific antibody comprises an anti-CD3 arm comprising a second binding domain comprising (a) a VH domain comprising an amino acid sequence having at least 95% sequence identity to the amino acid sequence of SEQ ID NO: 15; (b) a VL domain comprising an amino acid sequence having at least 95% sequence identity to the amino acid sequence of SEQ ID NO: 16; or (c) a VH domain as in (a) and a VL domain as in (b).

144. The method, bispecific antibody for use, or use of embodiment 143, wherein the second binding domain comprises a VH domain comprising an amino acid sequence of SEQ ID NO: 15 and a VL domain comprising an amino acid sequence of SEQ ID NO: 16.

145. The method, bispecific antibody for use, or use of any one of embodiments 1-144, wherein the bispecific antibody comprises (a) an anti-CD20 arm comprising (i) a heavy chain comprising an amino acid sequence having at least 95% sequence identity to the amino acid sequence of SEQ ID NO: 51, and (ii) a light chain comprising an amino acid sequence having at least 95% sequence identity to the amino acid sequence of SEQ ID NO: 52; and (b) an anti-CD3 arm comprising (i) a heavy chain comprising an amino acid sequence having at least 95% sequence identity to the amino acid sequence of SEQ ID NO: 53, and (ii) a light chain comprising an amino acid sequence having at least 95% sequence identity to the amino acid sequence of SEQ ID NO: 54.

146. The method, bispecific antibody for use, or use of embodiment 145, wherein (a) the anti-CD20 arm comprises a heavy chain comprising an amino acid sequence of SEQ ID NO: 51 and a light chain comprising an amino acid sequence of SEQ ID NO: 52, and (b) the anti-CD3 arm comprises a heavy chain comprising an amino acid sequence of SEQ ID NO: 53 and a light chain comprising an amino acid sequence of SEQ ID NO: 54.

147. The method, bispecific antibody for use, or use of any one of embodiments 1-146, wherein the bispecific antibody is a humanized antibody.

148. The method, bispecific antibody for use, or use of any one of embodiments 1-147, wherein the bispecific antibody is a chimeric antibody.

149. The method, bispecific antibody for use, or use of any one of embodiments 1-148, wherein the bispecific antibody is an antibody fragment that binds CD20 and CD3.

150. The method, bispecific antibody for use, or use of embodiment 149, wherein the antibody fragment is selected from the group consisting of Fab, Fab'-SH, Fv, scFv, and (Fab')$_2$ fragments.

151. The method, bispecific antibody for use, or use of any one of embodiments 1-148, wherein the bispecific antibody is a full-length antibody.

152. The method, bispecific antibody for use, or use of any one of embodiments 1-148 and 151, wherein the bispecific antibody is an IgG antibody.

153. The method, bispecific antibody for use, or use of embodiment 152, wherein the IgG antibody is an IgG1 antibody.

154. The method, bispecific antibody for use, or use of embodiment 152 or 153, wherein the IgG antibody comprises a mutation at amino acid residue N297 (EU numbering) that results in the absence of glycosylation.

155. The method, bispecific antibody for use, or use of embodiment 154, wherein the mutation at amino acid residue N297 is a substitution mutation.

156. The method, bispecific antibody for use, or use of embodiment 154 or 155, wherein the mutation at amino acid residue N297 reduces effector function of the Fc region.

157. The method, bispecific antibody for use, or use of any one of embodiments 154-156, wherein the mutation is an N297G or N297A mutation.

158. The method, bispecific antibody for use, or use of any one of embodiments 153-155, wherein the bispecific antibody comprises a mutation in the Fc region that reduces effector function.

159. The method, bispecific antibody for use, or use of embodiment 158, wherein the mutation is a substitution mutation.

160. The method, bispecific antibody for use, or use of embodiment 159, wherein the substitution mutation is at amino acid residue L234, L235, D265, and/or P329 (EU numbering).

161. The method, bispecific antibody for use, or use of embodiment 160, wherein the substitution mutation is selected from the group consisting of L234A, L235A, D265A, and P329G.

162. The method, bispecific antibody for use, or use of any one of embodiments 1-148 and 151-161, wherein the bispecific antibody comprises one or more heavy chain constant domains, wherein the one or more heavy chain constant domains are selected from a first CH1 (CH1$_1$) domain, a first CH2 (CH2$_1$) domain, a first CH3 (CH3$_1$) domain, a second CH1 (CH1$_2$) domain, second CH2 (CH2$_2$) domain, and a second CH3 (CH3$_2$) domain.

163. The method, bispecific antibody for use, or use of embodiment 162, wherein at least one of the one or more heavy chain constant domains is paired with another heavy chain constant domain.

164. The method, bispecific antibody for use, or use of embodiment 162 or 163, wherein the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain.

165. The method, bispecific antibody for use, or use of embodiment 164, wherein the CH3$_1$ and CH3$_2$ domains meet at an interface between the protuberance and cavity.

166. The method, bispecific antibody for use, or use of embodiment 140 or 141, wherein the anti-CD20 arm further comprises T366W and N297G substitution mutations (EU numbering).

167. The method, bispecific antibody for use, or use of embodiment 143 or 144, wherein the anti-CD3 arm further comprises T366S, L368A, Y407V, and N297G substitution mutations (EU numbering).

168. The method, bispecific antibody for use, or use of embodiment 145 or 146, wherein (a) the anti-CD20 arm further comprises T366W and N297G substitution mutations and (b) the anti-CD3 arm further comprises T366S, L368A, Y407V, and N297G substitution mutations (EU numbering).

169. The method, bispecific antibody for use, or use of any one of embodiments 1-138, wherein the bispecific antibody is mosunetuzumab 170. The method, bispecific antibody for use, or use of any one of embodiments 1-169, wherein the subject is a human.

171. The method of any one of embodiments 1, 5-24, 28-46, 50-67, 71, and 75-91, further comprising administering to the subject a PD-1 axis binding antagonist.

172. The method of embodiment 171, wherein the PD-1 axis binding antagonist is administered at a dose of between about 1100 mg to about 1300 mg.

173. The method of embodiment 172, wherein the PD-1 axis binding antagonist is administered at a dose of about 1200 mg.

174. The method of embodiment 172, wherein the PD-1 axis binding antagonist is administered on Day 1 of each dosing cycle after the first dosing cycle comprising administration of the bispecific antibody.

175. The bispecific antibody for use or use of any one of embodiments 2-23, 25-45, 47-66, 68-70, and 72-91, wherein the bispecific antibody is formulated for use with a PD-1 axis binding antagonist.

176. The bispecific antibody for use or use of embodiment 171, wherein the PD-1 axis binding antagonist is to be administered at a dose of between 1100 mg to about 1300 mg.

177. The bispecific antibody for use or use of embodiment 172, wherein the PD-1 axis binding antagonist is to be administered at a dose of about 1200 mg.

178. The bispecific antibody for use or use of embodiment 172, wherein the PD-1 axis binding antagonist is to be administered on Day 1 of each dosing cycle after the first dosing cycle comprising administration of the bispecific antibody.

179. The method, bispecific antibody of use, or use of any one of embodiments 171-178, wherein the PD-1 axis binding antagonist is atezolizumab.

180. The method, bispecific antibody of use, or use of any one of embodiments 171-179, wherein the subject is a human.

VII. Examples

The following are examples of the methods of the invention. It is understood that various other embodiments may be practiced, given the general description provided above.

Example 1. Step-Load-Base Dosing of Mosunetuzumab

This study evaluates the safety, tolerability, and pharmacokinetics of step-load-base dosing of mosunetuzumab in patients with relapsed or refractory (R/R) non-Hodgkin's lymphoma (NHL) and chronic lymphocytic leukemia (CLL). Patients are given step doses during the first two doses of Cycle 1, followed by two loading doses as the third dose of Cycle 1 and the first dose of Cycle 2, and then base doses during the subsequent cycles.

FIG. 1 depicts an overview of the dosing regimen of the study. The patients are administered a first step dose of about 1 mg mosunetuzumab on Cycle 1 Day 1, followed by a second step dose of about 2 mg mosunetuzumab on Cycle 1 Day 8. The patients are then administered a first loading dose of about 60 mg mosunetuzumab on Cycle 1 Day 15, followed by a second loading dose of about 60 mg mosunetuzumab on Cycle 2 Day 1. Thereafter, the patient is administered base doses of about 30 mg mosunetuzumab on Day 1 of each subsequent cycle. The patients are initially administered 6 base doses on Cycle 3 Day 1 to Cycle 8 Day 1. Patients who did not achieve CR following 8 cycles of treatment continue to receive base doses of about 30 mg mosunetuzumab for 6 or 15 additional cycles of treatment (for a total of 8 or 17 additional cycles, respectively).

Safety and tolerability of the step-load-base dosing of mosunetuzumab (e.g., C1D1: 1 mg, C1D8: 2 mg, C1D15: 60 mg, C2: 60 mg, C3+: 30 mg) was evaluated in patients with relapsed or refractory (R/R) non-Hodgkin's lymphoma (NHL) (n=153). Results are summarized below in Table 4:

TABLE 4

Safety and tolerability of step-load-base dosing of mosunetuzumab

| CRS | Cycle 1 D1-7 (n = 153) | D8-14 (n = 142) | D15-21 (n = 133) | Cycle 2 (n = 126) | Cycle 3+ (n = 94) |
| --- | --- | --- | --- | --- | --- |
| Any Grade | 22 (14.4%) | 10 (7%) | 39 (29.3%) | 6 (4.8%) | 2 (2.1%) |
| Grade 1 | 14 (9.2%) | 7 (4.9%) | 22 (16.5%) | 3 (2.4%) | 1 (1.1%) |
| Grade 2 | 8 (5.2%) | 3 (2.1%) | 15 (11.3%) | 1 (0.8%) | 1 (1.1%) |
| Grade 3 | 0 | 0 | 1 (0.8%) | 2 (1.6%) | 0 |
| Grade 4 | 0 | 0 | 1 (0.8%) | 0 | 0 |

Lee 2014 criteria: Lee et al., Blood, 124: 188-195, 2014.

The median onset to the first CRS event was 16 days (range 1 to 29 days). The median duration of a CRS event was 3 days (range 1 to 19 days).

Four Grade 3 or above CRS events were observed in three patients, one of whom experienced 2 such events. Both patients had disease features that increased the risk of severe CRS and had experienced CRS (Grade 2) after 1 mg dose on C1D1. The first patient, who experienced a Grade 4 CRS event, had 30% bone marrow infiltration, splenomegaly, and was in leukemic phase with 48% circulating malignant cells at baseline. On study day 23, Grade 4 CRS occurred after infusion of 11 mg out of a planned 60 mg dose (C1D15, dose delay of 8 days due to fever). The event resolved in 7 days. The patient received two additional cycles (Grade 3 CRS associated with C2D1 9 mg dose; resolved) prior to treatment discontinuation due to PD. The second patient, who experienced a Grade 3 CRS event, had 30% bone marrow infiltration, splenomegaly, and circulating abnormal lymphoid cells at baseline. On study day 28, Grade 3 CRS occurred (C2D1 60 mg dose administered on study day 26, dose delay of 4 days due to duodenal obstruction). The CRS event was characterized by Grade 4 transaminitis, without hypoxia or hypotension. The event resolved, and the patient continued study treatment, achieving partial response prior to pursuing allogeneic stem cell transplant. In all 153 R/R NHL patients treated at the registration dose, Grade 3 or above CRS occurred in 3/153 patients (2%).

Figure 2:
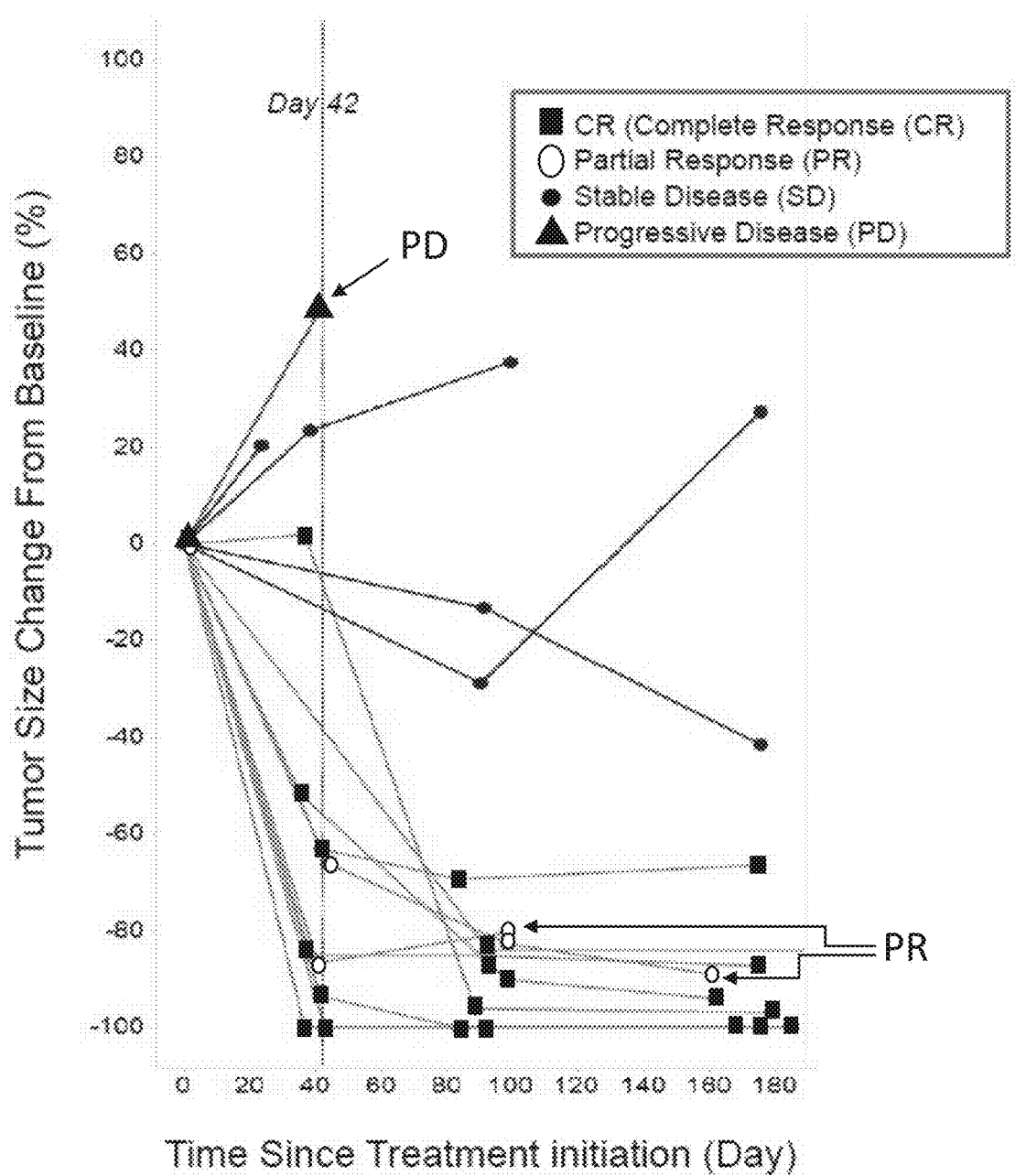
FIG. 2 is a graph showing % tumor change from base line in patients administered with step-load-base dosing of mosunetuzumab (i.e., 1/2/60/30 dosing). Arrows indicate lines representing patients with progressive disease (PD) or partial response (PR). Lines with solid rectangles represent patients with complete response (CR). Lines with hollow ovals indicate patients with PR. Lines with solid circles indicate patients with stable disease (SD). Lines with solid triangles indicate patients with PD.

Effects of the step-load-base dosing of mosunetuzumab was evaluated based on changes in tumor size at the 1/2/60/30 mg dose. Results are shown in FIG. 2. On average, >50% reduction in tumor size was observed following two 60 mg doses in responders by the end of Cycle 2 (i.e., on Day 42 or at the end of the first tumor scan). The proposed dose regimen of base doses of 30 mg after loading doses minimizes unnecessarily subjecting patients to high PK exposure over time and reduces potential risks of chronic or cumulative toxicity.

Example 2. An Open-Label, Multicenter, Phase I/Ib Trial Evaluating the Safety, Efficacy, and Pharmacokinetics of Escalating Doses of Mosunetuzumab (BTCT4465A) as a Single Agent and Combined with Atezolizumab in Patients with Relapsed or Refractory B-Cell Non-Hodgkin's Lymphoma and Chronic Lymphocytic Leukemia This Example describes GO29781, a Phase I/Ib, multicenter, open-label, dose-escalation study of mosunetuzumab administered as a single agent and in combination with atezolizumab in patients with R/R hematologic malignancies expected to express CD20, including B-cell non-Hodgkin's lymphoma (NHL) and chronic lymphocytic leukemia (CLL). The study enrolls approximately 130-226 patients during the dose-escalation stage (100-166 patients with NHL and 30-60 patients with CLL) and approximately 290-520 patients during the expansion stage at approximately 45-50 investigative sites globally.

A. Objectives

This study evaluates the safety, tolerability, and pharmacokinetics of mosunetuzumab in patients with relapsed or refractory (R/R) non-Hodgkin's lymphoma (NHL) and chronic lymphocytic leukemia (CLL) as described below:

Administered intravenously (IV) as a single agent on a Cycle 1 non-fractionated dose schedule (Group A);

Administered IV as a single agent on a Cycle 1 step-up dose schedule (Group B);

Administered IV as a single agent on a Cycle 1 step-up dose schedule with concurrent administration of atezolizumab starting in Cycle 2 (Group E).

This study determines the maximum tolerated dose (MTD) and dose-limiting toxicities (DLTs) of mosunetuzumab in patients with R/R NHL and CLL as described below:

Administered IV on a Cycle 1 non-fractionated dose schedule (Group A);

Administered IV on a Cycle 1 step-up dose schedule (Group B);

Administered IV as a single agent on a Cycle 1 step-up dose schedule with concurrent administration of atezolizumab starting in Cycle 2 (Group E).

This study identifies, on the basis of safety, pharmacokinetic (PK), and pharmacodynamic data, the recommended Phase II dose(s) and schedule(s) of mosunetuzumab as a single agent and in combination with atezolizumab in patients with R/R NHL and for CLL. In addition, this study evaluates the efficacy of mosunetuzumab using a Cycle 1 step-up dosing schedule as a single agent (Group B) and in combination with atezolizumab (Group E) in patients with R/R diffuse large B-cell lymphoma (DLBCL) and transformed follicular lymphoma (FL), and patients with R/R FL, as measured by Independent Review Facility-assessed complete response (CR) rate according to standard NHL response criteria.

This study assesses the incidence of anti-drug antibodies (ADAs) to mosunetuzumab and atezolizumab (when given in combination with mosunetuzumab), and their relationship to relevant clinical outcomes.

Where evaluation of efficacy of mosunetuzumab as single agent and in combination with atezolizumab is not a primary objective as described above, this study conducts a preliminary assessment of the anti-tumor activity of mosunetuzumab, as a single agent and in combination with atezolizumab, in patients with R/R NHL and CLL.

B. Study Design

Description of Study

Figure 3:
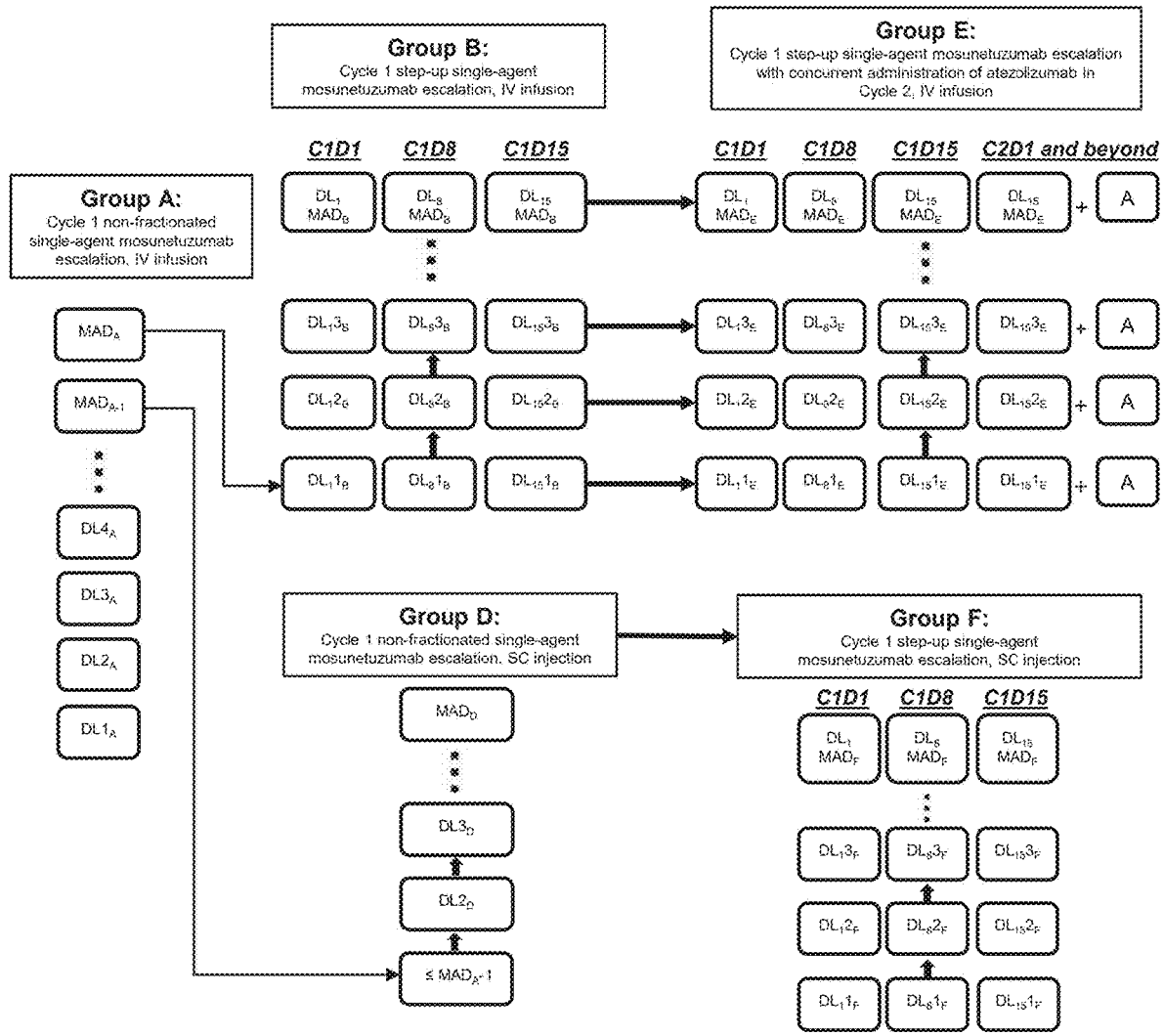
FIG. 3 is a schematic diagram showing the design of the dose escalation portion of the GO29781 study. Initially, mosunetuzumab is given as a single non-fractionated intravenous (IV) dose on Day 1 of each cycle (Group A). Cycle 1 dosing is subsequently modified such that Group A dose escalation stops and mosunetuzumab dose escalation is conducted as follows: Group B: mosunetuzumab dose escalation utilizing a Cycle 1 step-up IV dosing scheme; and Group E: mosunetuzumab dose escalation utilizing a Cycle 1 step-up IV dosing scheme with concurrent administration of atezolizumab (anti-PD-L1 monoclonal antibody (mAb) starting in Cycle 2 by IV infusion; for reference. A=atezolizumab; C=Cycle; D=Day; DL=dose level; MAD=maximum assessed dose.
Figure 4:
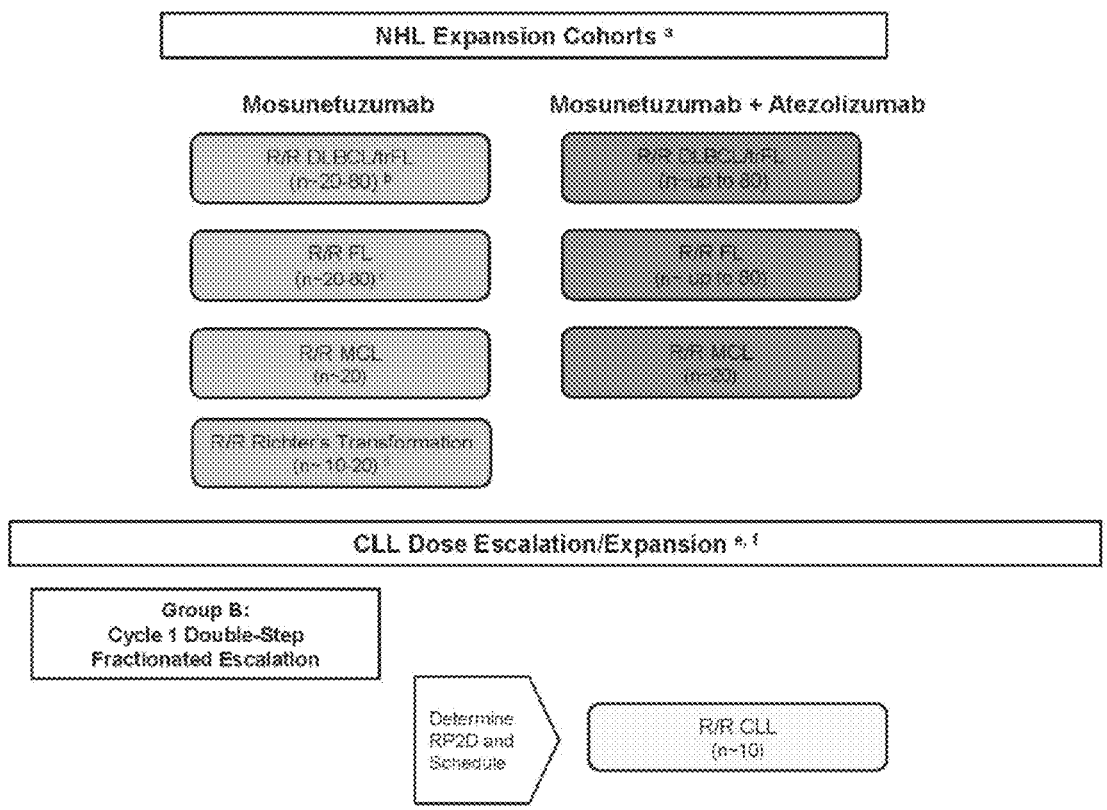
FIG. 4 is a schematic diagram showing the design of the non-Hodgkin's lymphoma (NHL) expansion cohorts and the chronic lymphocytic leukemia (CLL) dose escalation/expansion cohorts of the GO29781 study. DLBCL=diffuse large B-cell lymphoma; FL=follicular lymphoma; MCL=mantle cell lymphoma; NHL=Non-Hodgkin's Lymphoma; RP2D=recommended Phase II dose; R/R=relapsed/refractory; trFL=transformed follicular lymphoma. $^a$Multiple expansion cohorts based on Groups A, B, and E dose escalations may be tested. $^b$Expansion cohorts in R/R DLBCL/trFL enroll up to about 20 patients except for expansion cohort based on Group B RP2D, which enrolls up to about 80 patients. $^c$Expansion cohorts in R/R FL enroll up to about 20 patients except for expansion cohort based on Group B RP2D, which enrolls up to about 80 patients. $^d$Expansion cohort based on Group B dose escalation only is tested. $^e$Dose escalation conducted similarly to that for NHL (see FIG. 3). $^f$Multiple expansion cohorts based on Groups B dose escalation may be tested.

FIG. 3 provides an overview of the dose-escalation portion of the study, and FIG. 4 depicts the dose-expansion phase. Initially, mosunetuzumab is given as a single non-fractionated IV dose on Day 1 of each cycle (Group A). Cycle 1 dosing is subsequently modified such that Group A dose escalation stops and mosunetuzumab dose escalation is conducted as follows:

Mosunetuzumab dose escalation utilizing a Cycle 1 step-up IV dosing scheme (Group B).

Enrollment into escalation Group B may not necessarily begin concurrently.

Mosunetuzumab dose escalation in combination with atezolizumab (Group E) is also conducted based on mosunetuzumab dose levels tested in Group B escalation.

After the recommended Phase II doses (RP2Ds) and schedules have been identified for single-agent mosunetuzumab and for mosunetuzumab in combination with atezolizumab, further assessment of mosunetuzumab clinical activity as a single agent and in combination with atezolizumab is conducted in indication-specific expansion cohorts (FIG. 4).

In addition to dose escalation and expansion in NHL, separate escalation and expansions in CLL may also be conducted. The rules for dose escalation and dose expansion are identical to those described for NHL escalation and expansion.

Dose-Escalation Stage

The dose-escalation stage of the study assesses the safety, tolerability, and pharmacokinetics of mosunetuzumab administered by IV infusion. Up to five dose-escalation groups may be enrolled (FIG. 3):

Group A: Cycle 1 non-fractionated single-agent mosunetuzumab escalation, IV infusion (enrollment into dose-escalation Group A has stopped to prioritize assessment of other dosing schedule and route of mosunetuzumab);

Group B: Cycle 1 step-up single-agent mosunetuzumab escalation, IV infusion;

Group E: Cycle 1 step-up single-agent mosunetuzumab escalation with concurrent administration of atezolizumab starting in Cycle 2, IV infusion.

Dose-escalation Group C (Cycle 1 non-fractionated single-agent mosunetuzumab following a single dose of obinutuzumab; IV infusion) has been removed.

Initially, dose-escalation cohorts in Group A consist of 1 patient. Conversion to a standard 3+3 design occurs based on the criteria provided herein. Subsequently, dose-escalation cohorts consist of at least 3 patients, unless DLTs are observed in the first 2 patients prior to enrollment of a third patient, according to a standard 3+3 design.

Dose-escalation cohorts in Groups B and E are based on a standard 3+3 design from the outset.

For each dose-escalation cohort, treatment with the first dose of mosunetuzumab is staggered such that the second patient enrolled in the cohort receives mosunetuzumab at least 72 hours after the first enrolled patient receives the first dose of mosunetuzumab in order to assess for any severe and unexpected acute drug or infusion/injection-related toxicities; dosing in subsequent patients in each cohort is staggered by at least 24 hours from the end of the prior patients' administration. Staggered patient enrollment is not required for enrollment of additional patients to acquire additional safety and pharmacodynamic data at a dose level that has been shown to not exceed the MTD.

Patients exhibiting acceptable safety and evidence of clinical benefit (as defined herein) may continue to receive mosunetuzumab or mosunetuzumab combined with atezolizumab every 21 days up to a maximum of 8 or 17 cycles until confirmed objective disease progression or unacceptable toxicity, whichever occurs first. Re-treatment with mosunetuzumab or mosunetuzumab combined with atezolizumab based on clinical responses to initial treatment are detailed herein.

Prior clinical trial experience in hematologic malignancies suggests that different toxicity profiles may be observed depending on the patient population treated. Specifically, the toxicity of mosunetuzumab in CLL patients may be distinct from that of NHL patients due to the presence of a larger number of circulating tumor cells and/or differences in overall disease burden. Because of this potential difference in toxicity profile and/or MTD in CLL patients, separate dose escalations are provided for NHL and CLL patients. The initial dose escalation is conducted in NHL patients. Initiation of dose escalation in CLL patients is at the Sponsor's discretion and follows Group B dose-escalation rules as applicable. The cumulative Cycle 1 starting dose level in CLL is at least one dose level below the highest cumulative Cycle 1 dose that has cleared the DLT assessment window in the corresponding NHL dose escalation.

Mosunetuzumab dose levels are independent of patient weight (fixed/flat dosing). The starting dose of 50 μg is based on the minimal anticipated biologic effect level (MABEL) in humans.

Definition of Dose-Limiting Toxicity

Although CRS is graded according to the Modified Cytokine Release Syndrome Grading System (Table 5), for dose-escalation decisions, DLTs related to CRS are defined based on individual signs and symptoms and laboratory data according to the National Cancer Institute Common Terminology for Adverse Events (NCI CTCAE) v4.0. Dose-limiting toxicities (DLTs) are treated according to clinical practice and are monitored through their resolution. All adverse events should be considered related to mosunetuzumab unless such events are clearly attributed by the investigator to another clearly identifiable cause (e.g., documented disease progression, concomitant medication, or pre-existing medical condition). Decreases in B cells, lymphopenia, and/or leukopenia due to decreases in B cells will not be considered DLTs as they are expected pharmacodynamic outcomes of mosunetuzumab treatment.

TABLE 5

Modified cytokine release syndrome grading system

| Grade | Modified Cytokine Release Syndrome Grading System |
|---|---|
| Grade 1 | Symptoms are not life threatening and require symptomatic treatment only (e.g., fever, nausea, fatigue, headache, myalgia, malaise) |
| Grade 2 | Symptoms require and respond to moderate intervention<br>Oxygen requirement < 40%; or<br>Hypotension responsive to fluids or low dose of one vasopressor; or Grade 2 organ toxicity |
| Grade 3 | Symptoms require and respond to aggressive intervention<br>Oxygen requirement ≥ 40%; or<br>Hypotension requiring high dose or multiple vasopressors; or Grade 3 organ toxicity or Grade 4 transaminitis |
| Grade 4 | Life-threatening symptoms<br>Requirement for ventilation support or<br>Grade 4 organ toxicity (excluding transaminitis) |
| Grade 5 | Death |

Lee 2014 criteria: Lee et al., *Blood*, 124: 188-195, 2014.
Low-dose vasopressor: single vasopressor at doses below that shown in Table 6. High-dose vasopressor: as defined in Table 6.

TABLE 6

High-dose vasopressors

High-Dose Vasopressors (duration ≥ 3 hours)

| Pressor | Dose |
|---|---|
| Norepinephrine monotherapy | ≥20 µg/min |
| Dopamine monotherapy | ≥10 µg/kg/min |
| Phenylephrine monotherapy | ≥200 µg/min |
| Epinephrine monotherapy | ≥10 µg/min |
| If on vasopressin | Vasopressin + norepinephrine equivalent of ≥ 10 µg/min |
| If on combination or vasopressors (not vasopressin) | Norepinephrine equivalent of ≥ 20 µg/min $^a$ | min = minute; VASST = Vasopressin and Septic Shock Trial.
VASST vasopressor equivalent equation: norepinephrine equivalent dose = [norepinephrine (µg/min)] + [dopamine (µg/kg/min) ÷ 2] + [epinephrine (µg/min)] + [phenylephrine (µg/min) ÷ 10].

For dose-escalation purposes, the DLT assessment period is defined by the following time periods depending on the assigned dose-escalation group:
  Groups A and B: Cycle 1 Day 1 through Cycle 1 Day 21.
    For treatment Group B, the 21-day DLT assessment period is subdivided into three windows as described herein.
    For treatment Group B, in the case of dose delay for the C1D8, and/or C1D15 dosing, the DLT assessment period is extended accordingly to 7 days after the C1D15 administration date.
  Group E: Cycle 2 Day 1 through Cycle 2 Day 21
A DLT is defined as any of the following adverse events occurring during the DLT assessment period:
  Any Grade 4 adverse events not considered by the investigator to be attributable to another clearly identifiable cause, with the following exceptions:
    Grade 4 neutropenia that is not accompanied by temperature elevation (as a single oral temperature of 38.3° C. (101° F.) or an oral temperature of 38.0° C. (100.4° F.) sustained for 1 hour) and improves to Grade 2 (or to 80% of the baseline value, whichever is lower) within 1 week.
    Grade 4 lymphopenia, which is an expected outcome of therapy.
    Grade 4 leukopenia, which is an expected outcome of therapy.
    For CLL patients only: neutropenia is graded based on National Cancer Institute-sponsored Working Group (NCI-WG) definitions (Hallek et al., *Blood*, 111: 5446-5456, 2008); absolute neutrophil count (ANC) <1000/mm$^3$ due to bone marrow involvement prior to study treatment is not evaluable for DLT based on ANC
    For CLL patients only: thrombocytopenia is graded based on NCI-WG definitions (Hallek et al., *Blood*, 111: 5446-5456, 2008); platelet counts<20,000/µL due to bone marrow involvement prior to study treatment will not be evaluable for DLT based on platelet counts.
    For CLL patients only: anemia is graded based on NCI-WG definitions (Hallek et al., *Blood*, 111: 5446-5456, 2008); Grade 4 anemia that improves to Grade 3 within 1 week and further improves to Grade 2 within another week without red blood cell (RBC) transfusion will not be a DLT.
  Any Grade 3 hematologic adverse event not considered by the investigator to be attributable to another clearly identifiable cause, with the following exceptions:
    Grade 3 lymphopenia, which is an expected outcome of therapy.
    Grade 3 leukopenia, which is an expected outcome of therapy.
    Grade 3 neutropenia that is not accompanied by temperature elevation (as a single oral temperature of ≥38.3° C. (101° F.) or an oral temperature of ≥38.0° C. (100.4° F.) sustained for ≥1 hour) and improves to Grade≤2 (or to ≥80% of the baseline value, whichever is lower) within 1 week.
    For CLL patients only: neutropenia is graded based on the NCI-WG Grading Scale for Chronic Lymphocytic Leukemia (Hallek et al., *Blood*, 111: 5446-5456, 2008); ANC<1000/mm$^3$ due to bone marrow involvement prior to study treatment is not evaluable for DLT based on ANC.
    Grade 3 thrombocytopenia that improves to Grade≤2 (or to ≥80% of the baseline value, whichever is lower) within 1 week without platelet transfusion and is not associated with bleeding that is considered clinically significant by the investigator.
    For CLL patients only: thrombocytopenia is graded based on NCI-WG definitions (Hallek et al., *Blood*, 111: 5446-5456, 2008); a platelet count<20,000/µL due to bone marrow involvement prior to study treatment will not be evaluable for DLT based on platelet counts.
    For CLL patients only: Grade 3 anemia (based on the NCI-WG Grading Scale for Chronic Lymphocytic Leukemia (Hallek et al., *Blood*, 111: 5446-5456, 2008) that improves to Grade 2 within 1 week without RBC transfusion.
  Any Grade 3 non-hematologic adverse event not considered by the investigator to be attributable to another clearly identifiable cause, with the following exceptions:
    Grade 3 nausea or vomiting in the absence of premedication or that can be managed with resulting resolution to Grade≤2 with oral or IV anti-emetics within 24 hours. Grade 3 nausea or vomiting that requires total parenteral nutrition or hospitalization are not excluded and should be considered a DLT.
    Grade 3 fatigue lasting ≤3 days.
    Grade 3 (NCI CTCAE v4) individual signs and symptoms of CRS that occur in the context of Grade≤2 CRS (Table 5) and lasts <3 days will not be considered a DLT.

Grade 3 laboratory abnormality that is asymptomatic and deemed by the investigator not to be clinically significant.

Any hepatic function abnormality as defined by the following:

Aspartate transaminase (AST) or alanine aminotransferase (ALT)>3×the upper limit of normal (ULN) AND total bilirubin>2×ULN. Any AST or ALT 3×the ULN and total bilirubin>2×ULN where no individual laboratory value exceeds Grade 3 and lasts <3 days will not be considered a DLT.

Any Grade 3 AST or ALT elevation with the following exception: any Grade 3 AST or ALT elevation that lasts <3 days will not be considered a DLT.

Dose-Escalation Rules and Determination of the Maximum Tolerated Dose

Specific rules for Groups A, B, and E dose escalations are detailed below. Initiation of individual group dose escalations is at the Sponsor's discretion. Relevant demographic, AE, laboratory, dose administration, and available PK and pharmacodynamic data (e.g., serum cytokines and markers of T-cell activation) are reviewed prior to each dose-escalation decision.

Determination of whether a patient is evaluable for DLT assessment is made in accordance with the following rules:

Patients who receive study treatment and remain on study through the DLT assessment window are considered DLT-evaluable.

Patients who discontinue from treatment with single-agent mosunetuzumab or mosunetuzumab combined with atezolizumab prior to completing the DLT assessment window for reasons other than a DLT are considered non-evaluable for dose-escalation decisions and MTD determination and are replaced by an additional patient at that same dose level.

For patients enrolled into Group B only: patients who have dose delays exceeding 7 days following the scheduled C1D1, C1D8, or C1D15 dose for a non-DLT adverse event may be DLT unevaluable and may be replaced. For patients who have dose delays of 7 days or fewer, the DLT window will extend until 7 days following the actual C1D15 dose.

For patients in Group E only: if an enrolled patient experiences any treatment-emergent toxicity that does not completely resolve to baseline level prior to initiation of combination treatment in Cycle 2, that patient is considered unevaluable for dose-escalation decisions and MTD determination and is replaced by an additional patient at that same dose level and schedule.

Patients who receive supportive care during the DLT assessment window that confounds the evaluation of DLTs (not including supportive care described herein as part of the DLT definition) may be replaced.

On the basis of a review of real-time safety data and available preliminary PK data, dose escalation may be halted or modified as deemed appropriate.

To acquire additional safety and pharmacodynamic data to better fully inform the RP2D, additional patients may be enrolled at a dose level that has been shown to not exceed the MTD based on the dose-escalation criteria described above, and at which there is evidence of anti-tumor activity and/or pharmacodynamic biomarker modulation. Up to approximately three additional patients per dose level may be enrolled. For the purposes of dose-escalation decisions, these patients will not be included as part of the DLT-evaluable population.

C. Inclusion Criteria

Patients meet the following criteria for study entry:

Age≥18 years

Able to comply with the study protocol, in the investigator's judgment

Eastern Cooperative Oncology Group Performance Status of 0 or 1

Life expectancy of at least 12 weeks

History of one of the following histologically-documented hematologic malignancies that are expected to express the CD20 antigen who have relapsed after or failed to respond to at least one prior systemic treatment regimen and for whom there is no available therapy expected to improve survival (e.g., standard chemotherapy, autologous stem cell transplant (SCT), CAR-T):

Dose-escalation:
Grades 1-3b FL; marginal zone lymphoma (including splenic, nodal, and extra-nodal); transformed indolent NHL; Richter's transformation; DLBCL; primary mediastinal B-cell lymphoma; small lymphocytic lymphoma; or mantle cell lymphoma.

Dose-expansion:
DLBCL/transformed FL cohort: patients have relapsed after or failed to respond to at least two prior systemic treatment regimens (including at least one prior regimen containing anthracycline, and at least one containing an anti-CD20-directed therapy). The number of transformed FL patients enrolled in the study may be limited. Transformed FL is an eligible diagnosis for enrollment in the DLBCL cohort but are relapsed or refractory to standard therapies for transformed FL.

FL cohort: Grades 1, 2, 3a, or 3b FL; patients have relapsed after or failed to respond to at least two prior lines of systemic therapy and have received prior treatment with an anti-CD20-directed therapy and an alkylating agent. Patients in the FL expansion cohort may be refractory to both anti-CD20-directed therapy and an alkylating agent.

MCL cohort: patients have relapsed after or failed to respond to at least one prior treatment regimen containing an approved Bruton's tyrosine kinase (BTK) inhibitor. If BTK inhibitor was received during participation in a clinical trial, patients have received treatment at a therapeutic dose level.

Richter's transformation cohort: Patients have relapsed after or failed to respond to at least one prior systemic treatment regimen. Patients have received anthracycline and an anti-CD20-directed therapy in prior treatment regimen(s).

CLL:
A separate dose escalation may be initiated in CLL patients at the Sponsor's discretion after evidence of pharmacodynamic biomarker modulation and/or anti-tumor activity is observed in an NHL dose-escalation cohort in the absence of DLTs. CLL with Richter's transformation is an eligible diagnosis for enrollment in the CLL escalation cohorts.

NHL patients have at least one bi-dimensionally measurable lesion (>1.5 cm in its largest dimension for nodal lesions, or >1.0 cm in its largest dimension for extranodal lesions by computerized tomography (CT) scan or magnetic resonance imaging (MRI)).

For patients with DLBCL or transformed FL, the pathology report for the initial histopathology diagnosis is provided, if available. Patients with transformed FL also provide the pathology report at the time of disease transformation, if available. The results of all tests conducted on the tissue at initial diagnosis, including but not limited to tests assessing cell of origin, B-cell lymphoma 2 and MYC abnormalities, are provided if done.

Agreement to provide tumor samples as follows:

For NHL patients with more than one bi-dimensionally measurable lesion (>1.5 cm in the largest dimension for nodal lesions, or >1.0 cm in its largest dimension for extranodal lesions by CT scan or MRI), agreement to undergo biopsy from a safely accessible site per investigator determination. Biopsies obtained at any time between the last dose of last prior anti-cancer therapy and the first dose of mosunetuzumab may be acceptable.

For patients with CLL: bone marrow biopsy and aspirate.

Patients who are unable to undergo biopsy procedures may be eligible for study enrollment. In such cases archival tumor tissue samples (paraffin blocks or at least 15 unstained slides) should be made available.

Adverse events from prior anti-cancer therapy resolved to Grade 1.

CLL patients only: have a circulating lymphocyte count of >5000/μL blood. Measurable disease by CT scan is not required.

Laboratory values as follows:

Hepatic function
   AST and ALT≤3×the upper limit of normal (ULN)
   Total bilirubin≤1.5×ULN; patients with a documented history of Gilbert syndrome and in whom total bilirubin elevations are accompanied by elevated indirect bilirubin are eligible Hematologic function
   Platelet count≥75,000/mm³ without transfusion within 14 days prior to first dose of mosunetuzumab
   ANC≥1000/mm³
   Total hemoglobin 10 g/dL without transfusion within 21 days prior to first dose of mosunetuzumab.
   Patients who do not meet criteria for hematologic function because of extensive marrow involvement of NHL/CLL and/or disease-related cytopenias (e.g., immune thrombocytopenia) may be enrolled into the study.

Serum creatinine≤ULN or estimated creatinine CL≥60 mL/min by Cockcroft-Gault method or other institutional standard methods (e.g., based on nuclear medicine renal scan).

Patients treated with alemtuzumab, fludarabine, cladribine, or pentostatin within 6 months before first mosunetuzumab administration may be enrolled only after confirming with the Medical Monitor.

D. Exclusion Criteria

Patients who meet any of the following criteria are excluded from the study:

Inability to comply with protocol-mandated hospitalization and activities restrictions Pregnant or lactating, or intending to become pregnant during the study or within 3 months after the last dose of mosunetuzumab, and 3 months after the last dose of tocilizumab (if applicable)

Women who are not postmenopausal (12 months of non-therapy-induced amenorrhea) or surgically sterile (removal of ovaries and/or uterus) must have a negative serum pregnancy test result within 14 days prior to initiation of study drug.

If a serum pregnancy test has not been performed within 14 days prior to receiving first study treatment, a negative urine pregnancy test result (performed within 7 days prior to study treatment) must be available.

Prior use of any monoclonal antibody, radioimmunoconjugate or antibody-drug conjugate within 4 weeks before first mosunetuzumab administration Prior treatment with systemic immunotherapeutic agents for which the mechanism of action involves T cells, including but not limited to cytokine therapy and anti-CTLA-4, anti-PD-1 and anti-PD-L1 therapeutic antibodies, within 12 weeks or five half-lives of the drug, whichever is shorter, before first mosunetuzumab administration Treatment-emergent immune-related adverse events associated with prior immunotherapeutic agents (e.g., immune checkpoint inhibitor therapies) as follows:
   Grade≥3 adverse events with the exception of Grade 3 endocrinopathy managed with replacement therapy
   Grade 1-2 adverse events that did not resolve to baseline after treatment discontinuation
   For certain prior treatments, such as CAR-T cell therapies, patients with prior immune-related Grade 3 adverse events (e.g., CRS) may be allowed to enroll after discussion with and confirmation by the Medical Monitor.

Treatment with any chemotherapeutic agent, or treatment with any other anti-cancer agent (investigational or otherwise) within 4 weeks or five half-lives of the drug, whichever is shorter, prior to first mosunetuzumab administration Treatment with radiotherapy within 2 weeks prior to the first mosunetuzumab administration.

If patients have received radiotherapy within 4 weeks prior to the first mosunetuzumab administration, patients must have at least one measurable lesion outside of the radiation field. Patients who have only one measurable lesion that was previously irradiated but subsequently progressed are eligible.

Autologous SCT within 100 days prior to first mosunetuzumab administration

Prior treatment with CAR-T therapy within 30 days before first mosunetuzumab administration Current eligibility for autologous SCT in patients with R/R DLBCL or R/R transformed FL Prior allogeneic SCT Prior solid organ transplantation History of autoimmune disease, including but not limited to myocarditis, pneumonitis, myasthenia gravis, myositis, autoimmune hepatitis, systemic lupus erythematosus, rheumatoid arthritis, inflammatory bowel disease, vascular thrombosis associated with antiphospholipid syndrome, Wegener's granulomatosis, Sjögren's syndrome, Guillain-Barré syndrome, multiple sclerosis, vasculitis, or glomerulonephritis Patients with a remote history of, or well-controlled autoimmune disease, may be eligible to enroll after discussion with and confirmation by the Medical Monitor. Patients with controlled Type 1 diabetes mellitus who are on an insulin regimen are eligible for the study.

Patients with a history of autoimmune-related hypothyroidism on a stable dose of thyroid replacement hormone may be eligible for this study.

Patients with a history of disease-related immune thrombocytopenic purpura or autoimmune hemolytic anemia may be eligible for this study.

Patients with eczema, psoriasis, lichen simplex chronicus, or vitiligo with dermatologic manifestations only (e.g., patients with psoriatic arthritis are excluded) are eligible for the study provided all of following conditions are met:

Rash must cover <10% of body surface area
Disease is well controlled at baseline and requires only low-potency topical corticosteroids No occurrence of acute exacerbations of the underlying condition requiring psoralen plus ultraviolet A radiation, methotrexate, retinoids, biologic agents, oral calcineurin inhibitors, or high potency or oral corticosteroids within the previous 12 months Patients with history of macrophage activation syndrome (MAS)/hemophagocytic lymphohistiocytosis (HLH)

Patients with history of confirmed progressive multifocal leukoencephalopathy

History of severe allergic or anaphylactic reactions to monoclonal antibody therapy (or recombinant antibody-related fusion proteins)

History of other malignancy that could affect compliance with the protocol or interpretation of results Patients with a history of curatively treated basal or squamous cell carcinoma of the skin or in situ carcinoma of the cervix are allowed.

Patients with a malignancy that has been treated with curative intent will also be allowed if the malignancy has been in remission without treatment for ≥2 years prior to first mosunetuzumab administration.

Current or past history of CNS lymphoma
Current or past history of CNS disease, such as stroke, epilepsy, CNS vasculitis, or neurodegenerative disease Patients with a history of stroke who have not experienced a stroke or transient ischemic attack in the past 2 years and have no residual neurologic deficits as judged by the investigator are allowed.

Patients with a history of epilepsy who have had no seizures in the past 2 years while not receiving any anti-epileptic medications are allowed in the expansion cohorts only.

Significant cardiovascular disease such as New York Heart Association Class III or IV cardiac disease, myocardial infarction within the last 6 months, unstable arrhythmias, or unstable angina)

Significant active pulmonary disease (e.g., bronchospasm and/or obstructive pulmonary disease)

Known active bacterial, viral, fungal, mycobacterial, parasitic, or other infection (excluding fungal infections of nail beds) at study enrollment, or any major episode of infection requiring treatment with IV antibiotics or hospitalization (relating to the completion of the course of antibiotics) within 4 weeks prior to first mosunetuzumab administration Known or suspected chronic active Epstein Barr Virus infection Recent major surgery within 4 weeks prior to first mosunetuzumab administration Protocol-mandated procedures (e.g., tumor biopsies and bone marrow biopsies) are permitted.

Positive serologic or polymerase chain reaction (PCR) test results for acute or chronic hepatitis B virus (HBV) infection Patients whose HBV infection status cannot be determined by serologic test results (cdc.gov) must be negative for HBV by PCR to be eligible for study participation. Acute or chronic hepatitis C virus (HCV) infection Patients who are positive for HCV antibody must be negative for HCV by PCR to be eligible for study participation.

Positive serologic test results for HIV infection
Administration of a live, attenuated vaccine within 4 weeks before first dose of study treatment or anticipation that such a live attenuated vaccine will be required during the study Patients must not receive live, attenuated vaccines (e.g., FluMist®) while receiving study treatment or after the last dose until B-cell recovery to the normal ranges. Killed vaccines or toxoids should be given at least 4 weeks prior to the first dose of study treatment to allow development of sufficient immunity.

Inactivated influenza vaccination should be given during influenza season only.

Investigators should review the vaccination status of potential study patients being considered for this study and follow the U.S. Centers for Disease Control and Prevention guidelines for adult vaccination with any other non-live vaccines intended to prevent infectious diseases prior to study.

Drug Products

Mosunetuzumab

Flat dosing independent of body weight is used for mosunetuzumab. The dose of mosunetuzumab for each patient will depend on the dose level assignment as detailed in the protocol.

Mosunetuzumab is administered to patients either by IV infusion using standard medical syringes and syringe pumps or IV bags where applicable. Compatibility testing has shown that mosunetuzumab is stable in extension sets and polypropylene syringes. When administered IV, the Drug Product is delivered by syringe pump via an IV infusion set or IV bag with a final mosunetuzumab volume determined by the dose.

Mosunetuzumab is administered in a setting with immediate access to trained critical care personnel and facilities equipped to respond to and manage medical emergencies.

Mosunetuzumab is administered to well-hydrated patients. Corticosteroid premedication consisting of dexamethasone 20 mg IV or methylprednisolone 80 mg IV is administered 1 hour prior to the administration of each mosunetuzumab dose. This administration of corticosteroid premedication may be optional for Cycle 3 and beyond for patients in Group B or for Cycle 4 and beyond for patients in Group E based on investigator's assessment. However, if the patient experiences CRS, premedication with steroids is administered for the subsequent doses until no additional CRS events are observed. In addition, premedication with oral acetaminophen or paracetamol (e.g., 500-1000 mg) and/or 50-100 mg diphenhydramine may be administered per standard institutional practice prior to administration of mosunetuzumab. Decisions to modify the requirement for corticosteroid premedication will be made based on the recommendation of the IMC.

The recommended management of CRS is detailed in Table 7.

TABLE 7

Management of cytokine release syndrome for patients receiving mosunetuzumab

| CRS Grade | Action with Current Mosunetuzumab Infusion | Supportive Care | Anti-IL-6/Corticosteroid Therapy | Action for Next Mosunetuzumab Dose |
|---|---|---|---|---|
| Grade 1 Symptoms not life-threatening and require symptomatic treatment only | Slow infusion to 50% or interrupt infusion until symptoms resolve; re-start at same rate. If symptoms recur with rechallenge, interrupt study treatment, do not resume, and manage per Grade 2. | Symptomatic management of constitutional symptoms. Consider empiric broad-spectrum antibiotics. Consider G-CSF if neutropenic. Maintenance IV fluids for hydration. Consider hospitalization until symptoms completely resolve. | For prolonged CRS (>2 days) in patients with significant symptoms and/or comorbidities (per investigator discretion, e.g., impaired cardiovascular function, reduced pulmonary reserve), consider tocilizumab and corticosteroids as per Grade 2. | Administer premedications for next dose. Consider 50% (or lower) rate of infusion for next step-up dose in Cycle 1 or 50% rate of infusion if next dose is same dose level (beyond Cycle 1). Consider hospitalization for next dose |
| Grade 2 Symptoms require and respond to moderate intervention $O_2$ requirement < 40% OR hypotension responsive to fluids or low dose of one vasopressor OR Grade 2 organ toxicity | Hold further study treatment until symptoms resolved; consider re-starting infusion at 50% rate. If symptoms recur with rechallenge at decreased infusion rate, interrupt study treatment, do not resume, and manage per Grade 3. | Symptomatic management of constitutional symptoms and organ toxicities. Consider ICU admission for hemodynamic monitoring, For hypotension: IV fluid bolus as needed; for persistent refractory hypotension (e.g., after two fluid boluses and anti-IL-6 therapy), start vasopressors and manage per Grade 3. Rule out other inflammatory conditions which can mimic severe CRS (e.g., infections/sepsis). Consider empiric broad-spectrum antibiotics. If no improvement within 24 hours, initiate work up and assess for signs and symptoms of HLH. | Consider tocilizumab. For persistent refractory hypotension after 1-2 doses of anti-IL-6 therapy, consider dexamethasone 10 mg IV every 6 hours (or equivalent), Manage per Grade 3 if no improvement within 24 hours after starting tocilizumab. | May receive the next dose of mosunetuzumab if symptoms resolve to Grade ≤ 1 for 3 consecutive days with approval of Medical Monitor. Consider enhanced premedications for next dose. Consider 50% (or lower) rate of infusion for next step-up dose in Cycle 1 or 50% rate of infusion if next dose is same dose level (beyond Cycle 1). Consider hospitalization for next dose. |
| Grade 3 Symptoms require and respond to aggressive intervention $O_2$ requirement ≥ 40% OR hypotension requiring high dose or multiple vasopressors OR Grade 3 organ toxicity OR Grade 4 transaminitis | Stop infusion, do not resume. | Symptomatic management of organ toxicities, admit to ICU for hemodynamic monitoring. For hypotension: IV fluid bolus and vasopressors as needed. Rule out other inflammatory conditions which can mimic severe CRS (e.g., infections/sepsis), Consider empiric broad-spectrum antibiotics. If no improvement within 24 hours, initiate work up and assess for signs and symptoms of HLH. | Administer tocilizumab. Dexamethasone 10 mg IV every 6 hours (or equivalent). If refractory, manage as per Grade 4. Manage per Grade 4 if no improvement within 18-24 hours after second dose of tocilizumab. | May receive the next dose of mosunetuzumab if CRS event was responsive to treatment (i.e., clinical improvement within 8-12 hours following tocilizumab/corticosteroids administration) and symptoms resolve to Grade ≤_1 for 3 consecutive days with approval of Medical Monitor: Enhanced premedications for next dose Decrease to 50% (or lower) rate of infusion for next step-up dose in Cycle 1, or 50% rate of infusion if next dose is same dose level (beyond Cycle 1) Hospitalization for next dose The next dose should be reduced to the next lower dose level that has been previously cleared during dose escalation. Subsequent doses may not be re-escalated with signs/symptoms of Grade 3 or higher CRS at the reduced dose. |

TABLE 7-continued

Management of cytokine release syndrome for patients receiving mosunetuzumab

| CRS Grade | Action with Current Mosunetuzumab Infusion | Supportive Care | Anti-IL-6/Corticosteroid Therapy | Action for Next Mosunetuzumab Dose |
|---|---|---|---|---|
| Grade 4 Life-threatening symptoms Requirement for ventilator support OR Grade 4 organ toxicity (excluding transaminitis) | Stop infusion, do not resume. | ICU admission and hemodynamic monitoring. Mechanical ventilation as needed. IV fluids and vasopressors as needed. Symptomatic management of organ toxicities. Rule out other inflammatory conditions methylprednisolone which can mimic severe CRS (e.g., Infections/sepsis) Consider empiric broad-spectrum antibiotics. If no improvement within 24 hours, initiate work up and assess for signs and symptoms of HLH. | Administer tocilizumab. For patients refractory to tocilizumab, consider siltuximab, anakinra, and emapalumab, based on discretion of the investigator. Dexamethasone 10 mg IV every 6 hours (or equivalent). If refractory, consider 1000 mg/day IV. | If the reduced dose is tolerated with no signs/symptoms of Grade 3 or higher CRS, the patient may return to the next higher dose that has been previously cleared during dose escalation. If Grade 3 CRS recurs with subsequent doses, permanently discontinue mosunetuzumab. Permanently discontinue mosunetuzumab. |

BiPAP = bilevel positive airway pressure; CPAP = continuous positive airway pressure; CRS = cytokine release syndrome; G-CSF = granulocyte colony stimulating factor; HLH = hemophagocytic lymphohistiocytosis.

CRS grading per Lee et al., *Blood,* 124: 188-195, 2014.

Tocilizumab should be administered at a dose of 8 mg/kg IV (8 mg/kg for participants at a weight of ≥30 kg only; 12 mg/kg for participants at a weight of <30 kg; doses exceeding 800 mg per infusion are not recommended); repeat every 8 hours as necessary (up to a maximum of 4 doses).

Antifungal prophylaxis should be strongly considered in patients receiving steroids for treatment of CRS.

For example, methylprednisolone IV 1000 mg/day for 3 days, followed by rapid taper at 250 mg every 12 hours for 2 days, 125 mg every 13 hours for 2 days, and 60 mg every 12 hours for 2 days.

If Grade 3 CRS occurs in the step-up dosing cohorts following mosunetuzumab administration at Cycle 1 Day 1 or Cycle 1 Day 8, the next mosunetuzumab dose should be discussed with the Medical Monitor and a dose reduction should be considered. Exceptions may be considered to repeat the same step-up dose based on individual risk-benefit assessment.

Resumption of mosunetuzumab may be considered in patients who are deriving benefit and have fully recovered from the adverse event. Patients can be re-challenged with mosunetuzumab only after approval has been documented by both the investigator (or an appropriate delegate) and the Medical Monitor. Further treatment will not be considered unless all the criteria below are met:

Individual risk-benefit assessment by principal investigator/treating physician favors continued treatment;

The patient has recovered from previous toxicities and has sufficient organ function/reserve to receive subsequent doses;

The patient has been adequately consented for risks associated with continued treatment and decides to receive subsequent doses;

The above risk-benefit assessment and evaluation of patient's are discussed with the Sponsor;

Subsequent doses are well planned with precautionary measures, including dose reduction, slow infusion rate at 50% or lower, mandatory hospitalizations, and enhanced premedications.

For IV mosunetuzumab administration, initially, mosunetuzumab is infused over 4 hours±15 minutes. The infusion may be slowed or interrupted for patients experiencing infusion-associated symptoms. Following each mosunetuzumab dose, patients are observed at least 90 minutes for fever, chills, rigors, hypotension, nausea, or other signs and symptoms of CRS. In the absence of infusion related adverse events, the infusion time of mosunetuzumab in Cycle 2 and beyond may be reduced to 2 hours±15 minutes. Patients who undergo intra-patient dose escalation should receive the first higher infusion of mosunetuzumab over a minimum of 4 hours. Table 8 below lists management guidelines for handling injection-site reactions.

TABLE 8

Management guidelines for injection-site reactions

| Grade | Management |
|---|---|
| Grade 1 | Consider treatment with topical steroids. Continue mosunetuzumab in subsequent cycles. |
| Grade 2 | Initiate treatment with topical steroids. If progressive after 24 hours, consider prednisone or equivalent 10-30 mg/day. Continue mosunetuzumab in subsequent cycles after improvement to Grade ≤ 1. |
| Grade 3 | Withhold mosunetuzumab. Initiate prednisone 1 mg/kg/day or equivalent. Consult dermatology. Taper steroids after improvement to Grade ≤ 1. Continue mosunetuzumab in subsequent cycles after improvement to Grade ≤ 1. |
| Grade 4 | Management as for Grade 3. Permanently discontinue SC mosunetuzumab. Consider continuing study treatment with IV mosunetuzumab with approval by Medical Monitor. |

Atezolizumab and Tocilizumab

The dose level of atezolizumab in this study is 1200 mg administered by IV infusion on Day 1 of Cycle 2 and on Day 1 of each subsequent 21-day cycle.

Tocilizumab is formulated, prepared, and handled according to standard practice.

Mosunetuzumab in Combination with Atezolizumab Dosage, Administration, and Compliance When mosunetuzumab is given in combination with atezolizumab, mosunetuzumab should be administered as described above. The atezolizumab infusion should begin at least 1 hour after the completion of the mosunetuzumab infusion. The dose level of atezolizumab in this study is 1200 mg administered by IV infusion on Day 1 of Cycle 2 and on Day 1 of each subsequent 21-day (Q3W).

Initially, mosunetuzumab is infused over 4 hours±15 minutes when given in combination with atezolizumab in Cycle 2. Beginning in Cycle 3, in the absence of infusion-related adverse events, the infusion time of mosunetuzumab may be reduced to 2 hours±15 minutes.

Administration of atezolizumab is performed in a monitored setting where there is immediate access to trained personnel and adequate equipment and medicine to manage potentially serious reactions. Atezolizumab infusions are administered per the instructions outlined in Table 9.

TABLE 9

Administration of first and subsequent atezolizumab infusions

| First Infusion | Subsequent Infusions |
|---|---|
| No premedication is permitted prior to the atezolizumab infusion. Vital signs (pulse rate, respiratory rate, blood pressure, and temperature) should be recorded within 60 minutes prior to the infusion. Atezolizumab should be infused over 60 minutes (±15). If clinically indicated, vital signs should be recorded during the infusion at 15, 30, 45, and 60 minutes (±5 minutes for all timepoints) during the infusion and at 30 (±10) minutes after the infusion. Patients should be informed about the possibility of delayed post-infusion symptoms and instructed to contact their study physician if they develop such symptoms. | If the patient experienced an IRR with any previous infusion, premedication with antihistamines, antipyretics, and/or analgesics may be administered for subsequent doses at the discretion of the investigator. Vital signs should be recorded within 60 minutes prior to the infusion. Atezolizumab should be infused over 30 minutes (±10) if the previous infusion was tolerated without an IRR, or 60 minutes (±15) if the patient experienced an IRR with the previous infusion. If the patient experienced an IRR with the previous infusion or if clinically indicated, vital signs should be recorded during the infusion at 15, 30, 45, and 60 minutes (±5) for all timepoints during the infusion and at 30 minutes (±5) after the infusion. |

IRR = infusion-related reaction.

Guidelines for the management of specific adverse events are provided below. Guidelines for treatment interruption or discontinuation are provided in below. No dose modification for atezolizumab is allowed.

E. Concomitant Therapy

Concomitant therapy includes any medication (e.g., prescription drugs, over-the-counter drugs, herbal or homeopathic remedies, nutritional supplements) used by a patient from 7 days prior to screening to the study completion/discontinuation visit.

Patients who use oral contraceptives, hormone-replacement therapy, or other maintenance therapy should continue their use.

Concomitant use of hematopoietic growth factors such as erythropoietin, granulocyte/macrophage colony-stimulating factor (sargramostim), or thrombopoietin (oprelvekin, eltrombopag) should not be initiated or increased in dose from the start of the screening period until the completion of the DLT assessment period in the absence of a DLT. After the DLT assessment period has been completed or after a DLT has been documented, initiation or dose and schedule modifications of hematopoietic growth factors is allowed in accordance with instructions provided in the package inserts, institutional practice and/or published guidelines.

Prophylactic and therapeutic use of G-CSF (filgrastim, pegfilgrastim) is allowed in accordance with instructions provided in the package inserts, institutional practice, and/or published guidelines (Smith et al., 2015). Growth factor support should be started when absolute neutrophil count (ANC) is <500/mm$^3$, unless medically contraindicated; if growth factor is contraindicated, this should be discussed with the Medical Monitor.

Anti-infective prophylaxis for viral, fungal, bacterial or *pneumocystis* infections is permitted and should be instituted per institutional practice.

Patients who experience mosunetuzumab infusion-related symptoms may be treated symptomatically as described herein. Treatment of severe CRS or HLH according to published recommendations and/or institutional practice is permitted.

Given the expected pharmacology of mosunetuzumab, the transient release of cytokines may suppress CYP450 enzymes and cause drug-drug interactions. Based on nonclinical models, cytokine levels are likely to be highest during the first 24 hours of the first cycle. During subsequent cycles, with decreasing number of CD20+ cells, it is anticipated that the cytokine levels will be substantially reduced. Patients may be of highest risk of a drug-drug interaction are those receiving concomitant medications that are CYP450 substrates and have a narrow therapeutic index (Table 10). Such concomitant medications should be monitored for toxicity, and dose adjusted accordingly.

TABLE 10

Examples of sensitive in vivo CYP substrates and CYP substrates with narrow therapeutic range

| CYP Enzymes | Sensitive Substrates | Substrates With Narrow Therapeutic Range |
|---|---|---|
| CYP1A2 | Alosetron, caffeine, duloxetine, melatonin, ramelteon, tacrine, tizanidine | Theophylline, tizanidine |
| CYP2B6 | Bupropion, efavirenz | |
| CYP2C8 | Repaglinide | Paclitaxel |
| CYP2C9 | Celecoxib | Warfarin, phenytoin |
| CYP2C19 | Lansoprazole, omeprazole, S-mephenytoin | S-mephenytoin |
| CYP3A | Alfentanil, aprepitant, budesonide, buspirone, conivaptan, darifenacin, darunavir, dasatinib, dronedarone, eletriptan, eplerenone, everolimus, felodipine, indinavir, fluticasone, lopinavir, lovastatin, lurasidone, maraviroc, midazolam, nisoldipine, quetiapine, saquinavir, sildenafil, simvastatin, sirolimus, tolvaptan, tipranavir, triazolam, vardenafil | Alfentanil, astemizole, cisapride, cyclosporine, dihydroergotamine, ergotamine, fentanyl, pimozide, quinidine, sirolimus, tacrolimus, terfenadine |
| CYP2D6 | Atomoxetine, desipramine, dextromethorphan, metoprolol, nebivolol, perphenazine, tolterodine, venlafaxine | Thioridazine |

AUC = area under the concentration-time curve; P-g = P-glycoprotein.

Sensitive CYP substrates refer to drugs whose plasma AUC values have been shown to increase 5-fold or higher when co-administered with a known CYP inhibitor.

CYP substrates with narrow therapeutic range refers to drugs whose exposure-response relationship indicates that small increases in their exposure levels by the concomitant use of CYP inhibitors may lead to serious safety concerns (e.g., Torsades de Pointes).

The AUC of these substrates were not increased by 5-fold or more with a CYP2B6 inhibitor, but they represent the most sensitive substrates studied with available inhibitors evaluated to date.

Repaglinide is also a substrate for OATP1 B1, and it is only suitable as a CYP2C8 substrate if the inhibition of OATP1 B1 by the investigational drug has been ruled out.

Because a number of CYP3A substrates (e.g., darunavir, maraviroc) are also substrates of P-gp, the observed increase in exposure could be due to inhibition of both CYP3A and P-gp.

CYP450 enzymes in the liver are down-regulated by infection and inflammatory stimuli, including cytokines such as IL-6. Inhibition of IL-6 signaling in patients with rheumatoid arthritis who are treated with tocilizumab may restore CYP450 activities to higher levels than those patients not treated with tocilizumab, leading to increased metabolism of drugs that are CYP450 substrates. In vitro studies showed that tocilizumab has the potential to affect expression of multiple CYP enzymes, including CYP1A2, CY2B6, CYP2C9, CYP2C19, CYP2D6, and CYP3A4. The effects of tocilizumab on CYP2C8 or transporters are unknown. In vivo studies with omeprazole (metabolized by CYP2C19 and CYP3A4) and simvastatin (metabolized by CYP3A4) showed up to a 28% and 57% decrease in exposure 1 week following a single dose of tocilizumab, respectively.

The effect of tocilizumab on CYP enzymes may be clinically relevant for CYP450 substrates with narrow therapeutic index (Table 10), where the dose is individually adjusted:

Upon initiation or discontinuation of tocilizumab in patients being treated with these types of medicinal products, therapeutic monitoring of effect (e.g., warfarin) or drug concentration (e.g., cyclosporine or theophylline) should be performed and the individual dose of the medicinal product adjusted as needed.

Prescribers should exercise caution when tocilizumab is coadministered with CYP3A4 substrate drugs where a decrease in effectiveness is undesirable (e.g., oral contraceptives, lovastatin, atorvastatin).

The effect of tocilizumab on CYP450 enzyme activity may persist for several weeks after stopping therapy.

F. Rationale for Using a Modified Grading Scale for CRS

In this study, grading and treatment of the adverse event of CRS arising from mosunetuzumab treatment is based on published criteria of Lee et al., Blood, 124: 188-195, 2014 and is described in Table 5. For dose-escalation decisions, DLTs related to CRS are defined based on individual signs and symptoms and laboratory data according to NCI CTCAE v4.0.

The NCI CTCAE v4.0 CRS grading scale was based on characterizations of CRS following treatment with monoclonal antibodies (Lee et al., Blood, 124: 188-195, 2014). T-cell directed therapies, including bispecifics such as mosunetuzumab and adoptive cell therapies such as engineered T-cells expressing CARs, result in pharmacodynamic profiles of cytokine release from T-cell activation distinct from those associated with conventional monoclonal antibodies. Consequently, the clinical features of CRS as defined by NCI CTCAE v4.0 may not be applicable to those following T-cell directed therapy.

Several alternate grading scales have been proposed and published which are specifically geared toward evaluation of CRS for T-directed therapies (Davila et al., Sci Transl Med, 6:224ra25, 2014; Lee et al., Blood, 124: 188-195, 2014; Porter et al., Sci Transl Med, 7: 303ra139, 2015). The grading system of Lee et al., is based on CRS arising from treatment with CD19 directed CAR-T cell and blinatumomab. It is a modification of NCI CTCAE v4.0, which provides further diagnostic detail including accounting for transient elevations in liver transaminases that may occur in the setting of CRS. In addition to diagnostic criteria, recommendations on management of CRS based on its severity, including early intervention with corticosteroids and/or anti-cytokine therapy, are provided and referenced in Example 8C. Incorporation of the CRS grading scale therefore allows for alignment between reporting and management guidelines that have been published and widely adopted.

G. Outcome Measures

Safety Outcome Measures

The safety and tolerability of mosunetuzumab are assessed using the following primary safety outcome measures:
   Incidence and nature of DLTs when mosunetuzumab is given as a single agent IV or SC.
   Incidence and nature of DLTs when mosunetuzumab is given in combination with atezolizumab.

Safety and tolerability are additionally assessed using the following secondary safety outcome measures:
   Incidence, nature, and severity of adverse events (AEs).
   Incidence of anti-drug antibodies (ADAs) against mosunetuzumab and atezolizumab, and their relationship to clinical outcomes.
   Changes in vital signs and clinical laboratory values.

Pharmacokinetic Outcome Measures

The following PK parameters are derived from the serum concentration-time profiles of mosunetuzumab following administration, when appropriate as data allow:

Total exposure (area under the concentration-time curve [AUC])

Maximum serum concentration (Cmax)

Minimum serum concentration (Cmin)

Clearance (CL)

Volume of distribution at steady state (Vss).

Serum trough and maximum concentrations for atezolizumab and tocilizumab, where applicable, are summarized, as appropriate and as data allow. Compartmental, non-compartmental, and/or population methods may be considered. Other parameters, such as accumulation ratio, t½, and dose proportionality, may also be calculated.

Activity Outcome Measures

The activity outcome measures for this study are as follows:

- Investigator-assessed objective response, defined as a partial response (PR) or complete response (CR), as assessed by the investigator using standard criteria for NHL (Cheson et al., *J Clin Oncol*, 25: 579-586 2007) and CLL (Hallek et al., *Blood*, 111: 5446-5456, 2008).
- Investigator-assessed duration of objective response, defined as the first occurrence of a documented, objective response until the time of disease progression or relapse as assessed by the investigator, or death from any cause, whichever occurs first.
- Investigator-assessed PFS, defined as the time from the first study treatment to the first occurrence of disease progression as assessed by the investigator, or death from any cause, whichever occurs first.

Additional activity outcome measures in the Group B and Group E R/R DLBCL and transformed FL expansion cohorts, and R/R FL expansion cohorts, are as follows:

- Objective response by an Independent review facility (IRF), defined as a PR or CR, as assessed by an IRF using standard criteria for NHL (Cheson et al., *J Clin Oncol*, 25: 579-586 2007).
- IRF-assessed duration of objective response, defined as the first occurrence of a documented, objective response until the time of disease progression or relapse as assessed by an IRF, or death from any cause, whichever occurs first.
- IRF-assessed duration of CR, defined as the first occurrence of a documented CR until the time of disease progression or relapse as assessed by an IRF, or death from any cause, whichever occurs first.
- Investigator-assessed duration of CR, defined as the first occurrence of a documented CR until the time of disease progression or relapse as assessed by the investigator, or death from any cause, whichever occurs first.
- IRF-assessed PFS, defined as the time from the first study treatment to the first occurrence of disease progression as assessed by an IRF or death from any cause, whichever occurs first.
- OS, defined as the time from the first study treatment to the date of death from any cause.

Patient-Reported Outcome Measures

The health-related quality of life (HRQoL) and health status measures that are used in NHL expansion cohorts to evaluate patient-reported outcomes (PROs) are as follows:

- Summary statistics and change from baseline in HRQoL based on the European Organization for Research and Treatment of Cancer Quality of Life Questionnaire Core 30 (EORTC QLQ-C30).
- Summary statistics and change from baseline in disease-related symptoms based on the Functional Assessment of Cancer Therapy-Lymphoma (FACT-Lym) subscale.
- Descriptive results of the EQ-5D-5L data during patients' participation in the study.

Example 3. Study Design

Group A: Cycle 1 Non-Fractionated, Single-Agent Mosunetuzumab Escalation (IV Infusion)

Patients enrolled into dose-escalation Group A of the GO29781 study receive mosunetuzumab by IV infusion on Day 1 of each 21-day cycle. Mosunetuzumab administration should occur on Day 1 of each cycle, but may be given up to ±2 days from scheduled date (i.e., with a minimum of 19 days between doses) for logistic/scheduling reasons.

The starting dose of mosunetuzumab in Group A is 50 µg based on MABEL. Dose escalation depends on clinical observations during the DLT assessment window.

Group A dose escalation continues until a dose level is reached that is no higher than approximately 12.8 mg or a dose level where DLTs were observed in 17% of 6 patients is reached, whichever is lower.

Based on the cumulative safety data, and to prioritize assessment of Cycle 1 step-up dosing to mitigate cytokine-driven toxicities, enrollment into dose-escalation Group A has stopped, and subsequent patients treated with single-agent mosunetuzumab will be enrolled into dose-escalation Group B.

Group B: Cycle 1 Step-Up, Single-Agent Mosunetuzumab Escalation (IV Infusion)

Patients enrolled in dose-escalation Group B of the GO29781 study receive mosunetuzumab by IV infusion on Days 1, 8, and 15 of Cycle 1. In Cycle 2 and beyond, mosunetuzumab is given on Day 1 of each 21-day cycle, with Day 1 of Cycle 2 being 7 days after the Cycle 1, Day 15 dose. Mosunetuzumab may be given up to ±1 day from the scheduled date for Cycle 2 (i.e., with a minimum of 6 days after Cycle 1 Day 15 dosing), and ±2 days from the scheduled date for Cycle 3 and beyond (i.e., with a minimum of 19 days between doses) for logistic/scheduling reasons.

The cumulative starting Group B Cycle 1 dose is 50% greater than the highest cleared Group A Cycle 1 dose level. The starting Cycle 1 Day 1, Day 8, and Day 15 dose levels are based on the highest cleared Cycle 1 dose assessed in Group A dose escalation and are specified in Table 11, with the starting Cycle 1, Day 15 dose corresponding to the highest cleared Group A Cycle 1 dose. The Cycle 1, Day 15 dose is the dose level administered on Day 1 of subsequent cycle (Cycle 2 and beyond).

Figure 5:
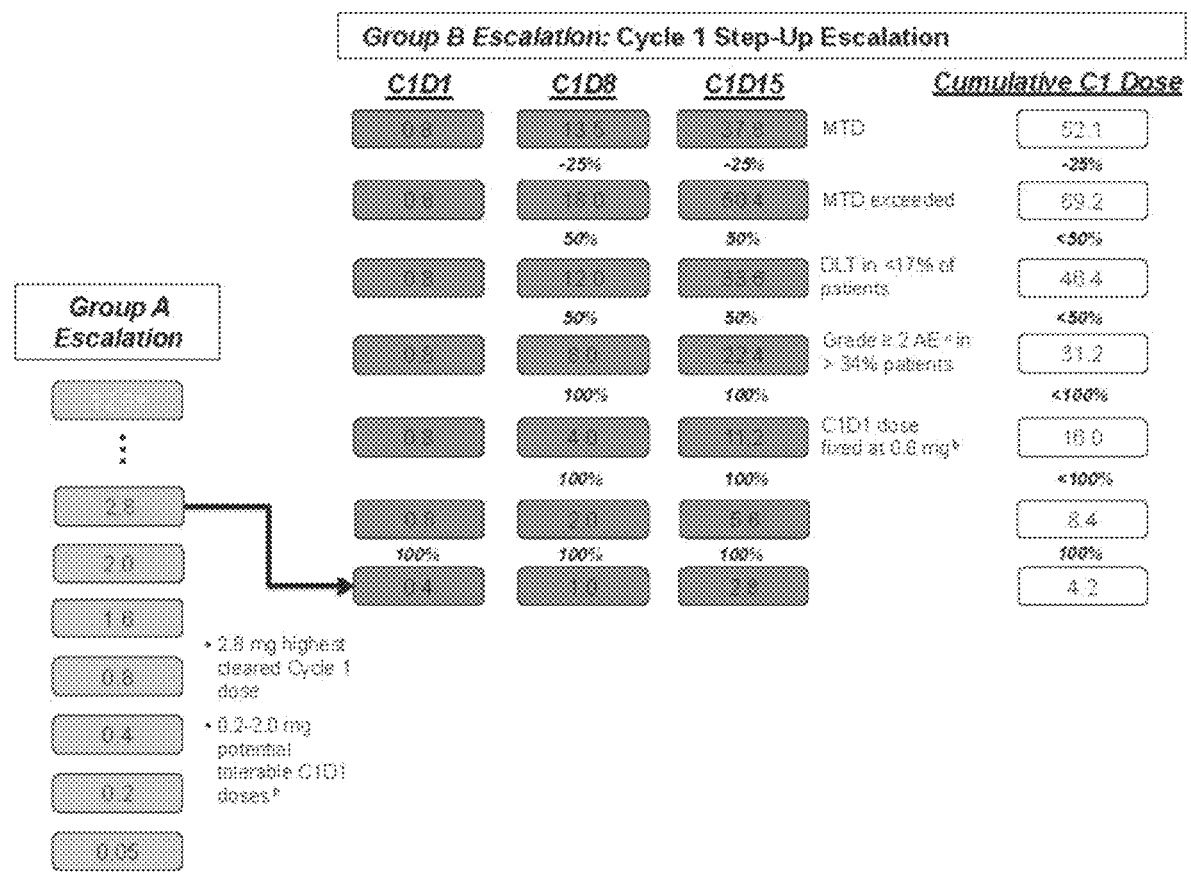
FIG. 5 is a schematic diagram showing an exemplary dose escalation progression for Group B of the GO29781 study. Doses listed are for illustrative purposes only. AE=adverse event; DLT=dose-limiting toxicity; HLH=hemophagocytic lymphohistiocytosis; MTD=maximum tolerated dose. Dose levels are in milligrams (mg). $^a$Protocol permits Group A escalation to a maximum of 12.8 mg; shown here is where 2.8 mg is the highest cleared C1 dose in Group A. $^b$Criteria for determination of the C1D1 dose are provided in the Examples. $^c$Adverse events associated with identified or potential risks of mosunetuzumab, e.g., cytokine release syndrome (CRS), HLH, neurologic toxicity, tumor lysis syndrome (TLS), neutropenia, thrombocytopenia, and elevated liver enzymes.

Dose escalation in Group B uses a standard 3+3 design. An example of a Group B dose-escalation progression is illustrated in FIG. 5. Doses listed in the figure are for illustrative purposes only. Starting Cycle 1 dose levels and subsequent adjustments to the doses of mosunetuzumab administered on Days 1, 8, and 15 of Cycle 1 are made in accordance to the rules described below (see also FIGS. 6A and 6B and Tables 12 and 13). On the basis of review of real-time safety data and preliminary PK data, dose escalation may be halted or modified as deemed appropriate. Dose escalation increments up to 100% of the preceding dose level may be recommended by the IMC based on review of the totality of data in dose escalation and expansion.

TABLE 11

Mosunetuzumab dose escalation: starting dose levels for step-up escalation (Group B)

| | Group B | | | | |
|---|---|---|---|---|---|
| Group A: Highest cleared C1 dose (mg) | Starting cumulative C1 dose (mg) | Starting Cycle 1, Day 1 dose (mg) | Starting Cycle 1, Day 8 dose (mg) | Starting Cycle 1, Day 15 dose (mg) | Starting Day 1 dose of C2 and beyond (mg) |
| 1.2 | 1.8 | 0.2 | 0.4 | 1.2 | 1.2 |
| 1.6 | 2.4 | 0.4 | 0.4 | 1.6 | 1.6 |
| 2.0 | 3.0 | 0.4 | 0.6 | 2.0 | 2.0 |
| 2.4 | 3.6 | 0.4 | 0.8 | 2.4 | 2.4 |
| 2.8 | 4.2 | 0.4 | 1.0 | 2.8 | 2.8 |
| 3.2 | 4.8 | 0.4 | 1.2 | 3.2 | 3.2 |
| 3.6 | 5.4 | 0.4 | 1.4 | 3.6 | 3.6 |

C = cycle; D = day.

Criteria for the determination of the Cycle 1, Day 1 dose are provided herein. The Cycle 1, Day 15 dose level is the dose level administered on Day 1 of Cycles 2 and beyond.

TABLE 12

Dose escalation rules for Cycle 1 step-up mosunetuzumab escalation, IV Infusion (Group B): DLT observed in < 17% of ≥ 3 DLT-evaluable patients in a given cohort

| Safety event | Timing of safety event | Cumulative C1 dose escalation | C1D1 dose escalation | C1D8 dose escalation | C1D15 dose escalation |
|---|---|---|---|---|---|
| Grade ≥ 2 non-DLT AE in ≤ 34% of ≥ 3 DLT-evaluable patients and no DLT | Any time during the DLT assessment period (Window A-Window C) | Cumulative C1 dose escalation increment ≤ 100% of previous cumulative C1 dose | If not previously fixed, continue dose escalation with increment ≤ 100% of previous C1D1 dose | Continue dose escalation with increment of ≤ 100% of previous C1D8 dose | Continue dose escalation with increment of ≤ 100% of previous C1D15 dose |
| Grade ≥ 2 non-DLT AE in > 34% of ≥ 3 DLT-evaluable patients or DLT in < 17% of ≥ 6 DLT-evaluable patients | If > 1 Grade ≥ 2 non-DLT AE occurs during Window A | Cumulative C1 dose escalation increment decreased to ≤ 50% of previous cumulative C1 dose | If not previously fixed, in subsequent cohorts C1D1 dose may be fixed at a previously tested C1D1 dose without safety event | Continue C1D8 dose escalation with increment ≤ 50% of previous C1D8 dose | Continue C1D15 dose escalation with increment ≤ 50% of previous C1D15 dose |
| | If ≤ 1 Grade ≥ 2 non-DLT AE occurs during Window A | | If not previously fixed, continue C1D1 dose escalation increment ≤ 50% of previous C1D1 dose | | |

AE = adverse event; C = cycle; D = day.

Dose adjustments are made on a per cohort basis.

Adverse events associated with potential risks of mosunetuzumab, e.g., CRS, HLH, elevated liver enzymes (e.g., aspartate aminotransferase (AST), alanine aminotransferase (ALT), or total bilirubin elevations that occur concurrently with signs or symptoms consistent with CRS or HLH and do not resolve within 72 hours and are not considered by the investigator to be attributable to another clearly identifiable cause), neurologic toxicity, TLS, worsening neutropenia and/or thrombocytopenia.

C1D1 dose may be fixed based on information from Group A escalation.

C1D1 dose may be fixed based on information from Group A escalation or based on totality of safety, PK, and pharmacodynamic data observed between C1D1 and C1D7 in cohorts assessed in Group B escalation.

The only exception to this rule is with the initial escalation of the C1D1 dose, which may be escalated from the starting dose of 0.4 mg to a dose of 1.0 mg provided the cumulative Cycle 1 dose increment is ≤100%; subsequent C1D1 dose escalation increments may not exceed 100% over the preceding C1D1 dose level.

The only exception to this rule is with the escalation of the C1D1 dose, which may be escalated from the starting dose of 0.4 mg to a dose of 1.0 mg provided the cumulative Cycle 1 dose increment is ≤50%; subsequent C1D1 dose-escalation increments may not exceed 50% over the preceding C1D1 dose level.

A DLT-evaluable patient is a patient who receives the C1D1, C1D8, and C1D15 doses.

Patients who discontinue study treatment prior to completing C1 dosing are not evaluable for DLTs.

Dose escalation increments up to 100% of the preceding dose level may be recommended by the IMC based on review of the totality of data in dose escalation and expansion.

Figure 6A:
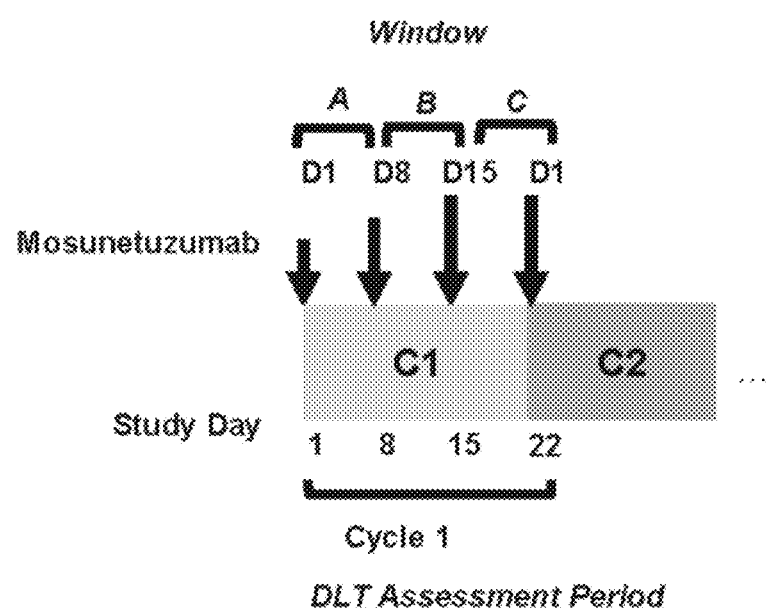
FIG. 6A is a schematic diagram showing dose-limiting toxicity (DLT) assessment windows in Cycle 1 dose escalation (Group B) in the GO29781 study. Window A: C1D1 through mosunetuzumab administration on C1D8; Window B: C1D8 through mosunetuzumab administration on C1D15; Window C: C1D15 through C1D21.
Figure 6B:
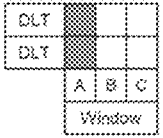
FIG. 6B is a set of schematic diagrams showing three exemplary scenarios for observation of DLTs in Cycle 1 dose escalation (Group B) in the GO29781 study. Diagrams represent examples illustrating the timing of two DLTs in a dose-escalation cohort of 6 patients and do not represent all possible scenarios. $^a$A DLT-evaluable patient is a patient who receives the C1D1, C1D8 and C1D15 doses, or develops a DLT.

Scenarios are described in FIG. 6B. AE=adverse event; C=cycle; D=day. Dose adjustments are made on a per cohort basis. Figures illustrate the timing of two DLTs in a dose escalation cohort of 6 patients.

A DLT-evaluable patient is a patient who receives the C1D1, C1D8 and C1D15 doses, or develops a DLT. Patients who discontinue study treatment prior to completing C1 dosing without a DLT are not evaluable for DLTs. If a patient develops a DLT and discontinues study treatment prior to completing C1 dosing, and the C1D1 and C1D8 combination MTD has not been exceeded, then an additional patient may be enrolled to allow evaluation of the cumulative C1 MTD.

By the posterior probability approach (Thall and Simon, *Biometrics*, 50(2): 337-349, 1994). For example, there is an ≥80% chance that true DLT rate≥20% if DLTs observed in 2/4, 2/5, 2/6, 3/7, 3/8, 3/9, 3/10, 4/11, 4/12, 4/13, 4/14, or 5/15 patients.

Dose escalation increments up to 100% of the preceding dose level may be recommended by the IMC based on review of the totality of data in dose escalation and expansion. Guidelines for dose escalation are outlined in Table 13 below.

TABLE 13

Dose escalation rules for Cycle 1 step-up mosunetuzumab escalation, IV Infusion (Group B): DLT observed in ≥ 17% of ≥ 3 DLT-evaluable patients in a given cohort

| Safety event/timing of safety event | C1D1 dose escalation/dose determination | C1D8 dose escalation/dose determination | C1D15 dose escalation/dose determination |
|---|---|---|---|
| Scenario 1 | If C1D1 MTD has not been exceeded, may continue C1D1 dose escalation with increment ≤ 50% of previous C1D1 dose. If the number of DLTs during Window A with a C1D1 dose level across all applicable cohorts has ≥ 80% chance that true DLT rate ≥ 20%, then C1D1 MTD has been exceeded. If C1D1 MTD has not been exceeded, may continue C1D1 dose escalation with increment ≤ 50% of previous C1D1 dose. Intermediate C1D1 doses may be tested if the C1D1 dose level at which the MTD is exceeded is ≥ 25% of the previous C1D1 dose level. | If C1D1 MTD has been exceeded, evaluate C1D8 dose with C1D1 dose that has not exceeded the C1D1 MTD; otherwise, continue C1D15 dose escalation with increment ≤ 50% of previous C1D8 dose. | If C1D1 MTD has been exceeded, evaluate C1D15 dose with C1D1 dose that has not exceeded the C1D1 MTD; otherwise, continue C1D15 dose escalation with increment ≤ 50% of previous C1D15 dose. |
| Scenario 2 | If the number of DLTs during Window A with a C1D1 dose level across all applicable cohorts has ≥ 80% chance that true DLT rate ≥ 20%, then C1D1 MTD has been exceeded. If the number of DLTs during Window B with a C1D1 and C1D8 dose combination across all applicable cohorts has ≥ 80% chance that true DLT rate ≥ 20%, then the C1D1 and C1D8 combination MTD has been exceeded. If C1D1 and C1D8 combination MTD has not been exceeded, may continue C1D1 and C1D8 escalation with increment ≤ 50% of previous C1D1 and C1D8 doses. Intermediate cumulative C1D1 and C1D8 doses may be tested if the cumulative C1D1 and C1D8 dose level at which the MTD is exceeded is ≥ 25% of the previous cumulative C1D1 and C1D8 dose level and C1D1 MTD not exceeded. | | If the C1D1 and C1D8 combination MTD has been exceeded, evaluate C1D15 dose with C1D1 and C1D8 doses that have not exceeded the C1D1 and C1D8 combination MTD; otherwise, continue C1D15 dose escalation with increment ≤ 50% of previous C1D15 dose. |
| Scenario 3 | No further escalation of individual C1D1, C1D8, and C1D15 doses. If a dose level is found to exceed the MTD, an additional 3 patients will be evaluated for DLTs at the preceding tested dose level to evaluate it as the MTD, unless 6 patients have already been evaluated at that dose level. Intermediate C1D1, C1D8, and C1D15 doses may be tested if the cumulative C1 dose level at which the MTD is exceeded is ≥ 25% of the previous cumulative C1 dose level and the C1D1 dose level does not exceed the C1D1 MTD. | | |

Cycle 1 dose escalation occurs according to the following rules based on the 3+3 dose-escalation design and is summarized in FIGS. 6A and 6B and Tables 12 and 13:
A minimum of 3 patients are initially enrolled in each cohort unless the first 2 enrolled patients experience a protocol-defined DLT in which case enrollment into the cohort is terminated.
Dose escalation may proceed with a cumulative Cycle 1 dose increment 100% over the preceding cumulative Cycle 1 dose if the following conditions during the DLT assessment window are met:
No DLT not considered by the investigator to be attributable to another clearly identifiable cause is observed in any patient;
Grade 2 or above adverse events that constitute potential risks attributable to mosunetuzumab based on its known mechanism of action (e.g., CRS, HLH, elevated liver enzymes (e.g., aspartate aminotransferase (AST), alanine aminotransferase (ALT), or total bilirubin elevations that occur concurrently with signs or symptoms consistent with CRS or HLH and do not resolve within 72 hours and are not considered by the investigator to be attributable to another clearly identifiable cause), neurologic toxicity, TLS, worsening neutropenia and/or thrombocytopenia) are observed in 34% of at least 3 patients.
Each of the individual Cycle 1 Day 1, Cycle 1 Day 8, and Cycle 1 Day 15 doses may be escalated by a dose increment 100% over the preceding corresponding dose level, provided that the cumulative Cycle dose increment remains at 100%.
The only exception to this rule is with the initial escalation of the Cycle 1 Day 1 dose, which may be escalated from the starting dose of 0.4 mg (Table 11) to a dose of 1.0 mg provided the cumulative Cycle 1 dose increment is 100%; subsequent Cycle 1 Day 1 dose escalation increments may not exceed 100% over the preceding Cycle 1 Day 1 dose level.
The Cycle 1 Day 1 dose may be fixed at a dose fulfilling the following criteria from Cycle 1 Day 1 Group A dose-escalation safety data:
The Cycle 1 Day 1 dose is no higher than the highest dose in Group A that did not have a DLT during the DLT assessment window (Days 1-21 of Cycle 1) in any patient.
The Cycle 1 Day 1 dose is no higher than the highest dose in Group A that had 34% of at least 3 patients experiencing Grade 2 AEs that constitute potential risks attributable to mosunetuzumab based on its known mechanism of action (e.g., CRS, HLH, elevated liver enzymes (e.g., aspartate aminotransferase (AST), alanine aminotransferase (ALT), or total bilirubin elevations that occur concurrently with signs or symptoms consistent with CRS or HLH and do not resolve within 72 hours and are not considered by the investigator to be attributable to another clearly identifiable cause), neurologic toxicity, TLS, worsening neutropenia and/or thrombocytopenia).
Escalation of the Cycle 1 Day 8 and Cycle 1 Day 15 doses may continue as appropriate.
If Grade 2 or above adverse events that constitute potential risks attributable to mosunetuzumab based on its mechanism of action (e.g., CRS, HLH, elevated liver enzymes (e.g., aspartate aminotransferase (AST), alanine aminotransferase (ALT), or total bilirubin elevations that occur concurrently with signs or symptoms consistent with CRS or HLH and do not resolve within 72 hours and are not considered by the investigator to be attributable to another clearly identifiable cause), neurologic toxicity, TLS, worsening neutropenia and/or thrombocytopenia) are observed in 34% of at least 3 patients, then:
The interval cumulative Cycle 1 increase between successive cohorts will be 50% of the preceding cumulative Cycle 1 dose level.
The interval increase of the individual Cycle 1 Day 1, Cycle 1 Day 8, and Cycle 1 Day 15 dose levels between successive cohorts will be 50% of the preceding corresponding dose levels.
The only exception to this rule is with the initial escalation of the Cycle 1 Day 1 dose, which may be escalated from the starting dose of 0.4 mg (Table 11) to a dose of 1.0 mg provided that no more than one of the above-mentioned Grade≥2 AEs occurs between Cycle 1 Day 1 and Cycle 1 Day 7, and that the cumulative Cycle 1 dose increment is ≤50%.
Subsequent Cycle 1 Day 1 dose escalation increments may not exceed 50% over the preceding Cycle 1 Day 1 dose level.
If the adverse events were observed between Cycle 1 Day 1 and Cycle 1 Day 7 and the Cycle 1 Day 1 dose was not previously fixed, then in subsequent cohorts the Cycle 1 Day 1 dose may be fixed at a previously tested Cycle 1 Day 1 dose level where no such defined adverse events were observed between Cycle 1 Day 1 and Cycle 1 Day 7. Escalation of the Cycle 1 Day 8 and Cycle 1 Day 15 dose may continue as appropriate.
If 1 of the first 3 DLT-evaluable patients experiences a DLT, the cohort is expanded to 6 patients. All patients are evaluated for DLTs before any dose-escalation decision.
If DLTs are observed in <17% of patients in a given cohort (e.g., DLTs observed in 1 of 6 DLT-evaluable patients), enrollment of the next cohort may proceed according to the dose escalation rules described in FIG. 6A and Table 12.
If DLTs are observed in 17% of patients in a given cohort, the dose-escalation rules described in FIG. 6B and Table 13 will apply.
The cumulative MTD is defined as the highest cumulative Cycle 1 dose level resulting in DLTs in <17% of a minimum of 6 patients during the period between Cycle 1, Day 15 and Cycle 1, Day 21 (Window C as detailed in FIG. 6B).
If a cumulative Cycle 1 dose is found to exceed the MTD, an additional 3 patients are evaluated for DLTs at the preceding tested cumulative Cycle 1 dose to evaluate it as the MTD, unless 6 patients have already been evaluated at that dose.
If the cumulative Cycle 1 dose level at which the MTD is exceeded is 25% higher than the preceding tested cumulative Cycle 1 dose, additional dose cohorts of at least 6 patients may be evaluated at intermediate cumulative Cycle 1 doses for evaluation as the MTD. The Cycle 1 Day 1 dose may not exceed the Cycle 1, Day 1 MTD.

Group E: Cycle 1 Step-Up, Single-Agent Mosunetuzumab Escalation with Concurrent Administration of Atezolizumab Starting in Cycle 2 (IV Infusion)
Group E dose escalation in the GO29781 study proceeds as corresponding Group B dose-escalation cohorts clear their Cycle 1 DLT assessment period (FIGS. 6A and 6B) and are shown to be safe and tolerable through Cycle 2 based on IMC review. The Cycle 1 Day 1, Day 8, and Day 15 dose levels of mosunetuzumab in Group E escalation are the same as those in the corresponding cohort in Group B escalation.

occur concurrently with signs or symptoms consistent with CRS or HLH and do not resolve within 72 hours and are not considered by the investigator to be attributable to another clearly identifiable cause), neurologic toxicity, TLS, worsening neutropenia and/or thrombocytopenia.

TABLE 14

Dose-escalation rules for Cycle 1 step-up mosunetuzumab escalation and concurrent administration of atezolizumab starting in Cycle 2, IV infusion (Group E)

| Time interval | Event | Mosunetuzumab dose escalation modifications (Group E) |
|---|---|---|
| Between C1D1 and C1D21 (X, Y) | Treatment-emergent toxicity that does not completely resolve to baseline level by C2D1 | Patient will be considered unevaluable for dose-escalation decisions and MTD determination and be replaced by an additional patient at that same dose level and schedule. |
| After combination administration (C2, Z) | Grade ≥ 2 non-DLT AE in ≤ 34% of ≥ 3 patients and no DLT | Proceed with dose escalation with increment ≤ 100% of the preceding dose level. |
| | Grade ≥ 2 non-DLT AE in > 34% of ≥ 3 patients | Proceed with dose escalation with increment ≤ 50% of the preceding dose level. |
| | First observed DLT | Expand cohort to ≥ 6 patients. If DLT in < 17% of ≥ 6 patients, proceed with dose escalation with increment ≤ 50% of the preceding dose level. |
| | DLT in ≥ 17% of ≥ 6 patients | 3 additional patients will be evaluated for DLTs at the preceding tested Cycle 2 dose, unless 6 patients have already been evaluated at that dose. Additional intermediate dose cohorts of at least 6 patients may be evaluated if the Cycle 2 dose at which the MTD is exceeded is ≥ 25% higher than the preceding Cycle 2 dose. A higher cumulative Cycle 1 dose level that has been cleared in Group B escalation may be tested using the highest cleared Cycle 2 mosunetuzumab dose level in combination with atezolizumab. |

Figure 7:
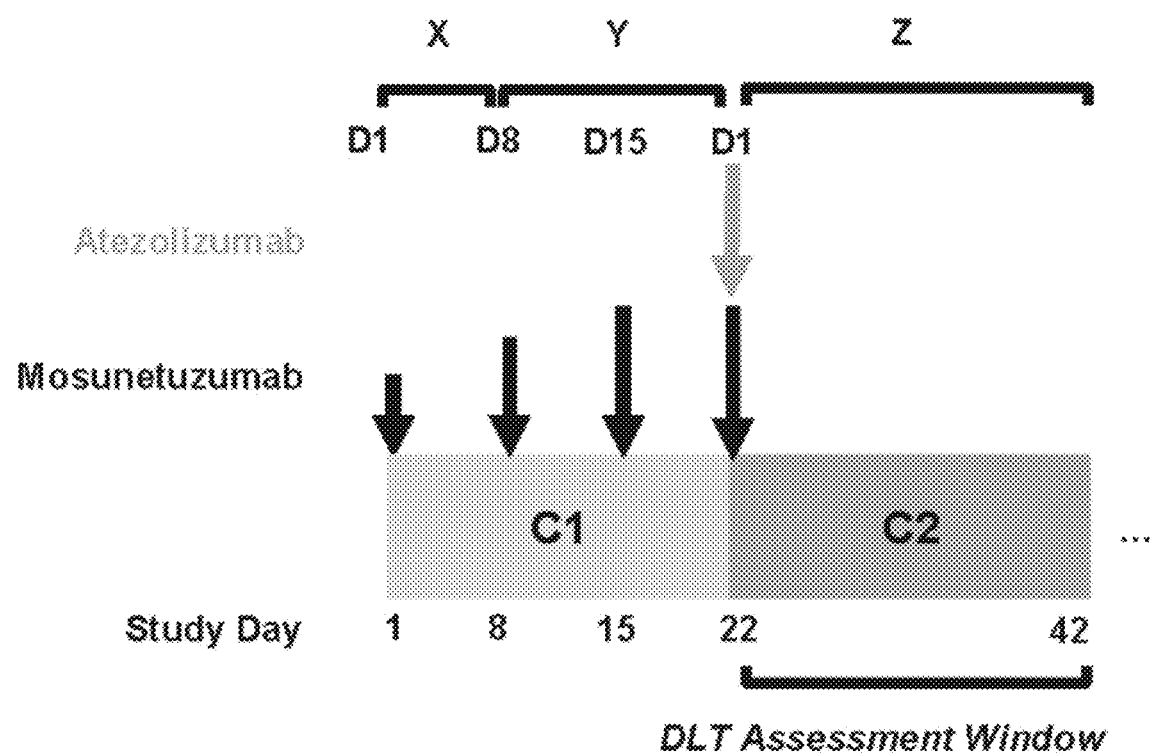
FIG. 7 is a schematic diagram showing assessment windows in Group E of the GO29781 study.

Windows are as provided in FIG. 7. AE = adverse event; C = Cycle; CRS = cytokine release syndrome; D = Day; DLT = dose-limiting toxicity; HLH = hemophagocytic lymphohistiocytosis; IMC = Internal Monitoring Committee; MTD = maximum tolerated dose; TLS = tumor lysis syndrome.
Note:
Dose adjustments are made on a per-cohort basis.

The Cycle 2 dose of mosunetuzumab in Group E escalation may not exceed the highest cleared Cycle 1 Day 15 dose from Group B escalation.

Mosunetuzumab is administered as a single agent by IV infusion based on a Cycle 1 step-up schedule as described for Group B escalation. Beginning with Cycle 2 Day 1 and on Day 1 of each subsequent cycle, atezolizumab is administered on the same day as mosunetuzumab. The mosunetuzumab dose is initially equal to the Cycle 1 Day 15 dose of mosunetuzumab. Mosunetuzumab is administered first, followed by atezolizumab, with atezolizumab infusion to begin at least 1 hour after the completion of the mosunetuzumab infusion. For logistic/scheduling reasons, Cycle 2 Day 1 administration of mosunetuzumab and atezolizumab may be given up to ±1 day from the scheduled date for Cycle 2, i.e., with a minimum of 6 days after Cycle 1 Day 15 dosing, and ±2 days from the scheduled date for Cycle 3 and beyond, i.e., with a minimum of 19 days between doses.

Figure 8:
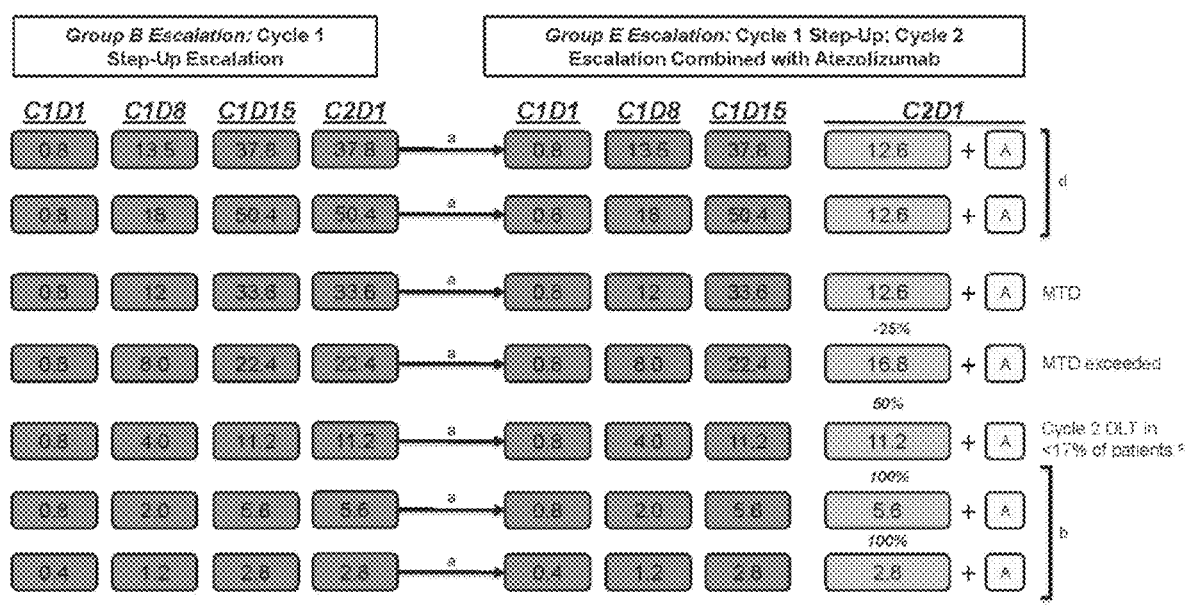
FIG. 8 is a schematic diagram showing an exemplary dose escalation progression for Group E of the GO29781 study. Doses listed are for illustrative purposes only. Dose levels are in mg. $^a$Initiation of a given Group E cohort is contingent on the following in Group B escalation: 1) clearing Cycle 1 DLT assessment period; and 2) demonstration of safety and tolerability in Cycle 2. $^b$In absence of DLT and Grade≥2 adverse events that constitute potential risks of mosunetuzumab, Cycle 2 mosunetuzumab escalation follows that of corresponding Group B dose. $^c$Cycle 2 DLT in <17% of patients results in decreasing Cycle 2 dose escalation increment to ≤50% over the preceding Cycle 2 Day 1 mosunetuzumab dose level. In this example, Cycle 2 dose escalation does not need to align with corresponding Cycle 2 dose level in Group B if Group B dose-escalation rules permit 100% dose-escalation increment. $^d$Once Cycle 2 MTD is reached, Cycle 2 dose level may not be further escalated. Higher Cycle 1 dose levels based on Group B escalation may be tested using the highest cleared Cycle 2 mosunetuzumab dose level in combination with atezolizumab.

The dose escalation rules for Group E dose escalation are listed below and are summarized in FIG. 7 and Table 14. An example of a Group E dose-escalation progression is illustrated in FIG. 8; doses listed in this figure are for illustrative purposes only.

Adverse events associated with identified or potential risks of mosunetuzumab, e.g., CRS, HLH, elevated liver enzymes (e.g., aspartate aminotransferase (AST), alanine aminotransferase (ALT), or total bilirubin elevations that Dose escalation increments may be recommended by the IMC based on review of the totality of data, as long as the recommended dose level does not exceed one dose level below the maximum assessed dose for mosunetuzumab in Group B.

The starting dose of mosunetuzumab is a dose that has been previously tested in Group B escalation, has cleared the Cycle 1 DLT assessment period, and has been shown to be safe and tolerable through Cycle 2. Atezolizumab is administered for the first time in combination with mosunetuzumab on Cycle 2 Day 1.

The DLT assessment period extends from Cycle 2 Day 1 through Cycle 2 Day 21. If an enrolled patient experiences any treatment-emergent toxicity during Cycle 1 (mosunetuzumab alone), that does not completely resolve to baseline level prior to scheduled initiation of combination treatment on Cycle 2 Day 1 (Study Day 22), that patient will be considered unevaluable for dose-escalation decisions and MTD determination and be replaced by an additional patient at that same dose level and schedule. Adverse events that are reported during Cycle 1 of Group E are not directly used for Group B dose-escalation decisions. However, based on the totality of available safety data, Group B dosing and schedules may be modified based on Cycle 1 treatment emergent toxicities in Group E Cycle 1 escalation.

Mosunetuzumab dose escalation in Group E will proceed as corresponding Group B dose-escalation cohorts clear their Cycle 1 DLT assessment period (FIG. 6) and shown to be safe and tolerable through Cycle 2 based on IMC review. The Cycle 2 dose of mosunetuzumab in Group E escalation may not exceed the highest cleared Cycle 1 Day 15 dose from Group B escalation.

The dose escalation in Group E initially follows the Group B rules. A dose increment over the preceding dose level may be recommended by the IMC based on review of totality of safety data in dose escalation and expansion, as long as the recommended dose level does not exceed one dose level below the maximum assessed dose for mosunetuzumab in Group B.

The MTD is defined as the highest Cycle 2 dose level resulting in DLTs in <17% of a minimum of 6 patients. If the Cycle 2 dose is found to exceed the MTD, an additional 3 patients are evaluated for DLTs at the preceding tested Cycle 2 dose to evaluate it as the MTD, unless 6 patients have already been evaluated at that dose.

- If the Cycle 2 dose at which the MTD is exceeded is 25% higher than the preceding tested Cycle 2 dose, additional dose cohorts of at least 6 patients may be evaluated at intermediate Cycle 2 doses for evaluation as the MTD.
- If the first tested Cycle 2 dose is found to exceed the MTD, a lower dose of mosunetuzumab may be tested. Decisions to test lower mosunetuzumab doses in combination with atezolizumab will be made based on review of the cumulative safety data by the IMC.
- If a higher cumulative Cycle 1 dose level has been cleared in Group B escalation, that Cycle 1 dose level and schedule may be tested using the highest cleared Cycle 2 mosunetuzumab dose level in combination with atezolizumab.
- The highest individual mosunetuzumab dose in tested Group E escalation may not exceed the highest individual dose identified as the MTD in Group B escalation.

Example 4. Intra-Patient Dose Escalation and Continued Dosing

A. Intra-Patient Dose Escalation

To maximize the collection of information at relevant doses and minimize the exposure of patients to sub-optimal doses of mosunetuzumab, intra-patient dose escalation may be permitted. Within each assigned dose-escalation Group, the dose of mosunetuzumab for an individual patient may be increased to the highest cleared dose level that is tolerated by completed cohorts through at least one cycle of mosunetuzumab administration. Patients are able to undergo intra-patient dose escalation after completing at least two cycles at their originally assigned dose level. Subsequent intra-patient dose escalations may occur after at least one cycle of any subsequently higher cleared dose level without any adverse event that meets the definition of a DLT or necessitates post-administration hospitalization.

Once the MTD is declared and the RP2D is determined, intra-patient dose escalation directly to the RP2D is permitted for patients who remain on study and continue to tolerate mosunetuzumab.

For patients in Group B dose escalation, intra-patient dose escalation is permitted beginning Cycle 3 (after step-fractionated dosing in Cycle 1 and non-fractionated dosing in Cycle 2). For patients in Group E, intra-patient dose escalation of mosunetuzumab is permitted beginning Cycle 4 (after mosunetuzumab single-agent dosing in Cycle 1 and dosing in combination with atezolizumab in Cycles 2 and 3). No escalation of atezolizumab is permitted.

B. Rules for Continued Dosing Beyond the Dose-Limiting Toxicity Observation Period Patients who do not experience a DLT during the DLT observation period are eligible to receive additional cycles of study treatment as follows:

- For patients enrolled in dose-escalation Group A, mosunetuzumab is given at the same dose level via the same administration route every 21 days (the day of administration being Day 1 of each cycle).
- For patients enrolled in dose-escalation Group B, mosunetuzumab is given at the same dose level as the Cycle 1 Day 15 dose every 21 days (the day of infusion being Day 1 of each cycle) beginning 7 days after the Cycle 1 Day 15 dose (study Day 22).
- For patients enrolled in dose-escalation Group E, mosunetuzumab is given in combination with atezolizumab every 21 days (the day of infusion being Day 1 of each cycle).
- Within each treatment group, the Sponsor retains the option to test a lower dose level on Day 1 of Cycle 3 or later to determine whether a lower dose during later cycles is sufficient to maintain clinical efficacy.

Additional doses of mosunetuzumab may be given provided the following criteria are met:

- Ongoing clinical benefit: Patients have no clinical signs or symptoms of progressive disease (PD); radiographic tumor assessments at the end of the DLT window are not required in order to minimize unnecessary radiation exposure. Patients are clinically assessed for disease progression on Day 1 of each cycle.
  - For NHL patients, disease progression should be confirmed by radiographic imaging as defined by the Revised Response Criteria for Malignant Lymphoma (Cheson et al., *J Clin Oncol,* 25: 579-586, 2007). NHL patients with radiographic disease progression prior to the completion of the study treatment period are generally ineligible to receive further mosunetuzumab treatment. However, in limited cases, treatment after apparent radiographic disease progression may be allowed.
  - CLL patients who experience disease progression as defined by the NCI-WG guidelines (Hallek et al., *Blood,* 111(12): 5446-5456, 2008) prior to the completion of the study treatment period are ineligible to receive further mosunetuzumab treatment.
- Acceptable toxicity: Patients who experience Grade 4 non-hematologic adverse events with the possible exception of Grade 4 tumor lysis syndrome (TLS) should discontinue study treatment and may not be re-treated. Patients who experience Grade 4 TLS may be considered for continued study treatment. All other study treatment related adverse events from prior study treatment administration have decreased to Grade≤1 or baseline grade by the next administration. Exceptions on the basis of ongoing overall clinical benefit may be allowed after a careful assessment and discussion of benefit-risk with the patient by the study investigator and with approval from the Medical Monitor. Dose reductions of mosunetuzumab may be allowed if it is determined that clinical benefit may be maintained according to the rules outlined herein.

Patients exhibiting acceptable safety and evidence of clinical benefit as described above may continue to receive study treatment as described herein. Patients who complete study treatment without disease progression will continue to be monitored, including regularly scheduled tumor assessments, until discontinuation from the post-treatment follow-up (e.g., due to progression). Patients have the option for re-treatment for development of recurrent disease as described herein.

Example 5. Treatment Following Disease Progression

A. Treatment of Non-Hodgkin's Lymphoma after Disease Progression

Experience with cancer immunotherapy for solid tumors has demonstrated that responding tumors may initially increase in size due to the influx of immune cells, a phenomenon known as "pseudoprogression" (Wolchok et al., *Clin Can Res,* 15(23): 7412-7420, 2009). Pseudoprogression has not been described in the context of lymphoma immunotherapy, but it is possible that mosunetuzumab and/or atezolizumab therapy may initially increase tumor size and metabolic activity by inducing the influx of T cells into the tumor. Given this, a repeat tumor biopsy, if clinical disease progression is observed, is strongly encouraged. Additionally, if the study investigator believes that an NHL patient is deriving clinical benefit despite radiographic evidence of progressive disease as defined by the Revised Response Criteria for Malignant Lymphoma (Cheson et al., *J Clin Oncol,* 25: 579-586, 2007), that patient may continue study treatment provided the following criteria are met:

There is an absence of symptoms and signs (including worsening of laboratory values) indicating unequivocal progression of disease.

There is no decline in Eastern Cooperative Oncology Group (ECOG) Performance Status.

There is an absence of tumor progression at critical anatomical sites including the central airway, the great vessels, and other organs or tissues where compromised function secondary to tumor progression would be expected to result acutely in severe and/or irreversible disability or death.

Patients continuing study treatment despite apparent radiographic progression are strongly encouraged to undergo a repeat tumor biopsy to assess whether increases in tumor volume are due to immune cell infiltration or neoplastic proliferation, provided that such a biopsy can be performed safely on a non-target lesion. If true progression is suspected based on the investigator's judgment, clinical factors, or biopsy findings that are consistent with neoplastic proliferation, or if radiographic disease progression is confirmed at a subsequent tumor assessment, the patient is ineligible to receive further study treatment under the currently assigned treatment group. Patients on single-agent mosunetuzumab may be considered for combination treatment with atezolizumab as described herein.

B. Mosunetuzumab/Atezolizumab Treatment Duration and Re-Treatment Following Disease Progression Patients who initially respond or have stable disease to mosunetuzumab as a single agent or in combination with atezolizumab may benefit from additional cycles beyond the initial eight cycles of study treatment, depending on anti-tumor responses to initial treatment. In addition, patients who develop progressive disease while receiving single-agent mosunetuzumab treatment may benefit from the addition of atezolizumab.

To test these hypotheses, patients are eligible for mosunetuzumab re-treatment or continued study treatment beyond the initial eight cycles, either as single-agent or combined with atezolizumab, as described herein. The study re-treatment dose and schedule is one that has been previously demonstrated in dose escalation to be safe, provided the following criteria are met:

Pertinent eligibility criteria are met at the time that mosunetuzumab treatment is re-initiated, with the following exceptions:

Prior therapy with mosunetuzumab is allowed

Serology tests to demonstrate human immunodeficiency virus (HIV), hepatitis C virus (HCV), and hepatitis B virus (HBV) status do not need to be repeated unless clinically indicated. EBV and cytomegalovirus (CMV) quantitative polymerase chain reaction (PCR) are repeated.

Manageable and reversible immune related adverse events with initial study treatment are allowed and do not constitute an exclusionary history of autoimmune disease.

Patients have not experienced Grade 4 non-hematologic adverse events that were not considered by the investigator to be attributable to another clearly identifiable cause during initial study treatment, with the possible exception of TLS.

Patients who experienced Grade 2 or Grade 3 AEs that were not considered by the investigator to be attributable to another clearly identifiable cause during initial treatment have resolved these toxicities to ≤Grade 1.

Patients may require hospitalization following the first re-treatment administration.

No intervening systemic anti-cancer therapy was administered between the completion of initial study treatment and re-initiation of study treatment.

Patients proceeding to re-treatment following disease progression are strongly encouraged to undergo a repeat tumor biopsy from a safely accessible site to assess: 1) CD20 expression status and 2) changes/status of the tumor and immune microenvironment. Patients who provide written informed consent but have no lesion amenable for biopsy at disease progression may still be considered for study drug re-treatment following a discussion between the study investigator and the Medical Monitor.

The dose and schedule of study treatment to be administered for patients receiving re-treatment is determined by the Medical Monitor and is on a previously tested dose and schedule that has cleared the DLT observation period.

Figure 9:
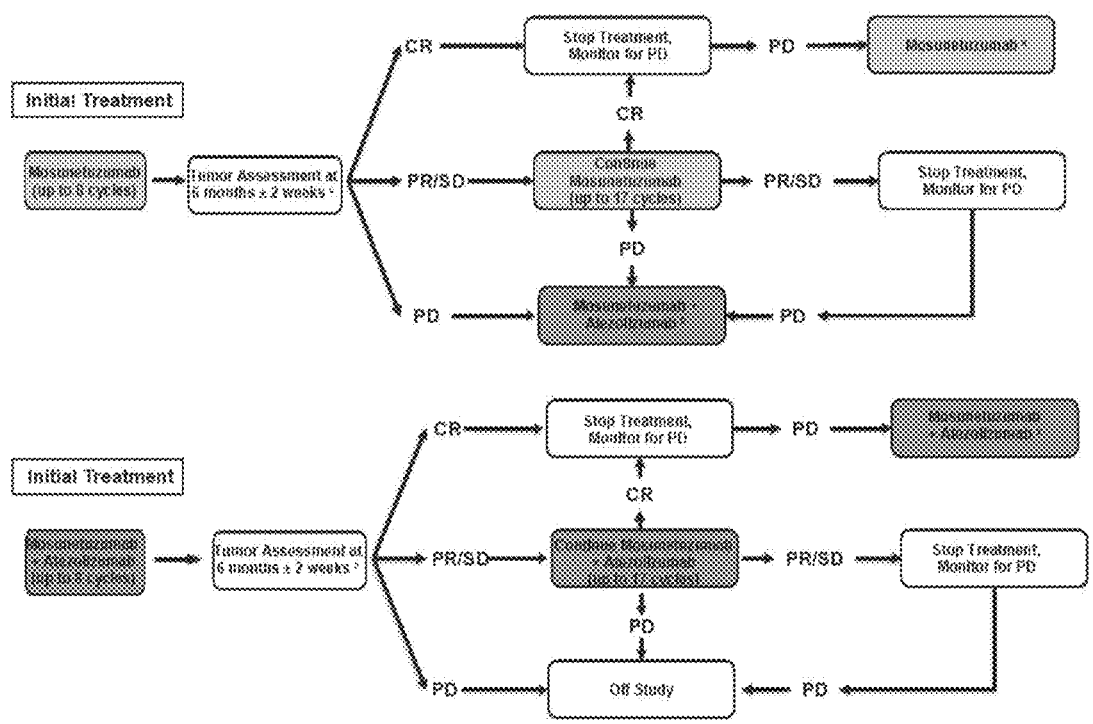
FIG. 9 is a schematic diagram showing the duration of initial study treatment in the GO29781 study and options for re-treatment or continued study treatment. CR=complete response; PD=progressive disease; PR=partial response; SD=stable disease. $^a$Additional rounds of re-treatment permitted, follow treatment flow for initial treatment. $^b$Follow treatment flow for mosunetuzumab+atezolizumab initial treatment. $^c$Scan should be scheduled to avoid/minimize any dose delay between Cycles 8 and 9 as much as possible.

The duration of initial study treatment and options for re-treatment or continued study treatment beyond the initial eight cycles of study treatment are described in FIG. 9. The dose and schedule/route of administration of mosunetuzumab with or without atezolizumab based on the nature and timing of study treatment is described in Table 12.

For patients initially receiving single-agent mosunetuzumab:

Mosunetuzumab is given for eight cycles unless PD or unacceptable toxicity is observed prior to completion of the eight cycles. If PD is observed, then patients are considered for treatment with mosunetuzumab combined with atezolizumab.

The tumor assessment at 6 months (±2 weeks) should be scheduled after Cycle 8 Day 1 but before Cycle 9 Day 1 in order to determine the duration of study treatment.

Patients who achieve a complete response (CR) after receiving eight cycles of treatment do not receive any additional cycles of mosunetuzumab and are monitored; if PD following completion of initial single-agent mosunetuzumab treatment is observed, single-agent mosunetuzumab re-treatment may be initiated.

Treatment may continue with mosunetuzumab for at least eight additional cycles.

Patients who achieve a PR or maintain stable disease (SD) after receiving eight cycles of treatment continue single-agent mosunetuzumab for up to a total of 17 cycles unless PD or unacceptable toxicity is observed.

If CR is achieved after 17 cycles of treatment, monitoring as described for patients who achieve a CR with mosunetuzumab is followed.

If PR or SD is achieved after 17 cycles of treatment, patients continue to be monitored.

If PD is observed, then patients are considered for treatment with mosunetuzumab combined with atezolizumab.

For patients initially receiving mosunetuzumab combined with atezolizumab (either as initial treatment or as re-treatment following PD on single-agent mosunetuzumab):

Combination treatment is given for eight cycles unless PD or unacceptable toxicity is observed prior to completion of the eight cycles. If PD is observed, then patients will discontinue study treatment.

The tumor assessment at 6 months (±2 weeks) should be scheduled after Cycle 8 Day 1 but before Cycle 9 Day 1 to determine the duration of study treatment.

Patients who achieve CR after receiving eight cycles of treatment do not receive any additional cycles of combination treatment and are monitored. If PD following completion of combination treatment is observed, combination re-treatment may be initiated.

Patients who achieve a PR or maintain SD after receiving eight cycles of treatment continue combination treatment for up to a total of 17 cycles unless PD or unacceptable toxicity is observed.

If CR is achieved after 17 cycles of treatment, monitoring as described for patients who achieve a CR with mosunetuzumab is followed.

If PR or SD is achieved by the completion of 17 total cycles, patients continue to be monitored.

If PD is observed on combination treatment, then patients will discontinue study treatment.

Study treatment may be discontinued at any time for unacceptable toxicity. At the discretion of the Medical Monitor and in consultation with the investigators, patients may be eligible for additional study re-treatment provided the aforementioned criteria for re-treatment continue to be met.

The schedule of assessments for patients who receive re-treatment follow the schedule of assessments currently implemented in dose escalation or expansion. For example, patients being re-treated following a Cycle 1 double-step fractionated schedule follow the Group B schedule of assessments.

The rules for study treatment duration and re-treatment apply both to dose-escalation and dose-expansion cohorts.

TABLE 15

Mosunetuzumab treatment/re-treatment: dose and schedule/route of administration

| Initial treatment | | | Re-treatment upon progressive disease (PD) with initial treatment | |
| --- | --- | --- | --- | --- |
| Agent(s) | Route of administration | Treatment-free interval | Agent(s) | Dose/schedule |
| mosunetuzumab | IV | ≥6 weeks | mosunetuzumab | Highest cleared Group B dose/schedule including Cycle 1 step-up dosing |
| mosunetuzumab | IV | <6 weeks | mosunetuzumab | Highest cleared Group B Cycle 2 dose every 21 days; no mosunetuzumab step-up dosing |
| mosunetuzumab | IV | ≥6 weeks | mosunetuzumab + atezolizumab | Highest cleared Group B dose/schedule including Cycle 1 single-agent mosunetuzumab step-up dosing |
| mosunetuzumab | IV | <6 weeks | mosunetuzumab + atezolizumab | Highest cleared Group E Cycle 2 dose every 21 days; no single-agent mosunetuzumab step-up dosing |
| mosunetuzumab + atezolizumab | IV | ≥6 weeks | mosunetuzumab + atezolizumab | Highest cleared Group E Cycle 2 dose/schedule Including Cycle 1 single-agent mosunetuzumab step-up dosing |
| mosunetuzumab + atezolizumab | IV | <6 weeks | mosunetuzumab + atezolizumab | Highest cleared Group E Cycle 2 dose every 21 days; no single-agent mosunetuzumab step-up dosing |

Example 6. Dose-Expansion Stage

The dose-expansion stage of this study is designed to obtain additional safety, tolerability, PK, and preliminary clinical activity data with study treatment at doses up to the MTD/maximal assessed dose (MAD).

All available safety data from the expansion cohorts is evaluated on an ongoing basis to assess the tolerability of the dose levels studied. At no time will a mosunetuzumab dose level studied in the expansion stage exceed the highest dose level that qualifies as an MTD in the dose-escalation stage. Additionally, for each expansion cohort, interim analyses are conducted in order to guide potential early stopping of enrollment in the event of excess toxicity.

Patients exhibiting acceptable safety and evidence of clinical benefit as described in the protocol may continue to receive mosunetuzumab every 21 days up to a maximum of 8 or 17 cycles (See FIG. 9) until objective disease progression is documented or unacceptable toxicity, whichever occurs first.

Evaluations for safety and efficacy are conducted according to the schedules of assessments. Additional assessments after the final dose of study treatment for patients who discontinue study treatment for reasons other than disease progression, including patients who complete initial mosunetuzumab treatment, are performed as outlined in the post-treatment schedule of assessments. Patients who complete study treatment continue to have tumor assessments until disease progression and are eligible for mosunetuzumab re-treatment as described herein.

A. Single-Agent Mosunetuzumab Dose-Expansion in NHL

Patients are enrolled to receive mosunetuzumab in the following separate indication-specific expansion cohorts:
- R/R DLBCL and transformed FL: expansion cohorts testing doses at or below the MTD from Groups A and B escalation may be enrolled. Each cohort may enroll up to approximately 20 patients, except the expansion cohort based on Group B RP2D which may enroll approximately 80 patients, assuming sufficient safety and activity as defined herein.
- R/R FL: expansion cohorts testing doses at or below the MTD from Groups A and B escalation may be enrolled. Each cohort may enroll up to approximately 20 patients, except the expansion cohort based on Group B RP2D which may enroll approximately 80 patients, assuming sufficient safety and activity as defined herein.
- R/R MCL: expansion cohorts testing doses at or below the MTD from Groups A and B escalation may be enrolled. Each cohort may enroll up to approximately 20 patients assuming sufficient safety and activity as defined herein.
- R/R Richter's transformation: An expansion cohort testing doses at or below the MTD from Group B escalation may be enrolled. The cohort may enroll approximately $10^{-20}$ patients assuming sufficient safety and activity as defined herein.

Mosunetuzumab doses and schedules to be assessed in dose expansion are determined by the IMC in consultation with the investigators (if necessary and possible from a timing perspective) following a review of cumulative safety data in dose escalation. More than one mosunetuzumab dose level and schedule may be assessed. Expansion cohorts may be initiated, prior to the identification of the RP2D, at doses previously determined to be safe and demonstrating evidence of clinical activity during dose escalation. The Sponsor may decide to initiate or suspend enrollment of any given expansion cohort (FIG. 4) based on ongoing review of clinical data.

B. Dose Expansions with Mosunetuzumab in Combination with Atezolizumab in NHL

Patients are enrolled in expansion cohorts that will receive atezolizumab and mosunetuzumab at doses below the mosunetuzumab Cycle 2 MTD determined in Group E escalation. The following indication-specific expansion cohorts are similarly sized as for single-agent mosunetuzumab:
- R/R DLBCL and transformed FL: expansion cohorts testing doses at or below the Cycle 2 MTD may be enrolled. Each cohort may enroll approximately 20 patients, except for the expansion cohort based on Group E RP2D, which may enroll approximately 80 patients assuming sufficient safety and activity as defined herein.
- R/R FL: expansion cohorts testing doses at or below the Cycle 2 MTD may be enrolled. Each cohort may enroll approximately 20 patients, except for the expansion cohort based on Group E RP2D, which may enroll approximately 80 patients assuming sufficient safety and activity as defined herein.
- R/R MCL: expansion cohorts testing Group E doses at or below the Cycle 2 MTD may be enrolled. Each cohort may enroll up to approximately 20 patients assuming sufficient safety and activity as defined herein.

Mosunetuzumab doses and schedules in combination with atezolizumab to be assessed in dose expansion are determined based on IMC recommendation and in consultation with the investigators (if necessary and possible from a timing perspective) following a review of cumulative safety data in dose escalation. More than one mosunetuzumab dose level and schedule in combination with atezolizumab may be assessed. Expansion cohorts may be initiated prior to the identification of the RP2D at doses previously determined to be safe and demonstrating evidence of clinical activity during dose escalation. The Sponsor may decide to initiate or suspend enrollment of any given expansion cohort (FIG. 4) based on ongoing review of clinical data.

C. Dose Escalation and Expansion in CLL

Dose-escalation rules for CLL patients are the same as those used for NHL patients. The starting dose for CLL patients is no higher than one dose level below that has cleared the DLT assessment window in the corresponding NHL dose escalation.

Expansion cohorts of up to approximately 10 patients assessing mosunetuzumab in CLL at doses determined to be safe and demonstrating of clinical activity during CLL Group B dose escalation may be tested. The CLL expansion cohorts occur independently and potentially with a different doses and schedules from those for NHL patients.

Example 7. Assessment of Safety

The following information describing management of safety concerns is based on anticipated pharmacology and mechanism of action, results from nonclinical studies, preliminary safety findings from the single-agent dose-escalation study, published data on similar molecules, and the established safety profile of atezolizumab.

Measures are taken to ensure the safety of patients participating in this trial, including the use of stringent inclusion and exclusion criteria and close monitoring, as described below. Enrollment of patients for DLT evaluation purposes is staggered such that the first 2 patients in each dose-escalation cohort have respective Cycle 1, Day 1 treatments administered ≥72 hours apart. Subsequent patients in each cohort are staggered such that their Cycle 1, Day 1 treatments are administered ≥24 hours apart.

All patients are monitored closely for toxicity. Patients are assessed clinically for toxicity prior to each dose using the NCI CTCAE v4.0 grading scale unless otherwise stated. CRS severity is graded according to the Modified Cytokine Release Syndrome Grading System (Table 5). All adverse events and serious adverse events are recorded during the trial and for up to 90 days after the last dose of study treatment or until the initiation of another systemic anti-cancer therapy, whichever occurs first. To mitigate potential unknown risks, at least in part, dosing beyond Cycle 1 is limited to patients who do not demonstrate unacceptable toxicity or compelling evidence of disease progression.

Specific anticipated or potential toxicities associated with administration of mosunetuzumab and atezolizumab, as well as the measures taken intended to avoid or minimize such toxicities in this trial, are described herein.

A. Mosunetuzumab and Atezolizumab Administrations and Hospitalization

Administration of mosunetuzumab and atezolizumab is performed in a clinical setting with immediate access to a critical care unit and staff who are trained to monitor for and respond to medical emergencies. Neurology consultation services should be readily available to address any neurologic adverse events that may arise as a result of mosunetuzumab treatment, and nephrology consultation with acute dialysis capabilities should be readily available to address any renal toxicity that might accompany tumor lysis syndrome (TLS).

All patients enrolled in Groups A dose escalation require inpatient monitoring, including hospitalization during or following mosunetuzumab administration, for the first mosunetuzumab administration through at least 72 hours after the completion of mosunetuzumab administration on Cycle 1 Day 1.

All patients enrolled in Group B dose escalation cohorts to receive mosunetuzumab on a double-step-fractionated schedule require inpatient monitoring, including hospitalization during or following mosunetuzumab administration, for mosunetuzumab infusion through at least 72 hours after the completion of mosunetuzumab infusion for any individual dose exceeding any previously tested dose level.

This dose generally corresponds to the dose of mosunetuzumab administered on Cycle 1 Day 15. Hospitalization for administration of previously assessed doses is not required unless clinically indicated at the study investigator's discretion and in consultation with the Medical Monitor. Examples where such hospitalization may be warranted include but are not limited to prior observed Grade 2 adverse events potentially attributable to mosunetuzumab (e.g., CRS, HLH, elevated liver enzymes (e.g., aspartate aminotransferase (AST), alanine aminotransferase (ALT), or total bilirubin elevations that occur concurrently with signs or symptoms consistent with CRS or HLH and do not resolve within 72 hours and are not considered by the investigator to be attributable to another clearly identifiable cause), neurologic toxicity, TLS, worsening neutropenia and/or thrombocytopenia) at the same or similar dose, and TLS monitoring and prophylaxis.

Based on available clinical safety data, for patients who receive mosunetuzumab at a dose level that has been tested to be safe and tolerable, hospitalization is not mandatory after any dosing day. This applies to patients enrolled in Group B dose-escalation backfill slots, Group B expansion cohorts, and to those patients who receive study the need for hospitalization, and patients should be hospitalized after mosunetuzumab administration whenever clinically indicated.

All patients enrolled in Group E dose escalation to receive mosunetuzumab in combination with atezolizumab beginning in Cycle 2 receive inpatient monitoring, including hospitalization during or following mosunetuzumab administration, for mosunetuzumab and atezolizumab infusions on Cycle 2 Day 1 through at least 72 hours after the completion of the mosunetuzumab and atezolizumab infusions.

Hospitalization requirements during subsequent cycles are determined on the basis of the clinical course during the first cycle (or the second cycle for Group E); patients with Grade 3 CRS, injection-site reactions, or TLS during Cycle 1, or during Cycle 2 for Group E, may also be hospitalized through at least 72 hours after the end of the administration of the subsequent dose, with considerations for dose reduction as described herein.

For all treatment groups, decisions to modify or discontinue the requirement for hospitalization in expansion cohorts are made based on the recommendation of the IMC and in consultation with study investigators (if necessary and possible from a timing perspective).

B. Dose and Schedule Modifications

Mosunetuzumab and atezolizumab (where applicable) dosing occur only if a patient's clinical assessment and laboratory test values are acceptable. If scheduled dosing coincides with a holiday that precludes dosing, dosing should commence on the nearest following date, with subsequent dosing continuing on a 21-day schedule as applicable.

Study treatment may be delayed as appropriate for management of toxicity. Specific guidelines for single-agent mosunetuzumab and atezolizumab combination therapy dose modifications are described below.

Management guidelines including study treatment dose and schedule modifications for specific adverse events are described below.

Mosunetuzumab Dose and Schedule Modifications

For patients who experience CRS with the first dose of mosunetuzumab or are at increased risk of recurrent CRS with subsequent doses, the time of infusion may be extended to up to 8 hours.

Patients who experience an adverse event that either meets the definition of a DLT, a Grade 3 adverse event or a serious adverse event are allowed to delay mosunetuzumab dosing for up to 2 weeks in order to recover from the toxicity.

During Cycle 1 double-step fractionation in Groups B and E, mosunetuzumab may be administered despite hematologic laboratory abnormalities if no clinically significant symptoms are present; for anemia and thrombocytopenia, no transfusions are required.

For those adverse events that are not considered by the investigator to be attributable to another clearly identifiable cause, (e.g., documented disease progression, concomitant medication, or pre-existing medical condition), patients may continue to receive additional doses of mosunetuzumab, provided that the toxicity has resolved to Grade≤1 within the time period stated above.

For decreased lab values, the abnormality should have resolved to the lower limit of Grade≤1, or return to ≥80% of the baseline value, whichever is lower.

For neutropenia, the ANC should resolve to Grade≤2 or return to ≥80% of the baseline value, whichever is lower.

For increased lab values the abnormality should have resolved to the upper limit of Grade≤1, or return to ≥120% of the baseline value, whichever is higher.

The dose for subsequent administration of mosunetuzumab in such patients should in general be reduced, e.g., to the next highest cleared dose level assessed during dose escalation. If the reduction is to a dose level where there is no evidence of mosunetuzumab pharmacodynamic activity, e.g., no evidence of changes in serum cytokine levels, the patient may be discontinued from study treatment.

Decisions on continued treatment at a reduced dose following a DLT or other study treatment related Grade 3 toxicity should be made following a careful assessment and discussion of risk versus benefit with the patient by the investigator and approval from the Medical Monitor with the following exceptions:

If an elevation of AST or ALT>3×ULN and/or total bilirubin>2×ULN, with no individual laboratory value exceeding Grade 3, occurs in the context of Grade 2 CRS (Table 5) which lasts <3 days, mosunetuzumab dosing may continue without dose reduction with approval of the Medical Monitor.

For Grade 3 CRS (Table 5), the next mosunetuzumab dose should be reduced, and subsequent doses may be increased if the lower dose was tolerated. If Grade 3 CRS occurs in the step-up dosing cohorts following mosunetuzumab administration at Cycle 1 Day 1 or Cycle 1 Day 8, the next mosunetuzumab dose should be discussed with the Medical Monitor, and a dose reduction should be considered (Table 7).

For Grade 3 (NCI CTCAE v4) individual signs and symptoms of CRS that occur in the context of Grade≤2 CRS (Table 5) which lasts <3 days, mosunetuzumab dosing may continue without dose reduction with approval of the Medical Monitor.

For patients enrolled into expansion cohorts, decisions regarding dose and schedule modifications are made following individual benefit-risk assessment by the investigator and in consultation with the Medical Monitor.

Any patient in whom similar toxicity recurs at a reduced dose should be discontinued from further mosunetuzumab treatment.

Patients may not be re-treated at the dose of mosunetuzumab at which the adverse event occurred unless the adverse event is attributed to another clearly identifiable cause.

Patients who do not fulfill the criteria for dosing after the additional 2 weeks elapse are discontinued from study treatment and followed for safety outcomes. Exceptions to this on the basis of ongoing clinical benefit may be allowed following investigator assessment of risk versus benefit with approval from the Medical Monitor. Delay of therapy because of toxicities not attributed to mosunetuzumab may not require discontinuation following investigator assessment of risk versus benefit with approval from the Medical Monitor.

For patients in Group B, if dose delay results in a treatment-free interval of 6 weeks or longer, double-step fractionation of mosunetuzumab is required on Days 1, 8, and 15 for the first cycle after the dose delay.

For patients in Group E, if dose delay results in a treatment-free interval of 6 weeks or longer, double-step fractionation of mosunetuzumab is required on Days 1, 8, and 15 for the first cycle after the dose delay, and continued treatment with atezolizumab should start in the second cycle after the dose delay.

For patients receiving mosunetuzumab on a Cycle 1 step-up schedule (Groups B and E escalation or expansion), if a serious adverse event or adverse event of special interest occurs following Cycle 1, Day 1, Cycle 1, Day 8, and/or Cycle 1, Day 15 dosing, a treatment delay of mosunetuzumab (and atezolizumab as applicable) up to 14 days and/or modification of the subsequent mosunetuzumab dose may occur at the discretion of the Medical Monitor following consultation with the treating investigator physician.

In the event that a patient has a toxicity in Cycle 1 necessitating mosunetuzumab interruption for >7 days, the Medical Monitor should be notified and the patient may be required to repeat mosunetuzumab at the highest dose previously tolerated prior to resuming the planned treatment schedule.

Patients who discontinue study treatment for reasons other than PD should continue to be followed.

Mosunetuzumab in Combination with Atezolizumab Dose and Schedule Modifications

Guidelines to delay or discontinue atezolizumab treatment following specific adverse events are outlined below.

During Cycle 2 and beyond, patients who experience a Grade 3-4 adverse event that is clearly attributed to mosunetuzumab or atezolizumab may continue treatment with the other agent following initial improvement of the adverse event and after discussion with and approval of the Medical Monitor.

C. Risks Associated with Mosunetuzumab

On the basis of clinical data to date with mosunetuzumab, the following known and suspected risks are described below.

Known Risks Associated with Mosunetuzumab

Cytokine Release Syndrome

The mechanism of action of mosunetuzumab is immune cell-activation against CD20-positive cells; therefore, a spectrum of events involving infusion-related reactions (IRRs), target-mediated cytokine release, and/or hypersensitivity with or without emergent ADAs, may occur. Other CD20-directed therapies and immunomodulatory therapies have been associated with IRRs, cytokine release syndrome (CRS), and/or hypersensitivity (RITUXAN® United States Package Insert (USPI); GAZYVA® USPI; BLINCYTO® USPI). CRS following mosunetuzumab administration has been reported in Study GO29781.

While CRS is a known risk associated with mosunetuzumab, comprehensive characterization is ongoing with accumulating clinical data. To date, CRS observed with mosunetuzumab have been mostly mild to moderate in severity, and include symptoms such as fever, headache, and myalgia, and respond to symptomatic treatment with analgesics, anti-pyretics, and antihistamines as indicated.

Severe or life-threatening presentations of CRS, such as hypotension, tachycardia, dyspnea, or chest discomfort, should be treated aggressively with supportive and resuscitative measures as indicated, including the use of tocilizumab and/or high dose corticosteroids, IV fluids, and other supportive measures per institutional practice. Severe CRS may be associated with other clinical sequelae such as disseminated intravascular coagulation, capillary leak syndrome, or may manifest as hemophagocytic lymphohistiocytosis (HLH). Standard of care for severe or life threatening CRS resulting from immune-based monoclonal antibody therapy has not been established; case reports and recommendations for CD19 CAR-T have been published (Teachey et al., *Blood,* 121(26): 5154-5157, 2013; Lee et al., *Blood,* 124(2): 188-195, 2014; Maude et al., *New Engl J Med,* 371(16): 1507-1517, 2014; Neelapu et al., *Nat Rev Clin Oncol,* 15: 47-62, 2018; also see FDA approval for two products describing risk management for CRS (YESCARTA® USPI; KYMRIAH® USPI)).

Disease-related factors that may be associated with an increased risk of severe CRS following chimeric antigen receptor (CAR)-T-cell therapy, and therefore, potentially other T-cell engaging therapies, include (but are not limited to) lymphoma bone marrow involvement, extranodal disease, Richter's transformation, B cell lymphocytosis, and the presence of circulating peripheral malignant cells.

To minimize the risk and sequelae of CRS, mosunetuzumab is administered over a minimum of 4 hours in a clinical setting. Corticosteroid premedication is administered as described herein. Management guidelines for CRS following mosunetuzumab are summarized in Table 7, with the grading of CRS following the modified grading scale described in Table 5. Given the mechanism of action of mosunetuzumab, IRRs and CRS may be indistinguishable, hence their evaluation and treatment are identical. Management of Grade≥3 CRS should be immediately discussed between the treating investigator and the Medical Monitor. As noted in Table 7, even moderate presentations of CRS in patients with extensive comorbidities should be monitored closely with consideration given to ICU admission and tocilizumab administration.

Infusion-Related Reactions/Cytokine Release Syndrome Occurring in Patients Receiving Mosunetuzumab in Combination with Atezolizumab In patients receiving mosunetuzumab combined with atezolizumab, attribution of an IRR/CRS event to either mosunetuzumab or atezolizumab may not be possible depending on the timing of the IRR/CRS event. Consequently, for patients who experience IRR or CRS events, management, including any modifications to dosing in subsequent cycles, will follow the following general guidelines:

During Cycle 1 (single-agent mosunetuzumab administration), patients who experience a Grade 3 CRS event (Table 7) may proceed to receive combination treatment in Cycle 2 and beyond with approval of the Medical Monitor. The dose of mosunetuzumab for subsequent cycles should be reduced as described herein. For step-up dosing cohorts, if the Grade 3 CRS event occurs during Cycle 1 Day 1 or Cycle 1 Day 8, the next dose of mosunetuzumab should be discussed with the Medical Monitor and a dose reduction should be considered. Mosunetuzumab infusion should be administered over a minimum of 4 hours.

During Cycle 2 and beyond, patients who experience a Grade 3 CRS event that begins during or after the mosunetuzumab infusion but prior to the atezolizumab infusion, and therefore attributed solely to mosunetuzumab, may receive mosunetuzumab in subsequent cycles following discussion between the investigator physician and the Medical Monitor. The next dose of mosunetuzumab should be reduced as described herein.

During Cycle 2 and beyond, for patients who experience a Grade 4 CRS event that begins during or after the mosunetuzumab infusion but prior to the atezolizumab infusion, and therefore attributed solely to mosunetuzumab, mosunetuzumab should be permanently discontinued per Table 7. Single-agent atezolizumab may continue to be administered in this situation following complete resolution of toxicity with the approval of the Medical Monitor.

During Cycle 2 and beyond, patients who experience a Grade 3 CRS event where the attribution to mosunetuzumab or atezolizumab cannot be distinguished may continue treatment in subsequent cycles and at a reduced dose of mosunetuzumab following discussion between the investigator physician and the Medical Monitor.

During Cycle 2 and beyond, for patients who experience a Grade 4 CRS event where the attribution to mosunetuzumab or atezolizumab cannot be distinguished, both atezolizumab and mosunetuzumab should be permanently discontinued.

Neutropenia

Neutropenia has a known class effect associated with other CD20-directed therapies as well as blinatumomab (BLINCYTO® USPI), and is a known risk for mosunetuzumab. Reversible neutropenia has been observed following mosunetuzumab treatment in Study GO29781. Some patients developing neutropenia have received growth factor support and/or temporary treatment holds.

Patients who experience Grade 3-4 neutropenia should be closely monitored with more frequent assessments as applicable. For treatment-emergent neutropenia events that are Grade 3 or higher, dose delay and/or dose modification as described herein should be considered.

Potential Risks Associated with Mosunetuzumab

Hemophagocytic Lymphohistiocytosis

CRS with features of adult-onset secondary or reactive macrophage activation syndrome/hemophagocytic lymphohistiocytosis (MAS/HLH) has been reported with blinatumomab as well as CAR adoptive T-cell therapy (BLINCYTO® USPI; Teachey et al., *Blood*, 121(26): 5154-5157, 2013; Lee et al., *Blood*, 124(2): 188-195, 2014). (Note: for the purposes of the GO29781 protocol, MAS and HLH are considered to be synonymous terms.) A fatal case of secondary HLH, in a patient with evidence of chronic active EBV infection (positive for EBV as assessed by EBV-encoded small RNA in situ hybridization), has been reported in Study GO29781.

While severe CRS and secondary HLH have overlapping presentation and symptoms, secondary HLH may be precipitated by other conditions including infections, autoimmune disease and malignancies (Ramos-Casals et al., *Lancet*, 383: 1503-1516, 2014). The prevalence of these conditions in the study patient population makes the distinction between severe CRS and HLH and identification of inciting factors challenging. For example, in one series, B-cell malignancies were the most common malignancy associated with reactive HLH (Rivière et al., *Am J Med*, 127: 1118-1125, 2014). Furthermore, active infection with EBV is one of the most common infectious causes of HLH (Hashemi-Sadraei et al., *Case Rep Hematol* 2015, 491567, 2015; Schram and Berliner, Blood, 125: 2908-2914, 2015), while reactivation of latent EBV may occur in patients with CLL (Rath et al., *Haematologica*, 93: 1424-1426, 2008), which in turn may lead to HLH (Lim et al., *Leuk Lymphoma*, 55: 2938-2941, 2014). It remains unknown whether mosunetuzumab treatment may further increase the risk of developing HLH in patients who have additional risk factors.

In the setting of T-cell engaging therapies including mosunetuzumab, CRS is much more likely compared with secondary HLH. Considering the overlapping presentation of symptoms, management of these patients should be primarily focused on treatment of CRS (see Table 7).

In atypical cases such as late onset CRS (past completion of step-up dosing with mosunetuzumab) or CRS that is refractory to treatment, work up for HLH should be initiated The supportive management of HLH is generally similar to that of CRS. Specific diagnostic, monitoring and management guidelines for HLH are described below.

A patient should be classified as having HLH if five of the following eight criteria are met:

Fever≥38.5° C.

Splenomegaly

Peripheral blood cytopenia consisting of at least two of the following:

Hemoglobin<90 g/L (9 g/dL) (<100 g/L (10 g/dL) for infants<4 weeks old)

Platelet count<100×10$^9$/L (100,000/μL)

ANC<1.0×10$^9$/L (1000/μL)

Fasting triglycerides>2.992 mmol/L (265 mg/dL) and/or fibrinogen<1.5 g/L (150 mg/dL)

Hemophagocytosis in bone marrow, spleen, lymph node, or liver

Low or absent natural killer cell activity

Ferritin>500 mg/L (500 ng/mL)

Soluble interleukin 2 (IL-2) receptor (soluble CD25) elevated 2 standard deviations above age-adjusted laboratory-specific norms Patients should be hospitalized with the following diagnostic and monitoring measures initiated:

Frequent (e.g., every 4 hours) vital signs and physical examination including evaluation for splenomegaly;

Serial (at least daily) monitoring of serum chemistries, complete blood counts, liver function tests (LFTs), ferritin, PT/PTT, fibrinogen, D-dimer and triglycerides;

Consideration of bone marrow and/or lymph node biopsy to assess for hemophagocytosis and active infection, including assessment of EBV protein localization in T/B/NK cells;

Complete infectious disease work-up including:

Blood cultures (bacterial and fungal)

Urine cultures and urinalysis

Radiographic assessments (e.g., chest X-ray or CT scan)

Assessment for active viral infections, including but not limited to EBV and CMV If available, assessment for soluble CD25 and assessment of NK cell function DNA for exploratory genetic testing of mutations potentially associated with HLH, e.g., PRF1, MUNC13-4, STXBP2 should be considered (Zhang et al., *Blood*, 118: 5794-5798, 2011).

Patients with suspected HLH should be treated according to the guidelines in Table 16. In the case of confirmed HLH, study treatment should be permanently discontinued.

have been observed (Assouline et al., *Lancet Haematol*, c128-338, 2016). Most of these were mild to moderate in severity (MABTHERA® European Medicines Agency, Summary of Product Characteristics (EMA SPC)). As CD4+ and CD8+ T-cells (Mueller et al., *Frontiers in Immunology*, 332, 2014) as well as B cells (Egbuniwe et al., *Trends Immunol*, 36: 102-111, 2015) reside in the skin, localized reactions following mosunetuzumab SC administration may occur. Consequently, the risk of injection-site reactions with mosunetuzumab is unknown. Patients who experience localized injection-site reactions following SC administration of mosunetuzumab should be managed according to the guidelines detailed in Table 8.

Neurologic Toxicity

Encephalopathy has been observed in in the setting of CRS and/or elevation in liver function tests (LFTs) following mosunetuzumab treatment.

Neurologic toxicity has been reported in cynomolgus monkeys administered mosunetuzumab and was frequently reported in patients treated with blinatumomab and CD19 CAR T-cell therapy (BLINCYTO® USPI; Kochenderfer et al., *J Clin Oncol*, published online before print Aug. 25, 2014; Maude et al., *New Engl J Med*, 371(16): 1507-1517, 2014). Reported symptoms in patients treated with blinatumomab or CAR T-cell therapy have included headache, confusion, aphasia, encephalopathy, tremor, seizure, and other neurologic events. The etiology of toxicity in these settings is uncertain and may not be responsive to cytokine directed therapy such as tocilizumab, but has generally improved with treatment discontinuations and corticosteroids (BLINCYTO® USPI; Viardot et al., *American Society of Hematology Annual Meeting* 2010, Abstract 2880, 2010; Kochenderfer et al., *J Clin Oncol*, published online before print Aug. 25, 2014). In patients with B-cell ALL treated with blinatumomab, neurologic toxicities were observed in approximately 50% of patients; Grade≥3 neurologic toxicity was observed in approximately 15% of patients. The majority of neurologic adverse events resolved following interruption of blinatumomab, with some patients requiring treatment discontinuation (BLINCYTO® USPI). Based on available clinical data, neurologic adverse events observed with mosunetuzumab have been mild in severity with early onset. The most frequent neurologic events include headache, dizziness, and insomnia.

Tumor Lysis Syndrome

TABLE 16

Management guidelines for suspected hemophagocytic lymphohistiocytosis

| Event | Management |
|---|---|
| Suspected HLH | Withhold study treatment. Consider patient referral to hematologist. Initiate supportive care, including intensive care monitoring if indicated per institutional guidelines. Consider treatment for HLH with appropriate therapy. |
| Confirmed HLH | Permanently discontinue study treatment. Refer patient to a hematologist. Institute appropriate supportive care, including intensive care monitoring, if indicated per the institutional guidelines. Treat with appropriate HLH therapy according to institutional standards or published references (Schram and Berliner, *Blood*, 125: 2908-2914, 2015; Vallurupalli and Berliner, *Blood*, 134(21): 1783-1786, 2019). |

Injection Site Reactions

Localized injection-site reactions following SC administration of the anti-CD20 monoclonal antibody rituximab Tumor lysis syndrome (TLS) is a known pharmacodynamic effect of anti-tumor therapy in hematologic malignancies including NHL. TLS has been reported with blinatumomab, CAR T-cell therapy, and other CD20 directed therapy (BLINCYTO® USPI; GAZYVA® USPI; RITUXAN® USPI; Porter et al., *N Engl J Med,* 365(8): 725-733, 2011). The inherent risk of TLS is dependent on the malignancy being treated and individual patient characteristics (Coiffier et al., *J Clin Oncol,* 26: 2767-2778, 2008). There is the theoretical risk of TLS if treatment with mosunetuzumab results in the rapid destruction of a large number of tumor cells.

The risk of TLS with mosunetuzumab in NHL patients is predicted to be highest for those with bulky disease (defined in the context of TLS as any lesion≥10 cm on the screening CT scan) and elevated pretreatment lactate dehydrogenase (LDH) levels, particularly in the presence of dehydration or compromised renal function. The risk of TLS with mosunetuzumab in CLL patients is predicted to be highest in patients with absolute lymphocyte counts≥25×10$^9$/L or those with any nodal lesion 10 cm, especially in the presence of dehydration or compromised renal function. While DLBCL, transformed lymphomas, and MCLs may be at higher risk of TLS as compared with follicular, marginal, and small cell lymphomas (Cairo et al., *Br J Haematol,* 149: 578-586, 2010), any risk stratification based on tumor type are to be considered along with the effectiveness of therapy (Howard et al., *New Engl J Med,* 364(19), 1844-1854, 2011).

As mosunetuzumab has the potential for potent B-cell killing, all patients will receive prophylaxis for TLS based on the prophylaxis guidelines below.

Upon hospital admission for Cycle 1 study treatment administration (or Cycle 2 for Group E) or hospitalization following dose escalation, the patient's serum chemistry and hematology laboratory samples should be obtained and reviewed and prophylactic measures initiated according to the guidelines described below.

All patients will receive prophylaxis for TLS prior to each mosunetuzumab administration at C1D1 for Group A at C1D1, C1D8, and C1D15 for Groups B and E, as well as the C2D1 infusion for Group E. Prophylaxis guidelines include the following:

Hydration, consisting of a fluid intake of approximately 2-3 L/day starting 24-48 hours prior to the first dose of mosunetuzumab.
  If a patient is hospitalized for the administration of study treatment, IV hydration at a rate of 150-200 mL/hour should begin at the conclusion of mosunetuzumab administration and continue for at least 24 hours thereafter.
  If a patient receives study treatment in the outpatient setting, fluid intake should be maintained at 2-3 L/day for at least 24 hours after mosunetuzumab administration.
  Modification of fluid rate should be considered for individuals with specific medical needs.
Administration of an agent to reduce uric acid:
  Allopurinol (e.g., 300 mg/day orally beginning 72 hours prior to dose and continuing for 3-7 days afterwards) for those patients judged to be of low or intermediate risk of developing TLS per the investigator's discretion.
  For patients with elevated uric acid levels prior to mosunetuzumab treatment, or considered to be at high risk for TLS: rasburicase (e.g., 0.2 mg/kg IV over 30 minutes prior to first dose mosunetuzumab and daily for up to 5 days thereafter) should be administered, unless contraindicated (ELITEK® USPI).
  Treatment with allopurinol/rasburicase should continue as specified above, or if laboratory evidence of TLS is observed until normalization of serum uric acid or other lab parameters.
  If treatment with allopurinol or rasburicase is contraindicated or is otherwise inappropriate in the view of the investigator, the Medical Monitor should be contacted for further guidance.

Infections

Due to its anticipated mode of action resulting in profound B-cell depletion, mosunetuzumab may be associated with an increased risk of infections. Infections have been reported in patients receiving other CD20 directed therapies as well as blinatumomab (BLINCYTO® USPI; GAZYVA® USPI; RITUXAN® USPI). Therefore, mosunetuzumab should not be administered in the presence of active severe infections.

Investigators should exercise caution when considering the use of mosunetuzumab in patients with history of recurring or chronic infections or with underlying conditions that may predispose patients to infections. Signs and symptoms of infection should result in prompt evaluation and appropriate samples for bacteriological investigation prior to starting antibiotic or other treatment.

Particular attention should be given to patients who have had significant prior immunosuppressive treatment such as high dose chemotherapy. Progressive multifocal leukoencephalopathy (PML) has been associated with treatment with CD20 directed therapies including rituximab and obinutuzumab. The diagnosis of PML should be considered in any patient presenting with new-onset neurologic manifestations and consultation with a neurologist and diagnostic procedures including brain MRI and lumbar puncture should be performed as clinically indicated. Note, however, that new onset neurologic adverse events following initial doses of mosunetuzumab may be more likely due to acute effects of mosunetuzumab, as PML associated with rituximab generally occurred following long-term exposure (Carson et al., *Blood,* 113(20): 4834-4840, 2009).

Thrombocytopenia

Thrombocytopenia is associated with other CD20 directed therapies as well as blinatumomab (BLINCYTO® USPI). Reversible thrombocytopenia has been observed following mosunetuzumab treatment in Study GO29781.

In nonclinical testing of mosunetuzumab in cynomolgus monkeys, hematology findings included transiently decreased WBC, lymphocyte, monocyte, eosinophil, basophil, and platelet counts within the first day of mosunetuzumab exposure, followed by recovery or rebound recovery between Days 4-8.

Patients should be closely monitored for thrombocytopenia; regular laboratory tests should be performed until the event resolves. Transfusion of blood products (e.g., platelet transfusion) according to institutional practice is at the discretion of the treating physician. Use of all concomitant therapies, which could possibly worsen thrombocytopenia-related events such as platelet inhibitors and anticoagulants, should also be taken into consideration.

For treatment-emergent thrombocytopenia events that are Grade 3 or higher, dose delay and/or dose modification should be considered.

Elevated Liver Enzymes and Hepatic Events

Elevated liver enzymes have been reported with blinatumomab (BLINCYTO® USPI), usually but not exclusively in the setting of CRS. Grade 3 liver enzyme elevations occurred in approximately 6% of patients outside the setting of CRS. Nearly all liver enzyme elevations resolved either with blinatumomab treatment interruption or while treatment continued. Some patients with resolved liver enzyme elevations were successfully rechallenged, suggesting a first-dose effect rather than direct toxicity (BLINCYTO® Drug Approval Package). Transient Grade 3 AST elevation in the setting of Grade 2 CRS as well as Grade 3 hepatic encephalopathy/Grade 4 elevation in LFTs have been observed following mosunetuzumab treatment.

In nonclinical testing with mosunetuzumab in cynomolgus monkeys, dose-dependent increases in serum total bilirubin along with CRP, fibrinogen, PT, and aPTT were observed, consistent with mosunetuzumab-induced cytokine release and an acute phase protein response, with minimal activation of the coagulation system. Possible drug-related microscopic findings in the liver included single-cell hepatocyte degeneration/necrosis and immune cell infiltration in the portal area. All findings showed evidence of reversibility.

Immunogenicity (Anti-Drug Antibodies)

As with any recombinant antibody, mosunetuzumab may elicit an immune response, and patients may develop antibodies against the molecule. Patients are closely monitored for any potential immune response to mosunetuzumab, which may have an impact on the benefit-risk profile of the agent.

Tumor Inflammation/Flare

Adverse events associated with tumor inflammation/flare have been reported in Study GO29781. Consistent with the mechanism of action of mosunetuzumab, tumor flare is likely due to the influx of T cells into tumor sites following mosunetuzumab administration and may be associated with pseudoprogression. Tumor flare-associated adverse events observed to date have had a short time to onset following initial mosunetuzumab administration. Tumor flare may additionally occur in patients who are retreated with mosunetuzumab following disease progression. On the basis of emerging safety data, tumor flare has manifested as tumor pain, increase in size of known nodal or extranodal lesions by clinical or radiographic assessment, as well as new or worsening pleural effusions. In addition, depending on tumor size and anatomic location, tumor flare may potentially result in mass effects on vital structures including airways, major blood vessels, gastrointestinal tract (risk of perforation and hemorrhage), and/or major organs. If such manifestations are temporally associated with early mosunetuzumab dosing, the treating physician/study investigator should consider those events to be tumor flare and report as "tumor flare" or "tumor inflammation". For patients with tumors at critical anatomic locations, the treating physician/study investigator should contact the Medical Monitor to discuss risk assessment and mitigation strategies prior to mosunetuzumab treatment and patients should be closely monitored for tumor flare.

D. Assessment of Severity and Causality of Adverse Events

The adverse event severity grading scale for the NCI CTCAE (v4.0) is used for assessing adverse event severity unless otherwise specified. Table 17 is used for assessing severity for adverse events that are not specifically listed in the NCI CTCAE.

TABLE 17

Adverse event severity grading scale for events not specifically listed in NCI CTCAE

| Grade | Severity |
|---|---|
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living |
| 3 | Severe or medically significant, but not immediately life-threatening; hospitalization or prolongation of hospitalization indicated; disabling; or limiting self-care activities of daily living Life-threatening consequences or urgent intervention indicated |

NCI CTCAE = National Cancer Institute Common Terminology Criteria for Adverse Events.
Note:
Based on the most recent version of NCI CTCAE (v5.0).

Instrumental activities of daily living refer to preparing meals, shopping for groceries or clothes, using the telephone, managing money, etc.

Examples of self-care activities of daily living include bathing, dressing and undressing, feeding oneself, using the toilet, and taking medications, as performed by patients who are not bedridden.

Investigators should use their knowledge of the patient, the circumstances surrounding the event, and an evaluation of any potential alternative causes to determine whether an adverse event is considered to be related to the study drug, indicating "yes" or "no" accordingly. The following guidance should be taken into consideration (see also Table 18):

Temporal relationship of event onset to the initiation of study drug

Course of the event, with special consideration of the effects of dose reduction, discontinuation of study drug, or reintroduction of study drug (as applicable)

Known association of the event with the study drug or with similar treatments

Known association of the event with the disease under study

Presence of risk factors in the patient or use of concomitant medications known to increase the occurrence of the event Presence of non-treatment-related factors that are known to be associated with the occurrence of the event

TABLE 18

Causal attribution guidance
Is the adverse event suspected to be caused by the study drug on the basis of facts, evidence, science-based rationales, and clinical judgment?

| | |
|---|---|
| YES | There is a plausible temporal relationship between the onset of the adverse event and administration of the study drug, and the adverse event cannot be readily explained by the patients clinical state, intercurrent illness, or concomitant therapies; and/or the adverse event follows a known pattern of response to the study drug; and/or the adverse event abates or resolves upon discontinuation of the study drug or dose reduction and, if applicable, reappears upon re-challenge. |

TABLE 18-continued

Causal attribution guidance
Is the adverse event suspected to be caused by the study drug on the basis of facts,
evidence, science-based rationales, and clinical judgment?

NO  An adverse event is considered related, unless it fulfills the criteria specified below.
Evidence exists that the adverse event has an etiology other than the study drug
(e.g., preexisting medical condition, underlying disease, intercurrent illness, or
concomitant medication); and/or the adverse event has no plausible temporal
relationship to administration of the study drug (e.g., cancer diagnosed 2 days
after first dose of study drug).

For patients receiving combination therapy, causality is assessed individually for each protocol-mandated therapy.

Example 8. Statistical Considerations and Analysis Plan

A. Determination of Sample Size

The sample size for the GO29781 trial is based on the dose-escalation rules described herein. The planned enrollment for the study is approximately 130-226 patients during the dose-escalation stage (100-166 patients with NHL and 30-60 patients with CLL) and approximately 290-520 patients during the expansion stage. Approximately 80 patients each are enrolled in R/R DLBCL/trFL and R/R FL expansion cohorts of Group B and Group E.

B. Dose-Escalation Stage

The dose-escalation stage of the study is primarily designed to assess safety, tolerability and pharmacokinetics. The trial initially utilizes single-patient dose-escalation cohorts but converts to a standard 3+3 design based on criteria described above. Table 19 provides the probability of not observing a DLT in 3 patients or observing ≤1 DLT in 6 patients given different underlying DLT rates. For example, if the true underlying DLT rate is 20%, then the probability of observing no DLT in 3 patients is 51% and the probability of observing ≤1 DLT in 6 patients is 66%.

TABLE 19

Probability of observing DLTs with different underlying DLT rates

| True Underlying DLT Rate | Probability of Observing No DLT in 3 Patients | Probability of Observing ≤ 1 DLT in 6 Patients |
| --- | --- | --- |
| 0.10 | 0.73 | 0.89 |
| 0.20 | 0.51 | 0.66 |
| 0.33 | 0.30 | 0.36 |
| 0.40 | 0.22 | 0.23 |
| 0.50 | 0.13 | 0.11 |
| 0.60 | 0.06 | 0.04 |

C. Dose-Expansion Stage

The dose-expansion stage of the study is designed to assess safety as well as efficacy signals.

Table 20 provides probabilities of observing at least one adverse event among 10, 20, 40, and 80 patients when true underlying probabilities of adverse events range from 1%-20%. For example, if the true underlying adverse event rate is 5%, then the probability of observing at least one adverse event in 40 patients is 87% and in 80 patients is 98%.

For the R/R DLBCL/trFL and the R/R FL expansion cohorts of Group B and Group E, the complete response rate will be estimated, along with the Clopper-Pearson exact 95% CI.

For the R/R DLBCL/trFL expansion cohorts of Group B and Group E: with observed CR rates of 30% and 35%, a sample size of 80 patients will result in 95% CIs of (20%, 41%) and (25%, 46%), respectively, i.e., a true CR rate below 20% is ruled out. Additionally, 80 patients will provide an 85% power to detect a 15% increase in CR rate from 20% to 35%, at the 5% two-sided significance level.

For the R/R FL expansion cohorts of Group B and Group E: with observed CR rates of 24% and 28%, a sample size of 80 patients will result in 95% CIs of (15%, 35%) and (18%, 39%), respectively, i.e., a true CR rate below 14% is ruled out. Additionally, 80 patients will provide an 83% power to detect a 14% increase in CR rate from 14% to 28%, at the 5% two-sided significance level.

For the R/R FL expansion cohorts of Group B and Group E: with observed CR rates of 24% and 28%, a sample size of 80 patients will result in 95% CIs of (15%, 35%) and (18%, 39%), respectively, i.e., a true CR rate below 14% is ruled out. Additionally, 80 patients will provide an 83% power to detect a 14% increase in CR rate from 14% to 28%, at the 5% two-sided significance level.

The Sponsor may enroll more than 80 patients in the R/R FL expansion cohorts of Group B and Group E to obtain data from at least 60 patients with R/R FL who are refractory to both anti-CD20 therapy and an alkylating agent to perform statistical analyses. With observed CR rates of 25%, a sample size of 60 patients will result in 95% CIs of (15%, 38%); that is, a true CR rate below 8% is ruled out.

Interim analyses to pause or stop patient enrollment for unacceptable toxicity and futility will be performed in the expansion stage of the study. In summary, continuous safety monitoring is performed and interim analyses are conducted periodically for futility at least once in each expansion cohort. Enrollment may be stopped in the event of unacceptable toxicity or a lower than expected response rate in the expansion cohorts.

TABLE 20

Probability of safety-signal detection with an expansion cohort of 10, 20, 40, and 80 patients

| True Underlying Probability of an AE | Probability of Observing at Least 1 AE in 10 Patients (%) | Probability of Observing at Least 1 AE in 20 Patients (%) | Probability of Observing at Least 1 AE in 40 Patients (%) | Probability of Observing at Least 1 AE in 80 Patients (%) |
|---|---|---|---|---|
| 0.01 | 10 | 18 | 33 | 55 |
| 0.05 | 40 | 64 | 87 | 98 |
| 0.1 | 65 | 88 | 99 | >99 |
| 0.15 | 80 | 96 | >99 | >99 |
| 0.2 | 89 | 99 | >99 | >99 |

D. Summaries of Treatment Group Comparability

Demographics and baseline characteristics such as age, sex, weight, type of malignancy, duration of malignancy, and baseline ECOG Performance Status are summarized using means, standard deviations, medians, and ranges for continuous variables and proportions for categorical variables. All summaries are presented overall and by dose level and arm.

Study drug administration data is summarized by dose level and arm.

The final analysis is based on patient data collected through the time of study discontinuation. All analyses are based on the safety-evaluable population, defined as patients who receive any amount of study treatment. All summaries are presented according to assigned dose level.

E. Safety Analyses

The safety analyses include all patients who received any amount of study treatment.

Safety is assessed through summaries of adverse events, changes in laboratory test results, changes in ECGs, changes in ADAs, and changes in vital signs.

All collected adverse event data are listed by assigned dose level and patient number. All adverse events occurring on or after treatment on Cycle 1 Day 1 are summarized by mapped term, appropriate thesaurus levels, and NCI CTCAE v4.0 toxicity grade. In addition, all serious adverse events, including deaths, are listed separately and summarized. DLTs and adverse events leading to treatment discontinuation are also separately listed.

F. Pharmacokinetic Analyses

Individual and mean serum concentration of mosunetuzumab versus time data are tabulated and plotted by dose level. The pharmacokinetics of mosunetuzumab are summarized by estimating total AUC, $C_{max}$, $C_{min}$, CL, and $V_{ss}$ (as appropriate for data collected). Estimates for these parameters are tabulated and summarized. Inter-patient variability and drug accumulation are evaluated.

Serum trough and maximum concentrations for atezolizumab and tocilizumab, where applicable, are summarized, as appropriate and as data allow. Compartmental, non-compartmental, and/or population methods may be considered. Additional PK analyses are conducted as appropriate.

G. Activity Analyses

Response assessment data, PFS, and duration of response, all assessed by the investigator, are summarized for all patients by dose level, schedule, and arm. The objective response rate (ORR) is estimated. Investigator-assessed objective response is defined as a CR or PR as determined by investigator assessment using standard criteria. Patients with missing or no response assessments are classified as non-responders.

Among patients with an investigator-assessed objective response, duration of response is defined as the time from the initial CR or PR to the time of disease progression as determined by the investigator, or death. If a patient does not experience disease progression or death from any cause before the end of the study, duration of response is censored at the day of the last tumor assessment.

Investigator-assessed PFS is defined as the time from the first day of study treatment (Cycle 1, Day 1) to disease progression as determined by the investigator, or death, whichever occurs first. If a patient has not experienced PD or death, PFS is censored at the day of the last tumor assessment.

H. Activity Analyses for the R/R DLBCL and Transformed FL Expansion Cohorts, and the R/R FL Expansion Cohorts at Group B RP2D and Group E RP2D Primary Efficacy Endpoint The primary efficacy endpoint is independent review facility (IRF)-assessed CR rate, defined as the proportion of patients whose best overall response is a CR based upon IRF assessment using standard criteria for NHL (Cheson et al., *J Clin Oncol*, 25: 579-586, 2007). Patients with missing or no response assessments are classified as non-complete responders.

Comparisons with respect to CR rate between the treated patient population and historical controls are tested. The control CR rate is assumed to be 20% for the R/R DLBCL and transformed FL expansion cohorts (see Table 21 for historical controls) and is assumed to be 14% for the R/R FL expansion cohorts (see Table 22 for historical controls).

TABLE 21

Summary of clinical trial data in patients with R/R DLBCL/transformed FL

| Therapy Regimen (n = patient number for efficacy assessment) | ORR (%) | CR (%) | NHL response criteria |
|---|---|---|---|
| Rituximab plus gemcitabine and oxaliplatin (n = 48) | 61% | CR = 23% CRu = 21% | International Working Group Criteria (Cheson et al., *J Clin Oncol*, 17: 1244, 1999) |

TABLE 21-continued

Summary of clinical trial data in patients with R/R DLBCL/transformed FL

| Therapy Regimen (n = patient number for efficacy assessment) | ORR (%) | CR (%) | NHL response criteria |
|---|---|---|---|
| Pixantrone (n = 64) | 41% | CR/CRu = 23% | International Working Group Criteria (Cheson et al., *J Clin Oncol*, 17: 1244, 1999) |
| Rituximab plus bendamustine (n = 137) | 48% | CR = 17% | Cheson et al., *J Clin Oncol*, 25: 579-586, 2007 |
| Blinatumomab (n = 21) | 43% | CR = 19% | Cheson et al., *J Clin Oncol*, 25: 579-586, 2007 |
| Blinatumomab (n = 11) | 55% | CR/CRu = 36% | International Working Group Criteria (Cheson et al., *J Clin Oncol*, 17: 1244, 1999) |
| Axicabtagene ciloleucel (n = 101) | 72% | 51% | Cheson et al., *J Clin Oncol*, 25: 579-586, 2007 |
| Polatuzumab vedotin plus bendamustine with rituximab (n = 40) | 63% | 50% | Modified Lugano 2014 |

CR: complete response as the best response;
CRu: unconfirmed complete response as the best response;
CT: computed tomography;
DLBCL: diffuse large B-cell lymphoma;
FL: follicular lymphoma;
NHL: non-Hodgkin's lymphoma;
ORR: objective response rate;
PET: positron emission tomography;
PR: partial response;
R/R DLBCL: relapsed/refractory diffuse large B-cell lymphoma.

Data for rituximab plus gemcitabine and oxaliplatin is from Mounier et al., *Haematologica*, 98: 1726-1731, 2013. Data for pixantrone includes 53 patients with DLBCL, 10 patients with transformed indolent lymphoma, and 1 patient with Grade 3 FL (Pettengell et al., *Lancet Oncol*, 13: 696-706, 2012). Data for Rituximab plus bendamustine is from Dang et al., *Br J Haematol*, doi: 10.1111/bjh.14820 [Epub ahead of print], 2017. Data for blinatumomab are from Viardot et al., *Blood*, 127: 1410-1416, 2016 and Goebeler et al., *J Clin Oncol*, 34: 1104-1111, 2016. Data for axicabtagene ciloleucel is from Neelapu et al., *Blood*, 128: LBA-6, 2016. Data for polatuzumab vedotin plus bendamustine with rituximab is from POLIVY™ USPI.

TABLE 22

Summary of clinical trial data in patients with R/R FL previously treated with two or more prior lines of systemic therapy

| Therapy Regimen (n = patient number for efficacy assessment) | ORR (%) | CR (%) | mDOR | Median PFS | Fatal and Serious Treatment-Emergent Adverse Events |
|---|---|---|---|---|---|
| Idelalisib (n = 72) | 54% | 8% | Median not evaluable | 11.0 months | Hepatotoxicity, 11%-18% Diarrhea/colitis, 14%-19% Pneumonitis, 4% Infections, 21%-36% Intestinal perforation |
| Copanlisib (n = 104) | 59% | 14% | 12.2 months | 11.2 months | Infections, 19% Hyperglycemia, 41% Hypertension, 26% Pneumonitis, 5% Neutropenia, 24% |

CR: complete response as the best response;
mDOR: median of duration of response;
FL: follicular lymphoma;
ORR: objective response rate;
mPFS: median of progression-free survival.

Accelerated approval was granted for idelalisib (ZYDE-LIG®; Gopal et al., *N Engl J Med,* 370: 1008-1018, 2014) and copanlisib (ALIQOPA™; Dreyling et al., *Ann Oncol,* 25: 76-82, 2017) for this indication based on overall response rate. Continued approval for this indication may be contingent upon verification and description of clinical benefit in a confirmatory trial.

The following hypothesis is tested at 0.05 level of significance in each of the R/R DLBCL and transformed FL expansion cohorts at Group B RP2D and Group E RP2D:

$H_0$: CR rate=20% versus $H_a$: CR rate≠20%

The following hypothesis is tested at 0.05 level of significance in each of the R/R FL expansion cohorts at Group B RP2D and Group E RP2D:

$H_0$: CR rate=14% versus Ha: CR rate≠14%

The exact 95% confidence intervals using the Clopper-Pearson method for CR rate are provided. The exact binomial test is used to evaluate whether single-agent mosunetuzumab treatment at Group B RP2D or mosunetuzumab in combination with atezolizumab at Group E RP2D results in a statistically significant increase in CR rate.

Secondary Efficacy Endpoints

The secondary efficacy endpoints include:

Investigator-assessed CR rate, defined as the proportion of patients whose best overall response is a CR based upon investigator assessment using standard criteria for NHL (Cheson et al., *J Clin Oncol,* 25: 579-586, 2007). The exact 95% confidence intervals using the Clopper-Pearson method for CR rate are provided.

ORR, defined as the proportion of patients whose best overall response is a PR or CR using standard criteria for NHL (Cheson et al., *J Clin Oncol,* 25: 579-586, 2007). ORR is assessed by the IRF and by the investigator. The exact 95% confidence intervals using the Clopper-Pearson method for ORR are provided.

Duration of complete response, defined as the time from the initial occurrence of a documented CR until documented disease progression or death due to any cause, whichever occurs first. Duration of complete response will be assessed by the IRF and by the investigator, using standard criteria for NHL. The Kaplan-Meier estimate is provided. The Brookmeyer-Crowley method is used to construct the 95% confidence interval for the median duration of complete response.

Duration of response, defined as the time from the initial occurrence of a documented PR or CR until documented disease progression or death due to any cause, whichever occurs first. Duration of response is assessed by the IRF and by the investigator, using standard criteria for NHL. The Kaplan-Meier estimate will be provided. The Brookmeyer-Crowley method is used to construct the 95% confidence interval for the median duration of response.

PFS, defined as the time from the first study treatment to the first occurrence of disease progression or death from any cause, whichever occurs first. PFS is assessed by the IRF and by the investigator, using standard criteria for NHL. The Kaplan-Meier estimate is provided. The Brookmeyer-Crowley method is used to construct the 95% confidence interval for the median PFS. Kaplan-Meier method is used to estimate 6-month PFS and 1-year PFS, along with the standard error and the corresponding 95% CIs using Greenwood's formula.

OS, defined as the time from the first study treatment to the date of death from any cause. The Kaplan-Meier estimate is provided. The Brookmeyer-Crowley method is used to construct the 95% confidence interval for the median OS. Kaplan-Meier method is used to estimate 6-month OS and 1-year OS, along with the standard error and the corresponding 95% CIs using Greenwood's formula.

I. Patient-Reported Outcomes Analysis

For all questionnaires, the patient-reported outcomes (PRO-evaluable population includes all patients in the NHL expansion cohorts with a baseline assessment and at least one post-baseline assessment. The EORTC QLQ-C30 and FACT-Lym subscale are scored according to user manuals. Summary statistics and changes from baseline scores are calculated for all timepoints. A repeated-measures mixed model is used to examine the longitudinal profiles for each cohort. The proportion of patients who report changes from baseline meeting or exceeding the minimal important difference for each measure is also reported in each cohort. For the EQ-5D-5L, summary statistics for the health status according to the VAS and changes in the index utility score from baseline are calculated. The results are used for more complete health economic data analysis.

J. Exploratory Pharmacodynamics Analysis

Exploratory pharmacodynamic analyses include assessments of pharmacodynamic biomarkers in both tumor tissue and blood when available. Additional pharmacodynamic analyses are conducted as appropriate.

K. Interim Analyses

Continuous safety monitoring and interim analyses are performed for the expansion portion of the study to guide potential early stopping of enrollment in the event of unacceptable toxicity in any given expansion cohort or a lower than expected response rate in the expansion cohorts.

A posterior probability approach (Thall and Simon, Biometrics, 50(2): 337-349, 1994) is used to evaluate toxicity in the expansion cohorts, including the rate of DLTs that occur during the DLT assessment periods for dose-escalation cohorts. If at any time in any expansion cohort, the number of observed DLTs indicates that there is an approximately 80% chance that the true DLT rate is 20%, accrual to the cohort may be paused, and the IMC will meet to determine whether further enrollment in the cohort should be halted and/or provide other recommendations as described herein.

Interim analyses are also conducted periodically for futility at least once in each of the expansion cohorts. If the interim analysis suggests that the ORR with study treatment is lower than that of historical controls, enrollment into the expansion cohort may be stopped. Specifically, enrollment may be stopped if there is an approximately 80% chance that the true ORR is 25%, using the posterior probability approach with non-informative prior. In all cases, decisions to stop enrollment into the expansion cohorts based on futility are made in consultation with study investigators.

L. Immunogenicity Analyses

Validated screening, titering, and confirmatory assays are employed to assess ADAs before, during, and after treatment with mosunetuzumab and atezolizumab. The immunogenicity analysis population consists of all patients with at least one ADA assessment. Patients are considered to be negative for ADAs if they are ADA negative at all timepoints. Patients are considered to be treatment unaffected if they are ADA positive at baseline but do not have any postbaseline samples with a titer that is at least 4-fold greater than the titer of the baseline sample. Patients are considered to have treatment-induced ADA responses if they are ADA negative or missing data at baseline and then develop an ADA response following study drug administration. Patients are considered to have treatment-enhanced ADA responses if they are ADA positive at baseline and the titer of one or more postbaseline samples is at least 4-fold greater (i.e., at least 0.60 titer unit) than the titer of the baseline sample.

The relationship between ADA status and safety, efficacy, PK, and biomarker endpoints may also be assessed as appropriate and reported in a descriptive manner via subgroup analyses.

Example 9. Summary of Clinical Data for Mosunetuzumab

Evaluation of mosunetuzumab in Study GO29781 is ongoing. In this study, mosunetuzumab has been studied according to the following dosing schedules in Groups A, B, and E. (Note: There is no Group C).

Administered intravenously as a single agent on a Cycle 1 non-fractionated dose schedule (Group A).

Administered intravenously as a single agent on a Cycle 1 step-up dose schedule, with escalating Cycle 1 Day 1, Cycle 1 Day 8, and Cycle 1 Day 15 dose levels, followed by administration of the highest dose level on Day 1 of subsequent cycles (Group B).

Administered intravenously as a single agent on a Cycle 1 step-up dose schedule with concurrent administration of atezolizumab starting in Cycle 2 (Group E).

A. Safety

Doses from 0.05 mg to 2.8 mg have been tested on the Group A dosing schedule. Dose escalation on the Group E dosing schedule is ongoing. The maximum tolerated dose (MTD) for mosunetuzumab has not been reached, based on any dosing schedule in the dose-escalation groups.

As of 21 Jan. 2020, a total of 432 patients have been treated with mosunetuzumab in Study GO29781. The most frequently observed adverse event considered related to mosunetuzumab is CRS, occurring in 31% of safety evaluable patients. Most of these events have been Grades 1-2 using the modified CRS grading system (Lee et al., Blood, 124(2): 188-195, 2014), except four Grade 3 events observed in patients treated in Group B at 1.0/2.0/13.5 mg, 1.0/2.0/27.0 mg, and 1.0/2.0/60.0/30.0 mg, and one Grade 4 event observed in a patient treated in Group B at 1.0/2.0/60.0/30.0 mg. Serious adverse events were reported in 174 patients (40%); in 90 patients (21%), the serious adverse events were related to mosunetuzumab by investigator assessment. Fifty patients have experienced adverse events with fatal outcome: 45 patients experienced malignant neoplasm progression (reported as adverse events), 1 patient had hemophagocytic lymphohistiocytosis (HLH), 1 patient had pneumonia, 2 patients had sepsis, and 1 patient had candida sepsis.

Figure 10:
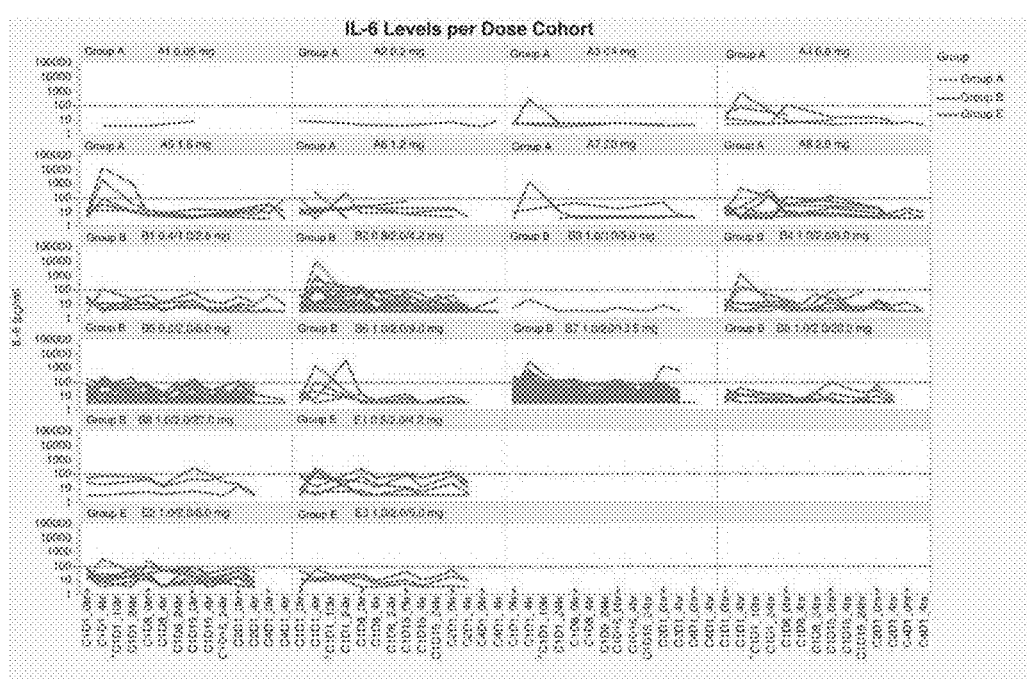
FIG. 10 is a set of graphs showing levels of IL-6 in plasma samples upon administration of mosunetuzumab with different dosing regimens in patients from Groups A, B, and E. Plasma samples are variously taken at 0 hrs (immediately), 4 hrs, 10 hrs, and 24 hrs after administration of the C1D1, C1D2, and C1D3 doses on days 1, 8, and 15 of Cycle 1 (labeled "C1D1," "C1D8," and "C1D15," respectively), as well as 0 hrs (immediately) and 4 hrs after administration of the C2D1 and C4D1 doses. Plasma IL-6 levels are reported in units of pg/mL.

Mosunetuzumab induced a transient elevation in plasma IL-6, with peak levels occurring in the majority of patients within 4 to 6 hours of Cycle 1 Day 1 dose and returning to baseline by 24 hours (FIG. 10). In Study GO29781, Group A, where patients received a single dose level of mosunetuzumab at all cycles, there was no clear dose dependence to the magnitude of IL-6 increase. In Groups B and E, maximum levels of IL-6 were observed after the first dose, even when subsequently higher doses of mosunetuzumab were administered during double-step fractionation and at later cycles. The kinetics as well as the fold-change of IL-6 relative to baseline were associated with the incidence of AEs, most notably CRS. Patients experiencing CRS exhibited a trend for higher peak levels of IL-6 during the first cycle; however, there is a significant overlap between patients with and without CRS. The IL-6 response, in combination with the safety profile, suggests that tolerable and potentially more efficacious higher doses of mosunetuzumab may be administered using the step-up dose scheme.

Figure 11:
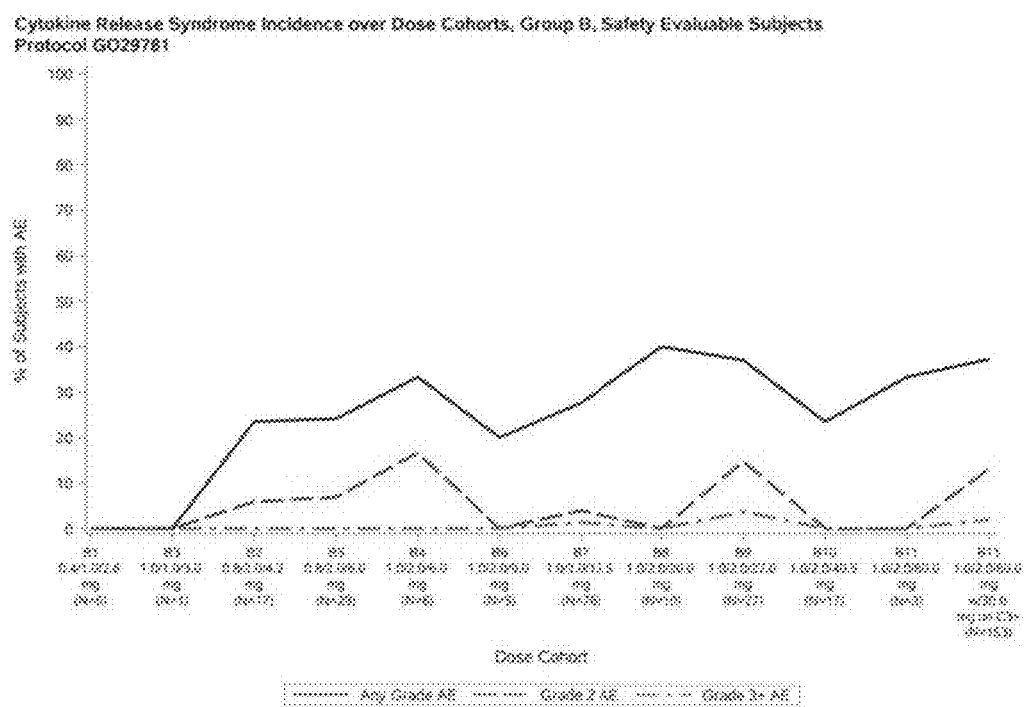
FIG. 11 is a graph showing rates of any Grade, Grade 2, and Grade 3+ cytokine release syndrome (CRS) in Group B patients administered different doses of mosunetuzumab (x-axis). AE=adverse event, i.e., CRS.
Figure 13:
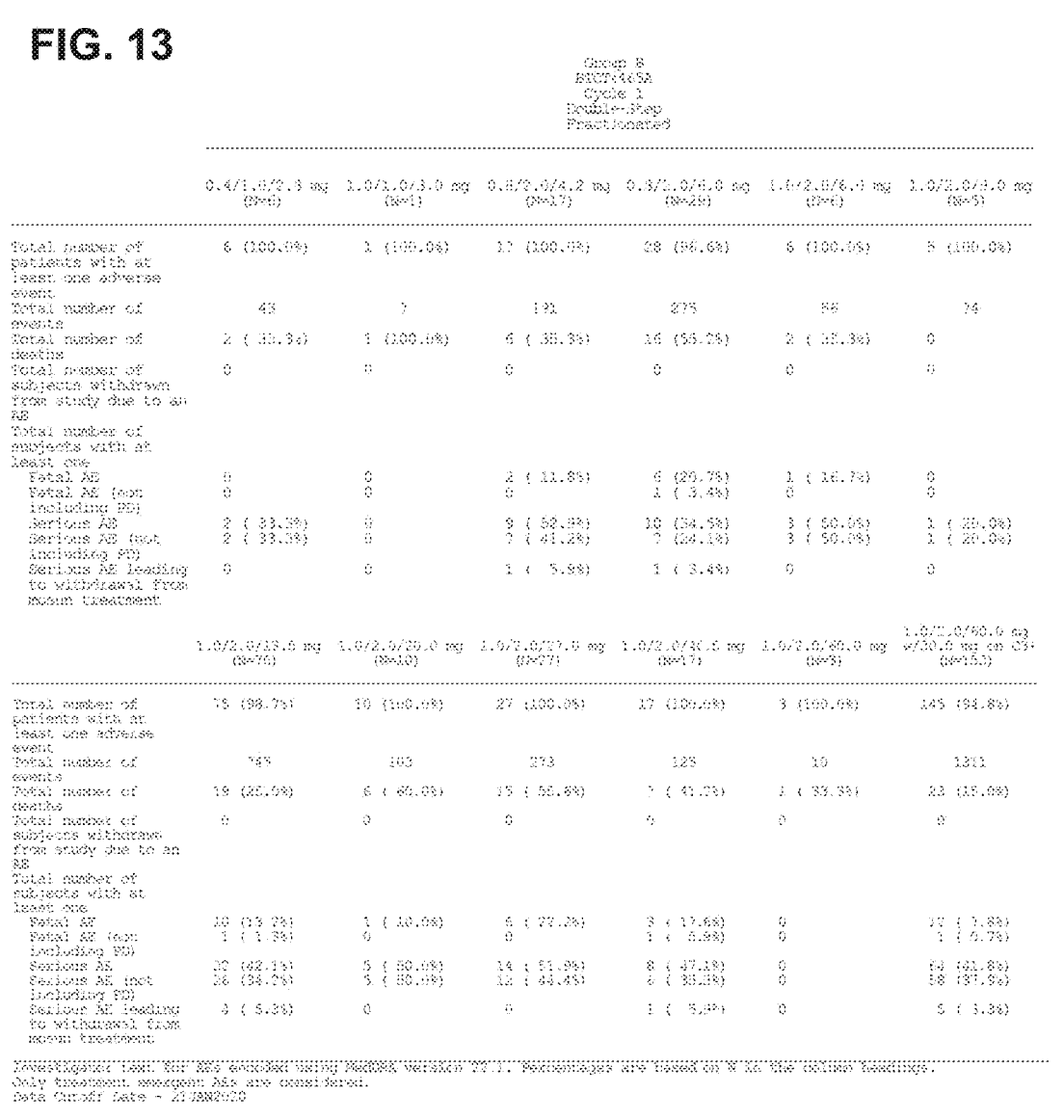

As of 21 Jan. 2020, no apparent association between patients with treatment-related AEs or Grade 3 AEs with mosunetuzumab dose levels was observed in Group B patients treated in Study GO29781 where mosunetuzumab was administered as a single agent using Cycle 1 step-up dosing regimen. The observed CRS incidence across different dose levels tested in Group B patients is provided in FIG. 11. This indicates that step-up dosing may be an effective safety mitigation strategy that can also provide a non-dose dependent exposure-safety profile. A summary of all adverse events in Groups A and B can be found in FIGS. 12 and 13, respectively.

In addition, adverse events observed in Group E have indicated that the overall safety profile when mosunetuzumab is administered subcutaneously or in combination with atezolizumab is not substantially worse than the safety profile observed in Group B at dose levels tested to date. Based on current data, no unexpected or unmanageable toxicities have been observed in Group E that have substantially differed from that of single-agent mosunetuzumab or known toxicities associated with atezolizumab.

Based on the overall safety, efficacy, and PK profile, the Group B Day 1 mosunetuzumab dose level has been fixed at 1 mg, the Day 8 dose level has been fixed at 2 mg, and only the Day 15 dose level has continued in dose escalation. As of 6 May 2019, the 1 mg/2 mg/60 mg dose level has cleared the dose-limiting toxicity (DLT) assessment period.

B. Activity

In Study GO29781 as of the clinical cutoff date of 21 Jan. 2020, of the 415 patients in the primary efficacy population across all treatment groups, 60 patients (39%) had investigator-assessed objective responses (CRs or partial responses (PRs)). Overall, 110 patients (27%) had CRs, 76 patients (18%) had PRs, 52 patients (13%) had stable disease (SD), and 160 patients (39%) had progressive disease (PD) as the best overall response assessed by the Investigator using the revised response criteria for malignant lymphoma (Cheson et al., *J Clin Oncol*, 25: 579-586, 2007). In Group A (Cycle 1 fixed mosunetuzumab dosing; n=33 patients), 5 patients (15.2%) had CRs, 1 patient (3%) had a PR, 6 patients (18.2%) had stable disease (SD), and 20 patients (60.6%) had progressive disease (PD). In Group B (Cycle 1 step-up mosunetuzumab dosing; n=336 patients), 92 patients (27%) had CRs, 63 patients (19%) had PRs, 41 patients (12%) had stable disease (SD), and 124 patients (37%) had progressive disease (PD). In Group E (Cycle 1 step-up mosunetuzumab dosing and Cycle 2+ mosunetuzumab+atezolizumab dosing; n=24 patients), 8 patients (33%) had CRs, 2 patients (8%) had PRs, 4 patients (17%) had stable disease (SD), and 10 patients (42%) had progressive disease (PD). Objective responses were observed in indolent and aggressive NHL histologies including FL, DLBCL, primary mediastinal B-cell lymphoma (PMBCL), Richter's transformation, MCL, marginal zone lymphoma (MZL), small lymphocytic lymphoma (SLL), transformed FL, and other transformed indolent NHL.

C. Clinical Pharmacokinetics and Immunogenicity

Clinical PK data from Group A (0.05 to 2.8 mg fixed dose, every 3 weeks (Q3W) dosing) and Group B (0.4/1/2.8 to 1/2/60 mg Cycle-1 step-up doses on Day 1/8/15, followed by Q3W dosing) were analyzed in the ongoing Phase I/Ib (GO29781) study.

Mosunetuzumab serum drug concentrations reach $C_{max}$ at the end of infusion (approximately 4 hours) and decline in a multi-phasic fashion, with an α half-life of about 3-4 days and apparent half-life ($t_{1/2}$) of approximately 6 to 11 days. The apparent $t_{1/2}$ estimates are shorter than the typical $t_{1/2}$ of 21 days for an IgG1 antibody, and likely reflect the impact on drug clearance due to target-mediated drug disposition at all tested dose levels. Mosunetuzumab PK exposure increased in an approximately dose-proportional manner over the dose range tested. Moderate pharmacokinetic variability was observed. The population PK following IV administrations of mosunetuzumab was well described by a 2 compartment PK model with time-dependent clearance. PK of mosunetuzumab remains similar when dosed in combination with atezolizumab.

Of 352 patients tested to date, anti-drug antibodies (ADAs) to mosunetuzumab were detected in 1 patient. This patient completed 8 cycles of mosunetuzumab SC treatment and was ADA negative throughout this period. After disease progression, the patient was then treated with mosunetuzumab in combination with atezolizumab for an additional 13 cycles, and the patient developed mosunetuzumab ADAs in cycles 2, 3, 4, 6, 8 and 12 during combination treatment. The presence of ADAs to mosunetuzumab had no apparent impact on drug exposure and safety. This patient tested negative for antibodies to atezolizumab.

VIII. Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a subject having a B cell proliferative disorder comprising administering to the subject a bispecific antibody that binds to CD20 and CD3 as a monotherapy for treating the B cell proliferative disorder in a dosing regimen comprising at least a first dosing cycle, a second dosing cycle, and a third dosing cycle, wherein:

(a) the first dosing cycle comprises a first dose (C1D1), a second dose (C1D2), and a third dose (C1D3) of the bispecific antibody, wherein the C1D1 is 1 mg, the C1D2 is 2 mg, and the C1D3 is 60 mg;

(b) the second dosing cycle comprises a single dose (C2D1) of the bispecific antibody, wherein the C2D1 is 60 mg; and (c) the third dosing cycle comprises a single dose (C3D1) of the bispecific antibody, wherein the C3D1 is 30 mg, wherein the B cell proliferative disorder is a diffuse large B cell lymphoma (DLBCL), a follicular lymphoma (FL), a mantle cell lymphoma (MCL), a marginal zone lymphoma (MZL), or a chronic lymphoid leukemia (CLL), wherein the bispecific antibody is a full-length antibody, and wherein the bispecific antibody comprises:

an anti-CD20 arm comprising a first binding domain comprising the following six hypervariable regions (HVRs):
  (a) an HVR-H1 comprising the amino acid sequence of GYTFTSYNMH (SEQ ID NO: 1);
  (b) an HVR-H2 comprising the amino acid sequence of AIYPGNGDTSYNQKFKG (SEQ ID NO: 2);
  (c) an HVR-H3 comprising the amino acid sequence of VVYYSNSYWYFDV (SEQ ID NO: 3);
  (d) an HVR-L1 comprising the amino acid sequence of RASSSVSYMH (SEQ ID NO: 4);
  (e) an HVR-L2 comprising the amino acid sequence of APSNLAS (SEQ ID NO: 5); and
  (f) an HVR-L3 comprising the amino acid sequence of QQWSFNPPT (SEQ ID NO: 6); and an anti-CD3 arm comprising a second binding domain comprising the following six HVRs:
  (a) an HVR-H1 comprising the amino acid sequence of NYYIH (SEQ ID NO: 9);
  (b) an HVR-H2 comprising the amino acid sequence of WIYPGDGNTKYNEKFKG (SEQ ID NO: 10);
  (c) an HVR-H3 comprising the amino acid sequence of DSYSNYYFDY (SEQ ID NO: 11);
  (d) an HVR-L1 comprising the amino acid sequence of KSSQSLLNSRTRKNYLA (SEQ ID NO: 12);
  (e) an HVR-L2 comprising the amino acid sequence of WASTRES (SEQ ID NO: 13); and
  (f) an HVR-L3 comprising the amino acid sequence of TQSFILRT (SEQ ID NO: 14).

2. The method of claim 1, wherein the C1D1, the C1D2, and the C1D3 are administered to the subject on Days 1, 8, and 15, respectively, of the first dosing cycle and/or the C2D1 is administered to the subject on Day 1 of the second dosing cycle and the C3D1 is administered to the subject on Day 1 of the third dosing cycle.

3. The method of claim 1, wherein the first, second, and third dosing cycles are 21-day dosing cycles or the first dosing cycle is a 21-day dosing cycle and the second and third dosing cycles are 28-day dosing cycles.

4. The method of claim 1, wherein the dosing regimen further comprises one or more additional dosing cycles beyond the third dosing cycle.

5. The method of claim 4, wherein the additional dosing cycles are 21-day dosing cycles or 28-day dosing cycles.

6. The method of claim 4, wherein one or more of the additional dosing cycles comprise an additional single dose of the bispecific antibody.

7. The method of claim 6, wherein the additional single dose of the bispecific antibody is administered to the subject on Day 1 of each additional dosing cycle and/or is equivalent in amount to the C3D1.

8. The method of claim 4, wherein the dosing regimen comprises from five to 14 additional dosing cycles beyond the third dosing cycle.

9. The method of claim 1, wherein the subject has received at least one prior systemic therapy for the B cell proliferative disorder.

10. The method of claim 9, wherein the prior systemic therapy comprises an anti-CD20 antibody, a chemotherapeutic agent, a radio-immunotherapy, a phosphoinositide 3-kinase inhibitor, an autologous stem cell transplant therapy, and/or a chimeric antigen receptor-T-cell (CAR-T) therapy.

11. The method of claim 9, wherein the prior systemic therapy comprises a Bruton's tyrosine kinase (BTK) inhibitor, an anthracycline, and/or an alkylating agent.

12. The method of claim 9, wherein the subject:
  (a) has received a first-line systemic therapy and a second-line systemic therapy for the B cell proliferative disorder; and/or
  (b) has exhibited progression of the B cell proliferative disorder within 24 months of any prior systemic therapy.

13. The method of claim 1, wherein the subject is a human.

14. The method of claim 1, wherein the bispecific antibody is administered intravenously.

15. The method of claim 1, wherein the B cell proliferative disorder is a CLL.

16. The method of claim 15, wherein the CLL is a relapsed or refractory CLL.

17. The method of claim 1, wherein the B cell proliferative disorder is a DLBCL, and wherein the DLBCL is a Richter's transformation.

18. The method of claim 1, wherein the B cell proliferative disorder is an FL, and wherein the FL is a Grade 1, 2, 3a, or 3b FL or a transformed FL.

19. The method of claim 1, wherein the bispecific antibody comprises an anti-CD20 arm comprising a first binding domain comprising: (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b).

20. The method of claim 19, wherein the bispecific antibody is an $IgG_1$ antibody, and wherein the anti-CD20 arm further comprises T366W and N297G substitution mutations, numbered according to EU numbering.

21. The method of claim 1, wherein the bispecific antibody comprises an anti-CD3 arm comprising a second binding domain comprising: (a) a VH domain comprising an amino acid sequence having at least 95% sequence identity to the amino acid sequence of SEQ ID NO: 15; (b) a VL domain comprising an amino acid sequence having at least 95% sequence identity to the amino acid sequence of SEQ ID NO: 16; or (c) a VH domain as in (a) and a VL domain as in (b).

22. The method of claim 21, wherein the bispecific antibody is an $IgG_1$ antibody, and wherein the anti-CD3 arm further comprises T366S, L368A, Y407V, and N297G substitution mutations, numbered according to EU numbering.

23. The method of claim 1, wherein the bispecific antibody comprises: (a) an anti-CD20 arm comprising: (i) a heavy chain comprising an amino acid sequence having at least 95% sequence identity to the amino acid sequence of SEQ ID NO: 51, and (ii) a light chain comprising an amino acid sequence having at least 95% sequence identity to the amino acid sequence of SEQ ID NO: 52; and (b) an anti-CD3 arm comprising: (i) a heavy chain comprising an amino acid sequence having at least 95% sequence identity to the amino acid sequence of SEQ ID NO: 53, and (ii) a light chain comprising an amino acid sequence having at least 95% sequence identity to the amino acid sequence of SEQ ID NO: 54.

24. The method of claim 1, wherein the bispecific antibody is a humanized antibody or a chimeric antibody.

25. The method of claim 1, wherein the bispecific antibody is an IgG antibody.

26. The method of claim 25, wherein the bispecific antibody is an IgG$_1$ antibody, wherein the IgG$_1$ antibody comprises a mutation at amino acid residue N297, numbered according to EU numbering, that results in the absence of glycosylation and/or is a substitution mutation that reduces effector function of the Fc region.

27. The method of claim 26, wherein the mutation is an N297G or N297A mutation.

28. The method of claim 25, wherein the bispecific antibody is an IgG$_1$ antibody, wherein the bispecific antibody comprises a mutation in the Fc region that reduces effector function and/or a substitution mutation at amino acid residue L234, L235, D265, and/or P329, numbered according to EU numbering.

29. The method of claim 28, wherein the substitution mutation is selected from the group consisting of L234A, L235A, D265A, and P329G.

30. The method of claim 1, wherein the bispecific antibody comprises one or more heavy chain constant domains, wherein the one or more heavy chain constant domains are selected from a first CH1 (CH1$_1$) domain, a first CH2 (CH2$_1$) domain, a first CH3 (CH3$_1$) domain, a second CH1 (CH1$_2$) domain, a second CH2 (CH2$_2$) domain, and a second CH3 (CH3$_2$) domain, wherein at least one of the one or more heavy chain constant domains is paired with another heavy chain constant domain and wherein:
  (a) the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain and the CH3$_1$ and CH3$_2$ domains meet at an interface between the protuberance and cavity; and/or
  (b) the CH2$_1$ and CH2$_2$ domains each comprise a protuberance or cavity, and wherein the protuberance or cavity in the CH2$_1$ domain is positionable in the cavity or protuberance, respectively, in the CH2$_2$ domain and the CH2$_1$ and CH2$_2$ domains meet at an interface between said protuberance and cavity.

31. The method of claim 1, wherein the bispecific antibody is mosunetuzumab.

32. The method of claim 1, wherein the bispecific antibody comprises:
  (a) an anti-CD20 arm comprising a first binding domain comprising a VH domain comprising the amino acid sequence of SEQ ID NO: 7 and a VL domain comprising the amino acid sequence of SEQ ID NO: 8; and
  (b) an anti-CD3 arm comprising a second binding domain comprising a VH domain comprising the amino acid sequence of SEQ ID NO: 15 and a VL domain comprising the amino acid sequence of SEQ ID NO: 16.

33. The method of claim 32, wherein the bispecific antibody is an IgG$_1$ antibody, wherein the anti-CD20 arm further comprises T366W and N297G substitution mutations, numbered according to EU numbering, and the anti-CD3 arm further comprises T366S, L368A, Y407V, and N297G substitution mutations, numbered according to EU numbering.

34. The method of claim 1, wherein the bispecific antibody comprises: (a) an anti-CD20 arm comprising: (i) a heavy chain comprising the amino acid sequence of SEQ ID NO: 51, and (ii) a light chain comprising the amino acid sequence of SEQ ID NO: 52; and (b) an anti-CD3 arm comprising: (i) a heavy chain comprising the amino acid sequence of SEQ ID NO: 53, and (ii) a light chain comprising the amino acid sequence of SEQ ID NO: 54.

35. The method of claim 1, wherein the subject is administered a corticosteroid, an antihistamine, or an antipyretic prior to administering the bispecific antibody.

36. The method of claim 35, wherein:
  (a) the corticosteroid is administered at least one hour prior to administering the bispecific antibody,
  (b) the antihistamine is administered prior to administering the bispecific antibody; and/or
  (c) the antipyretic is administered prior to administering the bispecific antibody.

37. The method of claim 35, wherein the corticosteroid is dexamethasone or methylprednisolone, the antihistamine is diphenhydramine, and the antipyretic is acetaminophen or paracetamol.

38. The method of claim 1, wherein the B cell proliferative disorder is an FL, and the FL is a relapsed or refractory FL.

39. The method of claim 38, wherein the subject has relapsed or refractory FL after one or more prior lines of systemic therapy.

40. The method of claim 38, wherein the subject has relapsed or refractory FL after two or more prior lines of systemic therapy.

41. The method of claim 1, wherein the B cell proliferative disorder is a DLBCL, and the DLBCL is a relapsed or refractory DLBCL.

42. The method of claim 41, wherein the subject has relapsed or refractory DLBCL after one or more prior lines of systemic therapy.

43. The method of claim 41, wherein the subject has relapsed or refractory DLBCL after two or more lines of systemic therapy.

44. A method of treating a subject having a B cell proliferative disorder comprising administering to the subject mosunetuzumab as a monotherapy for treating the B cell proliferative disorder in a dosing regimen comprising eight or more 21-day dosing cycles, wherein:
  (a) the first 21-day dosing cycle comprises a first dose (C1D1), a second dose (C1D2), and a third dose (C1D3) of mosunetuzumab, wherein the C1D1 is 1 mg, the C1D2 is 2 mg, and the C1D3 is 60 mg;
  (b) the second dosing cycle comprises a single dose (C2D1) of mosunetuzumab, wherein the C2D1 is 60 mg;
  (c) the third dosing cycle comprises a single dose (C3D1) of mosunetuzumab;
  (d) the fourth dosing cycle comprises a single dose (C4D1) of mosunetuzumab;
  (e) the fifth dosing cycle comprises a single dose (C5D1) of mosunetuzumab;
  (f) the sixth dosing cycle comprises a single dose (C6D1) of mosunetuzumab;
  (g) the seventh dosing cycle comprises a single dose (C7D1) of mosunetuzumab; and
  (h) the eighth dosing cycle comprises a single dose (C8D1) of mosunetuzumab,
  wherein the C3D1-C8D1 are each 30 mg, and wherein the B cell proliferative disorder is a DLBCL, an FL, an MCL, an MZL, or a CLL.

45. The method of claim 44, wherein the dosing regimen comprises up to nine additional dosing cycles beyond the eighth dosing cycle.

46. The method of claim 44, wherein the subject is administered a corticosteroid, an antihistamine, or an antipyretic prior to administering the bispecific antibody.

47. The method of claim 46, wherein:
(a) the corticosteroid is administered at least one hour prior to administering the bispecific antibody,
(b) the antihistamine is administered prior to administering the bispecific antibody; and/or
(c) the antipyretic is administered prior to administering the bispecific antibody.

48. The method of claim 46, wherein the corticosteroid is dexamethasone or methylprednisolone, the antihistamine is diphenhydramine, and the antipyretic is acetaminophen or paracetamol.

49. The method of claim 44, wherein the B cell proliferative disorder is an FL, and the FL is a relapsed or refractory FL.

50. The method of claim 49, wherein the subject has relapsed or refractory FL after one or more prior lines of systemic therapy.

51. The method of claim 49, wherein the subject has relapsed or refractory FL after two or more prior lines of systemic therapy.

52. The method of claim 44, wherein the B cell proliferative disorder is a DLBCL, and the DLBCL is a relapsed or refractory DLBCL.

53. The method of claim 52, wherein the subject has relapsed or refractory DLBCL after one or more prior lines of systemic therapy.

54. The method of claim 52, wherein the subject has relapsed or refractory DLBCL after two or more prior lines of systemic therapy.

55. The method of claim 44, wherein the C1D1, the C1D2, and the C1D3 are administered to the subject on Days 1, 8, and 15, respectively, of the first dosing cycle; and the C2D1-C8D1 are administered to the subject on Day 1 of the second to eighth dosing cycles, respectively.

56. The method of claim 55, wherein the B cell proliferative disorder is an FL.

57. The method of claim 56, wherein the FL is a Grade 1, 2, 3a, or 3b FL or a transformed FL.

58. The method of claim 56, wherein the FL is a relapsed or refractory FL.

59. The method of claim 58, wherein the subject has relapsed or refractory FL after one or more prior lines of systemic therapy.

60. The method of claim 58, wherein the subject has relapsed or refractory FL after two or more prior lines of systemic therapy.

61. The method of claim 55, wherein the B cell proliferative disorder is a DLBCL.

62. The method of claim 61, wherein the DLBCL is a relapsed or refractory DLBCL.

63. The method of claim 62, wherein the subject has relapsed or refractory DLBCL after one or more prior lines of systemic therapy.

64. The method of claim 62, wherein the subject has relapsed or refractory DLBCL after two or more prior lines of systemic therapy.

65. The method of claim 61, wherein the DLBCL is a Richer's transformation.

66. The method of claim 44, wherein the subject has received at least one prior systemic therapy for the B cell proliferative disorder.

67. The method of claim 66, wherein the prior systemic therapy comprises an anti-CD20 antibody, a chemotherapeutic agent, a radio-immunotherapy, a phosphoinositide 3-kinase inhibitor, autologous stem cell transplant therapy, and/or a chimeric antigen receptor-T-cell (CAR-T) therapy.

68. The method of claim 66, wherein the prior systemic therapy comprises a Bruton's tyrosine kinase (BTK) inhibitor, an anthracycline, and/or an alkylating agent.

69. The method of claim 66, wherein the subject:
(a) has received a first-line systemic therapy and a second-line systemic therapy for the B cell proliferative disorder; and/or
(b) has exhibited progression of the B cell proliferative disorder within 24 months of any prior systemic therapy.

70. The method of claim 44, wherein the subject is a human.

71. The method of claim 44, wherein mosunetuzumab is administered intravenously.

72. A method of treating a population of subjects having a B cell proliferative disorder comprising administering to the subjects a bispecific antibody that binds to CD20 and CD3 as a monotherapy for treating the B cell proliferative disorder in a dosing regimen comprising eight or more dosing cycles, wherein:
(a) the first dosing cycle comprises a first dose (C1D1), a second dose (C1D2), and a third dose (C1D3) of the bispecific antibody, wherein the C1D1 is 1 mg, the C1D2 is 2 mg, and the C1D3 is 60 mg;
(b) the second dosing cycle comprises a single dose (C2D1) of the bispecific antibody, wherein the C2D1 is 60 mg;
(c) the third dosing cycle comprises a single dose (C3D1) of the bispecific antibody,
(d) the fourth dosing cycle comprises a single dose (C4D1) of the bispecific antibody;
(e) the fifth dosing cycle comprises a single dose (C5D1) of the bispecific antibody;
(f) the sixth dosing cycle comprises a single dose (C6D1) of the bispecific antibody;
(g) the seventh dosing cycle comprises a single dose (C7D1) of the bispecific antibody; and
(h) the eighth dosing cycle comprises a single dose (C8D1) of the bispecific antibody,
wherein the C3D1-C8D1 are each 30 mg, wherein the B cell proliferative disorder is a DLBCL, an FL, an MCL, an MZL, or a CLL, wherein the bispecific antibody is a full-length antibody, and
wherein the bispecific antibody comprises:
an anti-CD20 arm comprising a first binding domain comprising the following six hypervariable regions (HVRs):
(a) an HVR-H1 comprising the amino acid sequence of GYTFTSYNMH (SEQ ID NO: 1);
(b) an HVR-H2 comprising the amino acid sequence of AIYPGNGDTSYNQKFKG (SEQ ID NO: 2);
(c) an HVR-H3 comprising the amino acid sequence of VVYYSNSYWYFDV (SEQ ID NO: 3);
(d) an HVR-L1 comprising the amino acid sequence of RASSSVSYMH (SEQ ID NO: 4);
(e) an HVR-L2 comprising the amino acid sequence of APSNLAS (SEQ ID NO: 5); and
(f) an HVR-L3 comprising the amino acid sequence of QQWSFNPPT (SEQ ID NO: 6); and
an anti-CD3 arm comprising a second binding domain comprising the following six HVRs:
(a) an HVR-H1 comprising the amino acid sequence of NYYIH (SEQ ID NO: 9);
(b) an HVR-H2 comprising the amino acid sequence of WIYPGDGNTKYNEKFKG (SEQ ID NO: 10);
(c) an HVR-H3 comprising the amino acid sequence of DSYSNYYFDY (SEQ ID NO: 11);

(d) an HVR-L1 comprising the amino acid sequence of KSSQSLLNSRTRKNYLA (SEQ ID NO: 12);
(e) an HVR-L2 comprising the amino acid sequence of WASTRES (SEQ ID NO: 13); and
(f) an HVR-L3 comprising the amino acid sequence of TQSFILRT (SEQ ID NO: 14).

73. The method of claim 72, wherein the population of subjects has:
(a) a complete response rate, wherein the complete response rate is the rate of subjects in the population having a complete response, and wherein the complete response rate is at least 15%;
(b) an objective response rate, wherein the objective response rate is the rate of subjects in the population having an objective response, and wherein the objective response rate is at least 60%;
(c) a median duration of response (mDOR), wherein the mDOR is the median of the durations of response of subjects in the population, and wherein mDOR is at least 12 months; and/or
(d) a duration of response (DOR) of at least 12 months, and wherein the rate of subjects in the population having a DOR of at least 12 months is at least 60%.

74. The method of claim 72, wherein the population of subjects exhibits cytokine release syndrome after administering the bispecific antibody, and wherein the rate of the cytokine release syndrome in the population of subjects is less than or equal to 40% and/or the rate of cytokine release syndrome having a grade of 2 or greater, as defined by the American Society for Transplantation and Cellular Therapy (ASTCT), is less than or equal to 20%.

75. The method of claim 72, wherein the bispecific antibody is administered intravenously.

76. The method of claim 72, wherein the dosing regimen comprises up to nine additional dosing cycles beyond the eighth dosing cycle.

77. The method of claim 72, wherein the subject is administered a corticosteroid, an antihistamine, or an antipyretic prior to administering the bispecific antibody.

78. The method of claim 77, wherein:
(a) the corticosteroid is administered at least one hour prior to administering the bispecific antibody,
(b) the antihistamine is administered prior to administering the bispecific antibody; and/or
(c) the antipyretic is administered prior to administering the bispecific antibody.

79. The method of claim 77, wherein the corticosteroid is dexamethasone or methylprednisolone, the antihistamine is diphenhydramine, and the antipyretic is acetaminophen or paracetamol.

80. A method of treating a subject having a B cell proliferative disorder comprising administering to the subject mosunetuzumab as a monotherapy for treating the B cell proliferative disorder in a dosing regimen comprising a 21-day dosing cycle and seven or more 28-day dosing cycles, wherein:
(a) the first 21-day dosing cycle comprises a first dose (C1D1), a second dose (C1D2), and a third dose (C1D3) of the bispecific antibody, wherein the C1D1 is 1 mg, the C1D2 is 2 mg, and the C1D3 is 60 mg;
(b) the second dosing cycle comprises a single dose (C2D1) of mosunetuzumab, wherein the C2D1 is 60 mg;
(c) the third dosing cycle comprises a single dose (C3D1) of mosunetuzumab;
(d) the fourth dosing cycle comprises a single dose (C4D1) of mosunetuzumab;
(e) the fifth dosing cycle comprises a single dose (C5D1) of mosunetuzumab;
(f) the sixth dosing cycle comprises a single dose (C6D1) of mosunetuzumab;
(g) the seventh dosing cycle comprises a single dose (C7D1) of mosunetuzumab; and
(h) the eighth dosing cycle comprises a single dose (C8D1) of mosunetuzumab,
wherein the C3D1-C8D1 are each 30 mg, and wherein the B cell proliferative disorder is a DLBCL, an FL, an MCL, an MZL, or a CLL.

* * * * *